US011045476B2

(12) United States Patent
Schultz et al.

(10) Patent No.: US 11,045,476 B2
(45) Date of Patent: Jun. 29, 2021

(54) COMPOUNDS AND METHODS FOR INDUCING CHONDROGENESIS

(71) Applicant: The Scripps Research Institute, La Jolla, CA (US)

(72) Inventors: Peter G. Schultz, La Jolla, CA (US); Arnab K. Chatterjee, San Diego, CA (US); Shoutian Zhu, Carlsbad, CA (US); Joshua Payette, Hollis, NH (US); Hongchul Yoon, San Diego, CA (US); Baiyuan Yang, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/685,555

(22) Filed: Nov. 15, 2019

(65) Prior Publication Data
US 2020/0188407 A1  Jun. 18, 2020

Related U.S. Application Data

(63) Continuation of application No. 14/774,673, filed as application No. PCT/US2014/026722 on Mar. 13, 2014, now Pat. No. 10,500,210.

(Continued)

(51) Int. Cl.
| A61K 31/54 | (2006.01) |
| C07C 255/60 | (2006.01) |
| A61K 31/277 | (2006.01) |
| A61K 31/192 | (2006.01) |
| C07D 295/26 | (2006.01) |
| A61K 31/5375 | (2006.01) |
| C07D 317/66 | (2006.01) |
| A61K 31/36 | (2006.01) |
| C07D 319/08 | (2006.01) |
| C07D 233/64 | (2006.01) |
| C07D 261/14 | (2006.01) |
| A61K 31/42 | (2006.01) |
| A61K 45/06 | (2006.01) |
| A61K 31/196 | (2006.01) |
| A61K 31/255 | (2006.01) |
| A61K 31/4035 | (2006.01) |
| C07C 271/20 | (2006.01) |

(Continued)

(52) U.S. Cl.
CPC .............. *A61K 31/54* (2013.01); *A61K 31/18* (2013.01); *A61K 31/192* (2013.01); *A61K 31/194* (2013.01); *A61K 31/196* (2013.01); *A61K 31/24* (2013.01); *A61K 31/255* (2013.01); *A61K 31/27* (2013.01); *A61K 31/277* (2013.01); *A61K 31/357* (2013.01); *A61K 31/36* (2013.01); *A61K 31/365* (2013.01); *A61K 31/402* (2013.01); *A61K 31/4035* (2013.01); *A61K 31/415* (2013.01); *A61K 31/4164* (2013.01); *A61K 31/42* (2013.01); *A61K 31/426* (2013.01); *A61K 31/433* (2013.01); *A61K 31/44* (2013.01); *A61K 31/495* (2013.01); *A61K 31/5375* (2013.01); *A61K 45/06* (2013.01); *C07C 233/66* (2013.01); *C07C 233/69* (2013.01); *C07C 233/73* (2013.01); *C07C 233/75* (2013.01); *C07C 233/76* (2013.01); *C07C 233/80* (2013.01); *C07C 233/81* (2013.01); *C07C 233/87* (2013.01); *C07C 235/52* (2013.01); *C07C 235/60* (2013.01); *C07C 235/84* (2013.01); *C07C 237/22* (2013.01); *C07C 251/48* (2013.01); *C07C 255/60* (2013.01); *C07C 271/20* (2013.01); *C07C 275/42* (2013.01); *C07C 311/05* (2013.01); *C07C 311/08* (2013.01); *C07C 311/13* (2013.01); *C07C 311/17* (2013.01); *C07C 311/21* (2013.01); *C07C 311/24* (2013.01); *C07C 311/46* (2013.01); *C07C 317/40* (2013.01); *C07D 207/27* (2013.01); *C07D 209/46* (2013.01); *C07D 209/48* (2013.01); *C07D 213/79* (2013.01); *C07D 231/40* (2013.01); *C07D 233/64* (2013.01); *C07D 261/14* (2013.01); *C07D 277/46* (2013.01); *C07D 285/135* (2013.01); *C07D 295/26* (2013.01); *C07D 307/88* (2013.01); *C07D 317/28* (2013.01); *C07D 317/66* (2013.01); *C07D 319/08* (2013.01); *C07D 319/18* (2013.01); *C12N 5/0655* (2013.01); *C12N 2506/1353* (2013.01)

(58) Field of Classification Search
USPC ........................................................ 514/577
See application file for complete search history.

(56) References Cited

U.S. PATENT DOCUMENTS 3,658,892 A  4/1972  Henry et al.
3,793,458 A  2/1974  Wermuth et al.
(Continued)

FOREIGN PATENT DOCUMENTS

CN  1264377 A  8/2000
CN  101094829 A  12/2007
(Continued)

OTHER PUBLICATIONS

Able et al. Receptor localization, native tissue binding and ex vivo occupancy for centrally penetrant P2X7antagonists in the rat, Br. J. Pharmacol, vol. 162, No. 2, pp. 405-414, Jan. 2011.
(Continued)

*Primary Examiner* — Kathrien A Cruz
(74) *Attorney, Agent, or Firm* — Wilson Sonsini Goodrich & Rosati

(57) ABSTRACT

Described herein are compounds and compositions for the amelioration of arthritis or joint injuries by inducing mesenchymal stem cells into chondrocytes.

13 Claims, No Drawings

Related U.S. Application Data

(60) Provisional application No. 61/794,094, filed on Mar. 15, 2013.

(51) Int. Cl.

| | | |
|---|---|---|
| *C07C 275/42* | (2006.01) | |
| *C07C 311/05* | (2006.01) | |
| *C07C 311/08* | (2006.01) | |
| *C07C 311/13* | (2006.01) | |
| *C07C 311/17* | (2006.01) | |
| *C07C 311/21* | (2006.01) | |
| *C07C 311/24* | (2006.01) | |
| *C07C 311/46* | (2006.01) | |
| *C07C 317/40* | (2006.01) | |
| *C07C 233/66* | (2006.01) | |
| *C07C 233/69* | (2006.01) | |
| *C07C 233/73* | (2006.01) | |
| *C07C 233/75* | (2006.01) | |
| *C07C 233/76* | (2006.01) | |
| *C07C 233/80* | (2006.01) | |
| *C07C 233/81* | (2006.01) | |
| *C07C 233/87* | (2006.01) | |
| *C07C 235/52* | (2006.01) | |
| *C07C 235/60* | (2006.01) | |
| *C07C 237/22* | (2006.01) | |
| *C07C 251/48* | (2006.01) | |
| *A61K 31/18* | (2006.01) | |
| *A61K 31/194* | (2006.01) | |
| *A61K 31/24* | (2006.01) | |
| *A61K 31/27* | (2006.01) | |
| *A61K 31/357* | (2006.01) | |
| *A61K 31/365* | (2006.01) | |
| *A61K 31/402* | (2006.01) | |
| *A61K 31/415* | (2006.01) | |
| *A61K 31/4164* | (2006.01) | |
| *A61K 31/426* | (2006.01) | |
| *A61K 31/433* | (2006.01) | |
| *A61K 31/44* | (2006.01) | |
| *A61K 31/495* | (2006.01) | |
| *C07C 235/84* | (2006.01) | |
| *C07D 207/27* | (2006.01) | |
| *C07D 209/46* | (2006.01) | |
| *C07D 209/48* | (2006.01) | |
| *C07D 213/79* | (2006.01) | |
| *C07D 231/40* | (2006.01) | |
| *C07D 277/46* | (2006.01) | |
| *C07D 285/135* | (2006.01) | |
| *C07D 307/88* | (2006.01) | |
| *C07D 317/28* | (2006.01) | |
| *C07D 319/18* | (2006.01) | |
| *C12N 5/077* | (2010.01) | |

(56) References Cited

U.S. PATENT DOCUMENTS

| | | | |
|---|---|---|---|
| 6,514,977 | B1 | 2/2003 | Anantanarayan et al. |
| 6,632,961 | B1 | 10/2003 | Kawai et al. |
| 7,776,869 | B2 | 8/2010 | Chaffee et al. |
| 9,452,170 | B2 | 9/2016 | Schultz et al. |
| 10,166,237 | B2 | 1/2019 | Schultz et al. |
| 10,500,210 | B2 | 12/2019 | Schultz et al. |
| 2003/0216434 | A1 | 11/2003 | Cherney |
| 2005/0049286 | A1 | 3/2005 | Wu et al. |
| 2006/0217380 | A1 | 9/2006 | Chaffee et al. |
| 2007/0142329 | A1 | 6/2007 | Dombroski et al. |
| 2007/0197516 | A1 | 8/2007 | Carter |
| 2009/0306078 | A1 | 12/2009 | Lee et al. |
| 2010/0087415 | A1 | 4/2010 | Whitten et al. |
| 2014/0113012 | A1 | 4/2014 | Schultz et al. |
| 2015/0329554 | A1 | 11/2015 | Choi et al. |
| 2016/0045514 | A1 | 2/2016 | Schultz et al. |
| 2017/0112843 | A1 | 4/2017 | Schultz et al. |

FOREIGN PATENT DOCUMENTS

| | | |
|---|---|---|
| DE | 1813727 B2 | 5/1977 |
| EP | 0347168 B1 | 9/1993 |
| EP | 2172198 A1 | 4/2010 |
| JP | H0959236 A | 3/1997 |
| WO | WO-9924416 A1 | 5/1999 |
| WO | WO-02060859 A2 | 8/2002 |
| WO | WO-2005013947 A2 | 2/2005 |
| WO | WO-2005021500 A1 | 3/2005 |
| WO | WO-2006039718 A2 | 4/2006 |
| WO | WO-2006062093 A1 | 6/2006 |
| WO | WO-2011147810 A1 | 12/2011 |
| WO | WO-2012129562 A2 | 9/2012 |
| WO | WO-2014151953 A1 | 9/2014 |

OTHER PUBLICATIONS

CAS Registry No. 717862-14-1. SciFinder. Accessed Apr. 10, 2019. 2 pages.
CAS Registry No. 897342-04-0 Benzoic acid, 2-[[[(3-acetylphenyl)amino]carbonyl]amino]-, methyl ester. STN Entry Date: Jul. 28, 2006.
CAS Registry No. 830338-61-9. SciFinder. Accessed Apr. 10, 2019. 2 pages.
CAS Registry No. 831243-94-8. SciFinder. Accessed Apr. 10, 2019. 2 pages.
Goldring, M.B., Articular cartilage and subchondral bone in the pathogenesis of osteoarthritis. Ann N Y Acad Sci, 2010. 1192(1): p. 230-237.
Grogan, S.P., et al., Mesenchymal progenitor cell markers in human articular cartilage: normal distribution and changes in osteoarthritis. Arthritis Res Ther, 2009. 11(3): p. R85.
Hunter, D.J., Pharmacologic therapy for osteoarthritis—the era of disease modification. Nat Rev Rheumatol, 2011. 7(1): p. 13-22.
International Application No. PCT/US2018/028939 International Search Report and Written Opinion dated Jul. 20, 2018.
International Search Report and Written Opinion for International Application No. PCT/US12/30567, dated Sep. 21, 2012.
International Search Report and Written Opinion for International Application No. PCT/US2014/026722 dated Jul. 18, 2014.
Irani, R.J., A simple method of preparation of N4-substituted disulfanilamido derivatives of some dibasic acids. Current Science, vol. 14, pp. 46-47, 1945.
Koelling, S., et al., Migratory chondrogenic progenitor cells from repair tissue during the later stages of human osteoarthritis. Cell Stem Cell, 2009. 4(4): p. 324-335.
Lewis, R. Hawley's Condensed Chemical Dictionary, 15th Edition p. 711 (2007).
Li, Z. et al. Microwave-Assisted Efficient and Convenient Synthesis of 2,4(1H,3H)-Quinazolinediones and 2-Thioxoquinazolines. Journal of Combinatorial Chremistry. 10(3):484-486 (May-Jun. 2008).
Nakamura et al. Studies on Antiinflammatory Agents. II. Synthesis and Pharmacological Properties 2'-(Phenylthio)methanesulfonanilides and Related Derivatives. Chem. Pharm. Bull. 41(5):894-906 (1993).
PCT/US2018/028939 International Preliminary Report on Patentability dated Oct. 29, 2019.
Pittenger, M.F., et al., Multilineage potential of adult human mesenchymal stem cells. Science, vol. 284, No. 5411, pp. 143-147, 1999.
Pubchem compound ID 78458 (create date: Mar. 26, 2005) (retreived from http://pubchem.ncbi.nlm.nih.gov/summary.cgi?cid=78458 on Oct. 22, 2015).
Reginster, J.Y. and N.G. Khaltaev, Introduction and WHO perspective on the global burden of musculoskeletal conditions. Rheumatology (Oxford), 2002. 41 Supp 1: p. 1-2.

(56) References Cited

OTHER PUBLICATIONS

Silva et al. Advances in Prodrug Design. Mini Reviews in Medicinal Chemistry 5:893-914 (2005).
Simonyi, Miklos and Maksay, Gabor. Chapter 21: "Stereochemical aspects of drug action II: Optical isomerism." The Practice of Medicinal Chemistry. First Edition. CG Wermuth Ed. San Diego: Academic Press Inc., 1996. 413-435. Print.
U.S. Appl. No. 14/007,306 Office Action dated Dec. 17, 2015.
U.S. Appl. No. 14/210,198 Final Office Action dated Jul. 12, 2016.
U.S. Appl. No. 14/210,198 Office Action dated Apr. 11, 2016.
U.S. Appl. No. 14/210,198 Restriction Requirement dated Oct. 19, 2015.
U.S. Appl. No. 14/774,673 Non-Final Office Action dated Aug. 24, 2018.
U.S. Appl. No. 15/256,230 Office Action dated Mar. 8, 2018.
Johnson et al., Stem Cell-Based Approach to Cartilage Repair. Science 336(6082): 717-721 (2012).

COMPOUNDS AND METHODS FOR INDUCING CHONDROGENESIS

CROSS-REFERENCE TO RELATED APPLICATIONS

This application is a continuation of U.S. application Ser. No. 14/774,673, filed Sep. 10, 2015, which is a U.S. National Stage entry of International Application No. PCT/US14/26722, filed Mar. 13, 2014, which claims the benefit of priority from U.S. Provisional Application No. 61/794,094, filed Mar. 15, 2013, all of which are hereby incorporated by reference in their entirety.

FIELD OF INVENTION

The present invention relates to compounds, compositions, preparations and their use for inducing chondrogenesis and for the treatment of arthritis or joint injury.

BACKGROUND OF THE INVENTION

Osteoarthritis (OA) represents the most common musculoskeletal disorder. Approximately 40 million Americans are currently affected and this number is predicted to increase to 60 million within the next twenty years as a result of the aging population and an increase in life expectancy, making it the fourth leading cause of disability. OA is characterized by a slow degenerative breakdown of the joint including both the articular cartilage (containing the cells and matrix which produce lubrication and cushioning for the joint) and the subchondral bone underlying the articular cartilage. Current OA therapies include pain relief with oral NSAIDs or selective cyclooxygenase 2 (COX-2) inhibitors, intra-articular (IA) injection with agents such as corticorsteroids and hyaluronan, and surgical approaches.

Mesenchymal stem cells (MSCs) are present in adult articular cartilage and upon isolation can be programmed in vitro to undergo differentiation to chondrocytes and other mesenchymal cell lineages. In part it is regulated by growth factors (TGFs, BMPs), serum conditions and cell-cell contact.

SUMMARY OF THE INVENTION

Provided herein is a method of ameliorating arthritis or joint injury in a mammal, the method including administering to a joint of the mammal a composition having a therapeutically effective amount of a compound disclosed herein.

Provided herein is a method of inducing differentiation of mesenchymal stem cells into chondrocytes, the method including contacting mesenchymal stem cells with a sufficient amount of a compound disclosed herein, thereby inducing differentiation of the stem cells into chondrocytes.

In one aspect, provided herein is a method of ameliorating arthritis or joint injury in a mammal, the method comprising administering to a joint of the mammal a composition comprising a therapeutically effective amount of a compound of Formula I, or a pharmaceutically acceptable salt, solvate, polymorph, prodrug, ester, metabolite, N-oxide, stereoisomer, or isomer thereof:

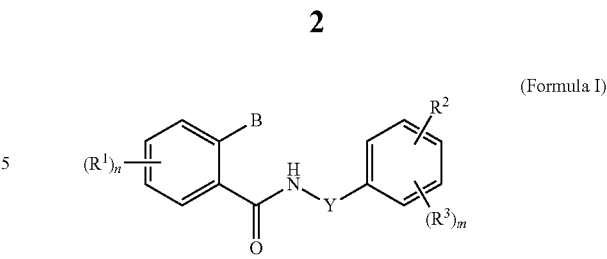

(Formula I)

wherein:
each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
n is 0, 1, 2, 3, or 4;
m is 1, 2, 3, or 4;
B is $CO_2R^4$, $CH_2CO_2H$, $CH_2CO_2R^4$, or optionally substituted phenyl;
Y is a bond, —$(CR^5R^6)$—, —$(CR^7R^8)(CR^9R^{10})$—, or —$(CR^7R^8)(CR^9R^{10})X$—;
X is O or $CR^5R^6$;
$R^2$ is halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
each $R^3$ is independently selected from H, CN, halo, $C(O)R^4$, $CO_2H$, $CO_2R^4$, $C(O)NR^4R^{11}$, alkyl, optionally substituted alkoxy, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$;
each $R^4$ is independently selected from H and optionally substituted alkyl;
each $R^5$, $R^6$, $R^7$, $R^8$, $R^9$, and $R^{10}$ is independently selected from H, halo, optionally substituted alkyl, OH, $CO_2R^4$, $NR^4R^{11}$, and optionally substituted alkoxy; and
$R^{11}$ is H, optionally substituted alkyl, $C(O)R^4$, $C(O)OR^4$, $C(O)NR^4R^4$, or $SO_2R^4$; provided that
a) if Y is a bond and m is 0, then $R^2$ is selected from $C(O)NR^4R^{11}$, $(CR^7R^8)OR^4$, $(CR^7R^8)(CR^9R^{10})OR^4$, $X(CR^7R^8)(CR^9)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$; and
$R^2$ is not $C(O)NH_2$, p-$CH_2OR^4$, p-$CH(OH)CH_2OH$, p-$CH_2CH_2OH$, or p-$CH_2CH_2CH_2OH$; and
b) the compound is not selected from

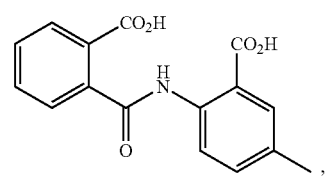

-continued

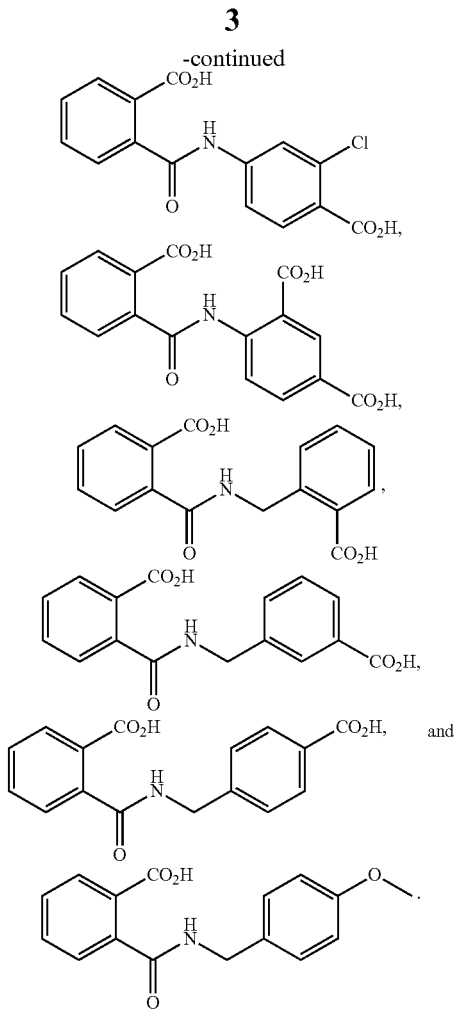

In another aspect, provided herein is a method of ameliorating arthritis or joint injury in a mammal, the method comprising administering to a joint of the mammal a composition comprising a therapeutically effective amount of a compound of Formula Ia, or a pharmaceutically acceptable salt, solvate, polymorph, prodrug, ester, metabolite, N-oxide, stereoisomer, or isomer thereof:

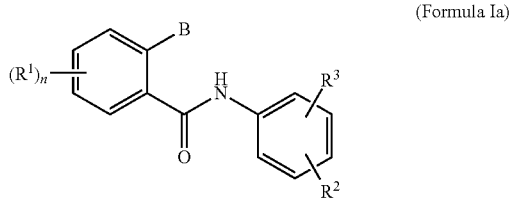

(Formula Ia)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
n is 0, 1, 2, 3, or 4;
B is $CO_2R^4$;
$R^2$ is halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
each $R^3$ is independently selected from CN, halo, $C(O)R^4$, $CO_2H$, $CO_2R^4$, $C(O)NR^4R^{11}$, alkyl, optionally substituted alkoxy, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$;
X is O or $CR^5R^6$;
each $R^4$ is independently selected from H and optionally substituted alkyl;
each $R^5$, $R^6$, $R^7$, $R^8$, $R^9$, and $R^{10}$ is independently selected from H, halo, optionally substituted alkyl, OH, $NR^4R^{11}$, and optionally substituted alkoxy; and
$R^{11}$ is H, optionally substituted alkyl, $C(O)R^4$, $C(O)OR^4$, $C(O)NR^4R^4$, or $SO_2R^4$;
provided that the compound is not selected from

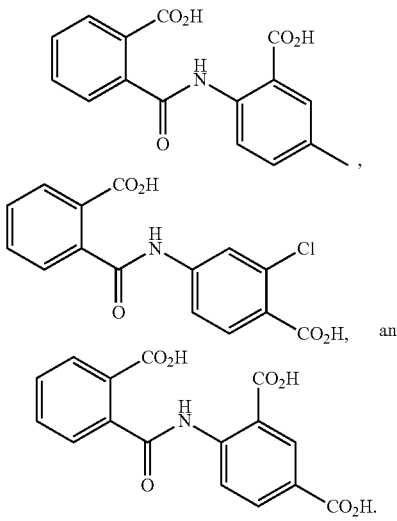

In another aspect, provided herein is a method of ameliorating arthritis or joint injury in a mammal, the method comprising administering to a joint of the mammal a composition comprising a therapeutically effective amount of a compound of Formula Ib, or a pharmaceutically acceptable salt, solvate, polymorph, prodrug, ester, metabolite, N-oxide, stereoisomer, or isomer thereof:

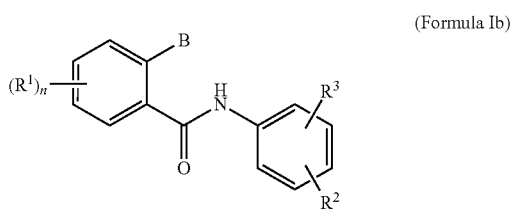

(Formula Ib)

wherein
  each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
  n is 0, 1, 2, 3, or 4;
  B is $CO_2R^4$;
  $R^2$ is $C(O)NR^4R^{11}$, $(CR^7R^8)OR^4$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
  $R^3$ is H;
  X is O or $CR^5R^6$;
  each $R^4$ is independently selected from H and optionally substituted alkyl;
  each $R^5$, $R^6$, $R^7$, $R^8$, $R^9$, and $R^{10}$ is independently selected from H, halo, optionally substituted alkyl, OH, $NR^4R^{11}$, and optionally substituted alkoxy; and
  $R^{11}$ is H, optionally substituted alkyl, $C(O)R^4$, $C(O)OR^4$, $C(O)NR^4R^4$, or $SO_2R^4$;
  provided that if n is 0, then $R^2$ is not $C(O)NH_2$, p-$CH_2OR^4$, p-$CH(OH)CH_2OH$, p-$CH_2CH_2OH$, or p-$CH_2CH_2CH_2OH$.

In another aspect, provided herein is a method of ameliorating arthritis or joint injury in a mammal, the method comprising administering to a joint of the mammal a composition comprising a therapeutically effective amount of a compound of Formula Ic, or a pharmaceutically acceptable salt, solvate, polymorph, prodrug, ester, metabolite, N-oxide, stereoisomer, or isomer thereof:

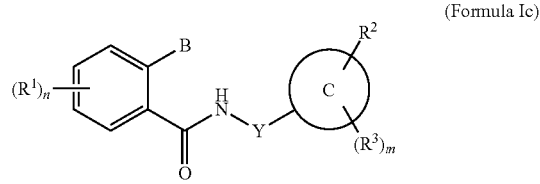

(Formula Ic)

wherein
  each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
  n is 0, 1, 2, 3, or 4;
  m is 1, 2, 3, or 4;
  B is $CO_2R^4$;
  Y is $-(CR^5R^6)-$;
  C is aryl or heteroaryl;
  X is O or $CR^5R^6$;
  $R^2$ is halo, $C(O)R^4$, $CO_2R^4$, $C(O)NR^4R^{11}$, alkyl, optionally substituted alkoxy, haloalkyl, $SO_2R^4$, $SO_2NH_2$, $SO_3H$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
  each $R^3$ is independently selected from H, CN, halo, $C(O)R^4$, $CO_2H$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$;
  each $R^4$ is independently selected from H and optionally substituted alkyl;
  each $R^5$, $R^6$, $R^7$, $R^8$, $R^9$, and $R^{10}$ is independently selected from H, halo, optionally substituted alkyl, OH, $CO_2R^4$, $NR^4R^{11}$, and optionally substituted alkoxy; and
  $R^{11}$ is H, optionally substituted alkyl, $C(O)R^4$, $C(O)OR^4$, $C(O)NR^4R^4$, or $SO_2R^4$; provided that the compound is not selected from

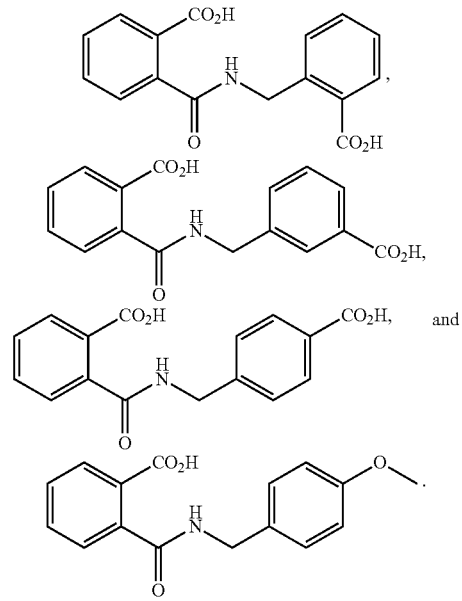

In another aspect, provided herein is a method of inducing differentiation of mesenchymal stem cells into chondrocytes, the method comprising contacting mesenchymal stem cells with a sufficient amount of a compound of Formula I, or a pharmaceutically acceptable salt, solvate, polymorph, prodrug, ester, metabolite, N-oxide, stereoisomer, or isomer thereof:

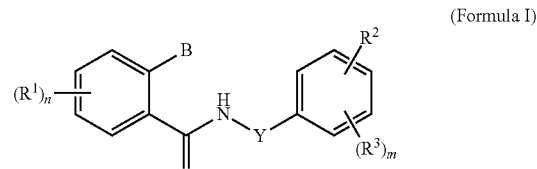

(Formula I)

wherein
  each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
  n is 0, 1, 2, 3, or 4;
  m is 1, 2, 3, or 4;

B is $CO_2R^4$, $CH_2CO_2H$, $CH_2CO_2R^3$, or optionally substituted phenyl;

Y is a bond, $-(CR^5R^6)-$, $-(CR^7R^8)(CR^9R^{10})-$, or $-(CR^7R^8)(CR^9R^{10})X-$;

X is O or $CR^5R^6$;

$R^2$ is halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;

each $R^3$ is independently selected from H, CN, halo, $C(O)R^4$, $CO_2H$, $CO_2R^4$, $C(O)NR^4R^{11}$, alkyl, optionally substituted alkoxy, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$;

each $R^4$ is independently selected from H and optionally substituted alkyl;

each $R^5$, $R^6$, $R^7$, $R^8$, $R^9$, and $R^{10}$ is independently selected from H, halo, optionally substituted alkyl, OH, $CO_2R^4$, $NR^4R^{11}$, and optionally substituted alkoxy; and $R^{11}$ is H, optionally substituted alkyl, $C(O)R^4$, $C(O)OR^4$, $C(O)NR^4R^4$, or $SO_2R^4$; provided that a) if Y is a bond and m is 0, then $R^2$ is selected from $C(O)NR^4R^{11}$, $(CR^7R^8)OR^4$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$; and $R^2$ is not $C(O)NH_2$, $p-CH_2OR^4$, $p-CH(OH)CH_2OH$, $p-CH_2CH_2OH$, or $p-CH_2CH_2CH_2OH$; and b) the compound is not selected from

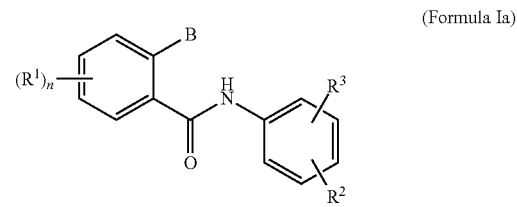

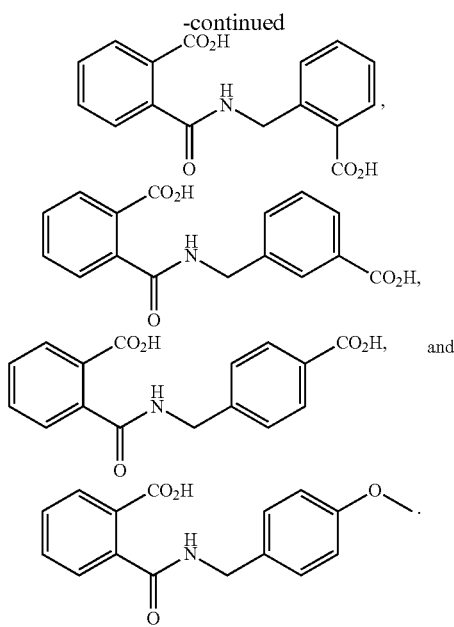

In another aspect, provided herein is a method of inducing differentiation of mesenchymal stem cells into chondrocytes, the method comprising contacting mesenchymal stem cells with a sufficient amount of a compound of Formula Ia, or a pharmaceutically acceptable salt, solvate, polymorph, prodrug, ester, metabolite, N-oxide, stereoisomer, or isomer thereof:

(Formula Ia)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;

n is 0, 1, 2, 3, or 4;

B is $CO_2R^4$;

$R^2$ is halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;

each $R^3$ is independently selected from CN, halo, $C(O)R^4$, $CO_2H$, $CO_2R^4$, $C(O)NR^4R^{11}$, alkyl, optionally substituted alkoxy, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, X(CR⁷R⁸)(CR⁹R¹⁰)C(O)R⁴, X(CR⁷R⁸)(CR⁹R¹⁰)C(O)OR⁴, X(CR⁷R⁸)(CR⁹R¹⁰)C(O)NR⁴R¹¹, (CR⁷R⁸)NR⁴SO₂R⁴, and C(=NOR⁴)R⁴;

X is O or CR⁵R⁶;

each R⁴ is independently selected from H and optionally substituted alkyl;

each R⁵, R⁶, R⁷, R⁸, R⁹, and R¹⁰ is independently selected from H, halo, optionally substituted alkyl, OH, NR⁴R¹¹, and optionally substituted alkoxy; and R¹¹ is H, optionally substituted alkyl, C(O)R⁴, C(O)OR⁴, C(O)NR⁴R⁴, or SO₂R⁴;

provided that the compound is not selected from

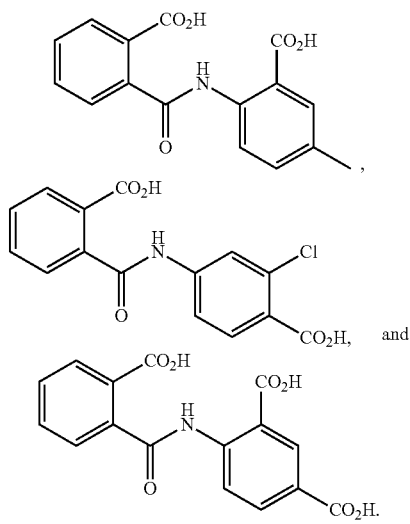

In another aspect, provided herein is a method of inducing differentiation of mesenchymal stem cells into chondrocytes, the method comprising contacting mesenchymal stem cells with a sufficient amount of a compound of Formula Ib, or a pharmaceutically acceptable salt, solvate, polymorph, prodrug, ester, metabolite, N-oxide, stereoisomer, or isomer thereof:

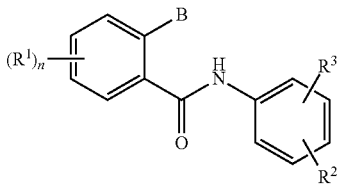

(Formula Ib)

wherein
each R¹ is independently halo, optionally substituted alkyl, optionally substituted alkoxy, optionally substituted aryloxy, CN, NO₂, SR⁴, S(O)R⁴, SO₂R⁴, NR⁴R¹¹, CO₂H, or CO₂R⁴;
n is 0, 1, 2, 3, or 4;
B is CO₂R⁴;
R² is C(O)NR⁴R¹¹, (CR⁷R⁸)OR⁴, (CR⁷R⁸)(CR⁹R¹⁰)OR⁴, X(CR⁷R⁸)(CR⁹R¹⁰)OR⁴, X(CR⁷R⁸)(CR⁹R¹⁰)NR⁴R¹¹, (CR⁷R⁸)C(O)R⁴, (CR⁷R⁸)C(O)OR⁴, (CR⁷R⁸)C(O)NR⁴R¹¹, X(CR⁷R⁸)C(O)R⁴, X(CR⁷R⁸)C(O)OR⁴, X(CR⁷R⁸)C(O)NR⁴R¹¹, X(CR⁷R⁸)(CR⁹R¹⁰)C(O)R⁴, X(CR⁷R⁸)(CR⁹R¹⁰)C(O)OR⁴, X(CR⁷R⁸)(CR⁹R¹⁰)C(O)NR⁴R¹¹, (CR⁷R⁸)NR⁴SO₂R⁴, or C(=NOR⁴)R⁴;

R³ is H;
X is O or CR⁵R⁶;
each R⁴ is independently selected from H and optionally substituted alkyl;
each R⁵, R⁶, R⁷, R⁸, R⁹, and R¹⁰ is independently selected from H, halo, optionally substituted alkyl, OH, NR⁴R¹¹, and optionally substituted alkoxy; and
R¹¹ is H, optionally substituted alkyl, C(O)R⁴, C(O)OR⁴, C(O)NR⁴R⁴, or SO₂R⁴;
provided that if n is 4 and R¹ is H, then R² is not C(O)NH₂, p-CH₂OR⁴, p-CH(OH)CH₂OH, p-CH₂CH₂OH, or p-CH₂CH₂CH₂OH.

In another aspect, provided herein is a method of inducing differentiation of mesenchymal stem cells into chondrocytes, the method comprising contacting mesenchymal stem cells with a sufficient amount of a compound of Formula Ic, or a pharmaceutically acceptable salt, solvate, polymorph, prodrug, ester, metabolite, N-oxide, stereoisomer, or isomer thereof:

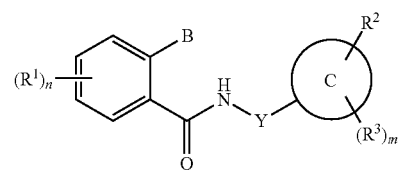

(Formula Ic)

wherein
each R¹ is independently halo, optionally substituted alkyl, optionally substituted alkoxy, optionally substituted aryloxy, CN, NO₂, SR⁴, S(O)R⁴, SO₂R⁴, NR⁴R¹¹, CO₂H, or CO₂R⁴;
n is 0, 1, 2, 3, or 4;
m is 1, 2, 3, or 4;
B is CO₂R⁴;
Y is —(CR⁵R⁶)—;
C is aryl or heteroaryl;
X is O or CR⁵R⁶;
R² is halo, C(O)R⁴, CO₂R⁴, C(O)NR⁴R¹¹, alkyl, optionally substituted alkoxy, haloalkyl, SO₂R⁴, SO₂NH₂, SO₃H, (CR⁷R⁸)OR⁴, (CR⁷R⁸)NR⁴R¹¹, (CR⁷R⁸)(CR⁹R¹⁰)OR⁴, X(CR⁷R⁸)(CR⁹R¹⁰)OR⁴, X(CR⁷R⁸)(CR⁹R¹⁰)NR⁴R¹¹, (CR⁷R⁸)C(O)R⁴, (CR⁷R⁸)C(O)OR⁴, (CR⁷R⁸)C(O)NR⁴R¹¹, X(CR⁷R⁸)C(O)R⁴, X(CR⁷R⁸)C(O)OR⁴, X(CR⁷R⁸)C(O)NR⁴R¹¹, X(CR⁷R⁸)(CR⁹R¹⁰)C(O)R⁴, X(CR⁷R⁸)(CR⁹R¹⁰)C(O)OR⁴, X(CR⁷R⁸)(CR⁹R¹⁰)C(O)NR⁴R¹¹, (CR⁷R⁸)NR⁴SO₂R⁴, or C(=NOR⁴)R⁴;
each R³ is independently selected from H, CN, halo, C(O)R⁴, CO₂H, CO₂R⁴, C(O)NR⁴R¹¹, alkyl, optionally substituted alkoxy, haloalkyl, SO₂R⁴, (CR⁷R⁸)OR⁴, (CR⁷R⁸)NR⁴R¹¹, (CR⁷R⁸)(CR⁹R¹⁰)OR⁴, X(CR⁷R⁸)(CR⁹R¹⁰)OR⁴, X(CR⁷R⁸)(CR⁹R¹⁰)NR⁴R¹¹, (CR⁷R⁸)C(O)R⁴, (CR⁷R⁸)C(O)OR⁴, (CR⁷R⁸)C(O)NR⁴R¹¹, X(CR⁷R⁸)C(O)R⁴, X(CR⁷R⁸)C(O)OR⁴, X(CR⁷R⁸)C(O)NR⁴R¹¹, X(CR⁷R⁸)(CR⁹R¹⁰)C(O)R⁴, X(CR⁷R⁸)(CR⁹R¹⁰)C(O)OR⁴, X(CR⁷R⁸)(CR⁹R¹⁰)C(O)NR⁴R¹¹, (CR⁷R⁸)NR⁴SO₂R⁴, and C(=NOR⁴)R⁴
each R⁴ is independently selected from H and optionally substituted alkyl;
each R⁵, R⁶, R⁷, R⁸, R⁹, and R¹⁰ is independently selected from H, halo, optionally substituted alkyl, OH, CO₂R⁴, NR⁴R¹¹, and optionally substituted alkoxy; and $R^{11}$ is H, optionally substituted alkyl, $C(O)R^4$, $C(O)OR^4$, $C(O)NR^4R^4$, or $SO_2R^4$;

provided that the compound is not selected from

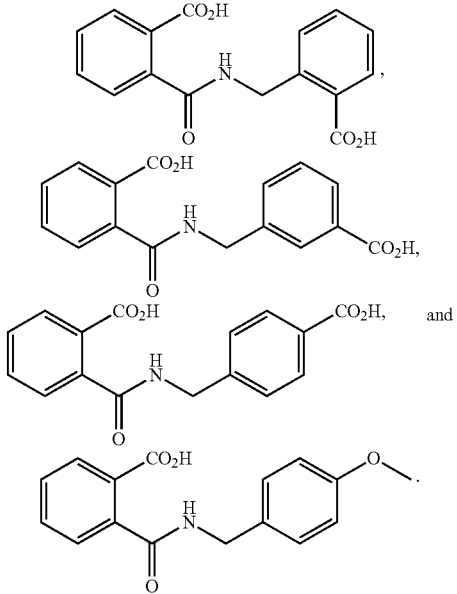

In some embodiments described above or below of a compound of Formula I or Ia:

$R^2$ is halo, $C(O)R^4$, alkyl, optionally substituted alkoxy, haloalkyl, $(CR^7R^8)OR^4$, $(CR^7R^8)(CR^9R^{10})OR^4$, $X(CR^7R^8)(CR^9R^{10})OR^4$, $X(CR^7R^8)C(O)OR^4$, or $X(CR^7R^8)C(O)NR^4R^{11}$; and each $R^3$ is independently selected from CN, halo, $C(O)R^4$, $CO_2H$, $C(O)NR^4R^{11}$, alkyl, or optionally substituted alkoxy;

or $R^3$ together with an adjacent $R^3$ or with $R^2$ form a ring.

In certain embodiments described above or below of a compound of Formula I or Ia:

$R^2$ is F, Cl, $C(O)CH_3$, $CH_3$, $CF_3$, $OCH_3$, OEt, OPr, $OCF_3$, $OCHF_2$, $(CR^7R^8)OR^4$, $(CR^7R^8)(CR^9R^{10})OR^4$, $X(CR^7R^8)(CR^9R^{10})OR^4$, $X(CR^7R^8)C(O)OR^4$, or $X(CR^7R^8)C(O)NR^4R^{11}$; and each $R^3$ is independently selected from CN, F, Cl, $C(O)CH_3$, $CO_2H$, $C(O)NH_2$, $CH_3$, $OCF_3$, or $OCH_3$;

or $R^3$ together with an adjacent $R^3$ or with $R^2$ form a ring.

In certain embodiments, $R^3$ is independently selected from CN, F, Cl, $C(O)CH_3$, or $CO_2H$. In certain embodiments, $R^2$ is F, Cl, $C(O)CH_3$, $CH_3$, $CF_3$, $OCH_3$, OEt, OPr, $OCF_3$, or $CH_2CH_2CH_2OH$.

In some embodiments described above or below of a compound of Formula Ib:

$R^2$ is $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)NR^4R^{11}$, $X(CR^7R^8)C(O)OR^4$, $X(CR^7R^8)C(O)NR^4R^{11}$, $(CR^7R^8)NR^4SO_2R^4$, or $C(=NOR^4)R^4$; and $R^3$ is H.

In certain embodiments, $R^2$ is $(CR^7R^8)(CR^9R^{10})OR^4$, $X(CR^7R^8)(CR^9R^{10})OR^4$, $X(CR^7R^8)(CR^9R^{10})NR^4R^{11}$, or $(CR^7R^8)NR^4SO_2R^4$. In certain embodiments, $R^2$ is $CH_2CH_2OH$, $CH_2CH_2OCH_3$, $CH_2CHCH_3OH$, $CHCH_3CH_2OH$, $CH_2CH_2CH_2OH$, $CH_2CH_2CH_2NH_2$, $CH_2CH_2CHCH_3OH$, $C(CH_3)_2CH_2CH_2OH$, $CH_2CH_2C(CH_3)_2OH$, $OCH_2CH_2OH$, $OCH_2CH_2OCH_3$, or $OCH_2CH_2NH_2$. In certain embodiments, $R^2$ is $(CR^7R^8)C(O)R^4$, $(CR^7R^8)C(O)NR^4R^{11}$, $X(CR^7R^8)C(O)R^4$, or $X(CR^7R^8)C(O)NR^4R^{11}$. In certain embodiments, $R^2$ is $CH_2C(O)CH_3$, $CH_2C(O)NH_2$, $CH_2CH_2C(O)CH_3$, or $CH_2CH_2C(O)NH_2$.

In some embodiments described above or below of a compound of Formula Ic, C is aryl. In certain embodiments, C is phenyl.

In some embodiments described above or below of a compound of Formula Ic, C is heteroaryl. In certain embodiments, C is pyridinyl, pyrimidinyl, pyridazinyl, or pyrazinyl.

In some embodiments described above or below of a compound of Formula Ic:

$R^2$ is halo, $C(O)R^4$, $CO_2R^4$, $C(O)NR^4R^{11}$, alkyl, optionally substituted alkoxy, haloalkyl, $SO_2NH_2$, $SO_3H$, $(CR^7R^8)C(O)R^4$, $(CR^7R^8)C(O)OR^4$, $(CR^7R^8)C(O)NR^4R^{11}$, $X(CR^7R^8)C(O)OR^4$, or $X(CR^7R^8)C(O)NR^4R^{11}$; and each $R^3$ is independently selected from H, CN, halo, $CO_2H$, or haloalkyl.

In certain embodiments described above or below of a compound of Formula Ic:

$R^2$ is Cl, F, $C(O)CH_3$, $CO_2H$, $C(O)NR^4R^{11}$, $CH_3$, optionally substituted alkoxy, $CF_3$, $SO_2NH_2$, $SO_3H$, $(CR^7R^8)C(O)R^4$, $(CR^7R^8)C(O)OR^4$, $(CR^7R^8)C(O)NR^4R^{11}$, $X(CR^7R^8)C(O)OR^4$, or $X(CR^7R^8)C(O)NR^4R^{11}$; and each $R^3$ is independently selected from H, CN, Cl, F, $CO_2H$, or $CF_3$.

In certain embodiments, $R^2$ is Cl, F, $C(O)CH_3$, $CO_2H$, $CH_3$, $OCH_3$, $CF_3$; and each $R^3$ is independently selected from H, CN, or $CO_2H$. In certain embodiments, $R^2$ is $CH_2C(O)NH_2$, $CH_2C(O)CH_3$, $CH_2C(O)OH$, $CH_2CH_2C(O)OH$, or $CH_2CH_2C(O)NH_2$.

In one aspect, provided herein is a method of ameliorating arthritis or joint injury in a mammal, the method comprising administering to a joint of the mammal a composition comprising a therapeutically effective amount of a compound of Formula II, or a pharmaceutically acceptable salt, solvate, polymorph, prodrug, ester, metabolite, N-oxide, stereoisomer, or isomer thereof:

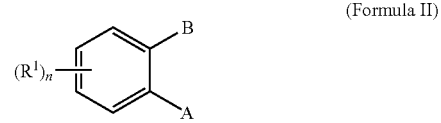

(Formula II)

wherein each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

B is $NHC(O)R^2$, $NR^3C(O)R^2$, $NHC(O)NH_2$, $NHC(O)NHR^2$, $NHC(O)NR^2R^4$, $NR^3C(O)NH_2$, $NR^3C(O)NHR^2$, $NR^3C(O)NR^2R^4$, $NHC(O)OR^2$, $NR^3C(O)OR^2$, $NHSO_2R^3$, $NR^3SO_2R^3$, $NHSO_2R^4$, $NR^3SO_2R^4$, $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$;

each $R^2$ and $R^4$ is independently optionally substituted phenyl, optionally substituted heteroaryl, optionally substituted heterocyclyl, optionally substituted aralkyl, or optionally substituted alkyl;

$R^3$ is optionally substituted alkyl or optionally substituted aralkyl;

$R^5$ is H, optionally substituted alkyl, $C(O)R^4$, $C(O)OR^4$, $C(O)NR^4R^4$, or $SO_2R^4$;

A is $CO_2H$, $CO_2R^3$, $C(O)NH_2$, $C(O)NHR^2$, $C(O)NR^2R^4$, or $SO_2NR^aR^b$; and each $R^a$ and $R^b$ is independently optionally substituted alkyl or together with the N to which they are attached make a ring;

provided that a) if B is $NHC(O)R^2$ or $NR^3C(O)R^2$, then A is not $CO_2H$; and b) the compound is not selected from

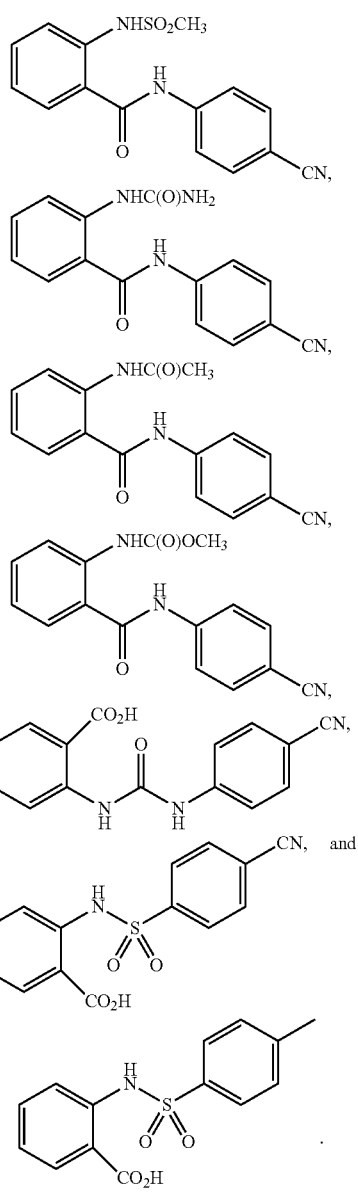

In another aspect, provided herein is a method of ameliorating arthritis or joint injury in a mammal, the method comprising administering to a joint of the mammal a composition comprising a therapeutically effective amount of a compound of Formula IIa, or a pharmaceutically acceptable salt, solvate, polymorph, prodrug, ester, metabolite, N-oxide, stereoisomer, or isomer thereof:

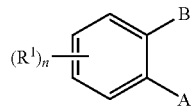

(Formula IIa)

wherein each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

B is $NHC(O)NH_2$, $NHC(O)NHR^2$, $NHC(O)NR^2R^4$, $NR^3C(O)NH_2$, $NR^3C(O)NHR^2$, or $NR^3C(O)NR^2R^4$;

each $R^2$ and $R^4$ is independently optionally substituted phenyl, optionally substituted heteroaryl, optionally substituted heterocyclyl, optionally substituted aralkyl, or optionally substituted alkyl;

$R^3$ is optionally substituted alkyl or optionally substituted aralkyl;

$R^5$ is H, optionally substituted alkyl, $C(O)R^4$, $C(O)OR^4$, $C(O)NR^4R^4$, or $SO_2R^4$; and A is $CO_2H$ or $CO_2R^3$;

provided that the compound is not

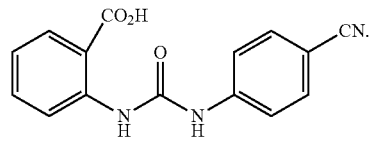 [SMILES: N#Cc1ccc(NC(=O)Nc2ccccc2C(=O)O)cc1]

In another aspect, provided herein is a method of ameliorating arthritis or joint injury in a mammal, the method comprising administering to a joint of the mammal a composition comprising a therapeutically effective amount of a compound of Formula IIb, or a pharmaceutically acceptable salt, solvate, polymorph, prodrug, ester, metabolite, N-oxide, stereoisomer, or isomer thereof:

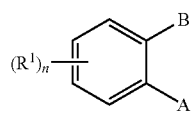

(Formula IIb)

wherein each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

B is $NHC(O)R^2$ or $NR^3C(O)R^2$;

$R^2$ is optionally substituted phenyl, optionally substituted heteroaryl, optionally substituted heterocyclyl, optionally substituted aralkyl, or optionally substituted alkyl;

$R^3$ is optionally substituted alkyl or optionally substituted aralkyl;

$R^5$ is H, optionally substituted alkyl, $C(O)R^4$, $C(O)OR^4$, $C(O)NR^4R^4$, or $SO_2R^4$;

A is $SO_2NR^aR^b$; and each $R^a$ and $R^b$ is independently optionally substituted alkyl or together with the N to which they are attached make a ring.

In another aspect, provided herein is a method of ameliorating arthritis or joint injury in a mammal, the method comprising administering to a joint of the mammal a composition comprising a therapeutically effective amount of a compound of Formula IIc, or a pharmaceutically acceptable salt, solvate, polymorph, prodrug, ester, metabolite, N-oxide, stereoisomer, or isomer thereof:

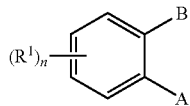

(Formula IIc)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

B is $NHSO_2R^3$, $NR^3SO_2R^3$, $NHSO_2R^4$, $NR^3SO_2R^4$, $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$;

each $R^2$ and $R^4$ is independently optionally substituted phenyl, optionally substituted heteroaryl, optionally substituted heterocyclyl, optionally substituted aralkyl, or optionally substituted alkyl;

each $R^3$ is independently optionally substituted alkyl or optionally substituted aralkyl;

$R^5$ is H, optionally substituted alkyl, $C(O)R^4$, $C(O)OR^4$, $C(O)NR^4R^4$, or $SO_2R^4$; and A is $C(O)NHR^2$ or $C(O)NR^2R^4$;

provided that the compound is not

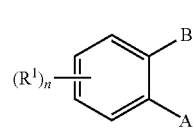

In another aspect provided herein is a method of inducing differentiation of mesenchymal stem cells into chondrocytes, the method comprising contacting mesenchymal stem cells with a sufficient amount of a compound of Formula II, or a pharmaceutically acceptable salt, solvate, polymorph, prodrug, ester, metabolite, N-oxide, stereoisomer, or isomer thereof:

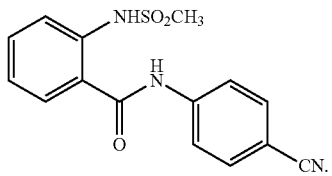

(Formula II)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

B is $NHC(O)R^2$, $NR^3C(O)R^2$, $NHC(O)NH_2$, $NHC(O)NHR^2$, $NHC(O)NR^2R^4$, $NR^3C(O)NH_2$, $NR^3C(O)NHR^2$, $NR^3C(O)NR^2R^4$, $NHC(O)OR^2$, $NR^3C(O)OR^2$, $NHSO_2R^3$, $NR^3SO_2R^3$, $NHSO_2R^4$, $NR^3SO_2R^4$, $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$;

each $R^2$ and $R^4$ is independently optionally substituted phenyl, optionally substituted heteroaryl, optionally substituted heterocyclyl, optionally substituted aralkyl, or optionally substituted alkyl;

$R^3$ is optionally substituted alkyl or optionally substituted aralkyl;

$R^5$ is H, optionally substituted alkyl, $C(O)R^4$, $C(O)OR^4$, $C(O)NR^4R^4$, or $SO_2R^4$;

A is $CO_2H$, $CO_2R^3$, $C(O)NH_2$, $C(O)NHR^2$, $C(O)NR^2R^4$, or $SO_2NR^aR^b$; and each $R^a$ and $R^b$ is independently optionally substituted alkyl or together with the N to which they are attached make a ring;

provided that a) if B is $NHC(O)R^2$ or $NR^3C(O)R^2$, then A is not $CO_2H$; and b) the compound is not selected from

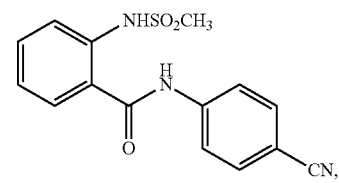

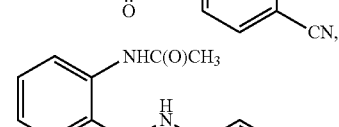

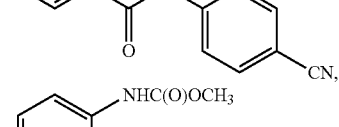

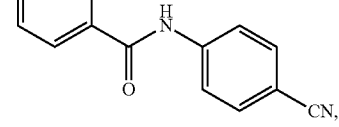

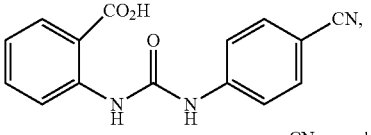, and

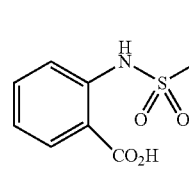

-continued

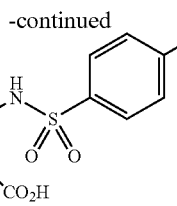

In another aspect, provided herein is a method of inducing differentiation of mesenchymal stem cells into chondrocytes, the method comprising contacting mesenchymal stem cells with a sufficient amount of a compound of Formula IIa, or a pharmaceutically acceptable salt, solvate, polymorph, prodrug, ester, metabolite, N-oxide, stereoisomer, or isomer thereof:

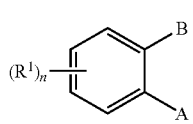
(Formula IIa)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
n is 0, 1, 2, 3, or 4;
B is $NHC(O)NH_2$, $NHC(O)NHR^2$, $NHC(O)NR^2R^4$, $NR^3C(O)NH_2$, $NR^3C(O)NHR^2$, or $NR^3C(O)NR^2R^4$;
each $R^2$ and $R^4$ is independently optionally substituted phenyl, optionally substituted heteroaryl, optionally substituted heterocyclyl, optionally substituted aralkyl, or optionally substituted alkyl;
$R^3$ is optionally substituted alkyl or optionally substituted aralkyl;
$R^5$ is H, optionally substituted alkyl, $C(O)R^4$, $C(O)OR^4$, $C(O)NR^4R^4$, or $SO_2R^4$; and
A is $CO_2H$ or $CO_2R^3$;
provided that the compound is not

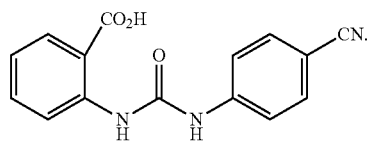 [SMILES: N#Cc1ccc(NC(=O)Nc2ccccc2C(=O)O)cc1]

In another aspect, provided herein is a method of inducing differentiation of mesenchymal stem cells into chondrocytes, the method comprising contacting mesenchymal stem cells with a sufficient amount of a compound of Formula IIb, or a pharmaceutically acceptable salt, solvate, polymorph, prodrug, ester, metabolite, N-oxide, stereoisomer, or isomer thereof:

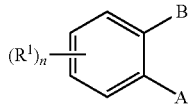
(Formula IIb)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
n is 0, 1, 2, 3, or 4;
B is $NHC(O)R^2$ or $NR^3C(O)R^2$;
$R^2$ is optionally substituted phenyl, optionally substituted heteroaryl, optionally substituted heterocyclyl, optionally substituted aralkyl, or optionally substituted alkyl;
$R^3$ is optionally substituted alkyl or optionally substituted aralkyl;
$R^5$ is H, optionally substituted alkyl, $C(O)R^4$, $C(O)OR^4$, $C(O)NR^4R^4$, or $SO_2R^4$;
A is $SO_2NR^aR^b$; and
each $R^a$ and $R^b$ is independently optionally substituted alkyl or together with the N to which they are attached make a ring.

In another aspect, provided herein is a method of inducing differentiation of mesenchymal stem cells into chondrocytes, the method comprising contacting mesenchymal stem cells with a sufficient amount of a compound of Formula IIc, or a pharmaceutically acceptable salt, solvate, polymorph, prodrug, ester, metabolite, N-oxide, stereoisomer, or isomer thereof:

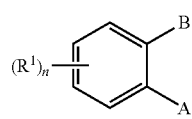
(Formula IIc)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
n is 0, 1, 2, 3, or 4;
B is $NHSO_2R^3$, $NR^3SO_2R^3$, $NHSO_2R^4$, $NR^3SO_2R^4$, $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$;
each $R^2$ and $R^4$ is independently optionally substituted phenyl, optionally substituted heteroaryl, optionally substituted heterocyclyl, optionally substituted aralkyl, or optionally substituted alkyl;
each $R^3$ is independently optionally substituted alkyl or optionally substituted aralkyl;
$R^5$ is H, optionally substituted alkyl, $C(O)R^4$, $C(O)OR^4$, $C(O)NR^4R^4$, or $SO_2R^4$; and
A is $C(O)NHR^2$ or $C(O)NR^2R^4$;
provided that the compound is not

In some embodiments described above or below of a compound of Formula IIa, B is $NHC(O)NHR^2$, $NHC(O)NR^2R^4$, $NR^3C(O)NHR^2$, or $NR^3C(O)NR^2R^4$. In certain embodiments, B is $NHC(O)NHR^2$ or $NR^3C(O)NHR^2$. In certain embodiments, B is NHC(O)NR²R⁴ or NR³C(O)NR²R⁴. In certain embodiments, B is NHC(O)NHR².

In some embodiments described above or below of a compound of Formula IIa, R² is optionally substituted phenyl. In certain embodiments, the phenyl of R² is bisubstituted. In certain embodiments, the phenyl of R² is monosubstituted. In certain embodiments, the phenyl of R² is independently selected from F, Cl, CO₂H, CN, OCH₃, C(O)CH₃, CF₃, CH₃, CH₂OH, CH₂CH₂OH, and CH₂CH₂CH₂OH.

In some embodiments described above or below of a compound of Formula IIb, B is NHC(O)R².

In some embodiments described above or below of a compound of Formula IIb, B is NR³C(O)R². In certain embodiments, R³ is optionally substituted alkyl.

In some embodiments described above or below of a compound of Formula IIb, each Rᵃ and Rᵇ is independently optionally substituted alkyl. In some embodiments described above or below of a compound of Formula IIb, Rᵃ and Rᵇ together with the N to which they are attached make a ring.

In some embodiments described above or below of a compound of Formula IIb, R² is optionally substituted phenyl. In certain embodiments, the phenyl of R² is bisubstituted. In certain embodiments, the phenyl of R² is monosubstituted. In certain embodiments, substitution on the phenyl of R² is independently selected from F, Cl, CO₂H, CN, OCH₃, C(O)CH₃, CF₃, CH₃, CH₂OH, CH₂CH₂OH, and CH₂CH₂CH₂OH.

In some embodiments described above or below of a compound of Formula IIc, B is NHSO₂R³, NR³SO₂R³, NHSO₂R⁴, or NR³SO₂R⁴. In certain embodiments, B is NHSO₂R³ or NR³SO₂R³. In certain embodiments, B is NHSO₂R³. In certain embodiments, R³ is optionally substituted alkyl. In certain embodiments, R³ is CH₃. In certain embodiments, B is NHSO₂R⁴ or NR³SO₂R⁴. In certain embodiments, R⁴ is optionally substituted phenyl.

In some embodiments described above or below of a compound of Formula IIc, B is NHSO₂NH₂, NHSO₂NHR², NHSO₂NR²R⁴, NR³SO₂NH₂, NR³SO₂NHR², or NR³SO₂NR²R⁴.

In some embodiments described above or below of a compound of Formula IIc, A is C(O)NHR². In some embodiments described above or below of a compound of Formula IIc, A is C(O)NR²R⁴. In certain embodiments, R² is optionally substituted phenyl. In certain embodiments, the phenyl of R² is bisubstituted. In certain embodiments, the phenyl of R² is monosubstituted. In certain embodiments, substitution on the phenyl of R² is independently selected from F, Cl, CO₂H, CN, OCH₃, C(O)CH₃, CF₃, CH₃, CH₂OH, CH₂CH₂OH, and CH₂CH₂CH₂OH.

In another aspect, provided herein is a method of ameliorating arthritis or joint injury in a mammal, the method comprising administering to a joint of the mammal a composition comprising a therapeutically effective amount of a compound of Formula III, or a pharmaceutically acceptable salt, solvate, polymorph, prodrug, ester, metabolite, N-oxide, stereoisomer, or isomer thereof:

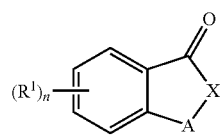

(Formula III)

wherein
each R¹ is independently halo, optionally substituted alkyl, optionally substituted alkoxy, optionally substituted aryloxy, CN, NO₂, SR⁴, S(O)R⁴, SO₂R⁴, NHR⁵, NR⁴R⁵, CO₂H, or CO₂R⁴;
n is 0, 1, 2, 3, or 4;
X is O, NH, or NR⁶;
A is C(O), CH₂, or CH—CR³R⁴—C(O)R²;
R² is optionally substituted aryl or optionally substituted heteroaryl;
each R³ and R⁴ is independently H or optionally substituted alkyl;
R⁵ is H, optionally substituted alkyl, C(O)R⁴, C(O)OR⁴, C(O)NR⁴R⁴, or SO₂R⁴; and
R⁶ is optionally substituted phenyl;
provided that
a) if A is CH—CR³R⁴—C(O)R², then X is O or NH;
b) if n is 0, A is CHCH₂C(O)R² and X is O, then R² is not

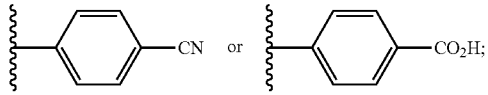

and
c) if A is C(O) or CH₂, then X is NR⁶ and R⁶ is not

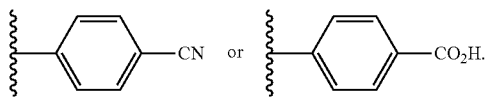

In another aspect, provided herein is a method of ameliorating arthritis or joint injury in a mammal, the method comprising administering to a joint of the mammal a composition comprising a therapeutically effective amount of a compound of Formula IIIa, or a pharmaceutically acceptable salt, solvate, polymorph, prodrug, ester, metabolite, N-oxide, stereoisomer, or isomer thereof:

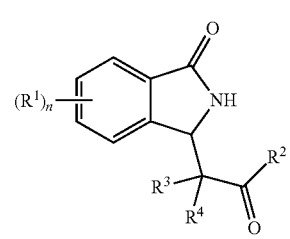

(Formula IIIa)

wherein
each R¹ is independently halo, optionally substituted alkyl, optionally substituted alkoxy, optionally substituted aryloxy, CN, NO₂, SR⁴, S(O)R⁴, SO₂R⁴, NHR⁵, NR⁴R⁵, CO₂H, or CO₂R⁴;
n is 0, 1, 2, 3, or 4;
R² is optionally substituted aryl or optionally substituted heteroaryl;
each R³ and R⁴ is independently H or optionally substituted alkyl; and
R⁵ is H, optionally substituted alkyl, C(O)R⁴, C(O)OR⁴, C(O)NR⁴R⁴, or SO₂R⁴.

In another aspect, provided herein is a method of inducing differentiation of mesenchymal stem cells into chondrocytes, the method comprising contacting mesenchymal stem cells with a sufficient amount of a compound of Formula III, or a pharmaceutically acceptable salt, solvate, polymorph, prodrug, ester, metabolite, N-oxide, stereoisomer, or isomer thereof:

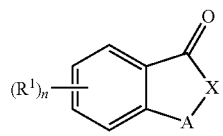

(Formula III)

wherein
    each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
    n is 0, 1, 2, 3, or 4;
    X is O, NH, or $NR^6$;
    A is C(O), $CH_2$, or CH—$CR^3R^4$—$C(O)R^2$;
    $R^2$ is optionally substituted aryl or optionally substituted heteroaryl;
    each $R^3$ and $R^4$ is independently H or optionally substituted alkyl;
    $R^5$ is H, optionally substituted alkyl, $C(O)R^4$, $C(O)OR^4$, $C(O)NR^4R^4$, or $SO_2R^4$; and
    $R^6$ is optionally substituted phenyl;
    provided that
        a) if A is CH—$CR^3R^4$—$C(O)R^2$, then X is O or NH;
        b) if n is 0, A is $CHCH_2C(O)R^2$ and X is O, then $R^2$ is not

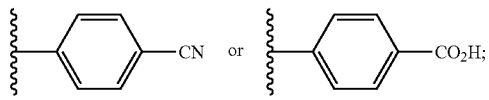

and
        c) if A is C(O) or $CH_2$, then X is $NR^6$ and $R^6$ is not

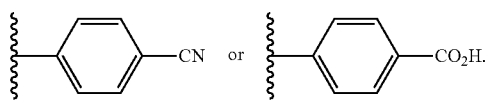

In another aspect, provided herein is a method of inducing differentiation of mesenchymal stem cells into chondrocytes, the method comprising contacting mesenchymal stem cells with a sufficient amount of a compound of Formula IIIa, or a pharmaceutically acceptable salt, solvate, polymorph, prodrug, ester, metabolite, N-oxide, stereoisomer, or isomer thereof:

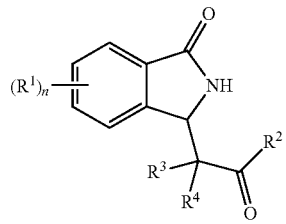

(Formula IIIa)

wherein
    each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
    n is 0, 1, 2, 3, or 4;
    $R^2$ is optionally substituted aryl or optionally substituted heteroaryl;
    each $R^3$ and $R^4$ is independently H or optionally substituted alkyl; and
    $R^5$ is H, optionally substituted alkyl, $C(O)R^4$, $C(O)OR^4$, $C(O)NR^4R^4$, or $SO_2R^4$.

In some embodiments described above or below of a compound of Formula III, X is $NR^6$ and A is C(O). In some embodiments described above or below of a compound of Formula III, X is $NR^6$ and A is $CH_2$. In some embodiments described above or below of a compound of Formula III, X is O and A is CH—$CR^3R^4$—$C(O)R^2$. In some embodiments described above or below of a compound of Formula III, X is NH and A is CH—$CR^3R^4$—$C(O)R^2$.

In some embodiments described above or below of a compound of Formula III or IIIa, $R^3$ and $R^4$ are both hydrogen. In some embodiments described above or below of a compound of Formula III or IIIa, $R^3$ is optionally substituted alkyl and $R^4$ is hydrogen. In some embodiments described above or below of a compound of Formula III or IIIa, $R^3$ and $R^4$ are independently optionally substituted alkyl.

In some embodiments described above or below of a compound of Formula III or IIIa, $R^2$ is optionally substituted heteroaryl. In certain embodiments, $R^2$ is optionally substituted pyridinyl, optionally substituted pyrimidinyl, optionally substituted pyridazinyl, or optionally substituted pyrazinyl.

In some embodiments described above or below of a compound of Formula III or IIIa, $R^2$ is phenyl. In certain embodiments, the phenyl of $R^2$ is bisubstituted. In certain embodiments, the phenyl of $R^2$ is monosubstituted. In certain embodiments, substitution on the phenyl is independently selected from F, Cl, $CO_2H$, CN, $OCH_3$, $C(O)CH_3$, $CF_3$, $CH_3$, $CH_2OH$, $CH_2CH_2OH$, and $CH_2CH_2CH_2OH$.

In some embodiments described above or below of a compound disclosed herein, B is $CO_2R^4$ and $R^4$ is optionally substituted alkyl. In some embodiments described above or below of a compound disclosed herein, B is $CO_2R^4$ and $R^4$ is hydrogen.

In some embodiments described above or below of a compound disclosed herein, n is 0, 1, or 2. In certain embodiments, n is 0. In certain embodiments, n is 1. In certain embodiments, $R^1$ is independently selected from Cl, F, $CH_2OH$, $CH_2NH_2$, $OCH_3$, $OCF_3$, $OCHF_2$, CN, $NO_2$, $CO_2H$, and $CO_2CH_3$.

In one aspect, provided herein is a method of ameliorating arthritis or joint injury in a mammal, the method comprising administering to a joint of the mammal a composition comprising a therapeutically effective amount of a compound, or a pharmaceutically acceptable salt, solvate, polymorph, prodrug, ester, metabolite, N-oxide, stereoisomer, or isomer thereof, selected from:
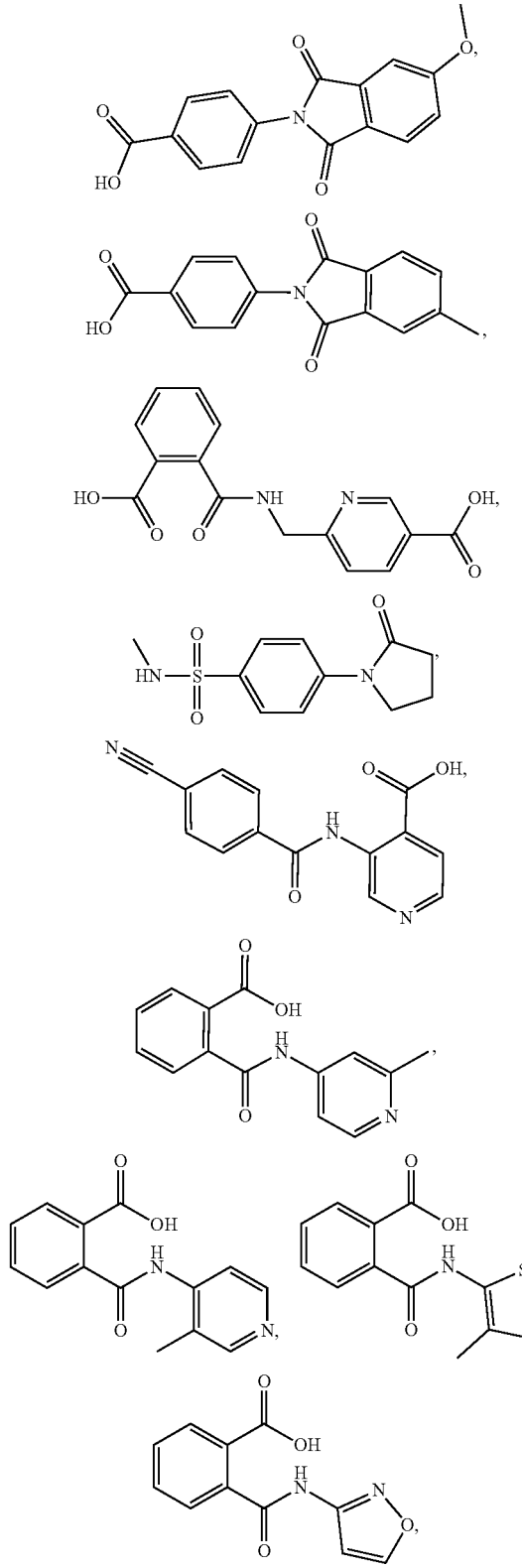
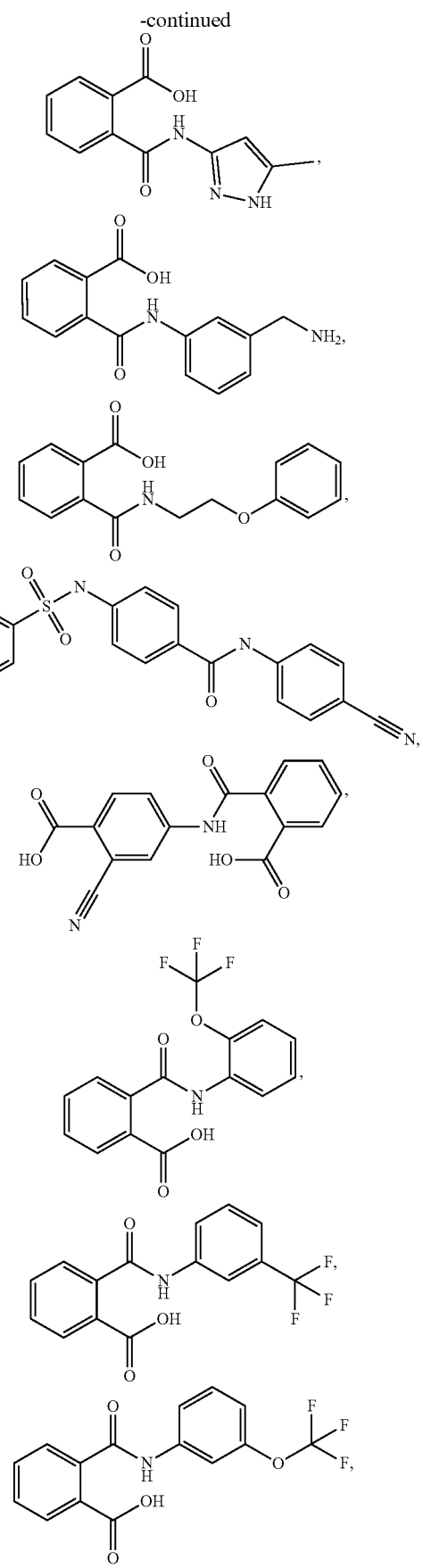

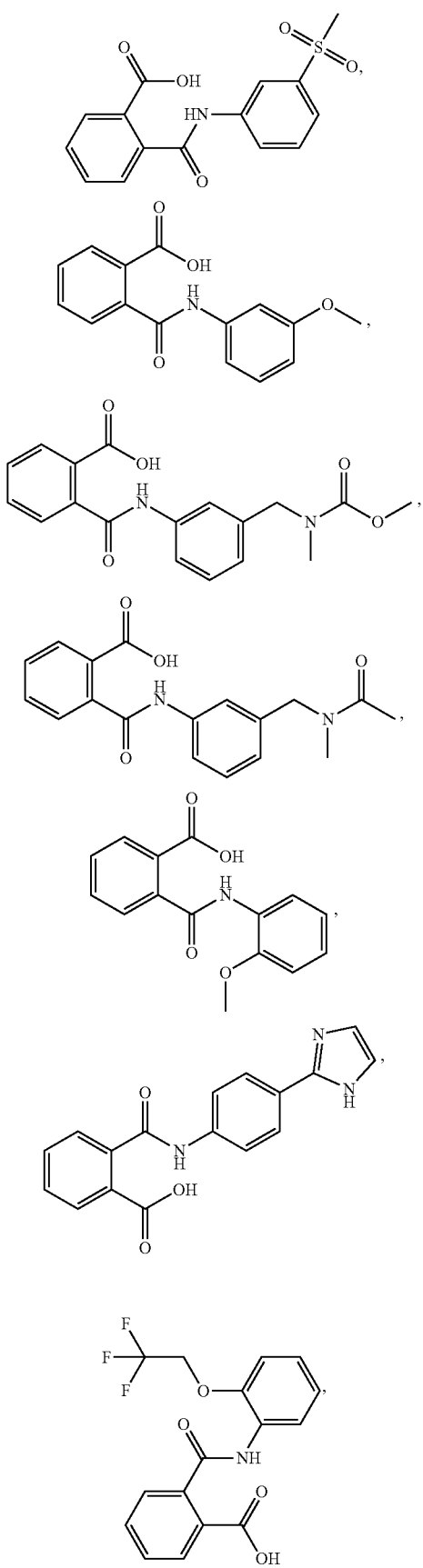
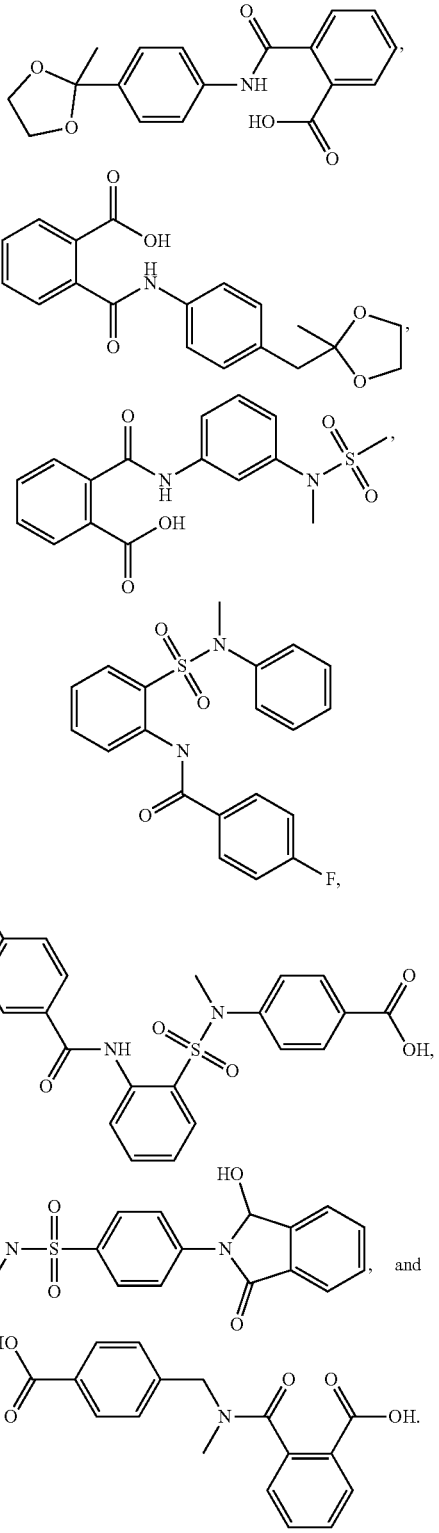

In another aspect, provided herein is a method of of inducing differentiation of mesenchymal stem cells into chondrocytes, the method comprising contacting mesenchymal stem cells with a sufficient amount of a compound, or a pharmaceutically acceptable salt, solvate, polymorph, prodrug, ester, metabolite. N-oxide stereoisomer, or isomer thereof, selected from:

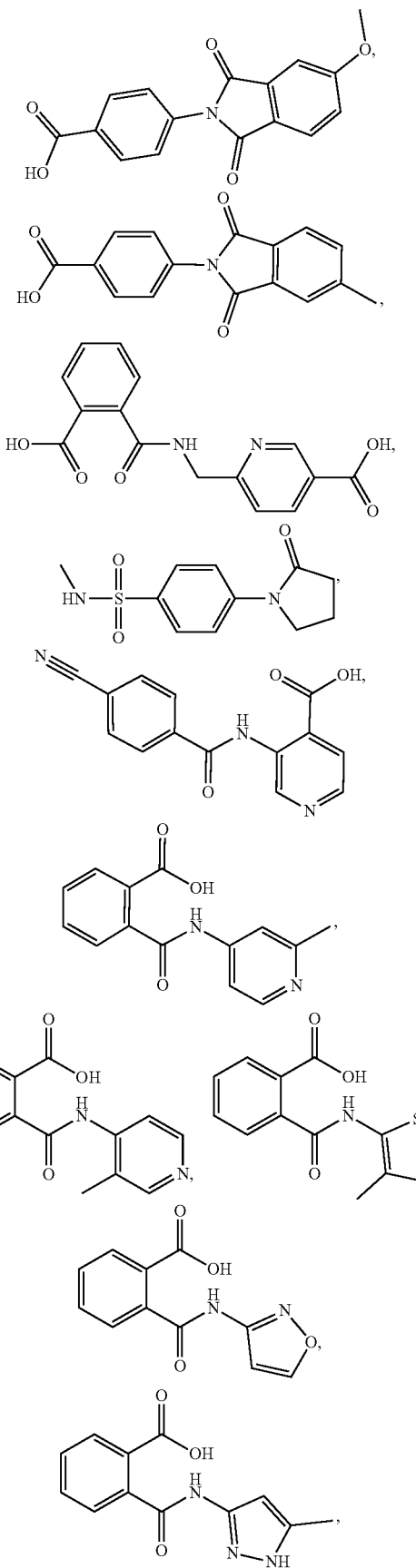
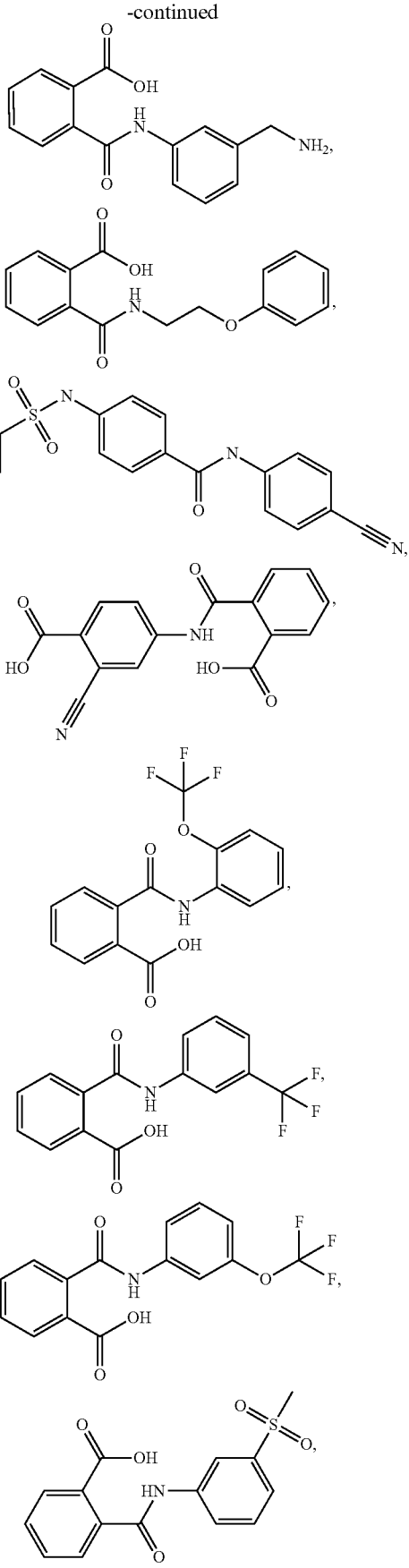

-continued

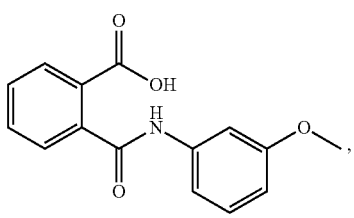

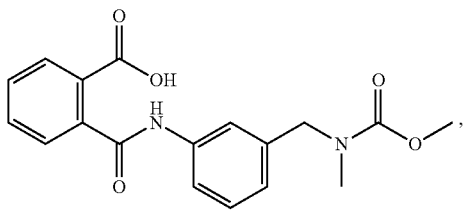

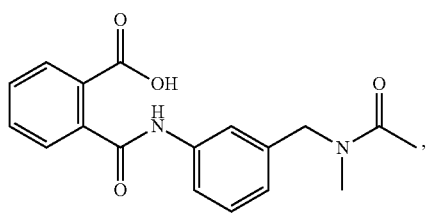

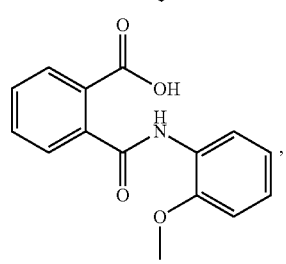

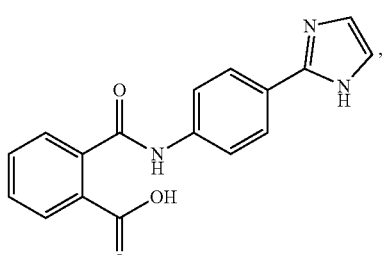

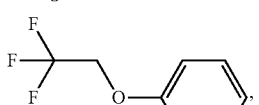

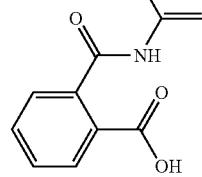

-continued

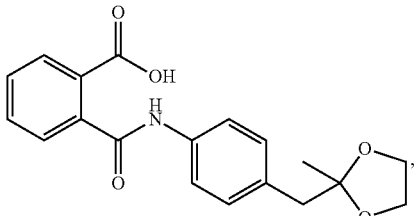

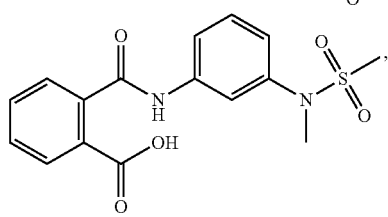

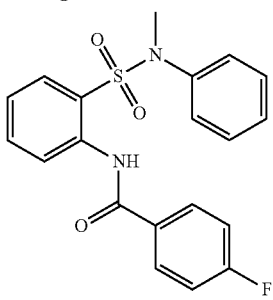

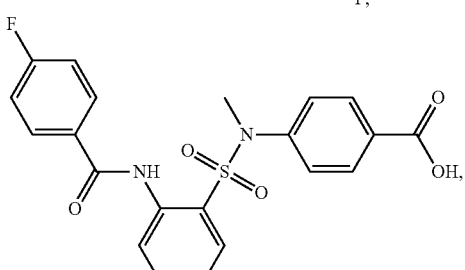

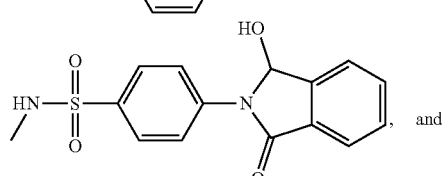

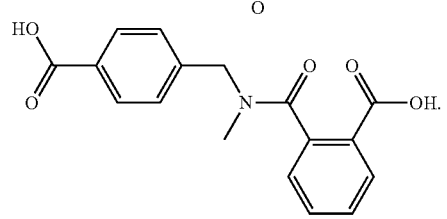

In some embodiments described above, the method is performed in vitro.

In some embodiments described above, the method is performed in vivo in a mammal and the stem cells are present in the mammal. In some embodiments, the mammal is a domesticated animal or livestock. In certain embodiments, the mammal is a human, a dog, a cat, or a horse.

In one aspect, provided herein are compounds of Formula I, or pharmaceutically acceptable salts, solvates, polymorphs, prodrugs, esters, metabolites, N-oxides, stereoisomers, or isomers thereof, selected from:

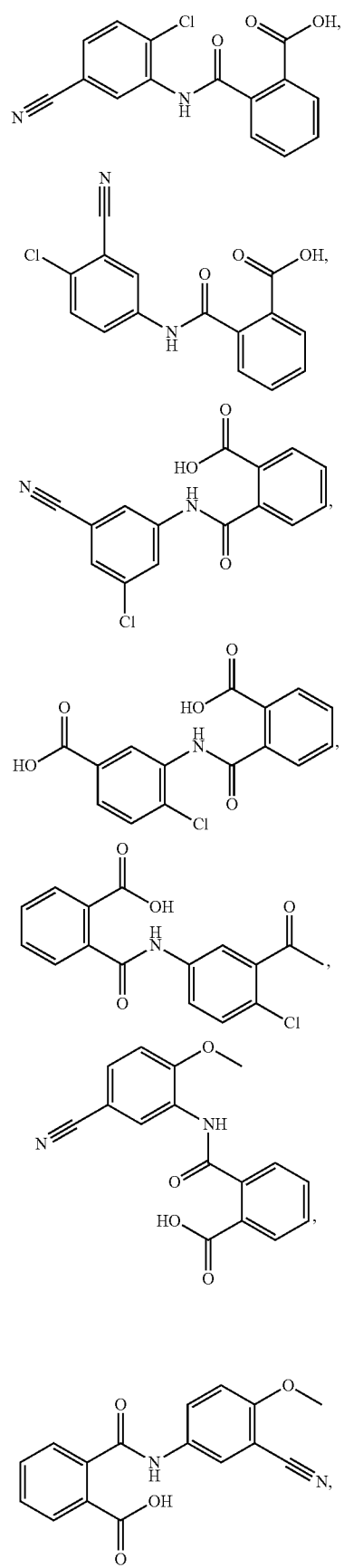
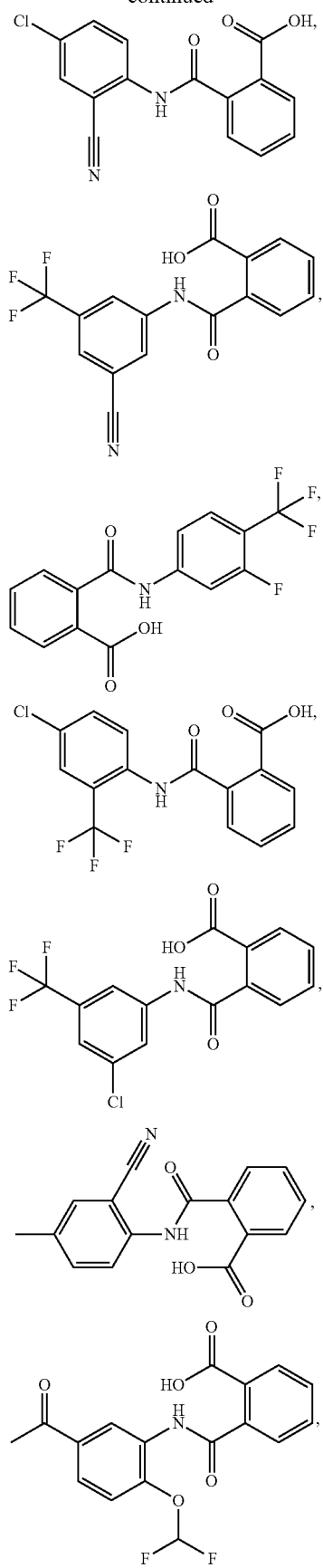

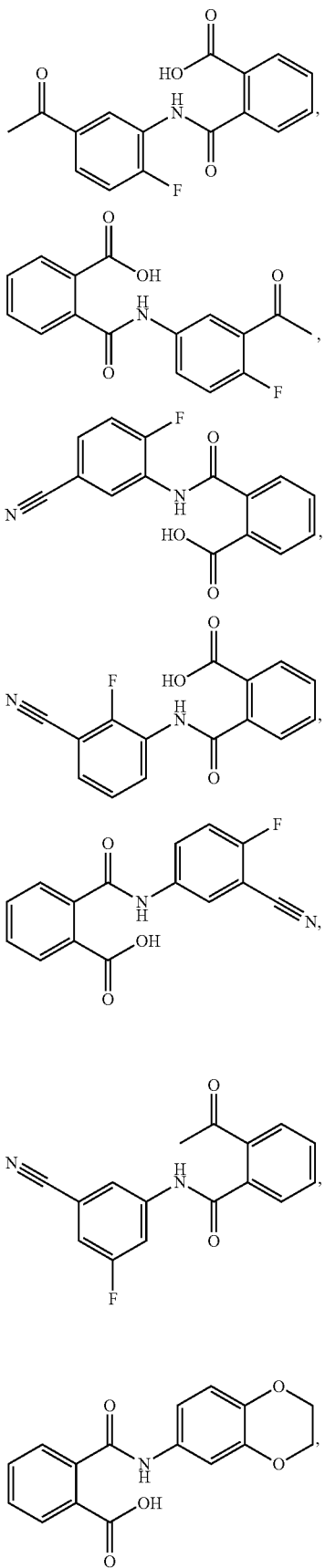
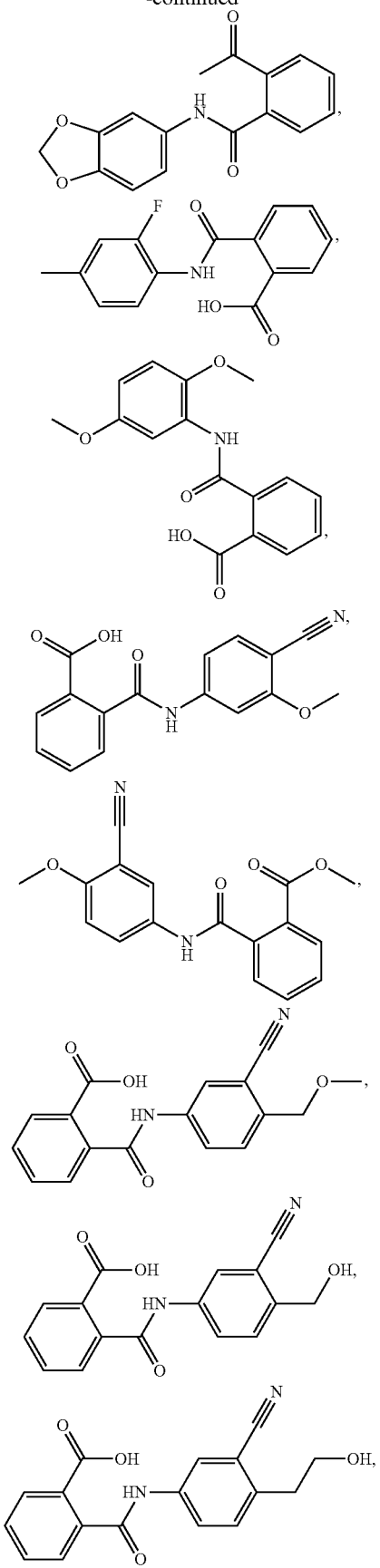

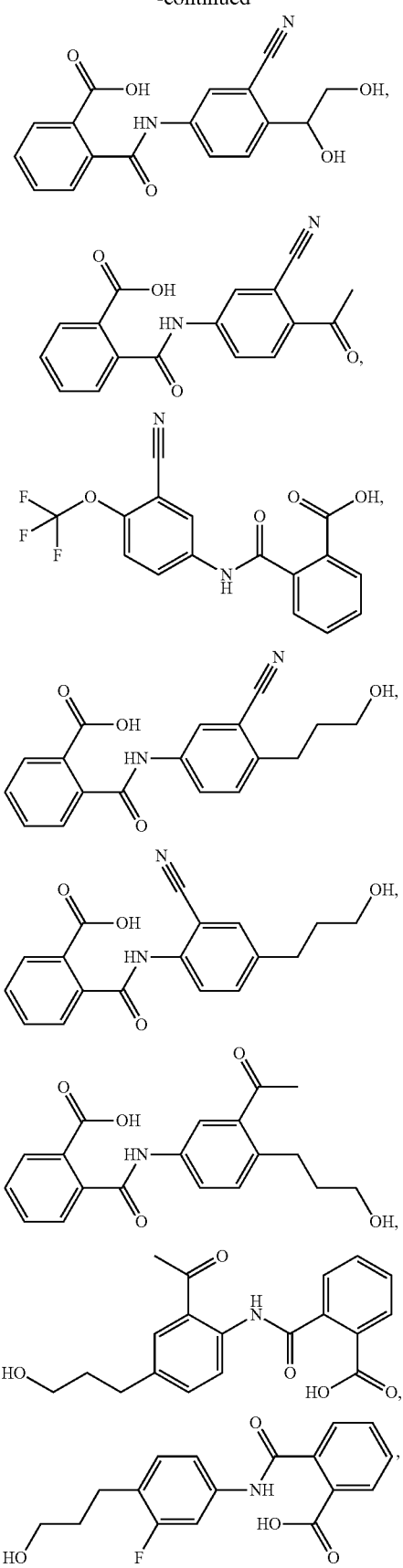
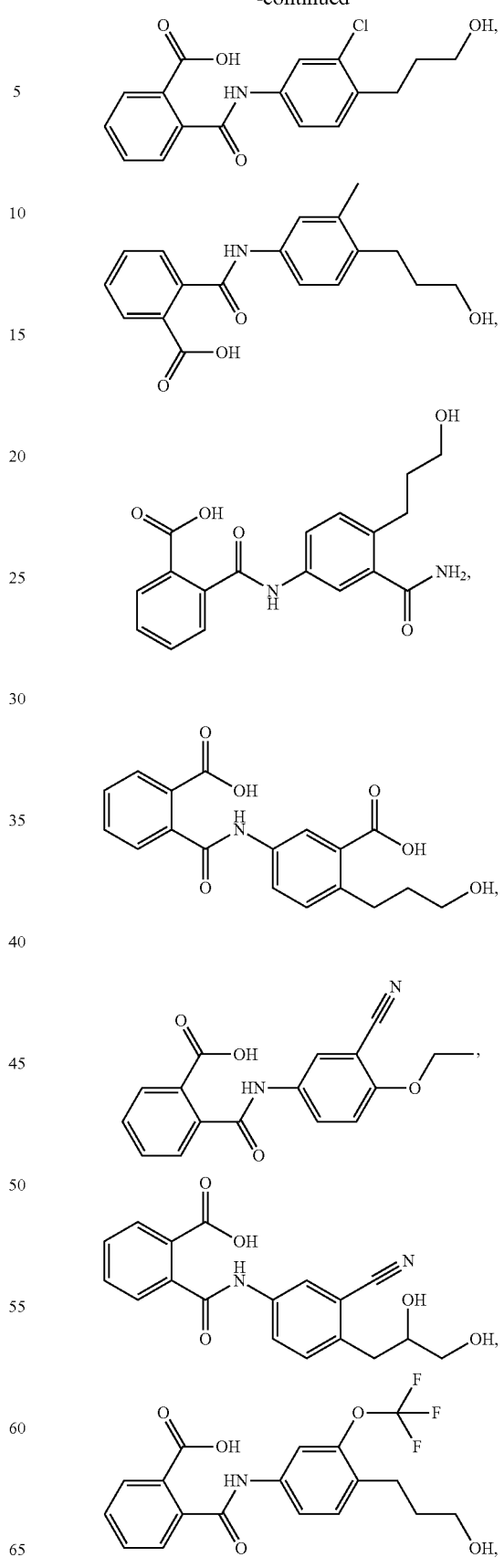

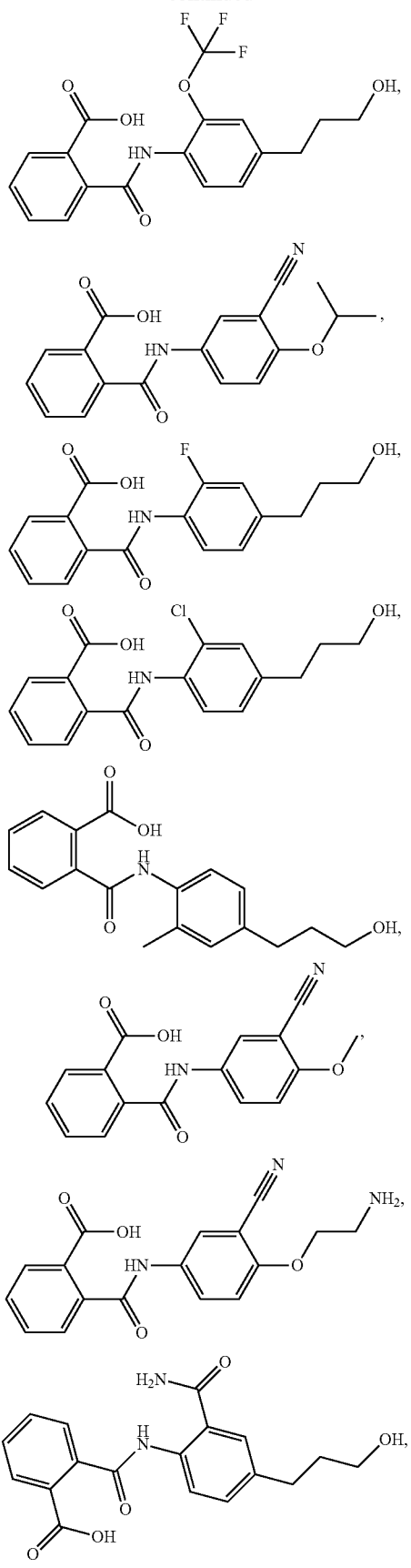
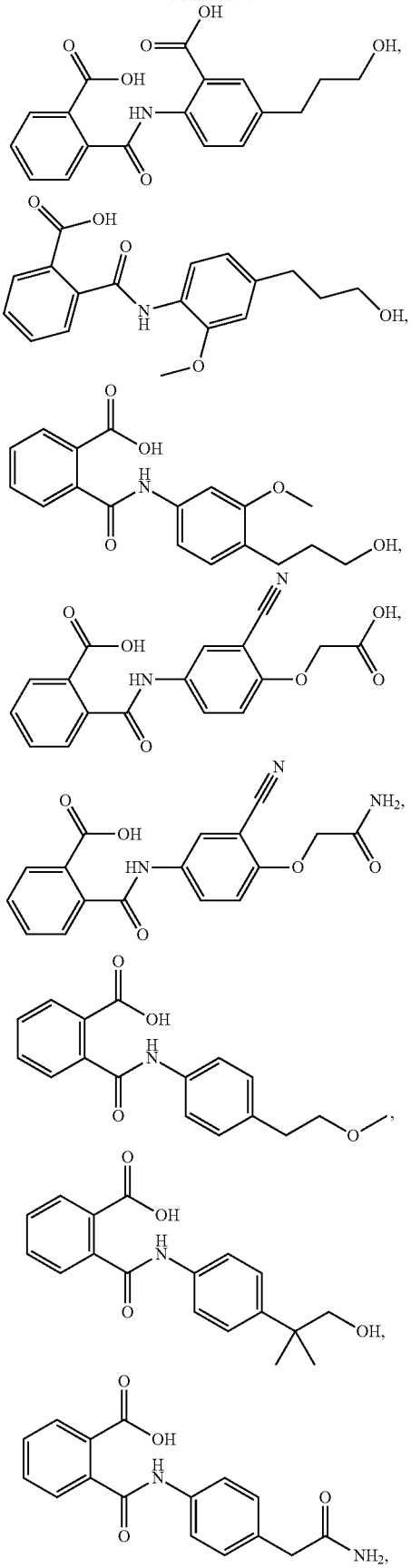

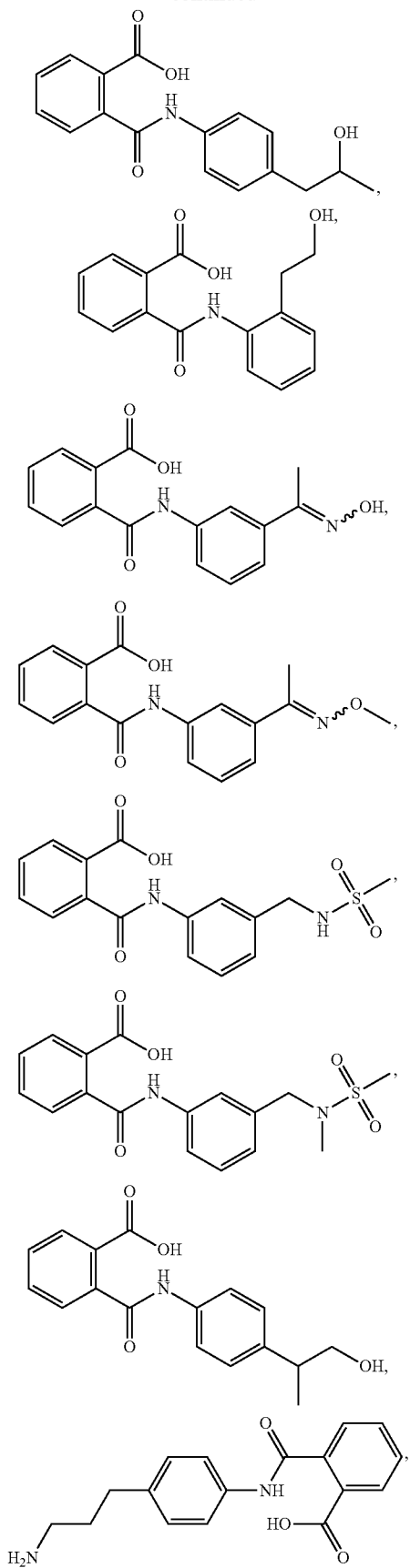
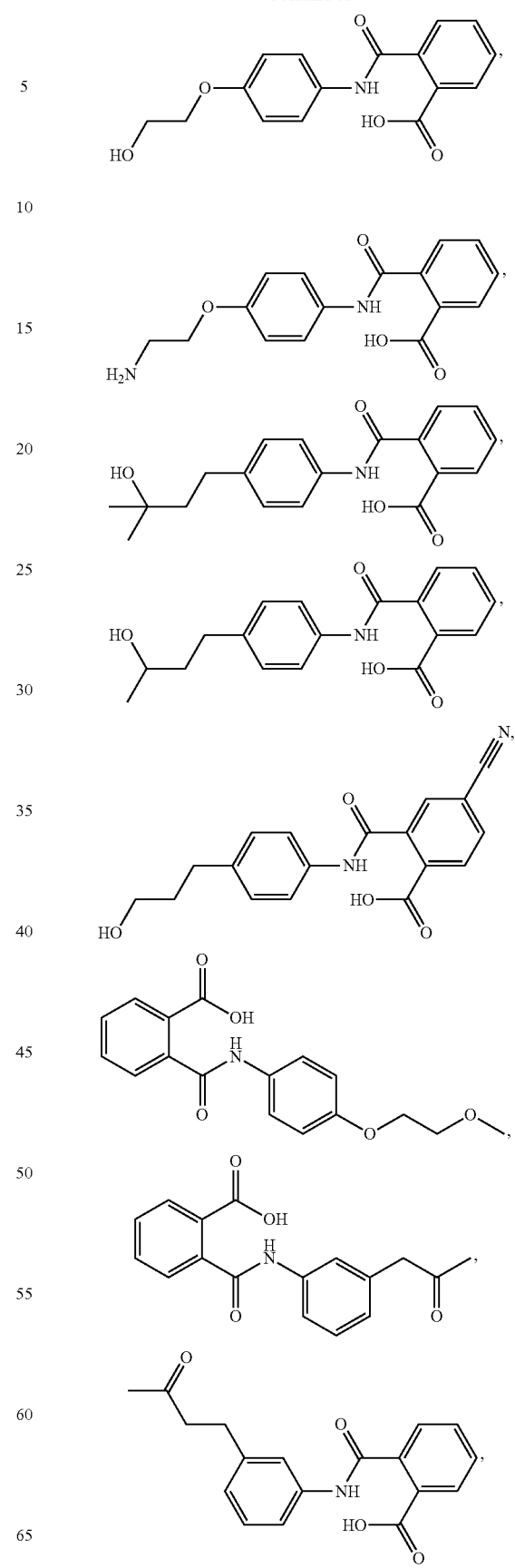

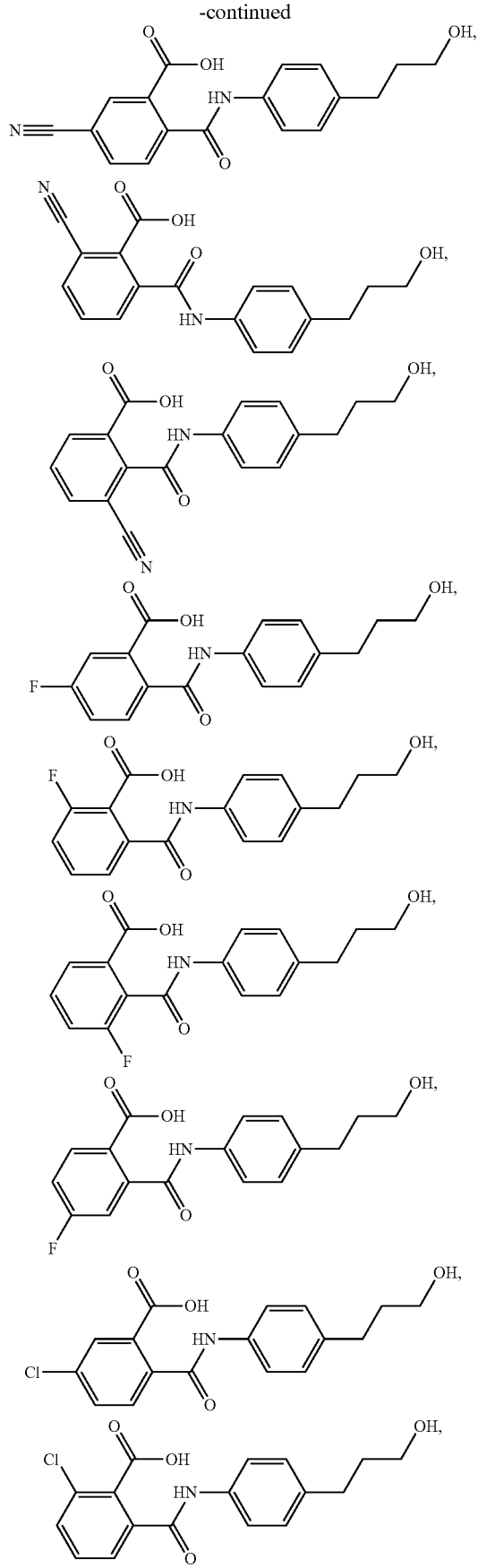
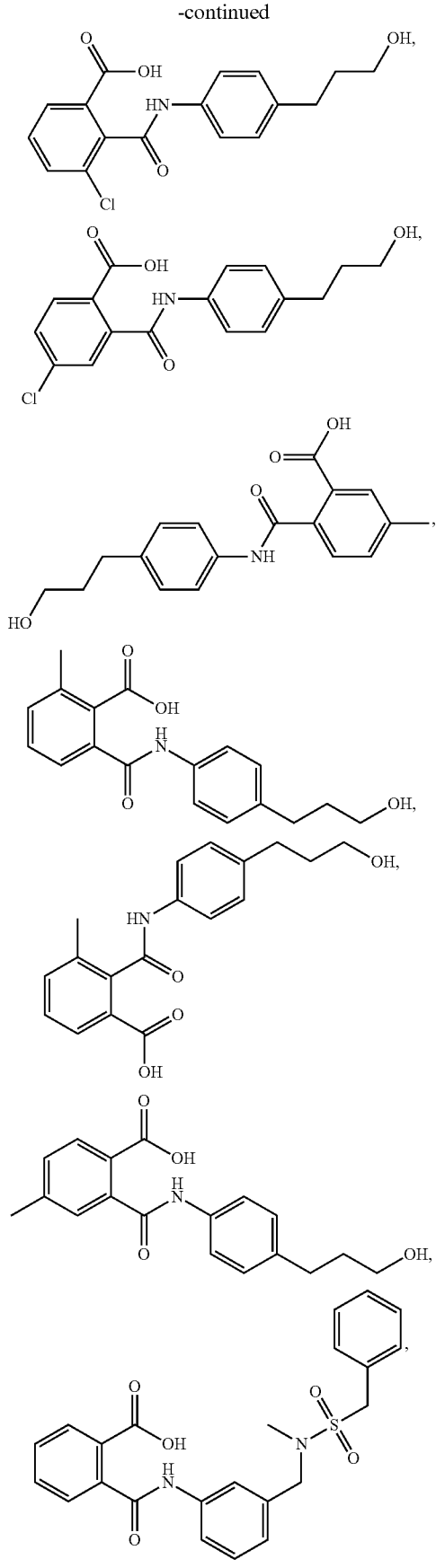

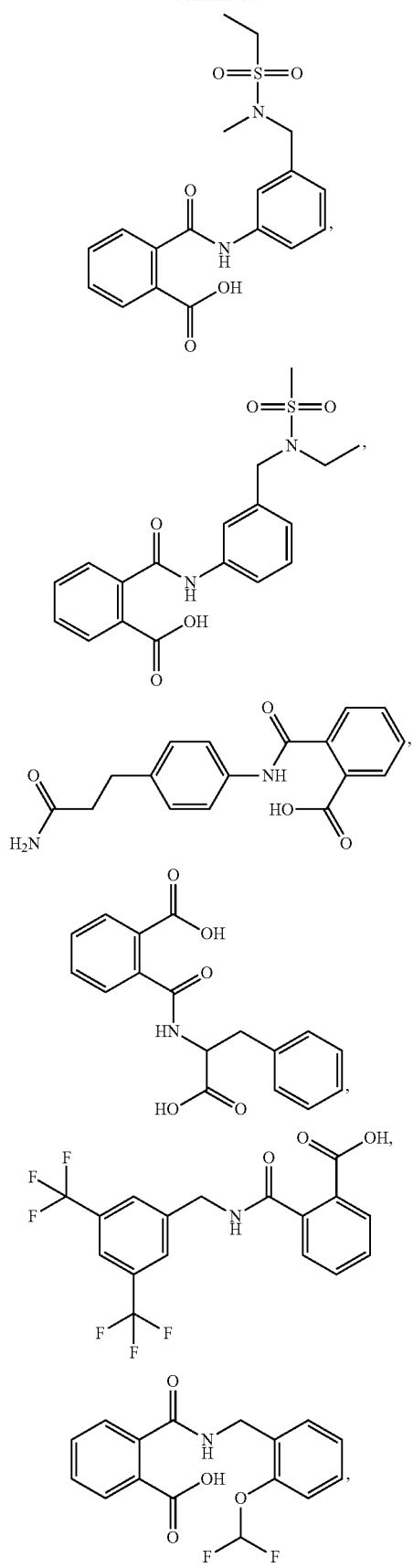
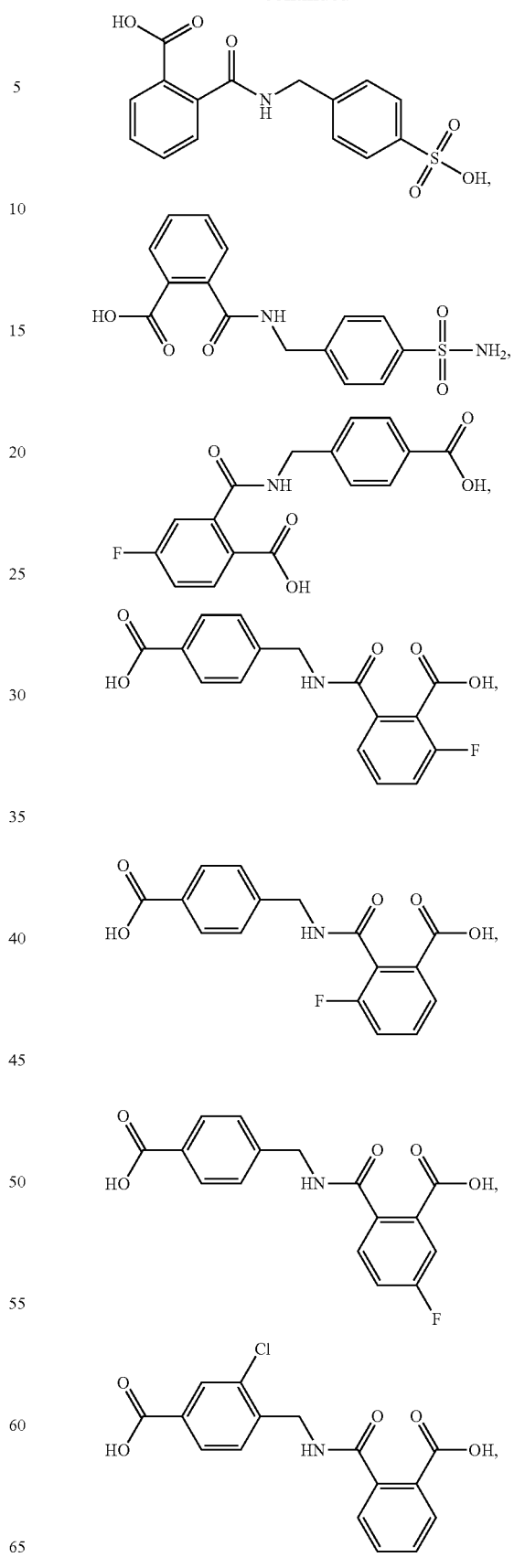

-continued
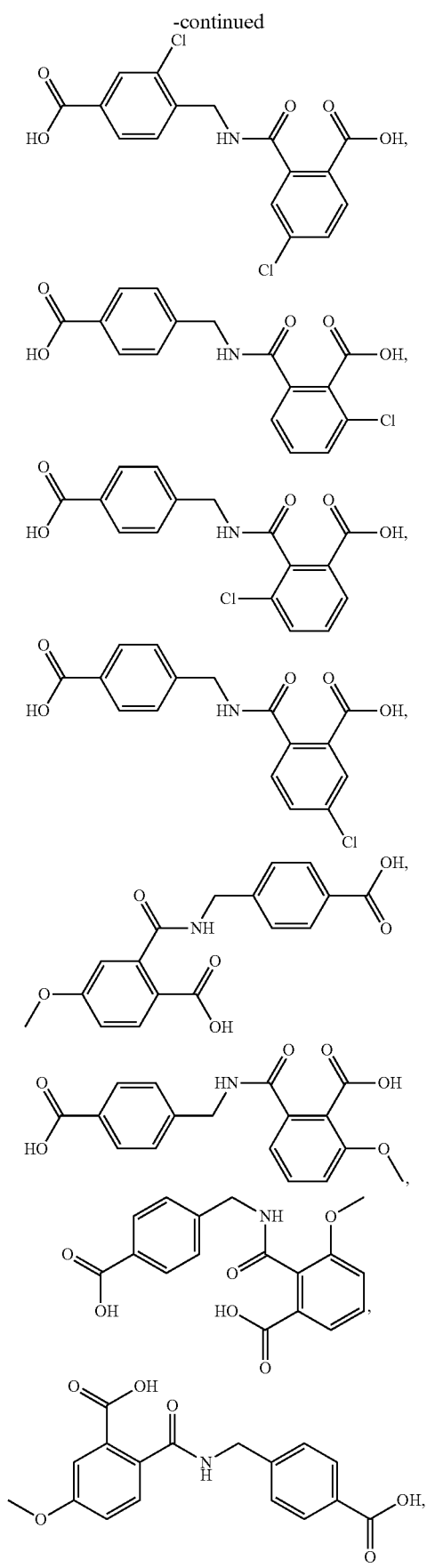
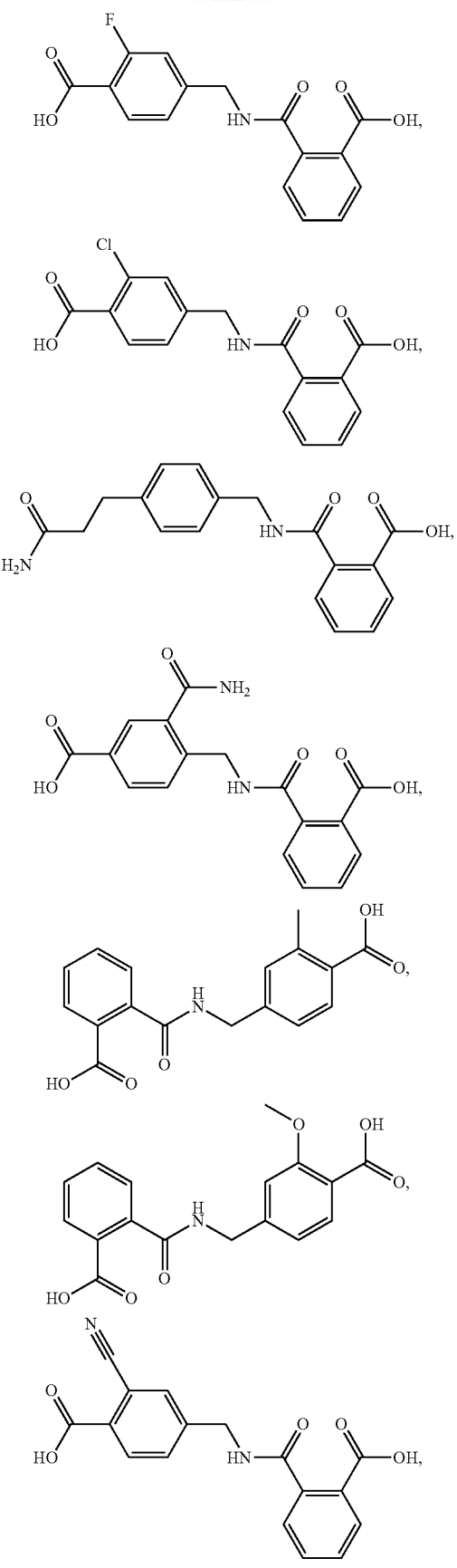

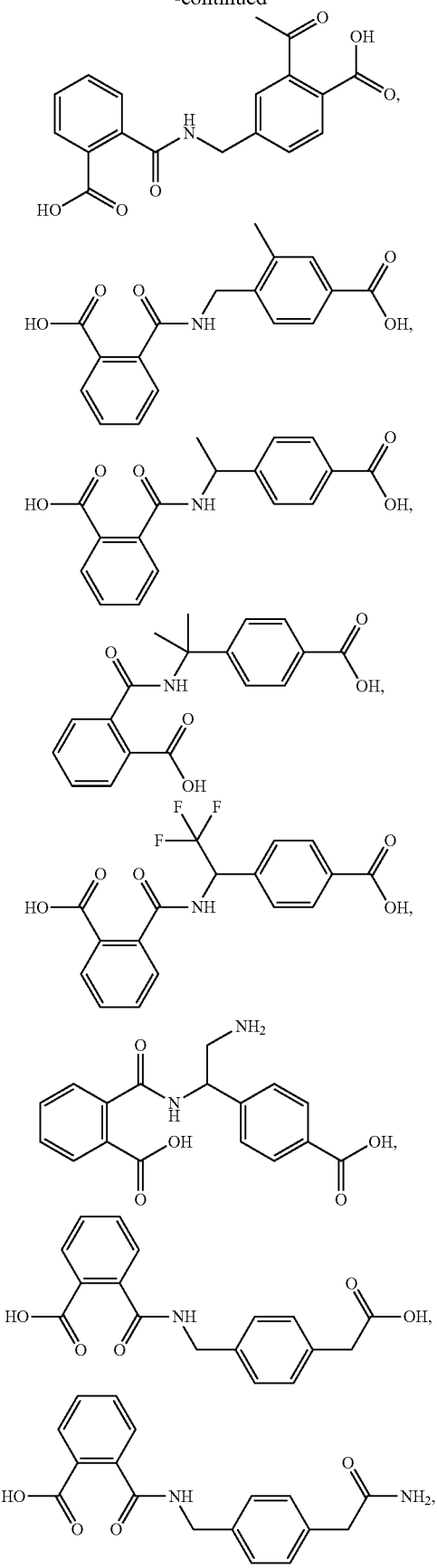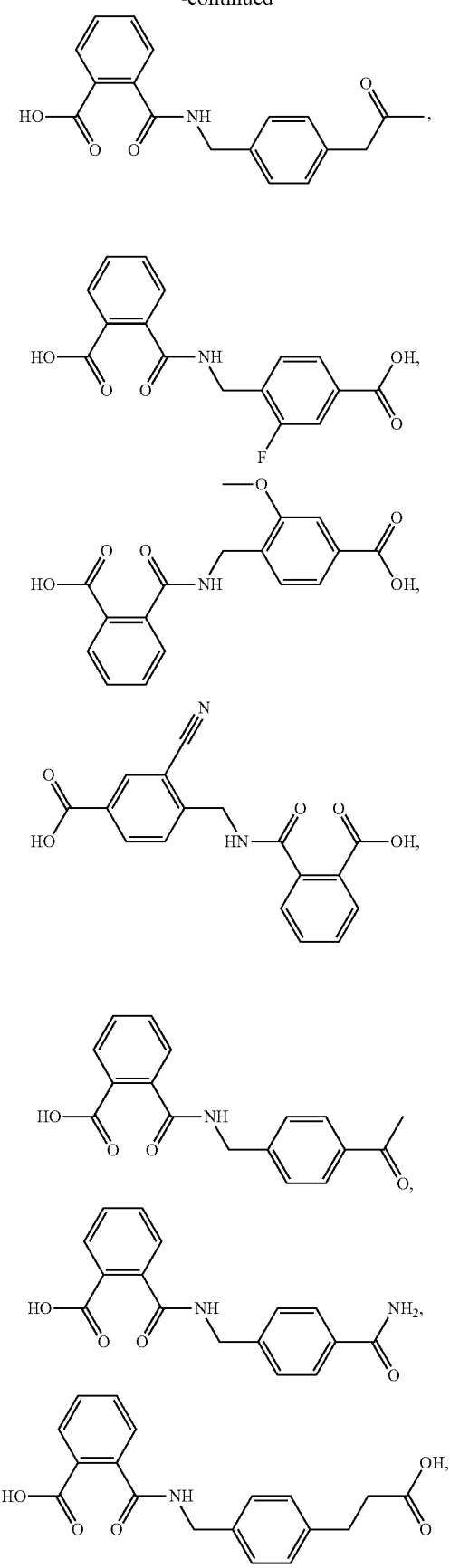

-continued
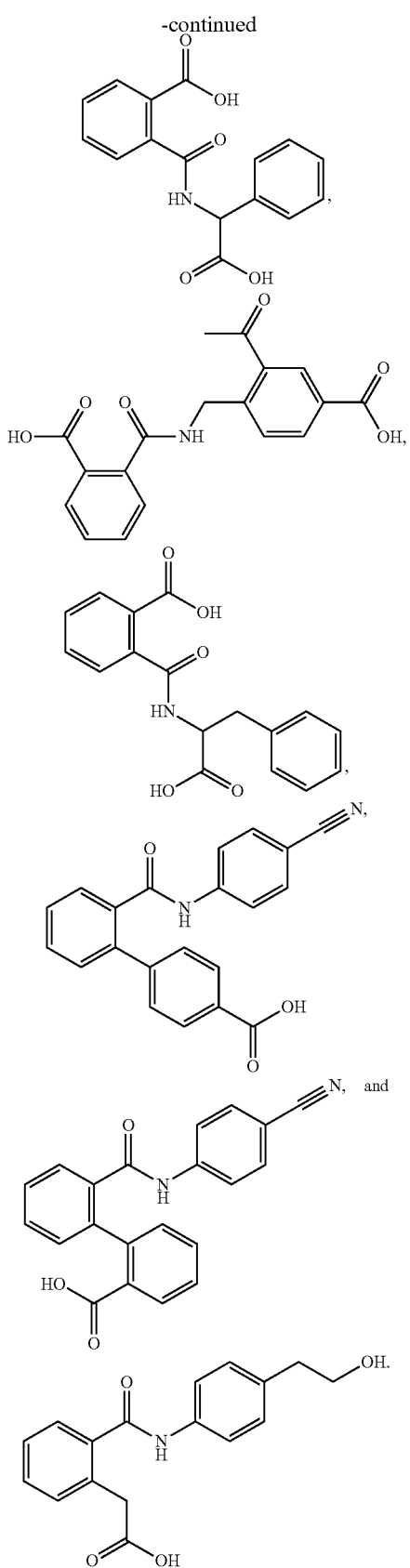
In another aspect, provided herein are compounds of Formula Ia, or pharmaceutically acceptable salts, solvates, polymorphs, prodrugs, esters, metabolites, N-oxides, stereoisomers, or isomers thereof, selected from:
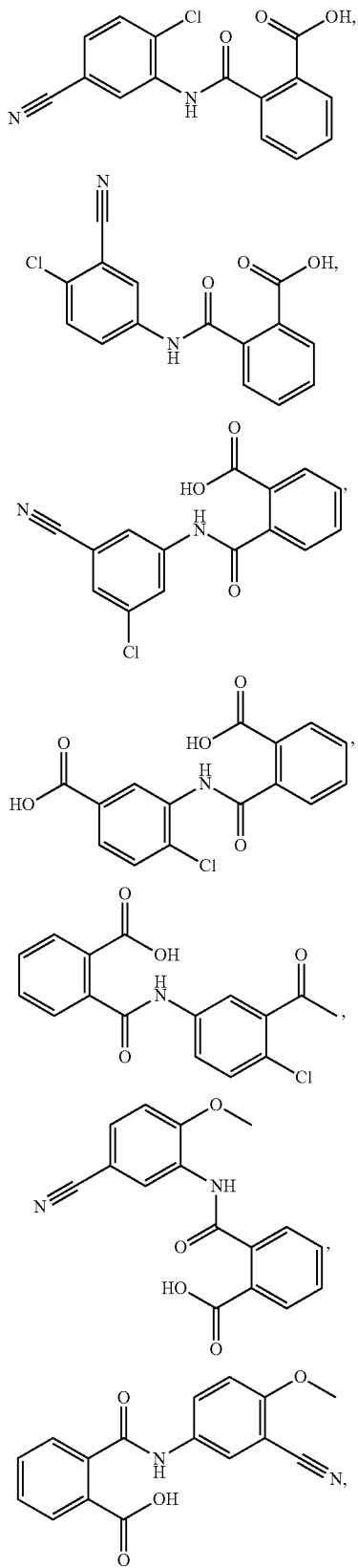

-continued
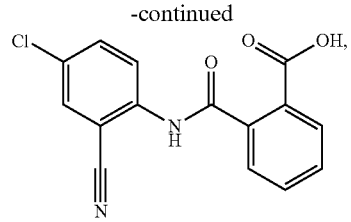
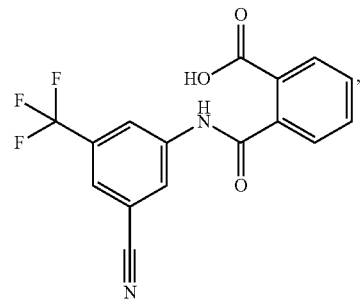
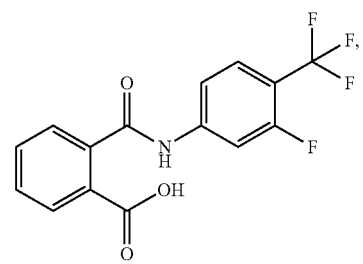
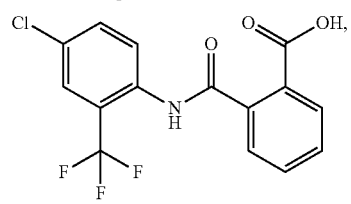
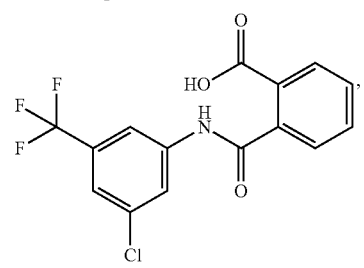
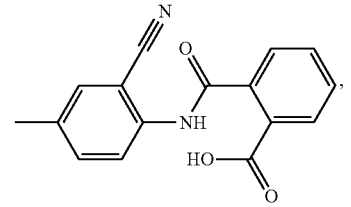
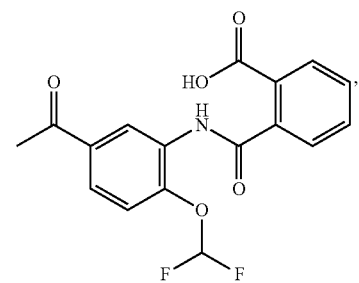
-continued
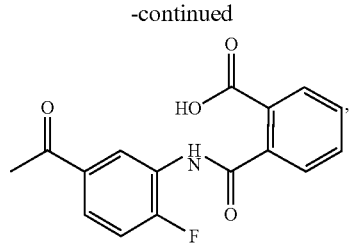
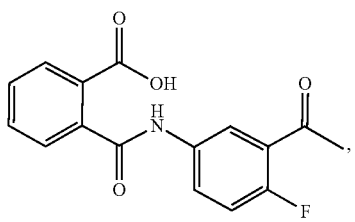
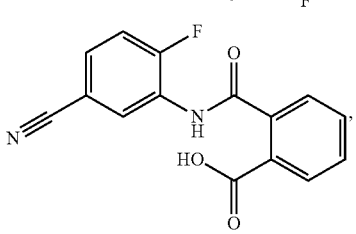
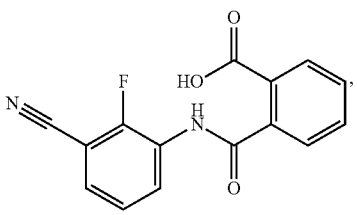
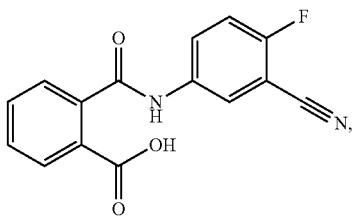
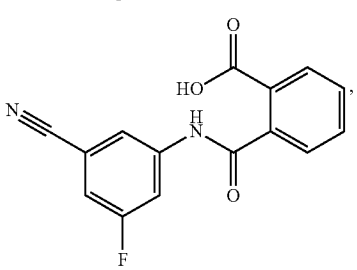
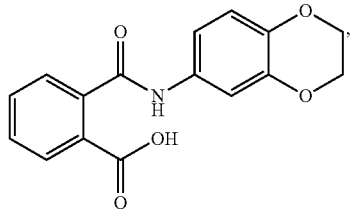

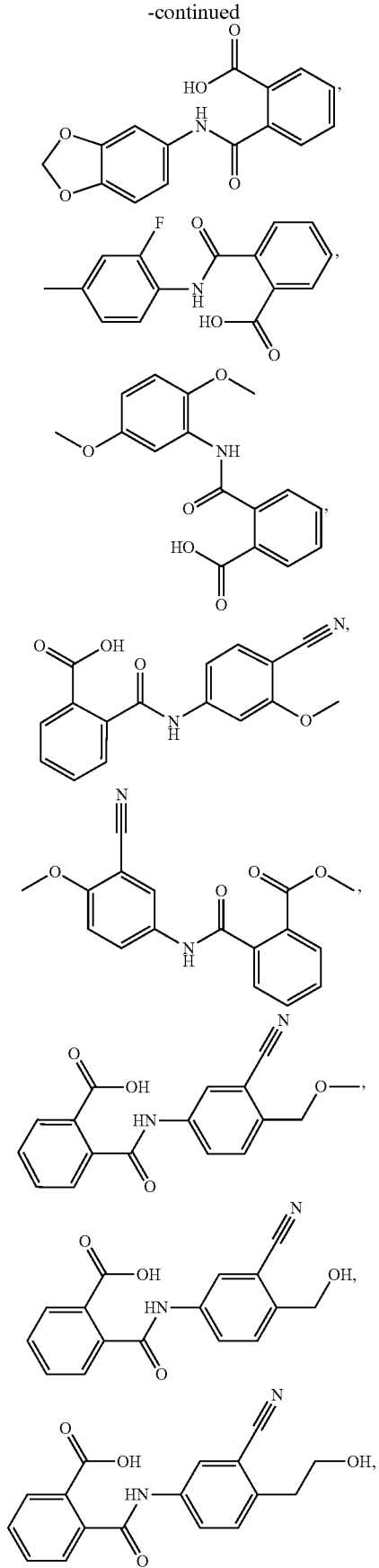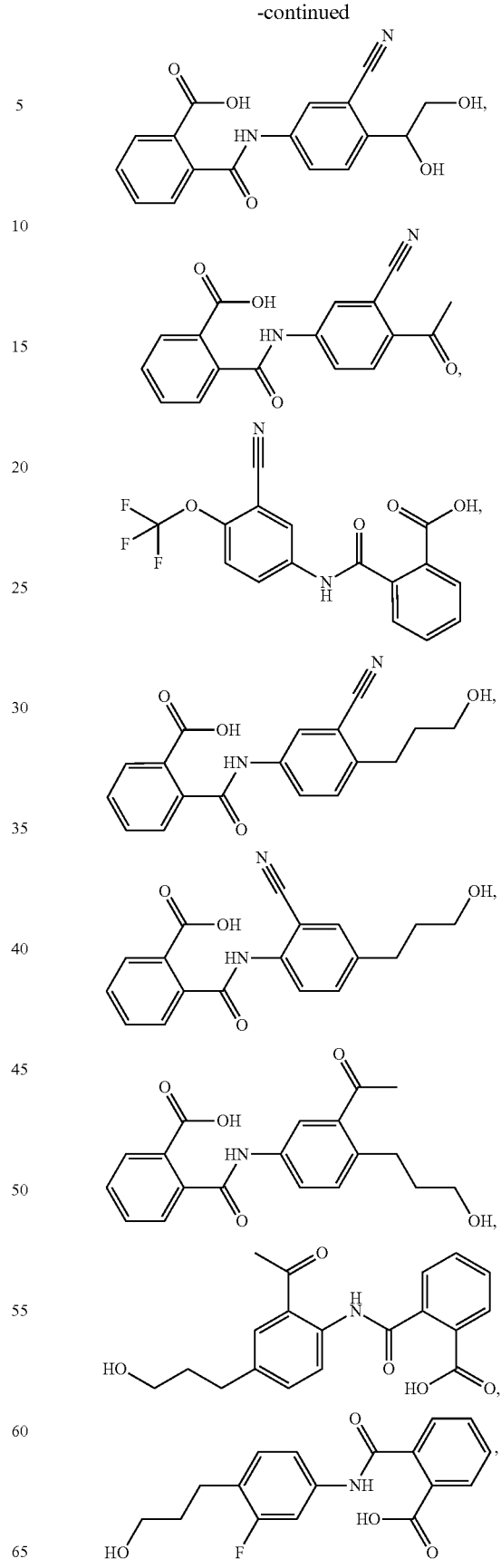

-continued
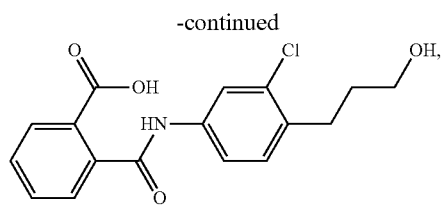
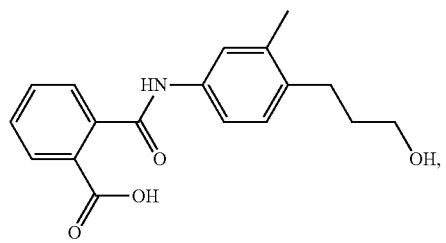
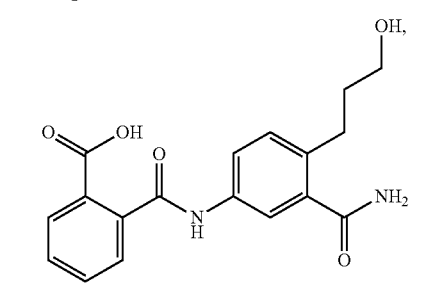
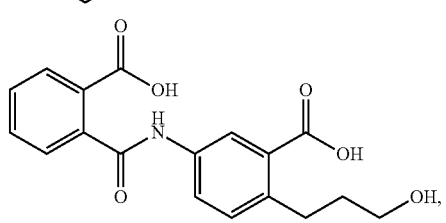
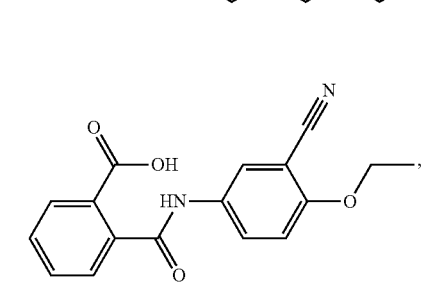
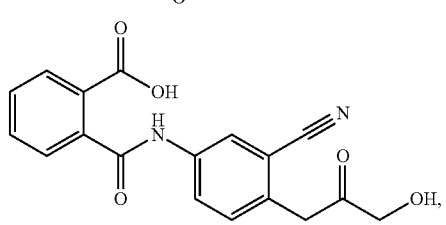
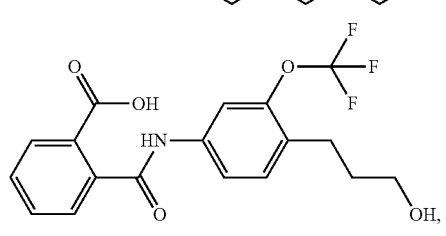
-continued
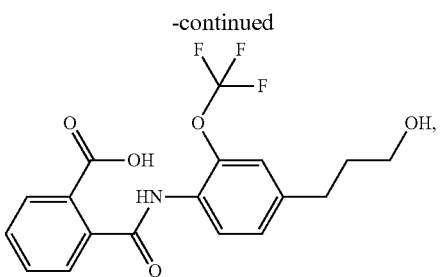
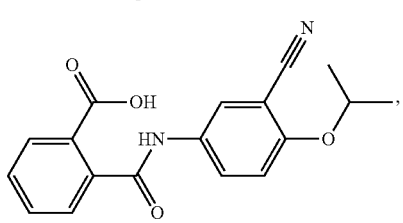
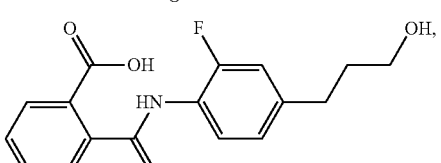
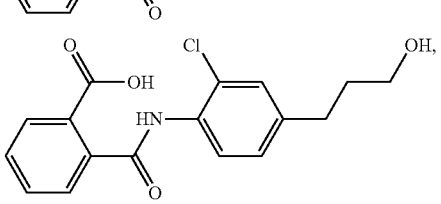
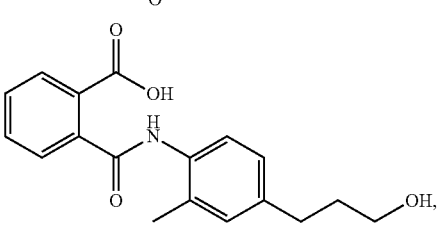
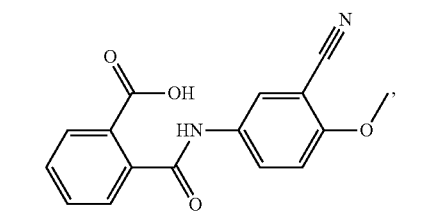
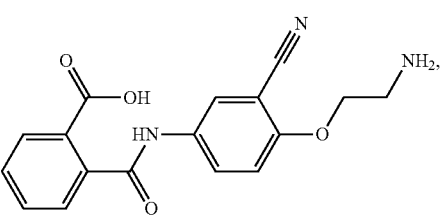

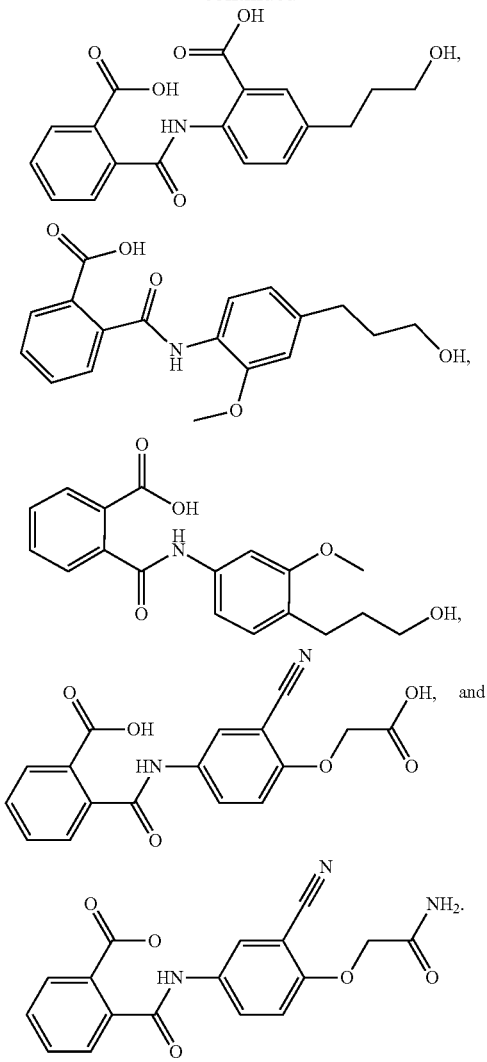
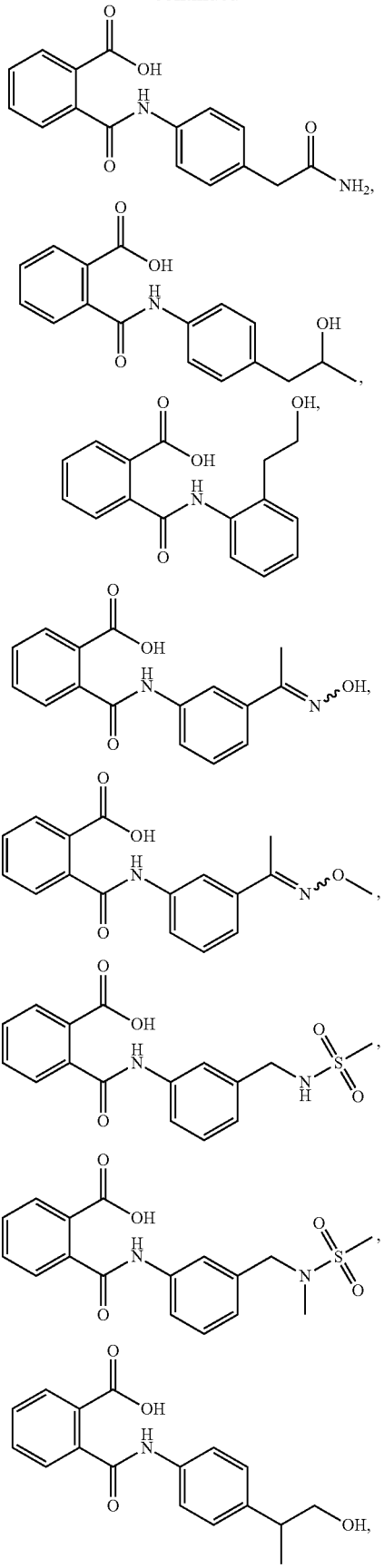
In another aspect, provided herein are compounds of Formula Ib, or pharmaceutically acceptable salts, solvates, polymorphs, prodrugs, esters, metabolites, N-oxides, stereoisomers, or isomers thereof, selected from:
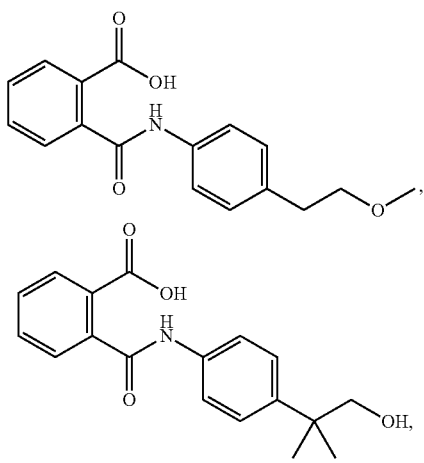

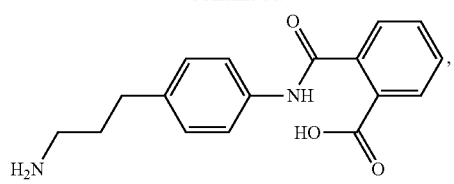
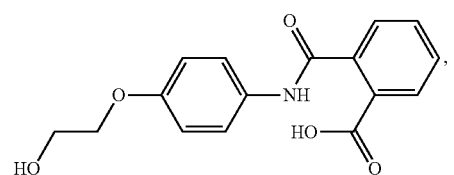
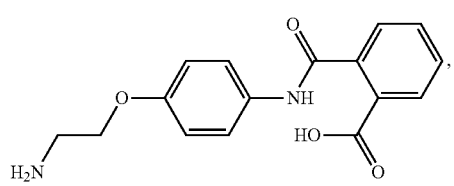
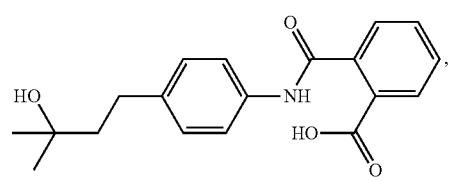
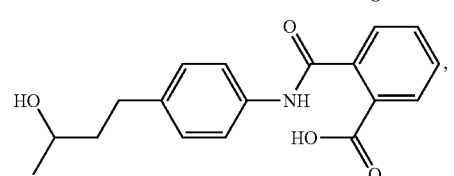
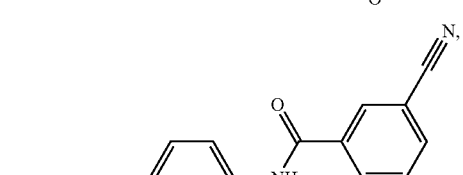
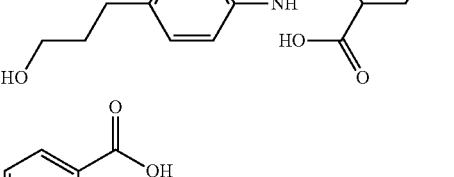
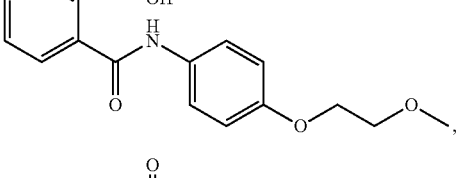
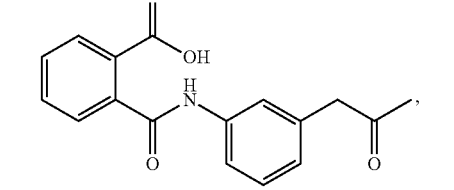
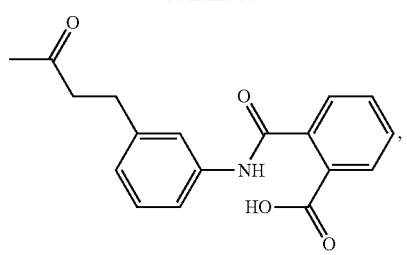
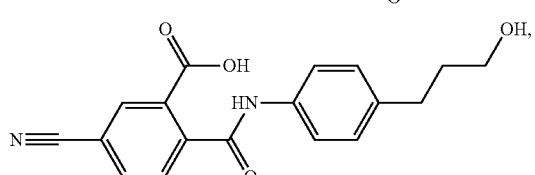
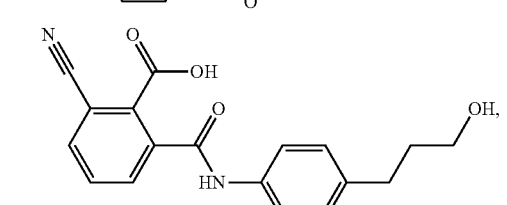
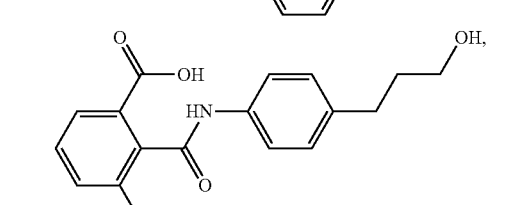
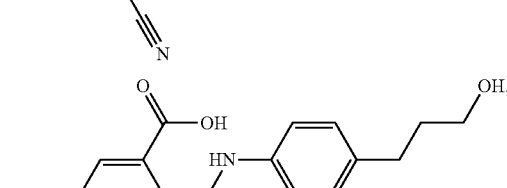
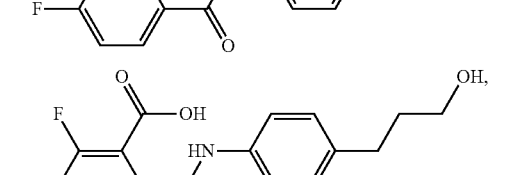
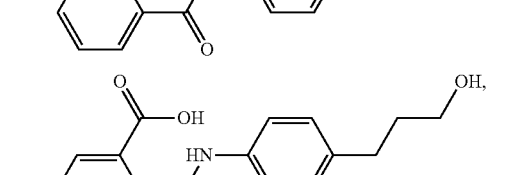
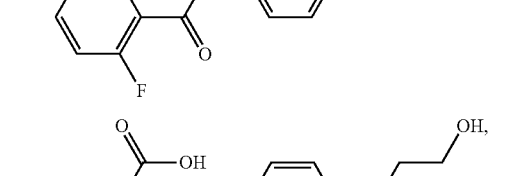
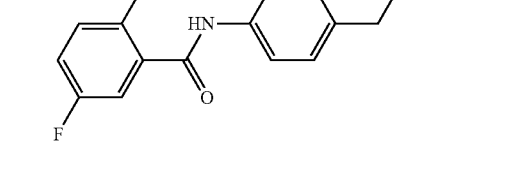

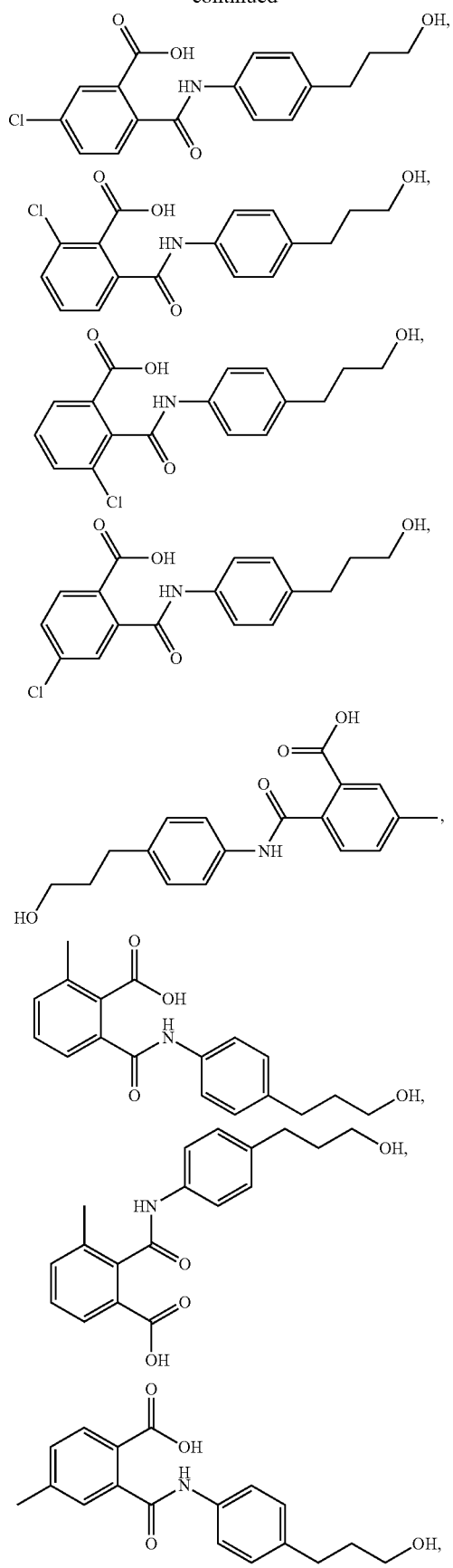
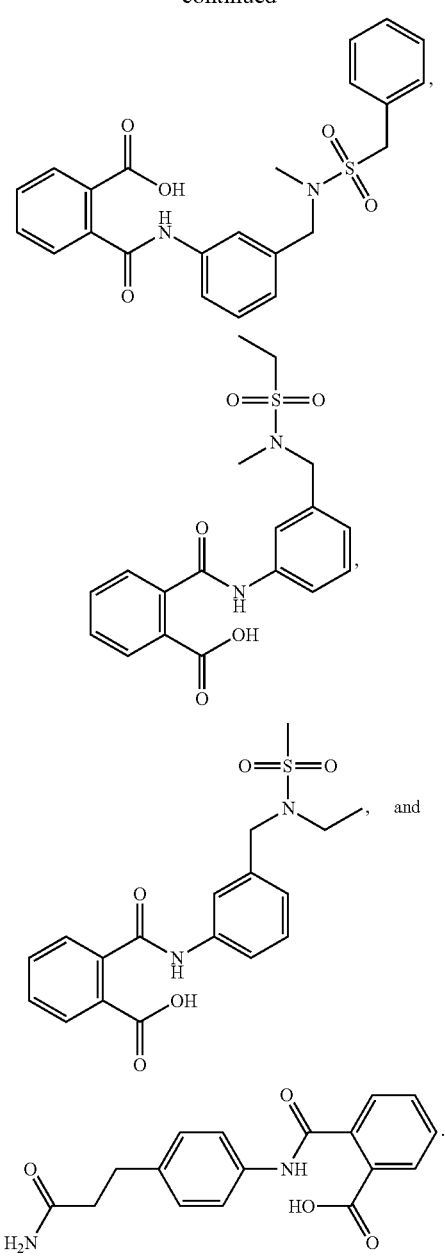
In another aspect, provided herein are compounds of Formula Ic, or pharmaceutically acceptable salts, solvates, polymorphs, prodrugs, esters, metabolites, N-oxides, stereoisomers, or isomers thereof, selected from:
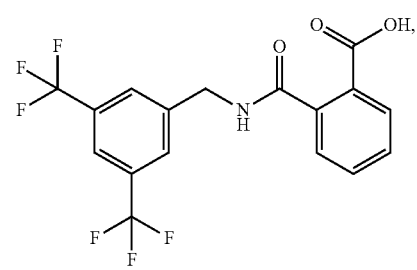

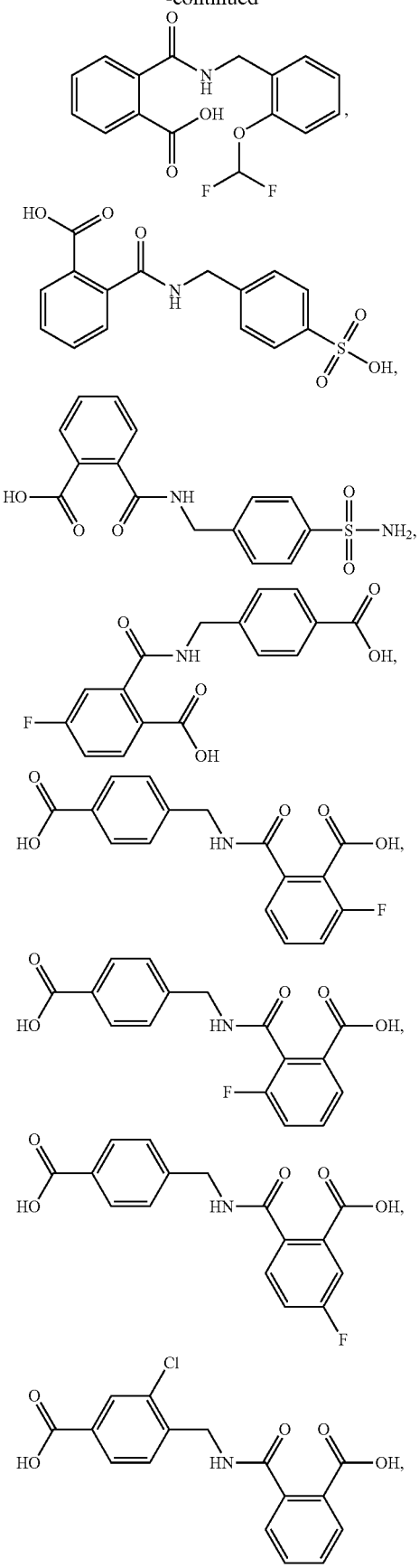
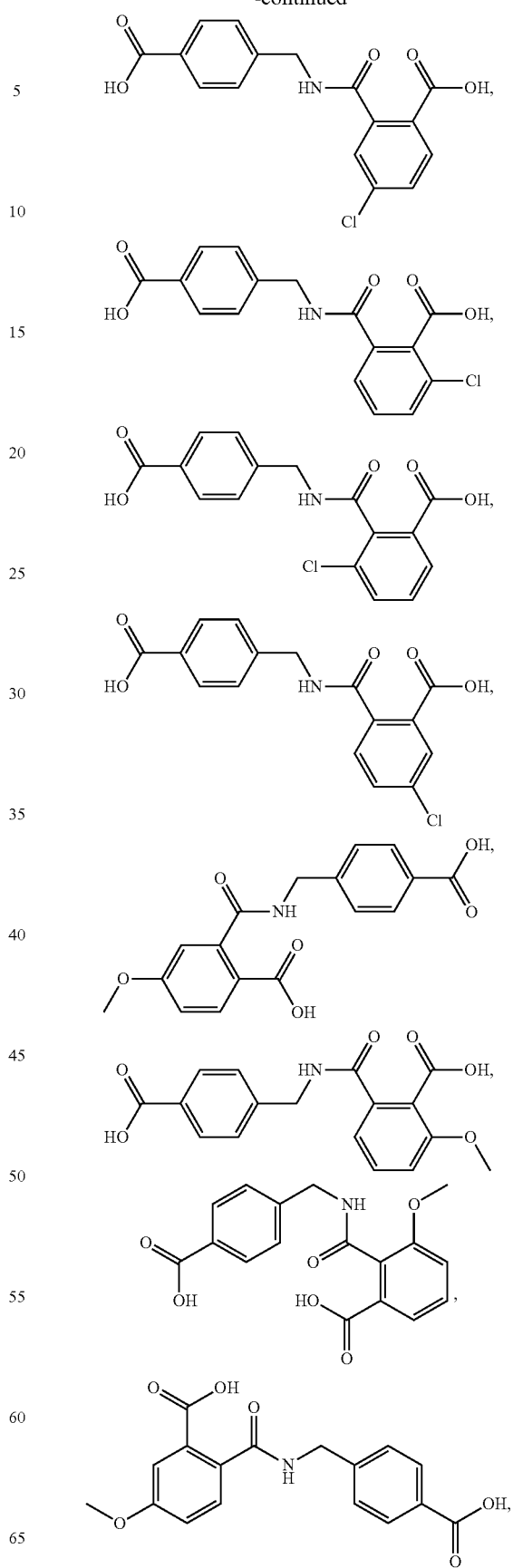

-continued
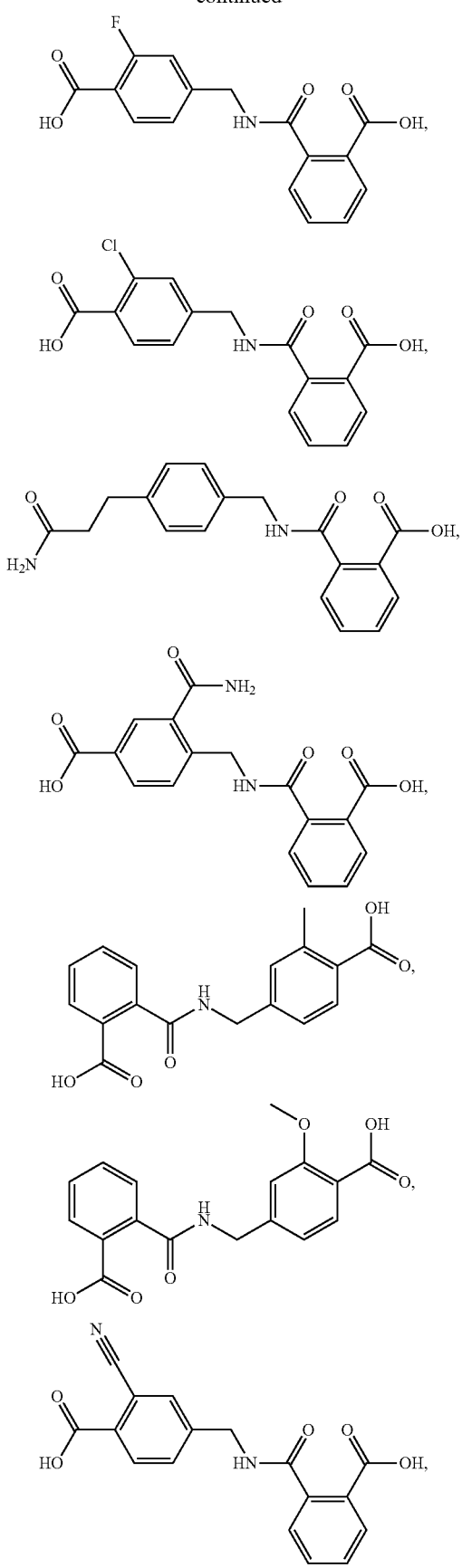
-continued
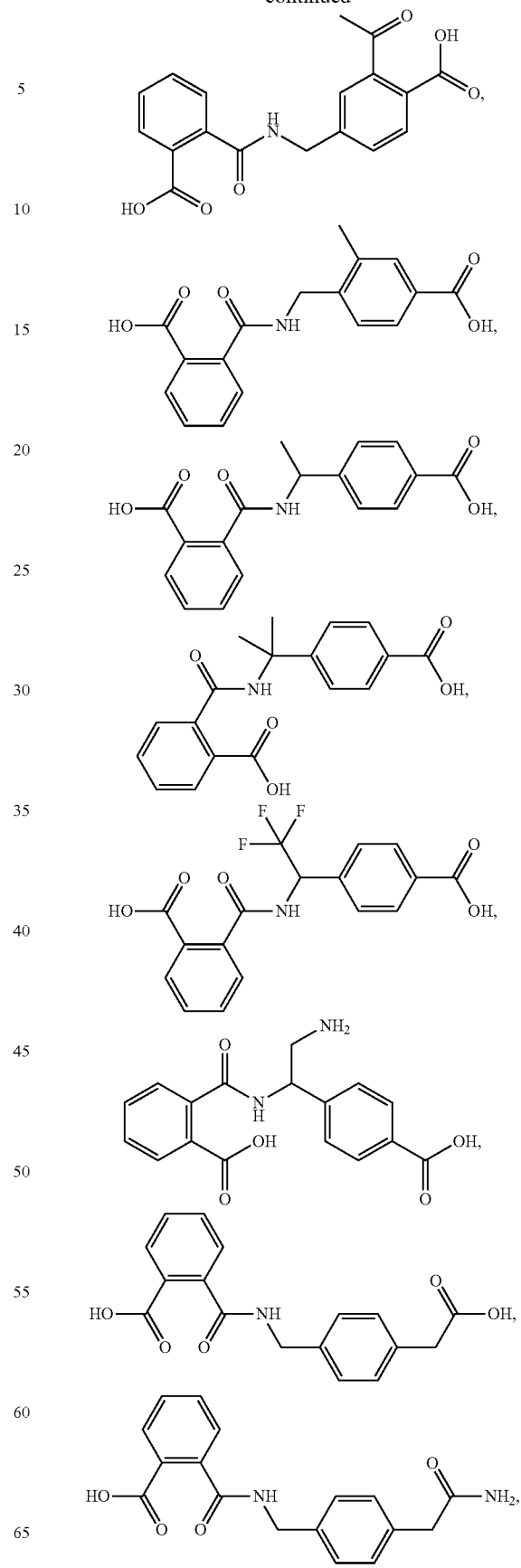

-continued
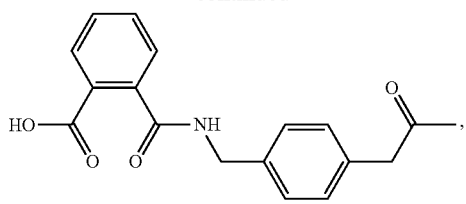
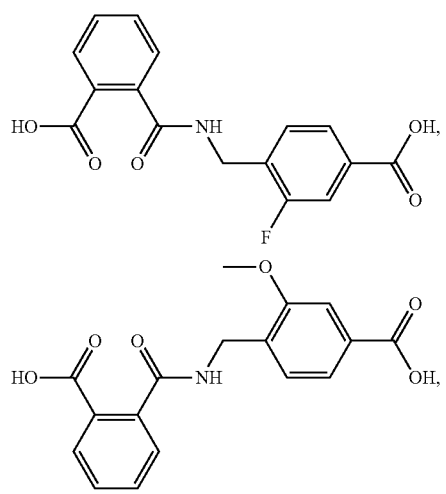
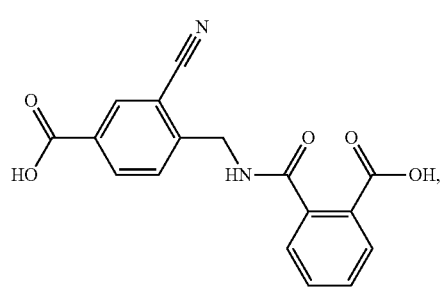
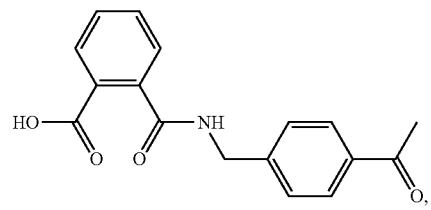
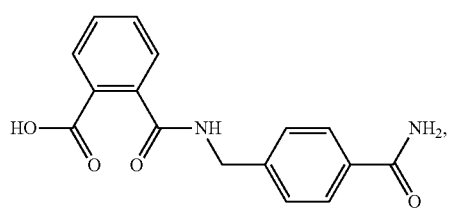
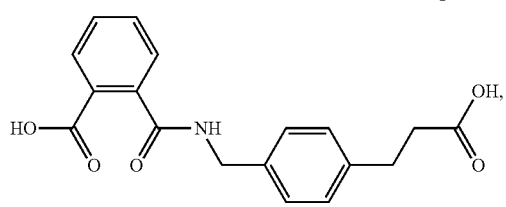
-continued
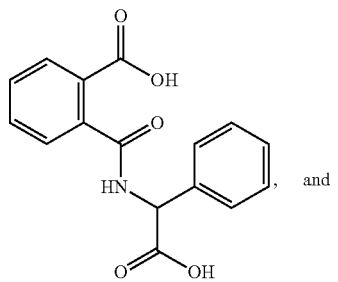
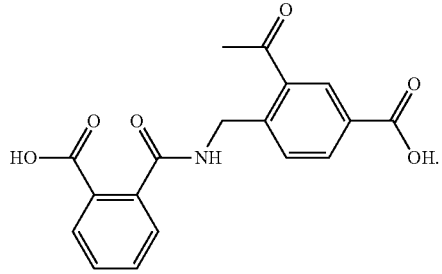
In another aspect, provided herein are compounds of Formula II, or pharmaceutically acceptable salts, solvates, polymorphs, prodrugs, esters, metabolites, N-oxides, stereoisomers, or isomers thereof, selected from:
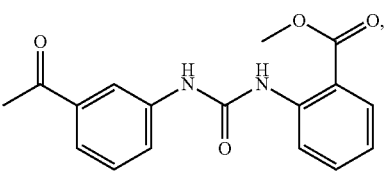
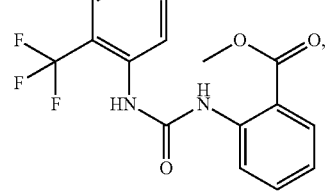
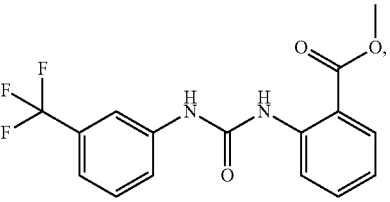
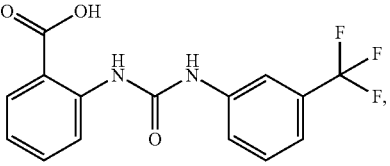
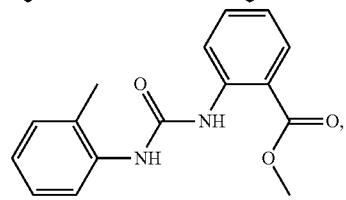

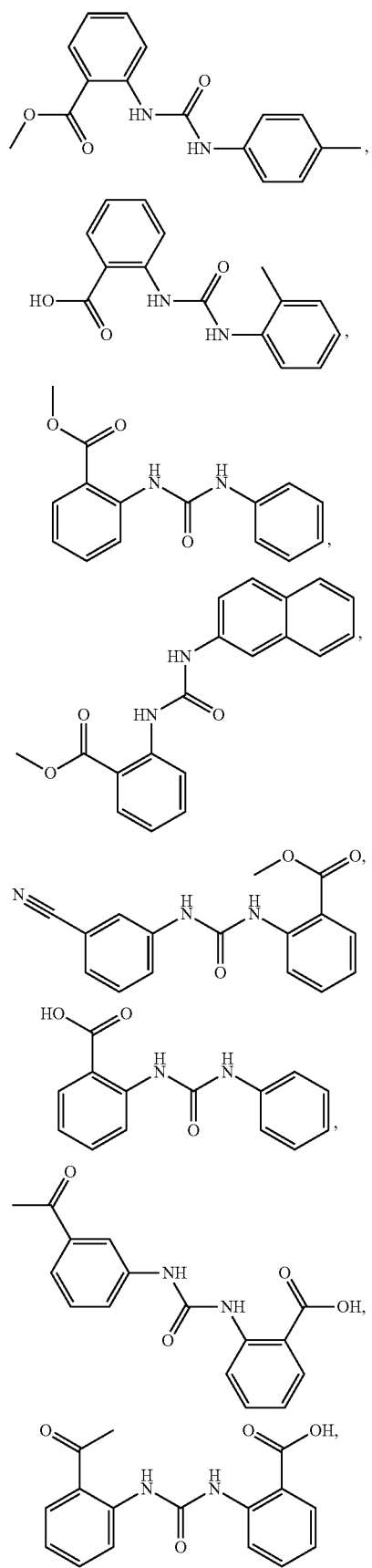
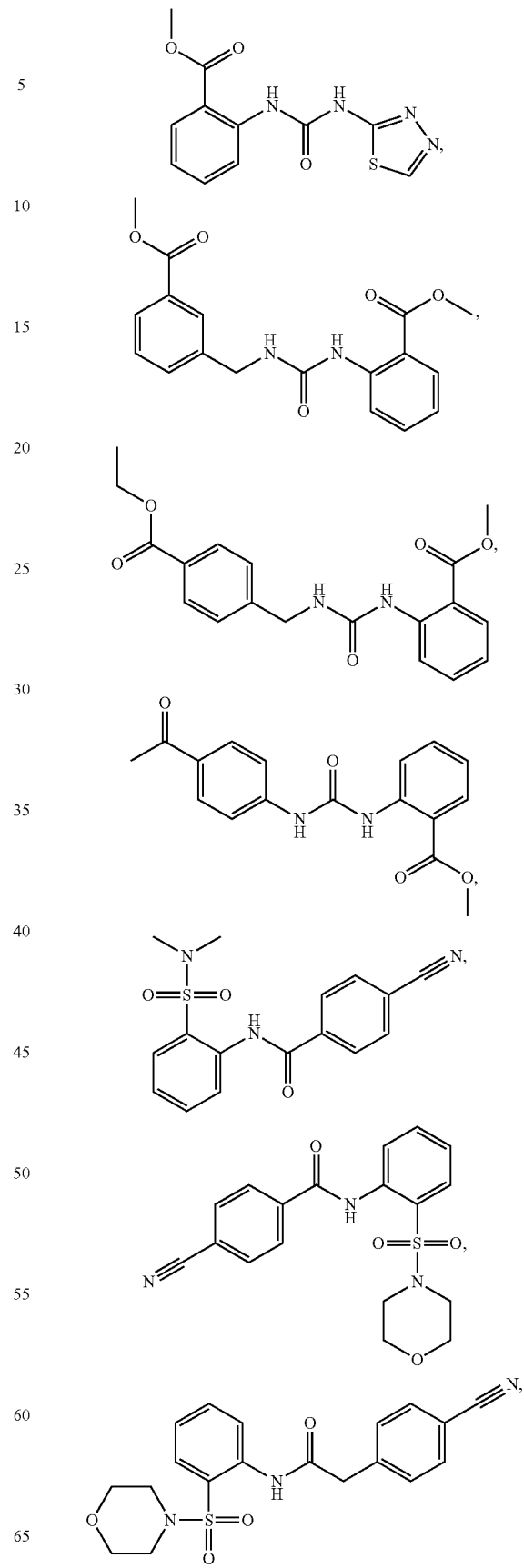

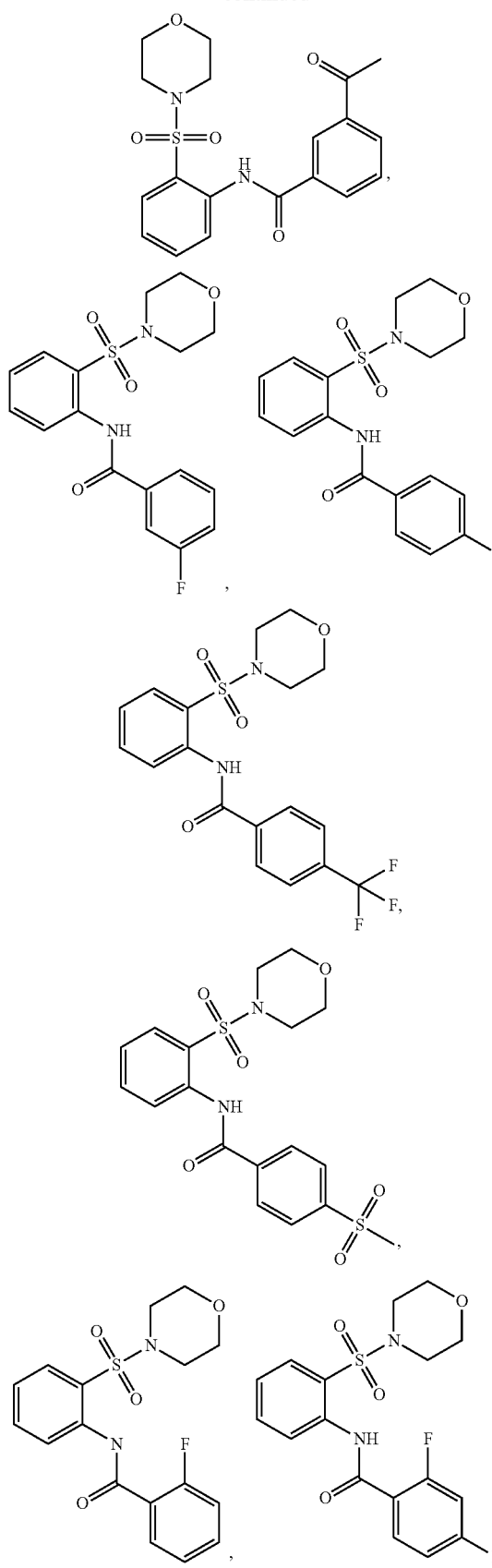
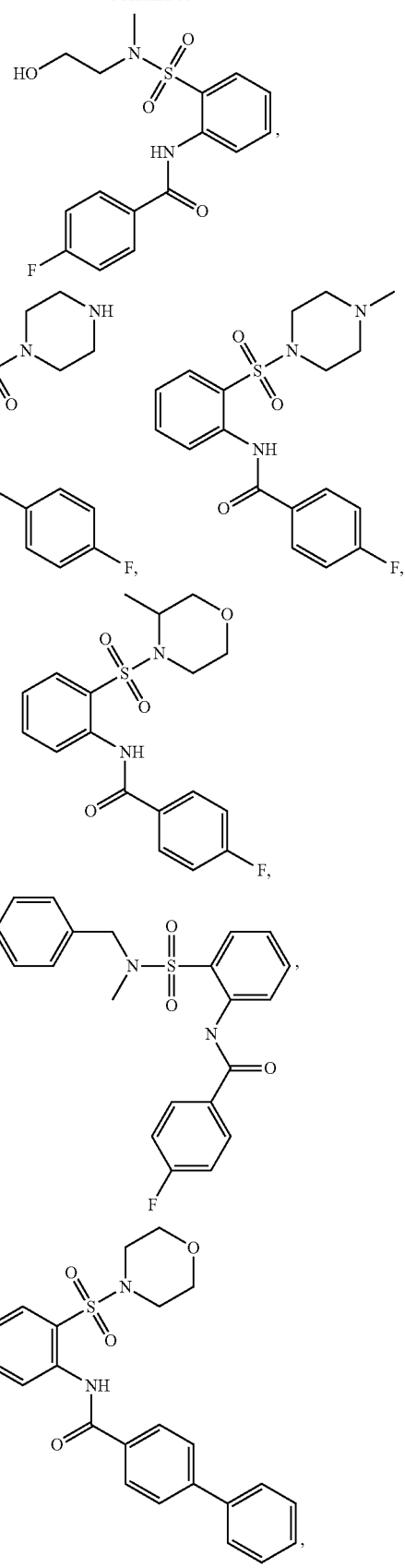

73
-continued
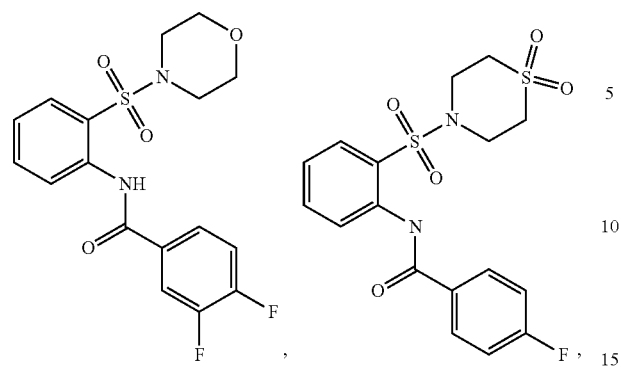
74
-continued
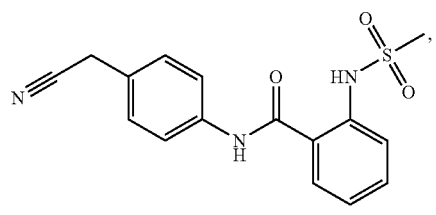
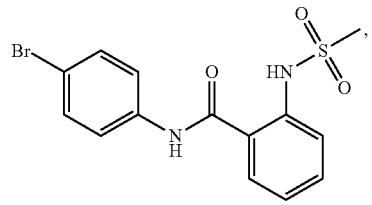
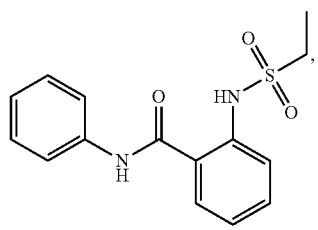
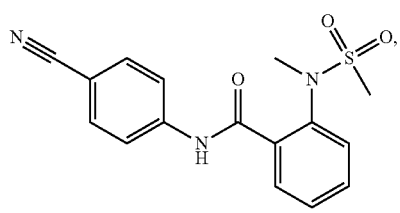
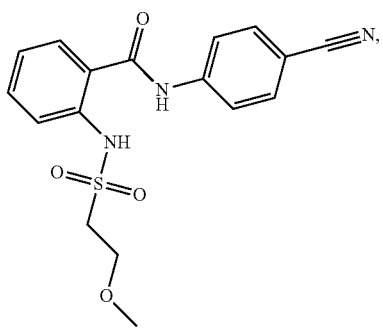
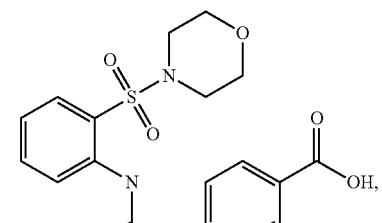
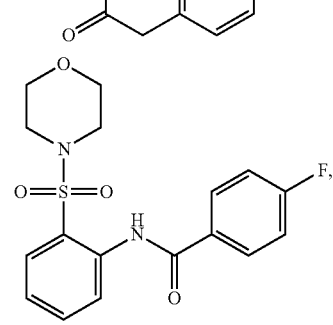
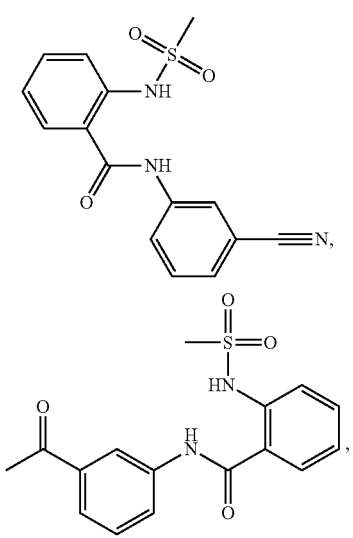

-continued
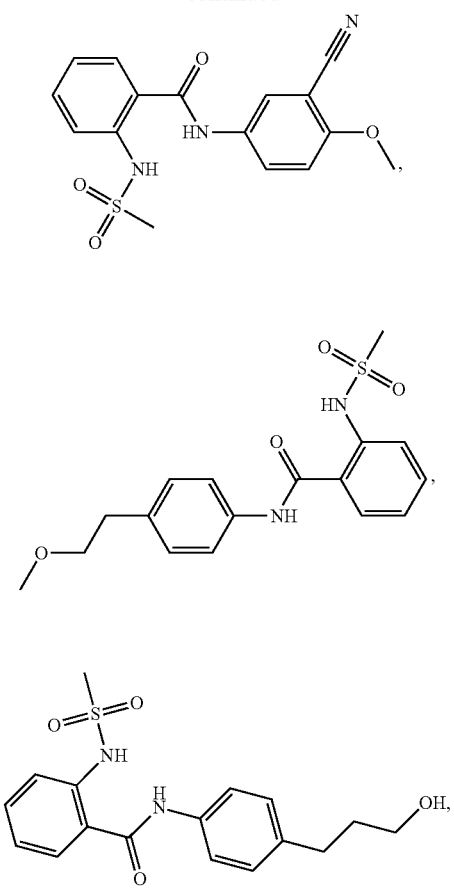
-continued
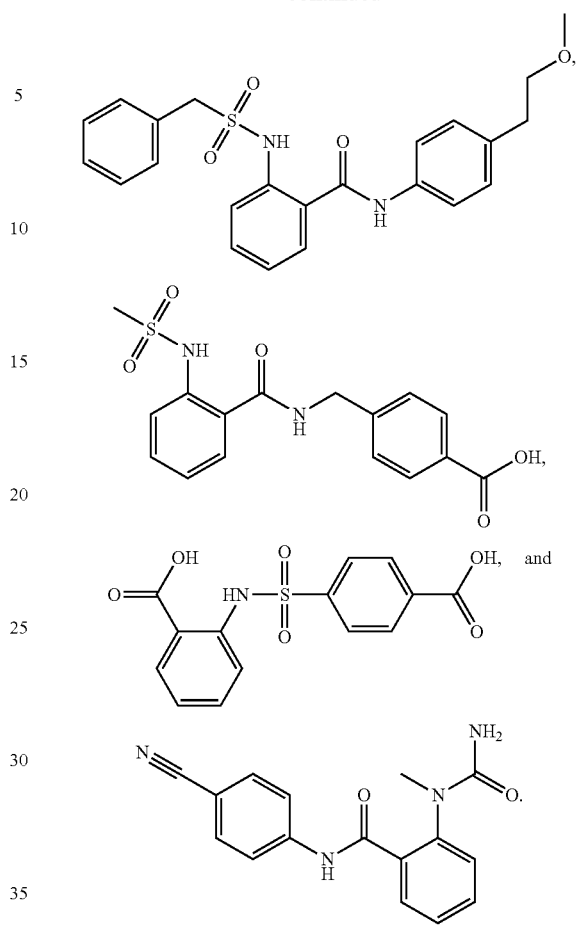
In another aspect, provided herein are compounds of Formula IIa, or pharmaceutically acceptable salts, solvates, polymorphs, prodrugs, esters, metabolites, N-oxides, stereoisomers, or isomers thereof, selected from:
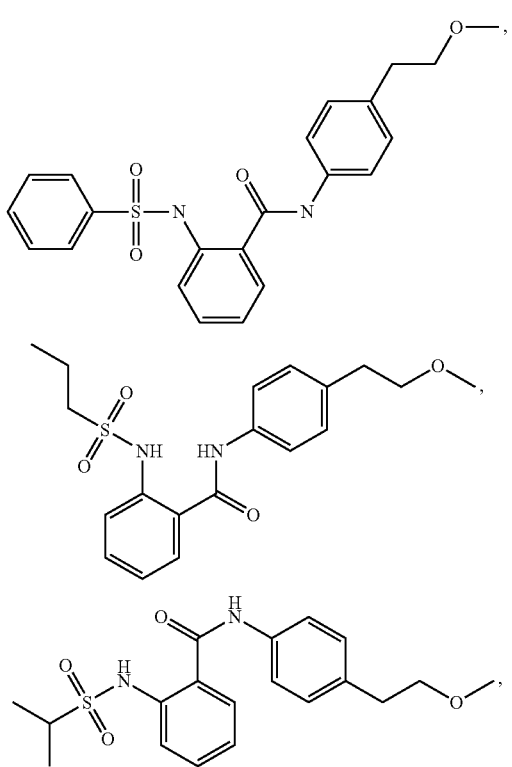
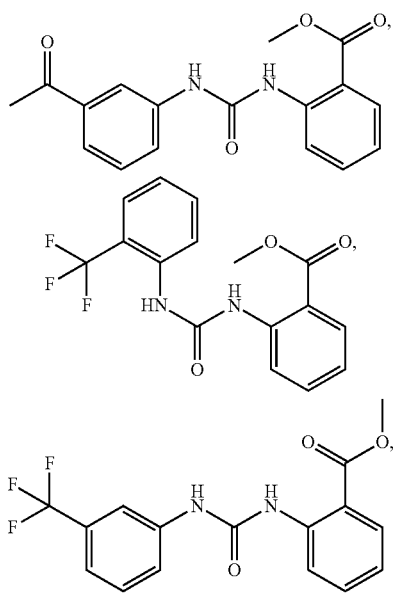

-continued
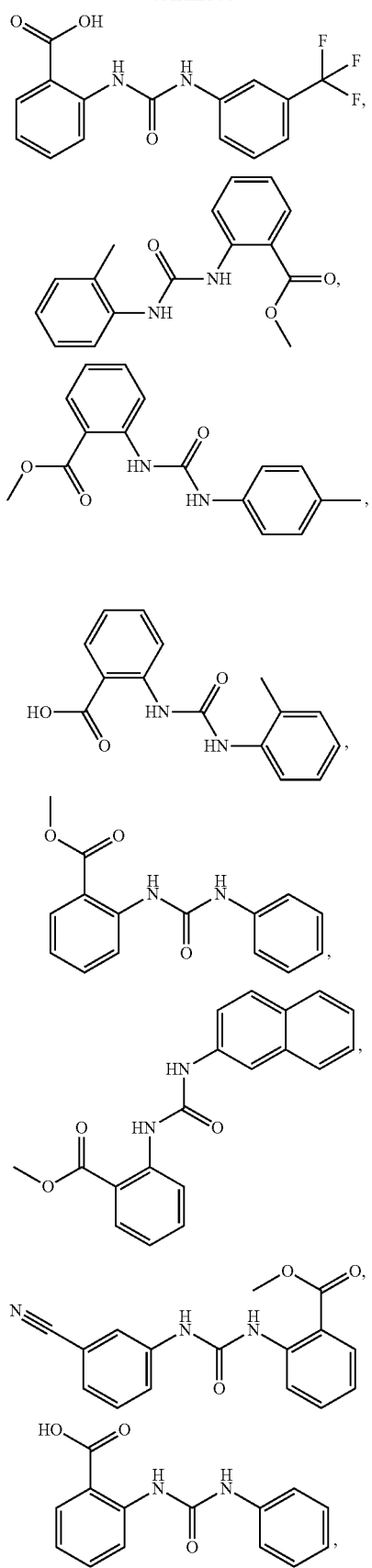
-continued
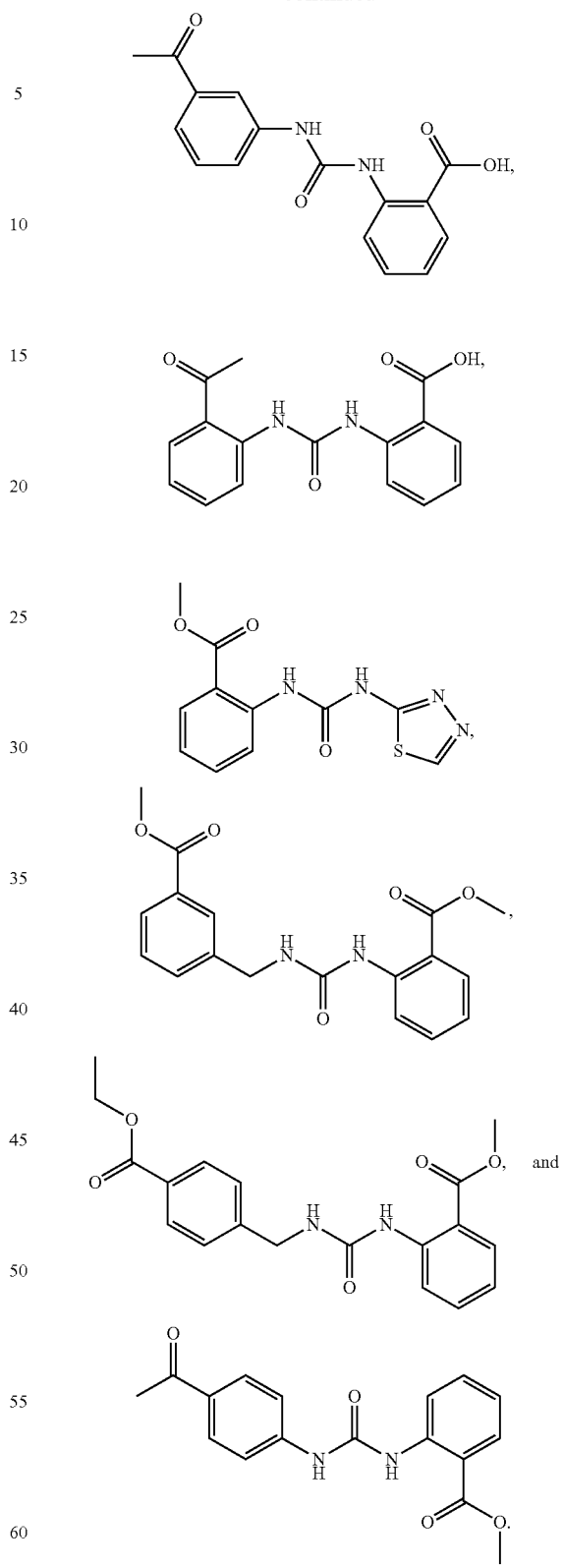
In another aspect, provided herein are compounds of Formula IIb, or pharmaceutically acceptable salts, solvates, polymorphs, prodrugs, esters, metabolites, N-oxides, stereoisomers, or isomers thereof, selected from:

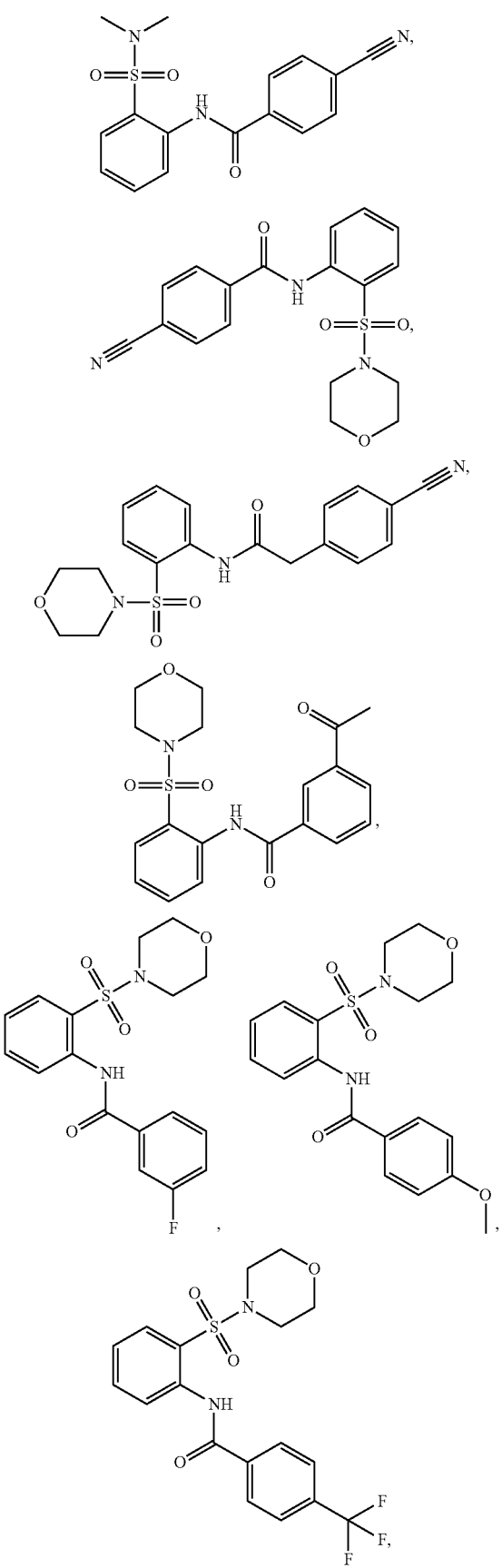
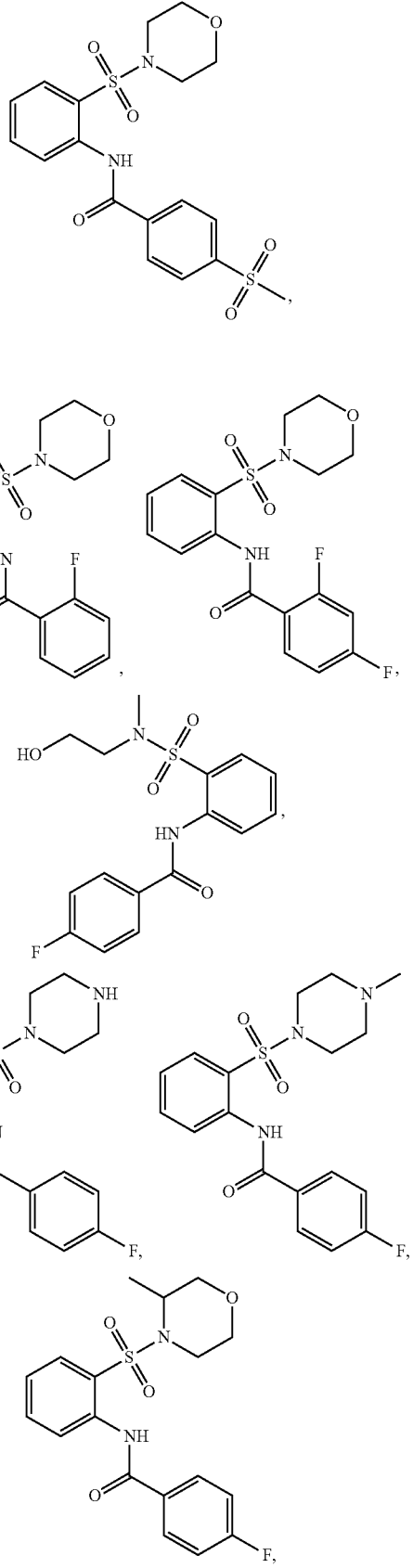

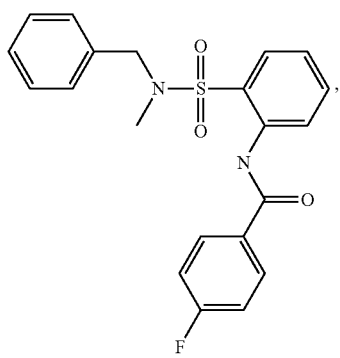
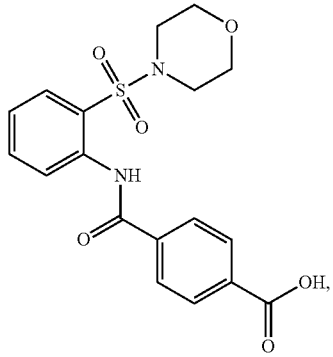
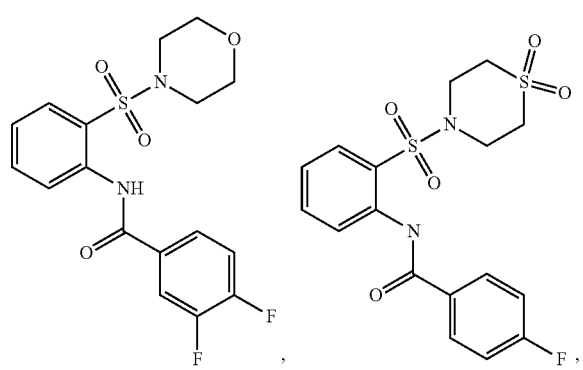
In another aspect, provided herein are compounds of Formula IIc, or pharmaceutically acceptable salts, solvates, polymorphs, prodrugs, esters, metabolites, N-oxides, stereoisomers, or isomers thereof, selected from:
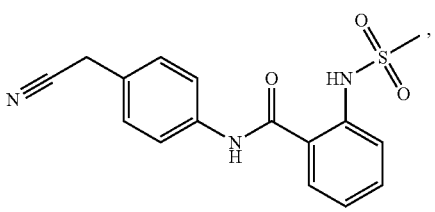
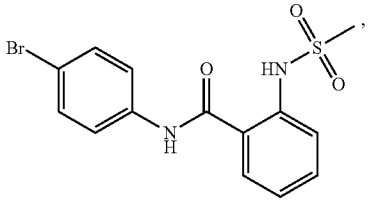
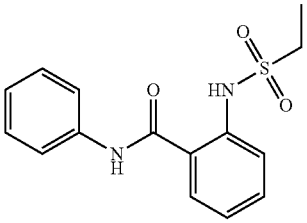

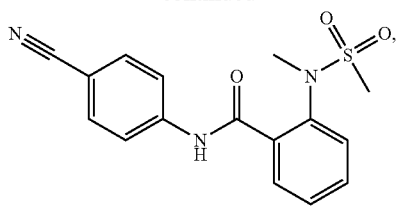
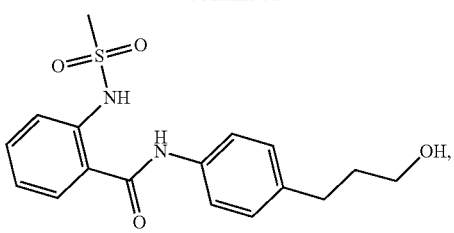
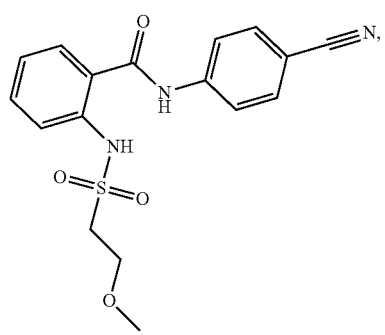
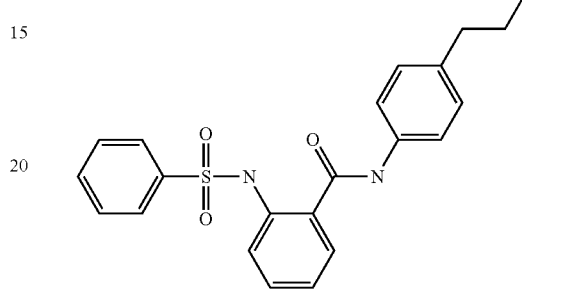
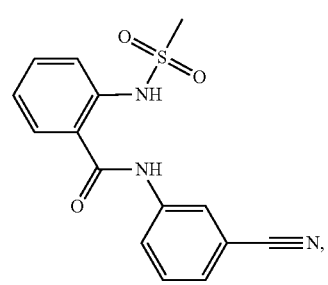
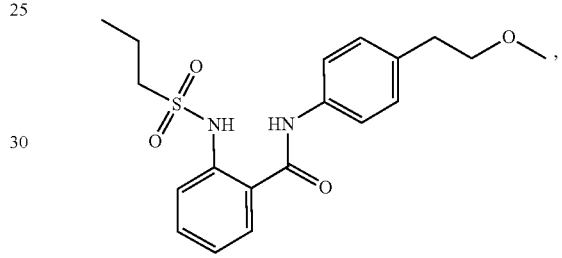
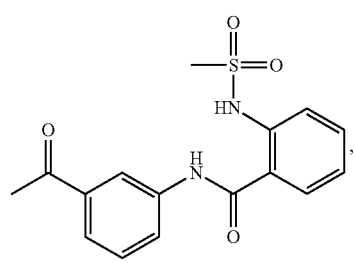
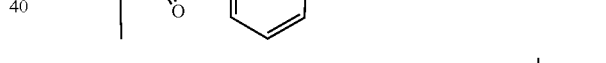
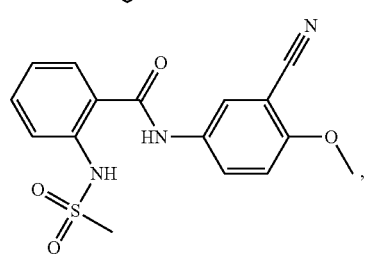
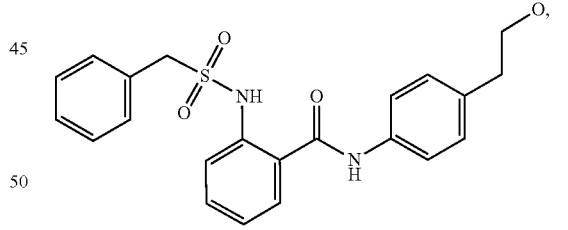
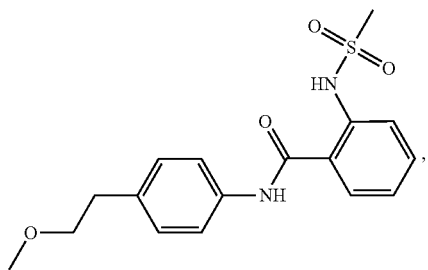
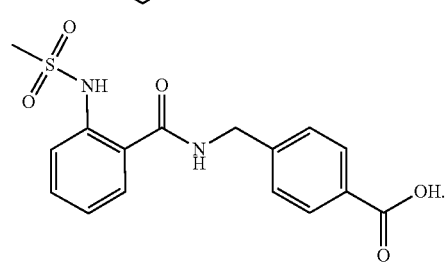
In another aspect, provided herein are compounds of Formula III, or pharmaceutically acceptable salts, solvates, polymorphs, prodrugs, esters, metabolites, N-oxides, stereoisomers, or isomers thereof, selected from:

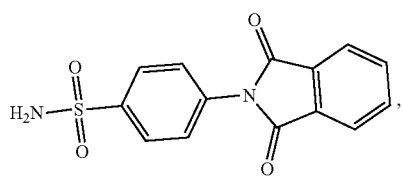
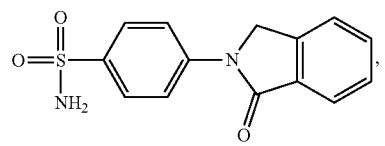
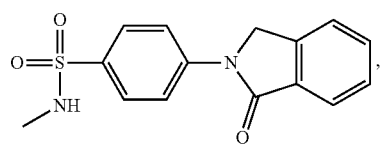
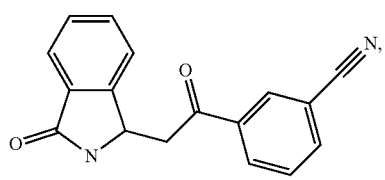
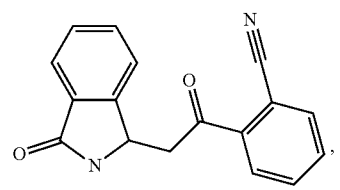
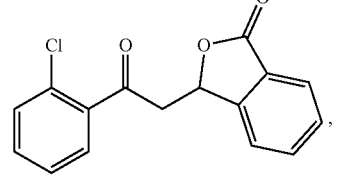
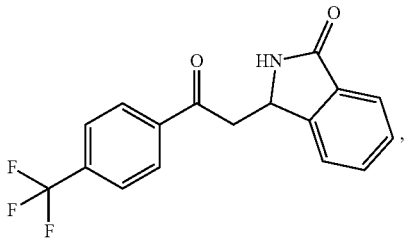
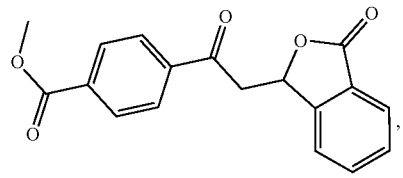
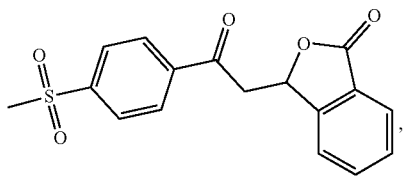
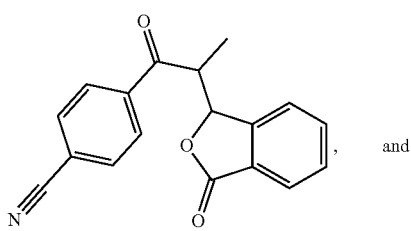
and
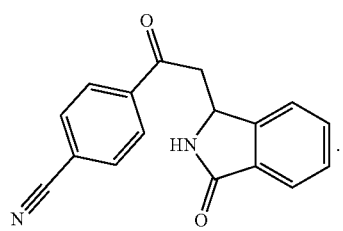
In another aspect, provided herein are compounds, or pharmaceutically acceptable salts, solvates, polymorphs, prodrugs, esters, metabolites, N-oxides, stereoisomers, or isomers thereof, selected from:
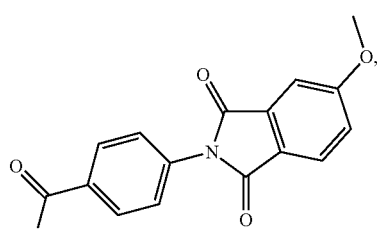
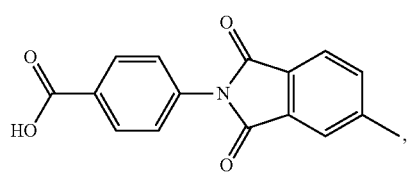
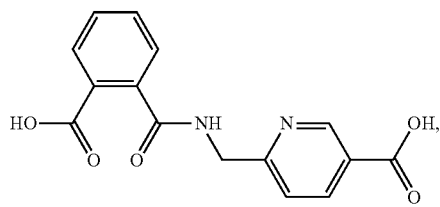
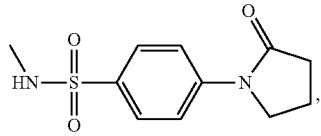
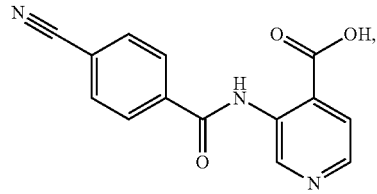

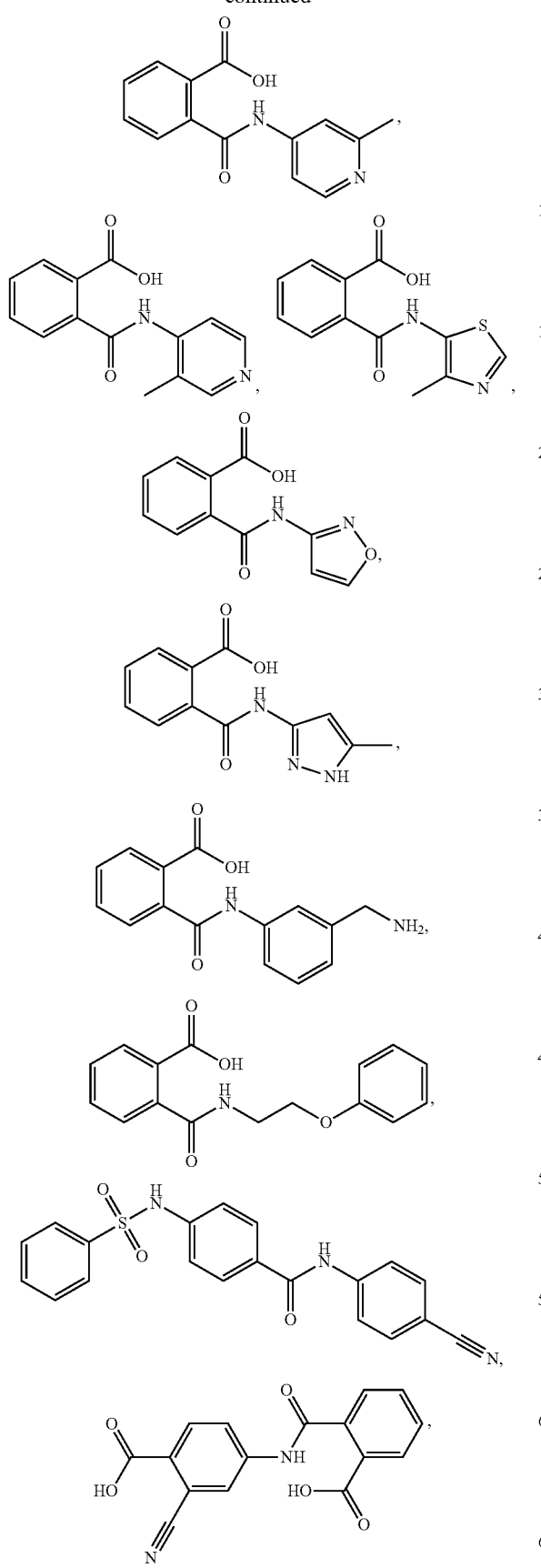
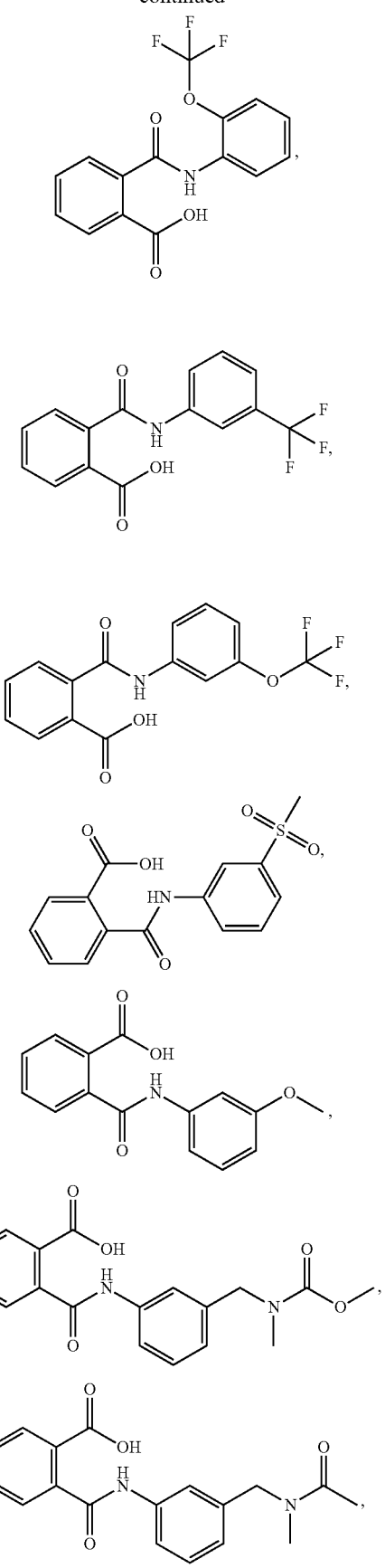

-continued

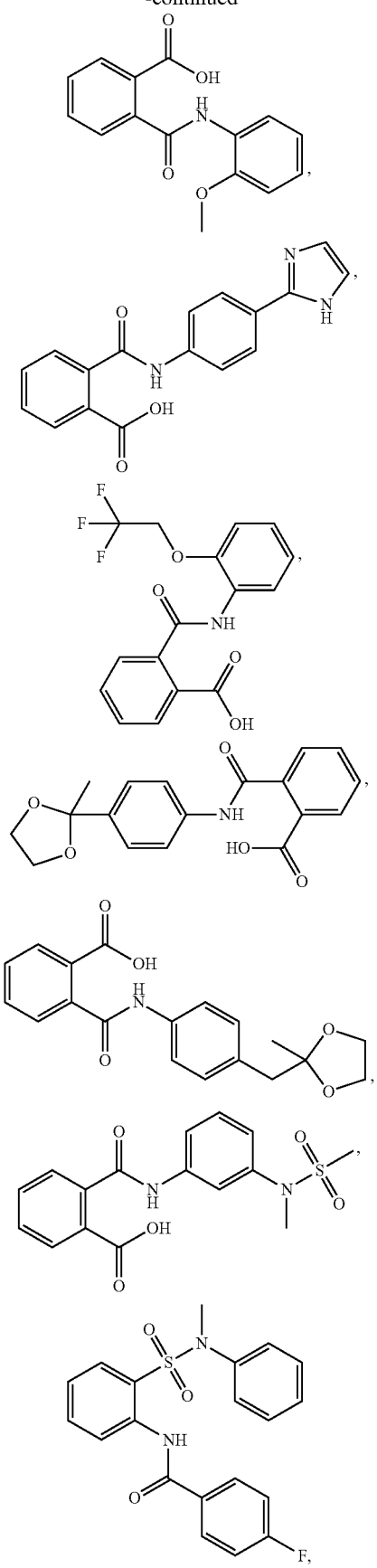

-continued

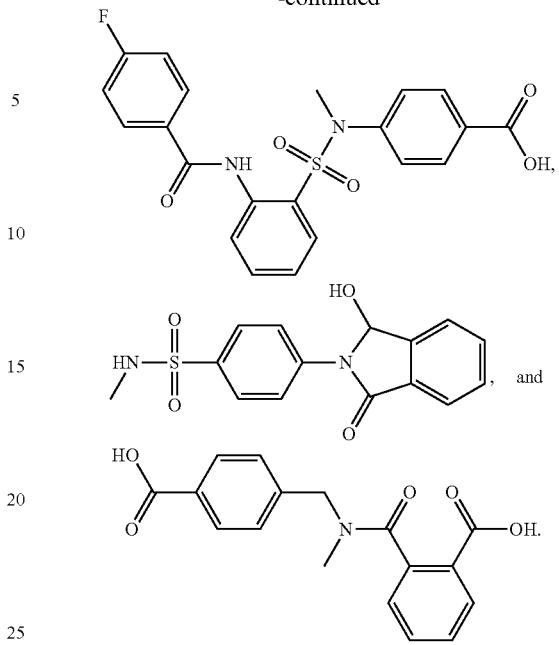

In one aspect, provided herein is a pharmaceutical composition comprising a compound disclosed herein, or a pharmaceutically acceptable salt, solvate, polymorph, prodrug, ester, metabolite, N-oxide, stereoisomer, or isomer thereof, and a pharmaceutically acceptable excipient. In certain embodiments, the pharmaceutical composition further comprises an additional compound which is therapeutically effective for the treatment of arthritis or joint injury and/or the symptoms associated with arthritis or joint injury in a mammal. In certain embodiments, the additional compound is selected from NSAIDS, analgesics, angiopoietin-like 3 protein (ANGPTL3) or chondrogenic variant thereof, oral salmon calcitonin, SD-6010 (iNOS inhibitor), vitamin D3 (choliecalciferol), apoptosis/caspase inhibitors (emricasan), collagen hydrolysate, FGF18, BMP7, avocado soy unsaponifiables (ASU), and hyaluronic acid. In some embodiments, the mammal is human. In other embodiments, the mammal is a companion animal or livestock. In further embodiments, the companion animal or livestock is a dog, cat, or horse.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Osteoarthritis (OA) is characterized by progressive breakdown of articular cartilage, and ultimately leads to functional failure of synovial joints [Reginster, J. Y. and N. G. Khaltaev, Introduction and WHO perspective on the global burden of musculoskeletal conditions. Rheumatology (Oxford), 2002. 41 Supp 1: p. 1-2]. OA is mediated by several pathogenic mechanisms including enzymatic degradation of extracellular matrix, deficient new matrix formation, cell death, and abnormal activation and hypertrophic differentiation of cartilage cells [Goldring, M. B. and S. R. Goldring, *Articular cartilage and subchondral bone in the pathogenesis of osteoarthritis*. Ann N Y Acad Sci, 2010. 1192(1): p. 230-7]. The only current therapeutic options for OA are pain management and surgical intervention [Hunter, D. J., *Pharmacologic therapy for osteoarthritis-the era of disease modification*. Nat Rev Rheumatol, 2011. 7(1): p. 13-22].

Mesenchymal stem cells (MSCs), residing in bone marrow and most adult tissues, are capable of self-renewal and differentiation into a variety of cell lineages including chondrocytes, osteoblasts and adipocytes [Pittenger, M. F., et al., *Multilineage potential of adult human mesenchymal stem cells*. Science, 1999. 284(5411): p. 143-7]. Recent studies found that adult articular cartilage contains MSCs (approximately 3% of the cells) that are capable of multi-lineage differentiation. In OA cartilage, the number of these cells approximately doubles. These resident stem cells still retain the capability to differentiate into chondrocytes and thus the capacity to repair the damaged cartilage [Grogan, S. P., et al., *Mesenchymal progenitor cell markers in human articular cartilage: normal distribution and changes in osteoarthritis*. Arthritis Res Ther, 2009. 11(3): p. R85; Koelling, S., et al., *Migratory chondrogenic progenitor cells from repair tissue during the later stages of human osteoarthritis*. Cell Stem Cell, 2009. 4(4): p. 324-35].

The present invention is based, in part, on the discovery that the compounds of the present invention stimulate chondrocyte differentiation in mesenchymal stem cells. Accordingly, the present invention provides for methods of induction of mesenchymal stem cell differentiation into chondrocytes. Further, the present invention provides for administration of compounds and compositions of the present invention to prevent or ameliorate arthritis or joint injury by administrating the compound or composition into a joint, the vertebrae, vertebral disc or systemically.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.

"Cyano" or "nitrile" refers to the —CN radical.

"Hydroxy" or "hydroxyl" refers to the —OH radical.

"Nitro" refers to the —$NO_2$ radical.

"Oxo" refers to the =O substituent.

"Oxime" refers to the =N—OH substituent.

"Thioxo" refers to the =S substituent.

"Alkyl" refers to a straight or branched hydrocarbon chain radical, which is fully saturated or comprises unsaturations, has from one to thirty carbon atoms, and is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, vinyl, allyl, propynyl, and the like. Alkyl comprising unsaturations include alkenyl and alkynyl groups. Unless stated otherwise specifically in the specification, an alkyl group may be optionally substituted as described below.

"Alkylene" or "alkylene chain" refers to a straight or branched divalent hydrocarbon chain, as described for alkyl above. Unless stated otherwise specifically in the specification, an alkylene group may be optionally substituted as described below.

"Alkoxy" refers to a radical of the formula —$OR_a$ where $R_a$ is an alkyl radical as defined.

Unless stated otherwise specifically in the specification, an alkoxy group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Cycloalkyl" or "carbocycle" refers to a stable, non-aromatic, monocyclic or polycyclic carbocyclic ring, which may include fused or bridged ring systems, which is saturated or unsaturated. Representative cycloalkyls or carbocycles include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyls or carbocycles include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0] nonane, cis-decalin, trans-decalin, bicyclo[2.1.1]hexane, bicyclo[2.2.1]heptane, bicyclo[2.2.2]octane, bicyclo[3.2.2] nonane, and bicyclo[3.3.2]decane, and 7,7-dimethyl-bicyclo [2.2.1]heptanyl. Unless otherwise stated specifically in the specification, a cycloalkyl or carbocycle group may be optionally substituted. Illustrative examples of cycloalkyl groups include, but are not limited to, the following moieties:

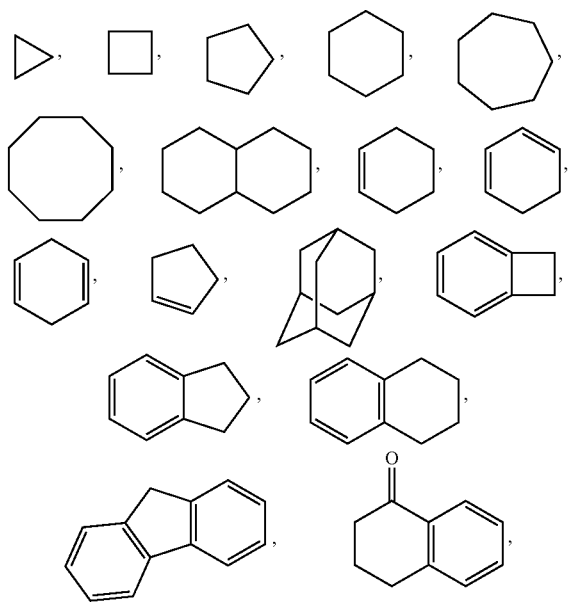

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

Unless stated otherwise specifically in the specification, a haloalkyl group may be optionally substituted.

"Haloalkoxy" similarly refers to a radical of the formula —OR$_a$ where R$_a$ is a haloalkyl radical as defined. Unless stated otherwise specifically in the specification, a haloalkoxy group may be optionally substituted as described below.

"Heterocycloalkyl" or "heterocyclyl" or "heterocyclic ring" or "heterocycle" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

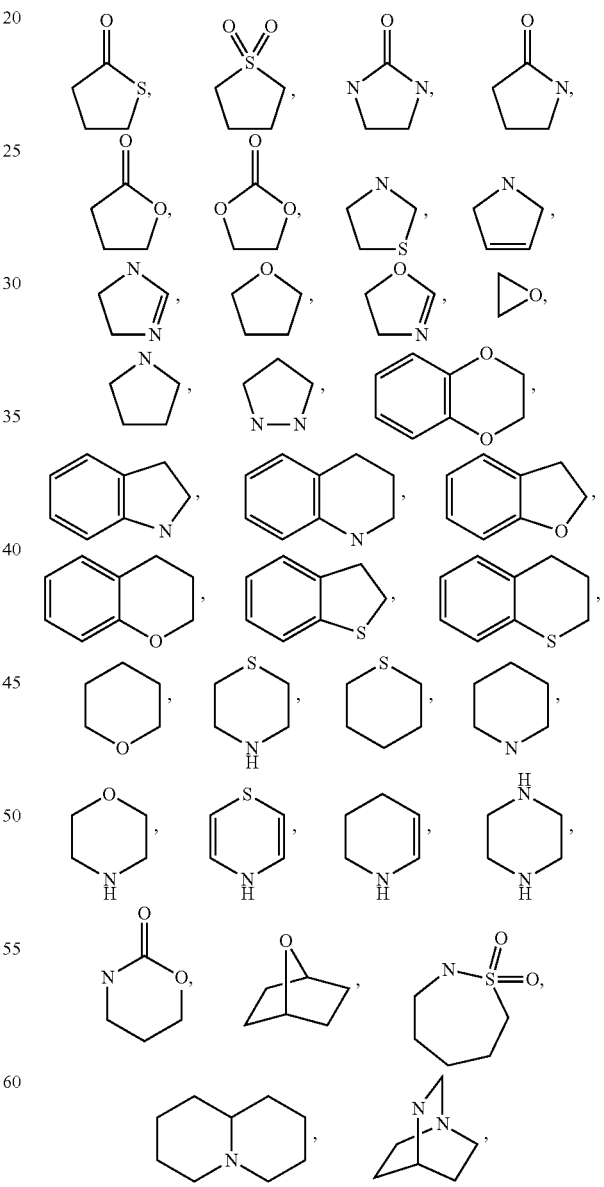

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (e.g, alkyl, alkylene, alkoxy, aryl, cycloalkyl, haloalkyl, heterocyclyl and/or heteroaryl) may be further functionalized wherein at least one hydrogen atom is replaced by a bond to a non-hydrogen atom substituent. Unless stated specifically in the specification, a substituted group may include one or more substituents selected from: oxo, amino, —CO$_2$H, nitrile, nitro, hydroxyl, thiooxy, alkyl, alkylene, alkoxy, aryl, cycloalkyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NH$_2$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen, sulfur, or nitrogen atoms. For example, an alkyl group may be substituted with one or more internal oxygen atoms to form an ether or polyether group. Similarly, an alkyl group may be substituted with one or more internal sulfur atoms to form a thioether, disulfide, etc.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In other embodiments, treatment also includes prophylactic treatment (e.g., administration of a composition described herein when an individual is suspected to be suffering from a bacterial infection).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

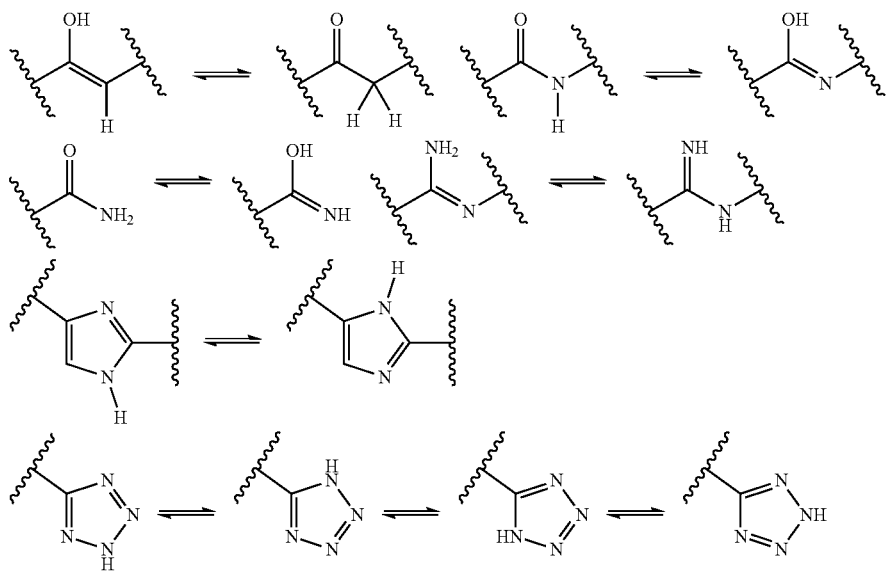

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

Methods

Provided herein is a method of ameliorating arthritis or joint injury in a mammal, the method including administering to a joint of the mammal a composition having a therapeutically effective amount of a compound disclosed herein.

Provided herein is a method of inducing differentiation of mesenchymal stem cells into chondrocytes, the method including contacting mesenchymal stem cells with a sufficient amount of a compound disclosed herein, thereby inducing differentiation of the stem cells into chondrocytes.

In one aspect, provided herein is a method of ameliorating arthritis or joint injury in a mammal, the method comprising administering to a joint of the mammal a composition comprising a therapeutically effective amount of a compound of Formula I, or a pharmaceutically acceptable salt, solvate, polymorph, prodrug, ester, metabolite, N-oxide, stereoisomer, or isomer thereof:

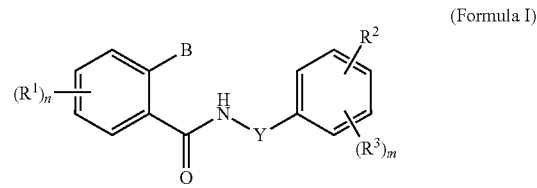

(Formula I)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
n is 0, 1, 2, 3, or 4;
m is 1, 2, 3, or 4;
B is $CO_2R^4$, $CH_2CO_2H$, $CH_2CO_2R^4$, or optionally substituted phenyl;
Y is a bond, —$(CR^5R^6)$—, —$(CR^7R^8)(CR^9R^{10})$—, or —$(CR^7R^8)(CR^9R^{10})X$—;
X is O or $CR^5R^6$;
$R^2$ is halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
each $R^3$ is independently selected from H, CN, halo, $C(O)R^4$, $CO_2H$, $CO_2R^4$, $C(O)NR^4R^{11}$, alkyl, optionally substituted alkoxy, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C$ (O)R$^4$, X(CR$^7$R$^8$)C(O)OR$^4$, X(CR$^7$R$^8$)C(O)NR$^4$R$^{11}$, X(CR$^7$R$^8$)(CR$^9$R$^{10}$)C(O)R$^4$, X(CR$^7$R$^8$)(CR$^9$R$^{10}$)C(O)OR$^4$, X(CR$^7$R$^8$)(CR$^9$R$^{10}$)C(O)NR$^4$R$^{11}$, (CR$^7$R$^8$)NR$^4$SO$_2$R$^4$, and C(=NOR$^4$)R$^4$;

or R$^3$ together with an adjacent R$^3$ or with R$^2$ form a ring;

each R$^4$ is independently selected from H and optionally substituted alkyl;

each R$^5$, R$^6$, R$^7$, R$^8$, R$^9$, and R$^{10}$ is independently selected from H, halo, optionally substituted alkyl, OH, CO$_2$R$^4$, NR$^4$R$^{11}$, and optionally substituted alkoxy; and R$^{11}$ is H, optionally substituted alkyl, C(O)R$^4$, C(O)OR$^4$, C(O)NR$^4$R$^4$, or SO$_2$R$^4$; provided that a) if Y is a bond and m is 0, then R$^2$ is selected from C(O)NR$^4$R$^{11}$, (CR$^7$R$^8$)OR$^4$, (CR$^7$R$^8$)(CR$^9$R$^{10}$)OR$^4$, X(CR$^7$R$^8$)(CR$^9$R$^{10}$)OR$^4$, X(CR$^7$R$^8$)(CR$^9$R$^{10}$)NR$^4$R$^{11}$, (CR$^7$R$^8$)C(O)R$^4$, (CR$^7$R$^8$)C(O)OR$^4$, (CR$^7$R$^8$)C(O)NR$^4$R$^{11}$, X(CR$^7$R$^8$)C(O)R$^4$, X(CR$^7$R$^8$)C(O)OR$^4$, X(CR$^7$R$^8$)C(O)NR$^4$R$^{11}$, X(CR$^7$R$^8$)(CR$^9$R$^{10}$)C(O)R$^4$, X(CR$^7$R$^8$)(CR$^9$R$^{10}$)C(O)OR$^4$, X(CR$^7$R$^8$)(CR$^9$R$^{10}$)C(O)NR$^4$R$^{11}$, (CR$^7$R$^8$)NR$^4$SO$_2$R$^4$, and C(=NOR$^4$)R$^4$; and R$^2$ is not C(O)NH$_2$, p-CH$_2$OR$^4$, p-CH(OH)CH$_2$OH, p-CH$_2$CH$_2$OH, or p-CH$_2$CH$_2$CH$_2$OH; and b) the compound is not selected from

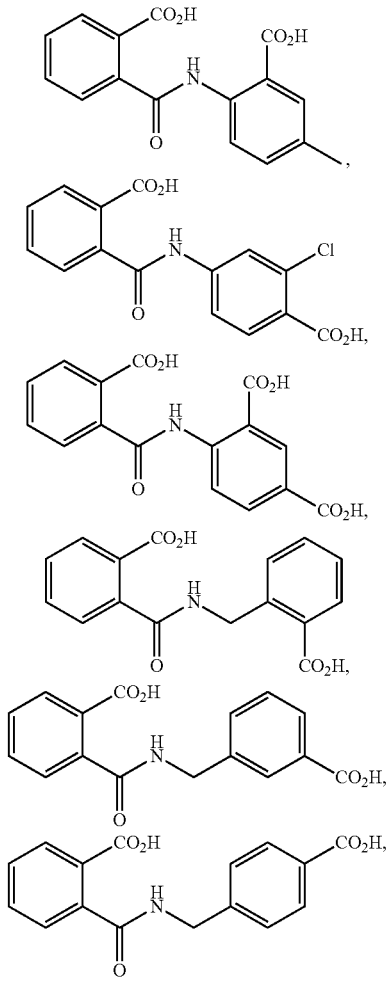

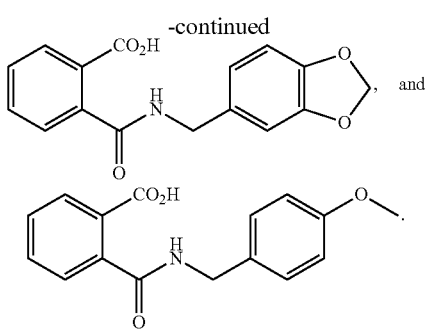

In another aspect, provided herein is a method of ameliorating arthritis or joint injury in a mammal, the method comprising administering to a joint of the mammal a composition comprising a therapeutically effective amount of a compound of Formula Ia, or a pharmaceutically acceptable salt, solvate, polymorph, prodrug, ester, metabolite, N-oxide, stereoisomer, or isomer thereof:

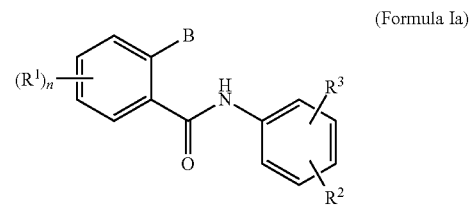

(Formula Ia)

wherein
each R$^1$ is independently halo, optionally substituted alkyl, optionally substituted alkoxy, optionally substituted aryloxy, CN, NO$_2$, SR$^4$, S(O)R$^4$, SO$_2$R$^4$, NR$^4$R$^{11}$, CO$_2$H, or CO$_2$R$^4$;

n is 0, 1, 2, 3, or 4;

B is CO$_2$R$^4$;

R$^2$ is halo, C(O)R$^4$, CO$_2$R$^4$, C(O)NR$^4$R$^{11}$, alkyl, optionally substituted alkoxy, haloalkyl, SO$_2$R$^4$, (CR$^7$R$^8$)OR$^4$, (CR$^7$R$^8$)NR$^4$R$^{11}$, (CR$^7$R$^8$)(CR$^9$R$^{10}$)OR$^4$, X(CR$^7$R$^8$)(CR$^9$R$^{10}$)OR$^4$, X(CR$^7$R$^8$)(CR$^9$R$^{10}$)NR$^4$R$^{11}$, (CR$^7$R$^8$)C(O)R$^4$, (CR$^7$R$^8$)C(O)OR$^4$, (CR$^7$R$^8$)C(O)NR$^4$R$^{11}$, X(CR$^7$R$^8$)C(O)R$^4$, X(CR$^7$R$^8$)C(O)OR$^4$, X(CR$^7$R$^8$)C(O)NR$^4$R$^{11}$, X(CR$^7$R$^8$)(CR$^9$R$^{10}$)C(O)R$^4$, X(CR$^7$R$^8$)(CR$^9$R$^{10}$)C(O)OR$^4$, X(CR$^7$R$^8$)(CR$^9$R$^{10}$)C(O)NR$^4$R$^{11}$, (CR$^7$R$^8$)NR$^4$SO$_2$R$^4$, or C(=NOR$^4$)R$^4$;

each R$^3$ is independently selected from CN, halo, C(O)R$^4$, CO$_2$H, CO$_2$R$^4$, C(O)NR$^4$R$^{11}$, alkyl, optionally substituted alkoxy, SO$_2$R$^4$, (CR$^7$R$^8$)OR$^4$, (CR$^7$R$^8$)NR$^4$R$^{11}$, (CR$^7$R$^8$)(CR$^9$R$^{10}$)OR$^4$, X(CR$^7$R$^8$)(CR$^9$R$^{10}$)OR$^4$, X(CR$^7$R$^8$)(CR$^9$R$^{10}$)NR$^4$R$^{11}$, (CR$^7$R$^8$)C(O)R$^4$, (CR$^7$R$^8$)C(O)OR$^4$, (CR$^7$R$^8$)C(O)NR$^4$R$^{11}$, X(CR$^7$R$^8$)C(O)R$^4$, X(CR$^7$R$^8$)C(O)OR$^4$, X(CR$^7$R$^8$)C(O)NR$^4$R$^{11}$, X(CR$^7$R$^8$)(CR$^9$R$^{10}$)C(O)R$^4$, X(CR$^7$R$^8$)(CR$^9$R$^{10}$)C(O)OR$^4$, X(CR$^7$R$^8$)(CR$^9$R$^{10}$)C(O)NR$^4$R$^{11}$, (CR$^7$R$^8$)NR$^4$SO$_2$R$^4$, and C(=NOR$^4$)R$^4$;

or R$^3$ together with an adjacent R$^3$ or with R$^2$ form a ring;

X is O or CR$^5$R$^6$;

each R$^4$ is independently selected from H and optionally substituted alkyl;

each R$^5$, R$^6$, R$^7$, R$^8$, R$^9$, and R$^{10}$ is independently selected from H, halo, optionally substituted alkyl, OH, NR$^4$R$^{11}$, and optionally substituted alkoxy; and R$^{11}$ is H, optionally substituted alkyl, C(O)R$^4$, C(O)OR$^4$, C(O)NR$^4$R$^4$, or SO$_2$R$^4$;

provided that the compound is not selected from

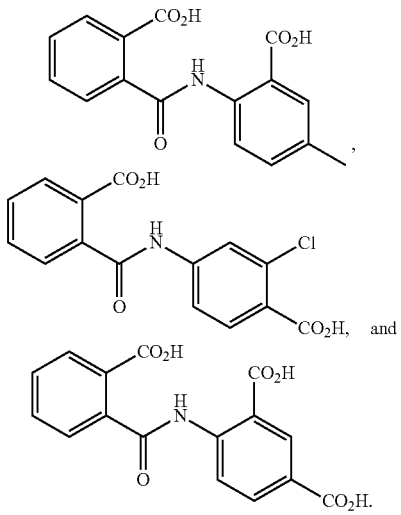

In another aspect, provided herein is a method of ameliorating arthritis or joint injury in a mammal, the method comprising administering to a joint of the mammal a composition comprising a therapeutically effective amount of a compound of Formula Ib, or a pharmaceutically acceptable salt, solvate, polymorph, prodrug, ester, metabolite, N-oxide, stereoisomer, or isomer thereof:

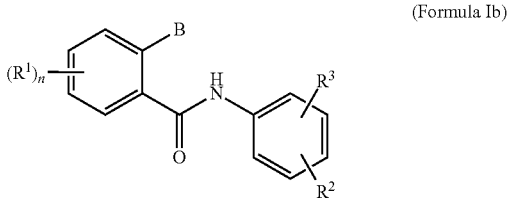

(Formula Ib)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
n is 0, 1, 2, 3, or 4;
B is $CO_2R^4$;
$R^2$ is $C(O)NR^4R^{11}$, $(CR^7R^8)OR^4$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
$R^3$ is H;
X is O or $CR^5R^6$;
each $R^4$ is independently selected from H and optionally substituted alkyl;
each $R^5$, $R^6$, $R^7$, $R^8$, $R^9$, and $R^{10}$ is independently selected from H, halo, optionally substituted alkyl, OH, $NR^4R^{11}$, and optionally substituted alkoxy; and
$R^{11}$ is H, optionally substituted alkyl, $C(O)R^4$, $C(O)OR^4$, $C(O)NR^4R^4$, or $SO_2R^4$;
provided that if n is 0, then $R^2$ is not $C(O)NH_2$, p-$CH_2OR^4$, p-$CH(OH)CH_2OH$, p-$CH_2CH_2OH$, or p-$CH_2CH_2CH_2OH$.

In another aspect, provided herein is a method of ameliorating arthritis or joint injury in a mammal, the method comprising administering to a joint of the mammal a composition comprising a therapeutically effective amount of a compound of Formula Ic, or a pharmaceutically acceptable salt, solvate, polymorph, prodrug, ester, metabolite, N-oxide, stereoisomer, or isomer thereof:

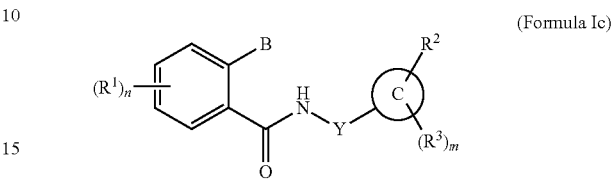

(Formula Ic)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
n is 0, 1, 2, 3, or 4;
m is 1, 2, 3, or 4;
B is $CO_2R^4$;
Y is —$(CR^5R^6)$—;
C is aryl or heteroaryl;
X is O or $CR^5R^6$;
$R^2$ is halo, $C(O)R^4$, $CO_2R^4$, $C(O)NR^4R^{11}$, alkyl, optionally substituted alkoxy, haloalkyl, $SO_2R^4$, $SO_2NH_2$, $SO_3H$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
each $R^3$ is independently selected from H, CN, halo, $C(O)R^4$, $CO_2H$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$;
or $R^3$ together with an adjacent $R^3$ or with $R^2$ form a ring;
each $R^4$ is independently selected from H and optionally substituted alkyl;
each $R^5$, $R^6$, $R^7$, $R^8$, $R^9$, and $R^{10}$ is independently selected from H, halo, optionally substituted alkyl, OH, $CO_2R^4$, $NR^4R^{11}$, and optionally substituted alkoxy; and
$R^{11}$ is H, optionally substituted alkyl, $C(O)R^4$, $C(O)OR^4$, $C(O)NR^4R^4$, or $SO_2R^4$;
provided that the compound is not selected from

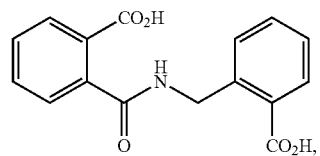

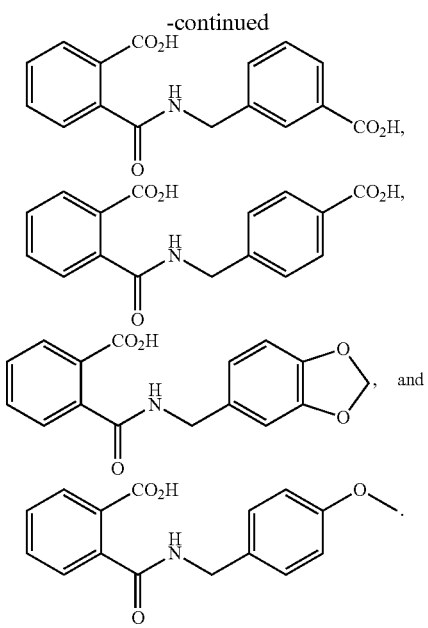

In another aspect, provided herein is a method of inducing differentiation of mesenchymal stem cells into chondrocytes, the method comprising contacting mesenchymal stem cells with a sufficient amount of a compound of Formula I, or a pharmaceutically acceptable salt, solvate, polymorph, prodrug, ester, metabolite, N-oxide, stereoisomer, or isomer thereof:

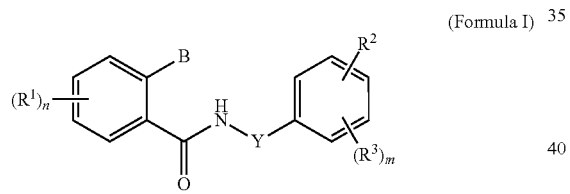

(Formula I)

wherein
  each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
  n is 0, 1, 2, 3, or 4;
  m is 1, 2, 3, or 4;
  B is $CO_2R^4$, $CH_2CO_2H$, $CH_2CO_2R^3$, or optionally substituted phenyl;
  Y is a bond, —$(CR^5R^6)$—, —$(CR^7R^8)(CR^9R^{10})$—, or —$(CR^7R^8)(CR^9R^{10})X$—;
  X is O or $CR^5R^6$;
  $R^2$ is halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
  each $R^3$ is independently selected from H, CN, halo, $C(O)R^4$, $CO_2H$, $CO_2R^4$, $C(O)NR^4R^{11}$, alkyl, optionally substituted alkoxy, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$;
  or $R^3$ together with an adjacent $R^3$ or with $R^2$ form a ring;
  each $R^4$ is independently selected from H and optionally substituted alkyl;
  each $R^5, R^6, R^7, R^8, R^9$, and $R^{10}$ is independently selected from H, halo, optionally substituted alkyl, OH, $CO_2R^4$, $NR^4R^{11}$, and optionally substituted alkoxy; and
  $R^{11}$ is H, optionally substituted alkyl, $C(O)R^4$, $C(O)OR^4$, $C(O)NR^4R^4$, or $SO_2R^4$; provided that
  a) if Y is a bond and m is 0, then $R^2$ is selected from $C(O)NR^4R^{11}$, $(CR^7R^8)OR^4$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$; and
  $R^2$ is not $C(O)NH_2$, p-$CH_2OR^4$, p-$CH(OH)CH_2OH$, p-$CH_2CH_2OH$, or p-$CH_2CH_2CH_2OH$; and
  b) the compound is not selected from

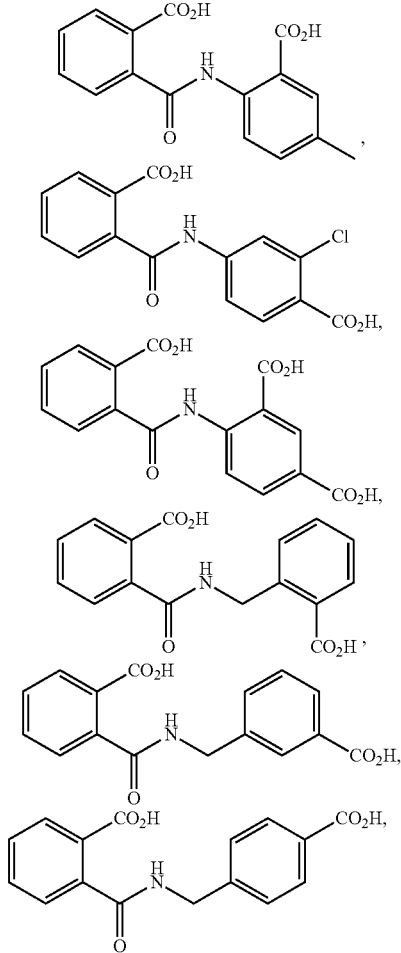

-continued

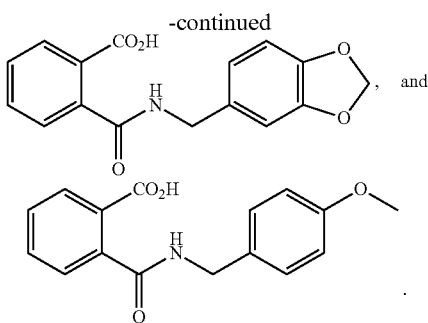

In another aspect, provided herein is a method of inducing differentiation of mesenchymal stem cells into chondrocytes, the method comprising contacting mesenchymal stem cells with a sufficient amount of a compound of Formula Ia, or a pharmaceutically acceptable salt, solvate, polymorph, prodrug, ester, metabolite, N-oxide, stereoisomer, or isomer thereof:

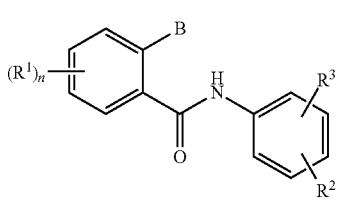

(Formula Ia)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
n is 0, 1, 2, 3, or 4;
B is $CO_2R^4$;
$R^2$ is halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
each $R^3$ is independently selected from CN, halo, $C(O)R^4$, $CO_2H$, $CO_2R^4$, $C(O)NR^4R^{11}$, alkyl, optionally substituted alkoxy, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$;
or $R^3$ together with an adjacent $R^3$ or with $R^2$ form a ring;
X is O or $CR^5R^6$;
each $R^4$ is independently selected from H and optionally substituted alkyl;
each $R^5$, $R^6$, $R^7$, $R^8$, $R^9$, and $R^{10}$ is independently selected from H, halo, optionally substituted alkyl, OH, $NR^4R^{11}$, and optionally substituted alkoxy; and
$R^{11}$ is H, optionally substituted alkyl, $C(O)R^4$, $C(O)OR^4$, $C(O)NR^4R^4$, or $SO_2R^4$;

provided that the compound is not selected from

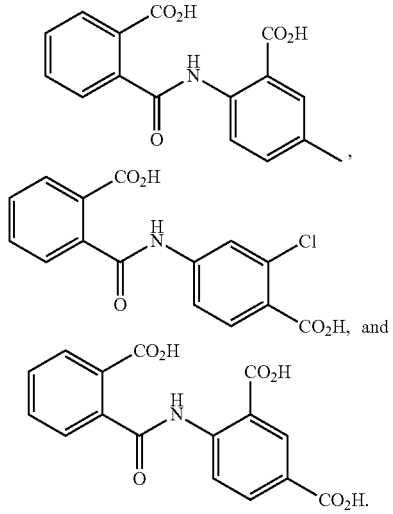

In another aspect, provided herein is a method of inducing differentiation of mesenchymal stem cells into chondrocytes, the method comprising contacting mesenchymal stem cells with a sufficient amount of a compound of Formula Ib, or a pharmaceutically acceptable salt, solvate, polymorph, prodrug, ester, metabolite, N-oxide, stereoisomer, or isomer thereof:

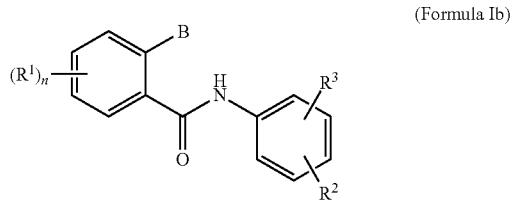

(Formula Ib)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
n is 0, 1, 2, 3, or 4;
B is $CO_2R^4$;
$R^2$ is $C(O)NR^4R^{11}$, $(CR^7R^8)OR^4$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
$R^3$ is H;
X is O or $CR^5R^6$;
each $R^4$ is independently selected from H and optionally substituted alkyl;
each $R^5$, $R^6$, $R^7$, $R^8$, $R^9$, and $R^{10}$ is independently selected from H, halo, optionally substituted alkyl, OH, $NR^4R^{11}$, and optionally substituted alkoxy; and
$R^{11}$ is H, optionally substituted alkyl, $C(O)R^4$, $C(O)OR^4$, $C(O)NR^4R^4$, or $SO_2R^4$;
provided that if n is 4 and $R^1$ is H, then $R^2$ is not $C(O)NH_2$, p-$CH_2OR^4$, p-$CH(OH)CH_2OH$, p-$CH_2CH_2OH$, or p-$CH_2CH_2CH_2OH$.

In another aspect, provided herein is a method of inducing differentiation of mesenchymal stem cells into chondrocytes, the method comprising contacting mesenchymal stem cells with a sufficient amount of a compound of Formula Ic, or a pharmaceutically acceptable salt, solvate, polymorph, prodrug, ester, metabolite, N-oxide, stereoisomer, or isomer thereof:

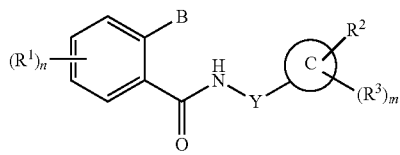

(Formula Ic)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NR^4R^{11}$, $CO_2H$, or $CO_2R^4$;
n is 0, 1, 2, 3, or 4;
m is 1, 2, 3, or 4;
B is $CO_2R^4$;
Y is —$(CR^5R^6)$—;
C is aryl or heteroaryl;
X is O or $CR^5R^6$;
$R^2$ is halo, $C(O)R^4$, $CO_2R^4$, $C(O)NR^4R^{11}$, alkyl, optionally substituted alkoxy, haloalkyl, $SO_2R^4$, $SO_2NH_2$, $SO_3H$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$;
each $R^3$ is independently selected from H, CN, halo, $C(O)R^4$, $CO_2H$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$
or $R^3$ together with an adjacent $R^3$ or with $R^2$ form a ring;
each $R^4$ is independently selected from H and optionally substituted alkyl;
each $R^5$, $R^6$, $R^7$, $R^8$, $R^9$, and $R^{10}$ is independently selected from H, halo, optionally substituted alkyl, OH, $CO_2R^4$, $NR^4R^{11}$, and optionally substituted alkoxy; and
$R^{11}$ is H, optionally substituted alkyl, $C(O)R^4$, $C(O)OR^4$, $C(O)NR^4R^4$, or $SO_2R^4$; provided that the compound is not selected from

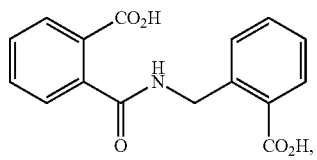

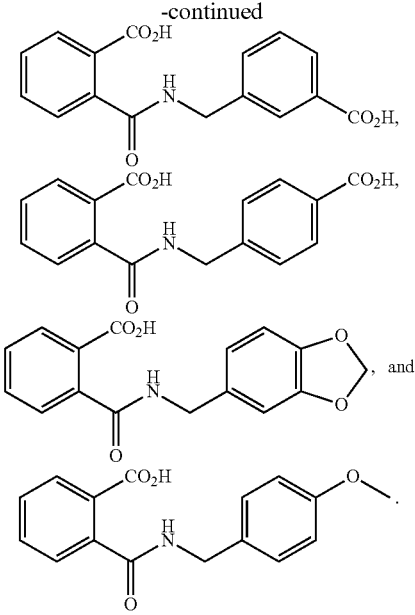

In some embodiments described above or below of a compound of Formula I or Ia:
$R^2$ is halo, $C(O)R^4$, alkyl, optionally substituted alkoxy, haloalkyl, $(CR^7R^8)OR^4$, $(CR^7R^8)(CR^9R^{10})OR^4$, $X(CR^7R^8)(CR^9R^{10})OR^4$, $X(CR^7R^8)C(O)OR^4$, or $X(CR^7R^8)C(O)NR^4R^{11}$; and
each $R^3$ is independently selected from CN, halo, $C(O)R^4$, $CO_2H$, $C(O)NR^4R^{11}$, alkyl, or optionally substituted alkoxy;
or $R^3$ together with an adjacent $R^3$ or with $R^2$ form a ring.

In certain embodiments described above or below of a compound of Formula I or Ia:
$R^2$ is F, Cl, $C(O)CH_3$, $CH_3$, $CF_3$, $OCH_3$, OEt, OPr, $OCF_3$, $OCHF_2$, $(CR^7R^8)OR^4$, $(CR^7R^8)(CR^9R^{10})OR^4$, $X(CR^7R^8)(CR^9R^{10})OR^4$, $X(CR^7R^8)C(O)OR^4$, or $X(CR^7R^8)C(O)NR^4R^{11}$; and
each $R^3$ is independently selected from CN, F, Cl, $C(O)CH_3$, $CO_2H$, $C(O)NH_2$, $CH_3$, $OCF_3$, or $OCH_3$;
or $R^3$ together with an adjacent $R^3$ or with $R^2$ form a ring.

In certain embodiments, $R^3$ is independently selected from CN, F, Cl, $C(O)CH_3$, or $CO_2H$. In certain embodiments, $R^3$ is CN or $CO_2H$. In certain embodiments, $R^2$ is F, Cl, $C(O)CH_3$, $CH_3$, $CF_3$, $OCH_3$, OEt, OPr, $OCF_3$, or $CH_2CH_2CH_2OH$. In certain embodiments, $R^2$ is $CH_2CH_2CH_2OH$. In certain embodiments, $R^3$ together with an adjacent $R^3$ or with $R^2$ form a ring.

In certain embodiments, $R^2$ is $(CR^7R^8)OR^4$, $(CR^7R^8)(CR^9R^{10})OR^4$, $X(CR^7R^8)(CR^9R^{10})OR^4$, $X(CR^7R^8)C(O)OR^4$, or $X(CR^7R^8)C(O)NR^4R^{11}$; and each $R^3$ is independently selected from CN, F, Cl, $C(O)CH_3$, $CO_2H$, $C(O)NH_2$, $CH_3$, $OCF_3$, or $OCH_3$. In certain embodiments, $R^2$ is F, Cl, $C(O)CH_3$, $CH_3$, $CF_3$, $OCH_3$, OEt, OPr, $OCF_3$, or $CH_2CH_2CH_2OH$; and $R^3$ is independently selected from CN, F, Cl, $C(O)CH_3$, or $CO_2H$. In certain embodiments, $R^2$ is F, Cl, $C(O)CH_3$, $CH_3$, $CF_3$, $OCH_3$, OEt, OPr, $OCF_3$, or $CH_2CH_2CH_2OH$; and $R^3$ is independently selected from CN or $CO_2H$. In certain embodiments, $R^2$ is $CH_2CH_2CH_2OH$ and $R^3$ is independently selected from CN, F, Cl, $C(O)CH_3$, or $CO_2H$.

In some embodiments described above or below of a compound of Formula I:

$R^2$ is halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$; and each $R^3$ is independently selected from CN, halo, $C(O)R^4$, $C(O)NR^4R^{11}$, alkyl, optionally substituted alkoxy, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$.

In some embodiments described above or below of a compound of Formula Ia:

$R^2$ is halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$; and each $R^3$ is independently selected from CN, halo, $C(O)R^4$, $C(O)NR^4R^{11}$, alkyl, optionally substituted alkoxy, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$.

In some embodiments described above or below of a compound of Formula Ib:

$R^2$ is $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)NR^4R^{11}$, $X(CR^7R^8)C(O)R^4$, $X(CR^7R^8)C(O)NR^4R^{11}$, $(CR^7R^8)NR^4SO_2R^4$, or $C(=NOR^4)R^4$; and $R^3$ is H.

In certain embodiments, $R^2$ is $(CR^7R^8)(CR^9R^{10})OR^4$, $X(CR^7R^8)(CR^9R^{10})OR^4$, $X(CR^7R^8)(CR^9R^{10})NR^4R^{11}$, or $(CR^7R^8)NR^4SO_2R^4$. In certain embodiments, $R^2$ is $CH_2CH_2OH$, $CH_2CH_2OCH_3$, $CH_2CHCH_3OH$, $CHCH_3CH_2OH$, $CH_2CH_2CH_2OH$, $CH_2CH_2CH_2NH_2$, $CH_2CH_2CHCH_3OH$, $C(CH_3)_2CH_2CH_2OH$, $CH_2CH_2C(CH_3)_2OH$, $OCH_2CH_2OH$, $OCH_2CH_2OCH_3$, or $OCH_2CH_2NH_2$. In certain embodiments, $R^2$ is $(CR^7R^8)C(O)R^4$, $(CR^7R^8)C(O)NR^4R^{11}$, $X(CR^7R^8)C(O)R^4$, or $X(CR^7R^8)C(O)NR^4R^{11}$. In certain embodiments, $R^2$ is $CH_2C(O)CH_3$, $CH_2C(O)NH_2$, $CH_2CH_2C(O)CH_3$, or $CH_2CH_2C(O)NH_2$.

In some embodiments described above or below of a compound of Formula Ic, C is aryl. In certain embodiments, C is phenyl. In certain embodiments, C is naphthyl.

In some embodiments described above or below of a compound of Formula Ic, C is heteroaryl. In certain embodiments, C is pyridinyl, pyrimidinyl, pyridazinyl, or pyrazinyl. In certain embodiments, C is pyridinyl. In certain embodiments, C is pyrimidinyl. In certain embodiments, C is pyridazinyl. In certain embodiments, C is a 5-membered heteroaryl ring. In certain embodiments, C is thiophene, benzofuran, pyrrole, thiazole, imidazole, oxazole, pyrazole, or triazole.

In some embodiments described above or below of a compound of Formula Ic:

$R^2$ is halo, $C(O)R^4$, $CO_2R^4$, $C(O)NR^4R^{11}$, alkyl, optionally substituted alkoxy, haloalkyl, $SO_2R^4$, $SO_2NH_2$, $SO_3H$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, or $C(=NOR^4)R^4$; and each $R^3$ is independently selected from H, CN, halo, $C(O)R^4$, $CO_2R^4$, $C(O)NR^4R^{11}$, alkyl, optionally substituted alkoxy, haloalkyl, $SO_2R^4$, $(CR^7R^8)OR^4$, $(CR^7R^8)NR^4R^{11}$, $(CR^7R^8)(CR^9R^{10})OR^4$, $X(CR^7R^8)(CR^9R^{10})OR^4$, $X(CR^7R^8)(CR^9R^{10})NR^4R^{11}$, $(CR^7R^8)C(O)R^4$, $(CR^7R^8)C(O)OR^4$, $(CR^7R^8)C(O)NR^4R^{11}$, $X(CR^7R^8)C(O)R^4$, $X(CR^7R^8)C(O)OR^4$, $X(CR^7R^8)C(O)NR^4R^{11}$, $X(CR^7R^8)(CR^9R^{10})C(O)R^4$, $X(CR^7R^8)(CR^9R^{10})C(O)OR^4$, $X(CR^7R^8)(CR^9R^{10})C(O)NR^4R^{11}$, $(CR^7R^8)NR^4SO_2R^4$, and $C(=NOR^4)R^4$;

provided that if n=0 and C is phenyl, $R^2$ is not $CO_2H$ or p-$OCH_3$.

In some embodiments described above or below of a compound of Formula Ic:

$R^2$ is halo, $C(O)R^4$, $CO_2R^4$, $C(O)NR^4R^{11}$, alkyl, optionally substituted alkoxy, haloalkyl, $SO_2NH_2$, $SO_3H$, $(CR^7R^8)C(O)R^4$, $(CR^7R^8)C(O)OR^4$, $(CR^7R^8)C(O)NR^4R^{11}$, $X(CR^7R^8)C(O)OR^4$, or $X(CR^7R^8)C(O)NR^4R^{11}$; and each $R^3$ is independently selected from H, CN, halo, $CO_2H$, or haloalkyl.

In certain embodiments described above or below of a compound of Formula Ic:

$R^2$ is Cl, F, $C(O)CH_3$, $CO_2H$, $C(O)NR^4R^{11}$, $CH_3$, optionally substituted alkoxy, $CF_3$, $SO_2NH_2$, $SO_3H$, $(CR^7R^8)C(O)R^4$, $(CR^7R^8)C(O)OR^4$, $(CR^7R^8)C(O)NR^4R^{11}$, $X(CR^7R^8)C(O)OR^4$, or $X(CR^7R^8)C(O)NR^4R^{11}$; and each $R^3$ is independently selected from H, CN, Cl, F, $CO_2H$, or $CF_3$.

In certain embodiments, $R^2$ is Cl, F, $C(O)CH_3$, $CO_2H$, $CH_3$, $OCH_3$, $CF_3$; and each $R^3$ is independently selected from H, CN, or $CO_2H$. In certain embodiments, $R^2$ is $CH_2C(O)NH_2$, $CH_2C(O)CH_3$, $CH_2C(O)OH$, $CH_2CH_2C(O)OH$, or $CH_2CH_2C(O)NH_2$. In certain embodiments, $R^2$ is $CO_2H$. In certain embodiments, $R^2$ is $CO_2H$ and each $R^3$ is independently selected from H, CN, Cl, F, or $CF_3$.

In certain embodiments described above or below of a compound of Formula Ic:

$R^2$ is Cl, F, $C(O)CH_3$, $CO_2H$, $C(O)NR^4R^{11}$, $CH_3$, optionally substituted alkoxy, $CF_3$, $SO_2NH_2$, $SO_3H$, $(CR^7R^8)C(O)R^4$, $(CR^7R^8)C(O)OR^4$, $(CR^7R^8)C(O)NR^4R^{11}$, $X(CR^7R^8)C(O)OR^4$, or $X(CR^7R^8)C(O)NR^4R^{11}$; and each $R^3$ is independently selected from H, CN, or $CO_2H$. In certain embodiments, $R^2$ is $CH_2C(O)NH_2$, $CH_2C(O)CH_3$, $CH_2C(O)OH$, $CH_2CH_2C(O)OH$, or $CH_2CH_2C(O)NH_2$; and each $R^3$ is independently selected from H, CN, or $CO_2H$.

In one aspect, provided herein is a method of ameliorating arthritis or joint injury in a mammal, the method comprising administering to a joint of the mammal a composition comprising a therapeutically effective amount of a compound of Formula II, or a pharmaceutically acceptable salt, solvate, polymorph, prodrug, ester, metabolite, N-oxide, stereoisomer, or isomer thereof:

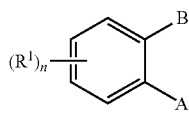

(Formula II)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
n is 0, 1, 2, 3, or 4;
B is $NHC(O)R^2$, $NR^3C(O)R^2$, $NHC(O)NH_2$, $NHC(O)NHR^2$, $NHC(O)NR^2R^4$, $NR^3C(O)NH_2$, $NR^3C(O)NHR^2$, $NR^3C(O)NR^2R^4$, $NHC(O)OR^2$, $NR^3C(O)OR^2$, $NHSO_2R^3$, $NR^3SO_2R^3$, $NHSO_2R^4$, $NR^3SO_2R^4$, $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$;
each $R^2$ and $R^4$ is independently optionally substituted phenyl, optionally substituted heteroaryl, optionally substituted heterocyclyl, optionally substituted aralkyl, or optionally substituted alkyl;
$R^3$ is optionally substituted alkyl or optionally substituted aralkyl;
$R^5$ is H, optionally substituted alkyl, $C(O)R^4$, $C(O)OR^4$, $C(O)NR^4R^4$, or $SO_2R^4$;
A is $CO_2H$, $CO_2R^3$, $C(O)NH_2$, $C(O)NHR^2$, $C(O)NR^2R^4$, or $SO_2NR^aR^b$; and
each $R^a$ and $R^b$ is independently optionally substituted alkyl or together with the N to which they are attached make a ring;
provided that
a) if B is $NHC(O)R^2$ or $NR^3C(O)R^2$, then A is not $CO_2H$; and
b) the compound is not selected from

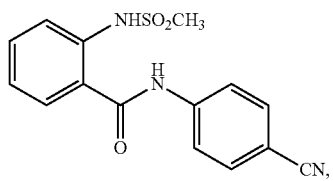

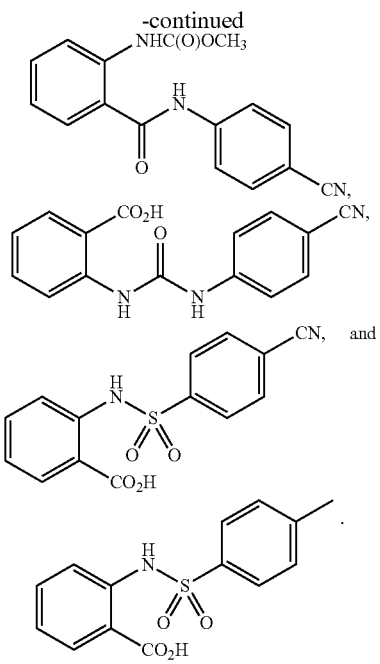

In another aspect, provided herein is a method of ameliorating arthritis or joint injury in a mammal, the method comprising administering to a joint of the mammal a composition comprising a therapeutically effective amount of a compound of Formula IIa, or a pharmaceutically acceptable salt, solvate, polymorph, prodrug, ester, metabolite, N-oxide, stereoisomer, or isomer thereof:

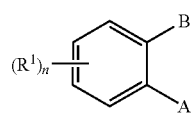

(Formula IIa)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
n is 0, 1, 2, 3, or 4;
B is $NHC(O)NH_2$, $NHC(O)NHR^2$, $NHC(O)NR^2R^4$, $NR^3C(O)NH_2$, $NR^3C(O)NHR^2$, or $NR^3C(O)NR^2R^4$;
each $R^2$ and $R^4$ is independently optionally substituted phenyl, optionally substituted heteroaryl, optionally substituted heterocyclyl, optionally substituted aralkyl, or optionally substituted alkyl;
$R^3$ is optionally substituted alkyl or optionally substituted aralkyl;
$R^5$ is H, optionally substituted alkyl, $C(O)R^4$, $C(O)OR^4$, $C(O)NR^4R^4$, or $SO_2R^4$; and
A is $CO_2H$ or $CO_2R^3$;
provided that the compound is not

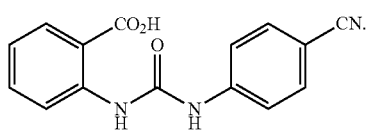 [SMILES: N#Cc1ccc(NC(=O)Nc2ccccc2C(=O)O)cc1]

In another aspect, provided herein is a method of ameliorating arthritis or joint injury in a mammal, the method comprising administering to a joint of the mammal a composition comprising a therapeutically effective amount of a compound of Formula IIb, or a pharmaceutically acceptable salt, solvate, polymorph, prodrug, ester, metabolite, N-oxide, stereoisomer, or isomer thereof:

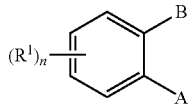

(Formula IIb)

wherein
- each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
- n is 0, 1, 2, 3, or 4;
- B is $NHC(O)R^2$ or $NR^3C(O)R^2$;
- $R^2$ is optionally substituted phenyl, optionally substituted heteroaryl, optionally substituted heterocyclyl, optionally substituted aralkyl, or optionally substituted alkyl;
- $R^3$ is optionally substituted alkyl or optionally substituted aralkyl;
- $R^5$ is H, optionally substituted alkyl, $C(O)R^4$, $C(O)OR^4$, $C(O)NR^4R^4$, or $SO_2R^4$;
- A is $SO_2NR^aR^b$; and
- each $R^a$ and $R^b$ is independently optionally substituted alkyl or together with the N to which they are attached make a ring.

In another aspect, provided herein is a method of ameliorating arthritis or joint injury in a mammal, the method comprising administering to a joint of the mammal a composition comprising a therapeutically effective amount of a compound of Formula IIc, or a pharmaceutically acceptable salt, solvate, polymorph, prodrug, ester, metabolite, N-oxide, stereoisomer, or isomer thereof:

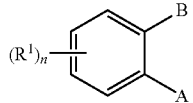

(Formula IIc)

wherein
- each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
- n is 0, 1, 2, 3, or 4;
- B is $NHSO_2R^3$, $NR^3SO_2R^3$, $NHSO_2R^4$, $NR^3SO_2R^4$, $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$;
- each $R^2$ and $R^4$ is independently optionally substituted phenyl, optionally substituted heteroaryl, optionally substituted heterocyclyl, optionally substituted aralkyl, or optionally substituted alkyl;
- each $R^3$ is independently optionally substituted alkyl or optionally substituted aralkyl;
- $R^5$ is H, optionally substituted alkyl, $C(O)R^4$, $C(O)OR^4$, $C(O)NR^4R^4$, or $SO_2R^4$; and
- A is $C(O)NHR^2$ or $C(O)NR^2R^4$;

provided that the compound is not

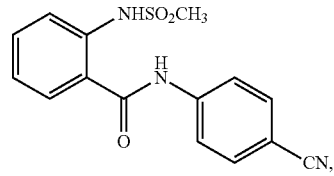

In another aspect provided herein is a method of inducing differentiation of mesenchymal stem cells into chondrocytes, the method comprising contacting mesenchymal stem cells with a sufficient amount of a compound of Formula II, or a pharmaceutically acceptable salt, solvate, polymorph, prodrug, ester, metabolite, N-oxide, stereoisomer, or isomer thereof:

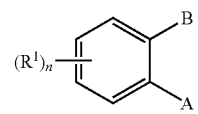

(Formula II)

wherein
- each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
- n is 0, 1, 2, 3, or 4;
- B is $NHC(O)R^2$, $NR^3C(O)R^2$, $NHC(O)NH_2$, $NHC(O)NHR^2$, $NHC(O)NR^2R^4$, $NR^3C(O)NH_2$, $NR^3C(O)NHR^2$, $NR^3C(O)NR^2R^4$, $NHC(O)OR^2$, $NR^3C(O)OR^2$, $NHSO_2R^3$, $NR^3SO_2R^3$, $NHSO_2R^4$, $NR^3SO_2R^4$, $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$;
- each $R^2$ and $R^4$ is independently optionally substituted phenyl, optionally substituted heteroaryl, optionally substituted heterocyclyl, optionally substituted aralkyl, or optionally substituted alkyl;
- $R^3$ is optionally substituted alkyl or optionally substituted aralkyl;
- $R^5$ is H, optionally substituted alkyl, $C(O)R^4$, $C(O)OR^4$, $C(O)NR^4R^4$, or $SO_2R^4$;
- A is $CO_2H$, $CO_2R^3$, $C(O)NH_2$, $C(O)NHR^2$, $C(O)NR^2R^4$, or $SO_2NR^aR^b$; and
- each $R^a$ and $R^b$ is independently optionally substituted alkyl or together with the N to which they are attached make a ring;

provided that
- a) if B is $NHC(O)R^2$ or $NR^3C(O)R^2$, then A is not $CO_2H$; and
- b) the compound is not selected from

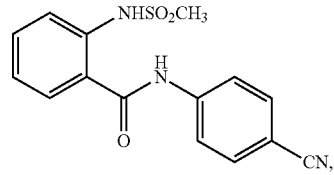

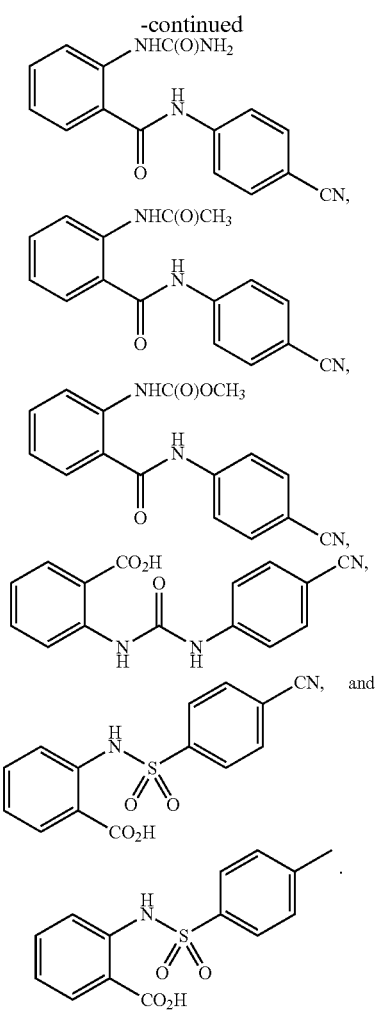

In another aspect, provided herein is a method of inducing differentiation of mesenchymal stem cells into chondrocytes, the method comprising contacting mesenchymal stem cells with a sufficient amount of a compound of Formula IIa, or a pharmaceutically acceptable salt, solvate, polymorph, prodrug, ester, metabolite, N-oxide, stereoisomer, or isomer thereof:

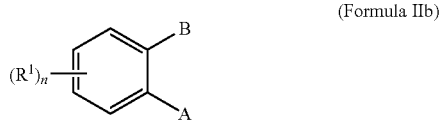

(Formula IIa)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
n is 0, 1, 2, 3, or 4;
B is $NHC(O)NH_2$, $NHC(O)NHR^2$, $NHC(O)NR^2R^4$, $NR^3C(O)NH_2$, $NR^3C(O)NHR^2$, or $NR^3C(O)NR^2R^4$;
each $R^2$ and $R^4$ is independently optionally substituted phenyl, optionally substituted heteroaryl, optionally substituted heterocyclyl, optionally substituted aralkyl, or optionally substituted alkyl;
$R^3$ is optionally substituted alkyl or optionally substituted aralkyl;
$R^5$ is H, optionally substituted alkyl, $C(O)R^4$, $C(O)OR^4$, $C(O)NR^4R^4$, or $SO_2R^4$; and
A is $CO_2H$ or $CO_2R^3$;
provided that the compound is not

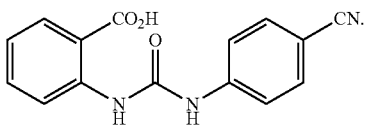 [SMILES: N#Cc1ccc(NC(=O)Nc2ccccc2C(=O)O)cc1]

In another aspect, provided herein is a method of inducing differentiation of mesenchymal stem cells into chondrocytes, the method comprising contacting mesenchymal stem cells with a sufficient amount of a compound of Formula IIb, or a pharmaceutically acceptable salt, solvate, polymorph, prodrug, ester, metabolite, N-oxide, stereoisomer, or isomer thereof:

(Formula IIb)

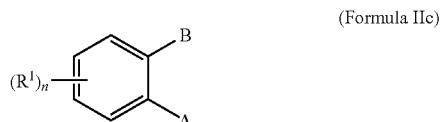

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
n is 0, 1, 2, 3, or 4;
B is $NHC(O)R^2$ or $NR^3C(O)R^2$;
$R^2$ is optionally substituted phenyl, optionally substituted heteroaryl, optionally substituted heterocyclyl, optionally substituted aralkyl, or optionally substituted alkyl;
$R^3$ is optionally substituted alkyl or optionally substituted aralkyl;
$R^5$ is H, optionally substituted alkyl, $C(O)R^4$, $C(O)OR^4$, $C(O)NR^4R^4$, or $SO_2R^4$;
A is $SO_2NR^aR^b$; and
each $R^a$ and $R^b$ is independently optionally substituted alkyl or together with the N to which they are attached make a ring.

In another aspect, provided herein is a method of inducing differentiation of mesenchymal stem cells into chondrocytes, the method comprising contacting mesenchymal stem cells with a sufficient amount of a compound of Formula IIc, or a pharmaceutically acceptable salt, solvate, polymorph, prodrug, ester, metabolite, N-oxide, stereoisomer, or isomer thereof:

(Formula IIc)

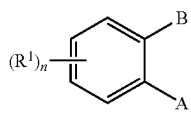

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

B is $NHSO_2R^3$, $NR^3SO_2R^3$, $NHSO_2R^4$, $NR^3SO_2R^4$, $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$;

each $R^2$ and $R^4$ is independently optionally substituted phenyl, optionally substituted heteroaryl, optionally substituted heterocyclyl, optionally substituted aralkyl, or optionally substituted alkyl;

each $R^3$ is independently optionally substituted alkyl or optionally substituted aralkyl;

$R^5$ is H, optionally substituted alkyl, $C(O)R^4$, $C(O)OR^4$, $C(O)NR^4R^4$, or $SO_2R^4$; and A is $C(O)NHR^2$ or $C(O)NR^2R^4$;

provided that the compound is not

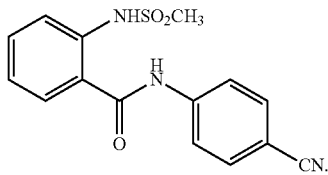

In some embodiments described above or below of a compound of Formula IIa, B is $NHC(O)NHR^2$, $NHC(O)NR^2R^4$, $NR^3C(O)NHR^2$, or $NR^3C(O)NR^2R^4$. In certain embodiments, B is $NHC(O)NHR^2$ or $NR^3C(O)NHR^2$. In certain embodiments, B is $NHC(O)NR^2R^4$ or $NR^3C(O)NR^2R^4$. In certain embodiments, B is $NHC(O)NHR^2$.

In some embodiments described above or below of a compound of Formula IIa, B is $NHC(O)NHR^2$, $NHC(O)NR^2R^4$, $NR^3C(O)NHR^2$, or $NR^3C(O)NR^2R^4$; and A is $CO_2H$. In certain embodiments, B is $NHC(O)NHR^2$ or $NR^3C(O)NHR^2$; and A is $CO_2H$. In certain embodiments, B is $NHC(O)NHR^2$ and A is $CO_2H$. In certain embodiments, B is $NHC(O)NHR^2$ and A is $CO_2H^3$, wherein $R^2$ is optionally substituted phenyl.

In some embodiments described above or below of a compound of Formula IIa, B is $NHC(O)NHR^2$, $NHC(O)NR^2R^4$, $NR^3C(O)NHR^2$, or $NR^3C(O)NR^2R^4$; and A is $CO_2R^3$. In certain embodiments, B is $NHC(O)NHR^2$ or $NR^3C(O)NHR^2$; and A is $CO_2R^3$. In certain embodiments, B is $NHC(O)NHR^2$ and A is $CO_2R^3$. In certain embodiments, B is $NHC(O)NHR^2$ and A is $CO_2R^3$, wherein $R^2$ is optionally substituted phenyl.

In some embodiments described above or below of a compound of Formula IIa, $R^2$ is optionally substituted phenyl. In certain embodiments, the phenyl of $R^2$ is bisubstituted. In certain embodiments, the phenyl of $R^2$ is monosubstituted. In certain embodiments, substitution on the phenyl of $R^2$ is independently selected from optionally substituted alkyl, optionally substituted alkoxy, optionally substituted aryloxy, halo, CN, $CO_2H$, amino, monoalkylamine, dialkylamine, monoarylamine, alkylarylamine, cycloalkyl, hydroxy, C(O)-(optionally substituted alkyl), $C(O)NH_2$, C(O)NH-(optionally substituted alkyl), alkylthioether, alkylsulfoxide, alkylsulfone, C(O)-(optionally substituted aryl), C(O)NH-(optionally substituted aryl), arylthioether, arylsulfoxide, or arylsulfone. In certain embodiments, substitution on the phenyl of $R^2$ is independently selected from F, Cl, $CO_2H$, CN, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of CN and a group selected from F, Cl, $CO_2H$, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of $CO_2H$ and a group selected from F, Cl, CN, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of $CH_2CH_2CH_2OH$ and a group selected from F, Cl, CN, $OCH_3$, $C(O)CH_3$, $CF_3$, $CH_3$, $CH_2OH$, $CH_2CH_2OH$, and $CO_2H$.

In some embodiments described above or below of a compound of Formula IIa, $R^2$ is optionally substituted naphthyl.

In some embodiments described above or below of a compound of Formula IIa, $R^2$ is optionally substituted heteroaryl. In certain embodiments, $R^2$ is optionally substituted pyridinyl, optionally substituted pyrimidinyl, optionally substituted pyridazinyl, or optionally substituted pyrazinyl. In certain embodiments, $R^2$ is an optionally substituted 5-membered heteroaryl ring. In certain embodiments, the 5-membered heteroaryl ring is thiophene, benzofuran, pyrrole, thiazole, imidazole, oxazole, pyrazole, or triazole. In certain embodiments, $R^2$ is an optionally substituted bicyclic heteroaryl. In certain embodiments, the bicyclic heteroaryl is benzimidazole, benzthiazole, benzoxazole, indazole, quinoline, or naphthyridine.

In some embodiments described above or below of a compound of Formula IIb, B is $NHC(O)R^2$. In certain embodiments, B is $NHC(O)R^2$ and $R^2$ is optionally substituted phenyl. In certain embodiments, B is $NHC(O)R^2$ and $R^2$ is optionally substituted heteroaryl.

In some embodiments described above or below of a compound of Formula IIb, B is $NR^3C(O)R^2$. In certain embodiments, $R^3$ is optionally substituted alkyl.

In some embodiments described above or below of a compound of Formula IIb, each $R^a$ and $R^b$ is independently optionally substituted alkyl. In certain embodiments, each $R^a$ and $R^b$ is independently alkyl. In some embodiments described above or below of a compound of Formula IIb, $R^a$ and $R^b$ together with the N to which they are attached make a ring. In certain embodiments, the ring is morpholinyl, thiomorpholinyl, piperidinyl, pyrrolidinyl, azetidinyl, aziridinyl, azepanyl, homopiperazinyl, or piperazinyl.

In some embodiments described above or below of a compound of Formula IIb, $R^2$ is optionally substituted phenyl. In certain embodiments, the phenyl of $R^2$ is bisubstituted. In certain embodiments, the phenyl of $R^2$ is monosubstituted. In certain embodiments, substitution on the phenyl of $R^2$ is independently selected from optionally substituted alkyl, optionally substituted alkoxy, optionally substituted aryloxy, halo, CN, $CO_2H$, amino, monoalkylamine, dialkylamine, monoarylamine, alkylarylamine, cycloalkyl, hydroxy, C(O)-(optionally substituted alkyl), $C(O)NH_2$, C(O)NH-(optionally substituted alkyl), alkylthioether, alkylsulfoxide, alkylsulfone, C(O)-(optionally substituted aryl), C(O)NH-(optionally substituted aryl), arylthioether, arylsulfoxide, or arylsulfone. In certain embodiments, substitution on the phenyl of $R^2$ is independently selected from F, Cl, $CO_2H$, CN, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of CN and a group selected from F, Cl, $CO_2H$, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of $CO_2H$ and a group selected from F, Cl, CN, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of $CH_2CH_2CH_2OH$ and a group selected from F, Cl, CN, $OCH_3$, $C(O)CH_3$, $CF_3$, $CH_3$, $CH_2OH$, $CH_2CH_2OH$, and $CO_2H$.

In some embodiments described above or below of a compound of Formula IIb, $R^2$ is optionally substituted naphthyl.

In some embodiments described above or below of a compound of Formula IIb, $R^2$ is optionally substituted heteroaryl. In certain embodiments, $R^2$ is optionally substituted pyridinyl, optionally substituted pyrimidinyl, optionally substituted pyridazinyl, or optionally substituted pyrazinyl. In certain embodiments, $R^2$ is an optionally substituted 5-membered heteroaryl ring. In certain embodiments, the 5-membered heteroaryl ring is thiophene, benzofuran, pyrrole, thiazole, imidazole, oxazole, pyrazole, or triazole. In certain embodiments, $R^2$ is an optionally substituted bicyclic heteroaryl. In certain embodiments, the bicyclic heteroaryl is benzimidazole, benzthiazole, benzoxazole, indazole, quinoline, or naphthyridine.

In some embodiments described above or below of a compound of Formula IIc, B is $NHSO_2R^3$, $NR^3SO_2R^3$, $NHSO_2R^4$, or $NR^3SO_2R^4$. In certain embodiments, B is $NHSO_2R^3$ or $NR^3SO_2R^3$. In certain embodiments, B is $NHSO_2R^3$. In certain embodiments, $R^3$ is optionally substituted alkyl. In certain embodiments, $R^3$ is alkyl. In certain embodiments, $R^3$ is $CH_3$. In certain embodiments, B is $NHSO_2R^4$ or $NR^3SO_2R^4$. In certain embodiments, $R^4$ is optionally substituted phenyl. In certain embodiments, $R^4$ is optionally substituted naphthyl. In certain embodiments, $R^4$ is optionally substituted heteroaryl. In certain embodiments, $R^4$ is optionally substituted heterocyclyl.

In some embodiments described above or below of a compound of Formula IIc, B is $NHSO_2R^3$, $NR^3SO_2R^3$, $NHSO_2R^4$, or $NR^3SO_2R^4$ and A is $C(O)NHR^2$. In certain embodiments, B is $NHSO_2R^3$ or $NR^3SO_2R^3$ and A is $C(O)NHR^2$. In certain embodiments, B is $NHSO_2R^3$ and A is $C(O)NHR^2$. In certain embodiments, B is $NHSO_2R^3$ and A is $C(O)NHR^2$, wherein $R^3$ is optionally substituted alkyl. In certain embodiments, B is $NHSO_2R^3$ and A is $C(O)NHR^2$, wherein $R^3$ is optionally substituted alkyl and $R^2$ is optionally substituted phenyl. In certain embodiments, B is $NHSO_2R^3$ and A is $C(O)NHR^2$, wherein $R^3$ is optionally substituted alkyl and $R^2$ is optionally substituted heteroaryl.

In some embodiments described above or below of a compound of Formula IIc, B is $NHSO_2R^3$, $NR^3SO_2R^3$, $NHSO_2R^4$, or $NR^3SO_2R^4$ and A is $C(O)NR^2R^4$. In certain embodiments, B is $NHSO_2R^3$ or $NR^3SO_2R^3$ and A is $C(O)NR^2R^4$. In certain embodiments, B is $NHSO_2R^3$ and A is $C(O)NR^2R^4$. In certain embodiments, B is $NHSO_2R^3$ and A is $C(O)NR^2R^4$, wherein $R^3$ is optionally substituted alkyl. In certain embodiments, B is $NHSO_2R^3$ and A is $C(O)NR^2R^4$, wherein $R^3$ is optionally substituted alkyl and $R^2$ is optionally substituted phenyl. In certain embodiments, B is $NHSO_2R^3$ and A is $C(O)NR^2R^4$, wherein $R^3$ is optionally substituted alkyl and $R^2$ is optionally substituted heteroaryl.

In some embodiments described above or below of a compound of Formula IIc, B is $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$. In certain embodiments, B is $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$ and A is $C(O)NHR^2$. In certain embodiments, B is $NHSO_2NH_2$, $NHSO_2NHR^2$, $NHSO_2NR^2R^4$, $NR^3SO_2NH_2$, $NR^3SO_2NHR^2$, or $NR^3SO_2NR^2R^4$ and A is $C(O)NR^2R^4$.

In some embodiments described above or below of a compound of Formula IIc, A is $C(O)NHR^2$. In some embodiments described above or below of a compound of Formula IIc, A is $C(O)NR^2R^4$. In certain embodiments, $R^2$ is optionally substituted phenyl. In certain embodiments, the phenyl of $R^2$ is bisubstituted. In certain embodiments, the phenyl of $R^2$ is monosubstituted. In certain embodiments, substitution on the phenyl of $R^2$ is independently selected from optionally substituted alkyl, optionally substituted alkoxy, optionally substituted aryloxy, halo, CN, $CO_2H$, amino, monoalkylamine, dialkylamine, monoarylamine, alkylarylamine, cycloalkyl, hydroxy, C(O)-(optionally substituted alkyl), $C(O)NH_2$, C(O)NH-(optionally substituted alkyl), alkylthioether, alkylsulfoxide, alkylsulfone, C(O)-(optionally substituted aryl), C(O)NH-(optionally substituted aryl), arylthioether, arylsulfoxide, or arylsulfone. In certain embodiments, substitution on the phenyl of $R^2$ is independently selected from F, Cl, $CO_2H$, CN, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of CN and a group selected from F, Cl, $CO_2H$, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of $CO_2H$ and a group selected from F, Cl, CN, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of $CH_2CH_2CH_2OH$ and a group selected from F, Cl, CN, $OCH_3$, $C(O)CH_3$, $CF_3$, $CH_3$, $CH_2OH$, $CH_2CH_2OH$, and $CO_2H$. In certain embodiments, $R^2$ is optionally substituted naphthyl.

In some embodiments described above or below of a compound of Formula IIc, $R^2$ is optionally substituted heteroaryl. In certain embodiments, $R^2$ is optionally substituted pyridinyl, optionally substituted pyrimidinyl, optionally substituted pyridazinyl, or optionally substituted pyrazinyl. In certain embodiments, $R^2$ is an optionally substituted 5-membered heteroaryl ring. In certain embodiments, the 5-membered heteroaryl ring is thiophene, benzofuran, pyrrole, thiazole, imidazole, oxazole, pyrazole, or triazole. In certain embodiments, $R^2$ is an optionally substituted bicyclic heteroaryl. In certain embodiments, the bicyclic heteroaryl is benzimidazole, benzthiazole, benzoxazole, indazole, quinoline, or naphthyridine.

In another aspect, provided herein is a method of ameliorating arthritis or joint injury in a mammal, the method comprising administering to a joint of the mammal a composition comprising a therapeutically effective amount of a compound of Formula III, or a pharmaceutically acceptable salt, solvate, polymorph, prodrug, ester, metabolite, N-oxide, stereoisomer, or isomer thereof:

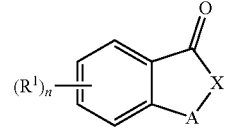

(Formula III)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
n is 0, 1, 2, 3, or 4;
X is O, NH, or $NR^6$;
A is C(O), $CH_2$, or $CH-CR^3R^4-C(O)R^2$;
$R^2$ is optionally substituted aryl or optionally substituted heteroaryl;
each $R^3$ and $R^4$ is independently H or optionally substituted alkyl;

$R^5$ is H, optionally substituted alkyl, $C(O)R^4$, $C(O)OR^4$, $C(O)NR^4R^4$, or $SO_2R^4$; and $R^6$ is optionally substituted phenyl;

provided that a) if A is CH—$CR^3R^4$—$C(O)R^2$, then X is O or NH;

b) if n is 0, A is $CHCH_2C(O)R^2$ and X is O, then $R^2$ is not

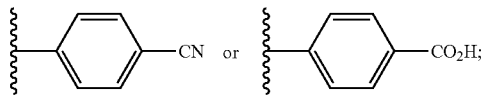

and c) if A is C(O) or $CH_2$, then X is $NR^6$ and $R^6$ is not

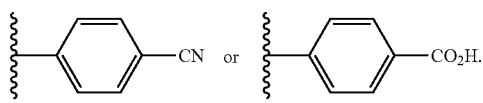

In another aspect, provided herein is a method of ameliorating arthritis or joint injury in a mammal, the method comprising administering to a joint of the mammal a composition comprising a therapeutically effective amount of a compound of Formula IIIa, or a pharmaceutically acceptable salt, solvate, polymorph, prodrug, ester, metabolite, N-oxide, stereoisomer, or isomer thereof:

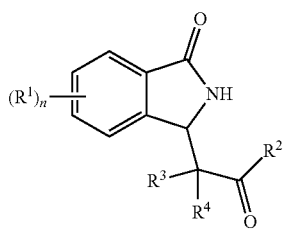

(Formula IIIa)

wherein each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

$R^2$ is optionally substituted aryl or optionally substituted heteroaryl;

each $R^3$ and $R^4$ is independently H or optionally substituted alkyl; and $R^5$ is H, optionally substituted alkyl, $C(O)R^4$, $C(O)OR^4$, $C(O)NR^4R^4$, or $SO_2R^4$.

In another aspect, provided herein is a method of inducing differentiation of mesenchymal stem cells into chondrocytes, the method comprising contacting mesenchymal stem cells with a sufficient amount of a compound of Formula III, or a pharmaceutically acceptable salt, solvate, polymorph, prodrug, ester, metabolite, N-oxide, stereoisomer, or isomer thereof:

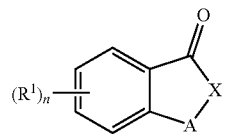

(Formula III)

wherein each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

X is O, NH, or $NR^6$;

A is C(O), $CH_2$, or CH—$CR^3R^4$—$C(O)R^2$;

$R^2$ is optionally substituted aryl or optionally substituted heteroaryl;

each $R^3$ and $R^4$ is independently H or optionally substituted alkyl;

$R^5$ is H, optionally substituted alkyl, $C(O)R^4$, $C(O)OR^4$, $C(O)NR^4R^4$, or $SO_2R^4$; and $R^6$ is optionally substituted phenyl;

provided that d) if A is CH—$CR^3R^4$—$C(O)R^2$, then X is O or NH;

e) if n is 0, A is $CHCH_2C(O)R^2$ and X is, then $R^2$ is not

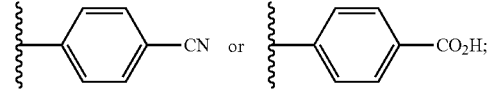

and if A is C(O) or $CH_2$, then X is $NR^6$ and $R^6$ is not

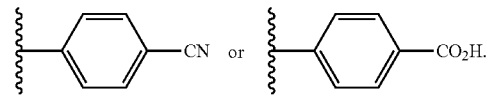

In another aspect, provided herein is a method of inducing differentiation of mesenchymal stem cells into chondrocytes, the method comprising contacting mesenchymal stem cells with a sufficient amount of a compound of Formula IIIa, or a pharmaceutically acceptable salt, solvate, polymorph, prodrug, ester, metabolite, N-oxide, stereoisomer, or isomer thereof:

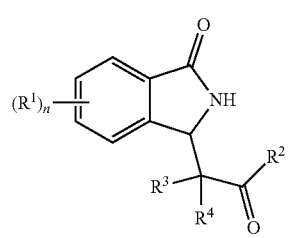

(Formula IIIa)

wherein each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

$R^2$ is optionally substituted aryl or optionally substituted heteroaryl;

each $R^3$ and $R^4$ is independently H or optionally substituted alkyl; and $R^5$ is H, optionally substituted alkyl, $C(O)R^4$, $C(O)OR^4$, $C(O)NR^4R^4$, or $SO_2R^4$.

In some embodiments described above or below of a compound of Formula III, X is $NR^6$ and A is $C(O)$. In some embodiments described above or below of a compound of Formula III, X is $NR^6$ and A is $CH_2$. In some embodiments described above or below of a compound of Formula III, X is O and A is $CH-CR^3R^4-C(O)R^2$. In some embodiments described above or below of a compound of Formula III, X is NH and A is $CH-CR^3R^4-C(O)R^2$.

In some embodiments described above or below of a compound of Formula III or IIIa, $R^3$ and $R^4$ are both hydrogen. In some embodiments described above or below of a compound of Formula III or IIIa, $R^3$ is optionally substituted alkyl and $R^4$ is hydrogen. In some embodiments described above or below of a compound of Formula III or IIIa, $R^3$ and $R^4$ are independently optionally substituted alkyl.

In some embodiments described above or below of a compound of Formula III or IIIa, $R^2$ is heteroaryl. In certain embodiments, $R^2$ is optionally substituted optionally substituted pyridinyl, optionally substituted pyrimidinyl, optionally substituted pyridazinyl, or optionally substituted pyrazinyl. In certain embodiments, $R^2$ is 5-membered heteroaryl. In certain embodiments, the 5-membered heteroaryl is thiophene, benzofuran, pyrrole, thiazole, imidazole, oxazole, pyrazole, or triazole. In certain embodiments, $R^2$ is bicyclic heteroaryl. In certain embodiments, the bicyclic heteroaryl is benzimidazole, benzthiazole, benzoxazole, indazole, quinoline, or naphthyridine.

In some embodiments described above or below of a compound of Formula III or IIIa, $R^2$ is phenyl. In certain embodiments, the phenyl of $R^2$ is bisubstituted. In certain embodiments, the phenyl of $R^2$ is monosubstituted. In certain embodiments, substitution on the phenyl of $R^2$ is independently selected from optionally substituted alkyl, optionally substituted alkoxy, optionally substituted aryloxy, halo, CN, $CO_2H$, amino, monoalkylamine, dialkylamine, monoarylamine, alkylarylamine, cycloalkyl, hydroxy, C(O)-(optionally substituted alkyl), $C(O)NH_2$, C(O)NH-(optionally substituted alkyl), alkylthioether, alkylsulfoxide, alkylsulfone, C(O)-(optionally substituted aryl), C(O)NH-(optionally substituted aryl), arylthioether, arylsulfoxide, or arylsulfone.

In certain embodiments, substitution on the phenyl is independently selected from F, Cl, $CO_2H$, CN, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of CN and a group selected from F, Cl, $CO_2H$, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of $CO_2H$ and a group selected from F, Cl, CN, $OCH_3$, $C(O)CH_3$, $CF_3$, $CH_3$, $CH_2OH$, $CH_2CH_2OH$, and $CH_2CH_2CH_2OH$. In certain embodiments, bisubstitution on the phenyl of $R^2$ consists of $CH_2CH_2CH_2OH$ and a group selected from F, Cl, CN, $OCH_3$, $C(O)CH_3$, $CF_3$, $CH_3$, $CH_2OH$, $CH_2CH_2OH$, and $CO_2H$.

In some embodiments described above or below of a compound of Formula III or IIIa, $R^2$ is naphthyl.

In some embodiments described above or below of a compound disclosed herein, B is $CO_2R^4$ and $R^4$ is optionally substituted alkyl. In some embodiments described above or below of a compound disclosed herein, B is $CO_2R^4$ and $R^4$ is hydrogen.

In some embodiments described above or below of a compound disclosed herein, n is 0, 1, or 2. In certain embodiments, n is 0. In certain embodiments, n is 1. In certain embodiments, $R^1$ is independently selected from Cl, F, $CH_2OH$, $CH_2NH_2$, $OCH_3$, $OCF_3$, $OCHF_2$, CN, $NO_2$, $CO_2H$, and $CO_2CH_3$.

In some embodiments described above or below of a compound of Formula I, the compound is selected from:

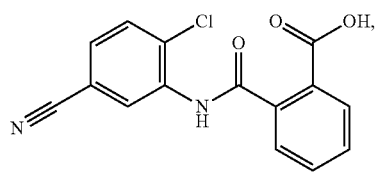

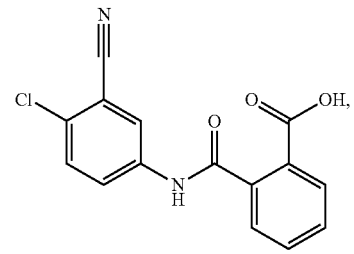

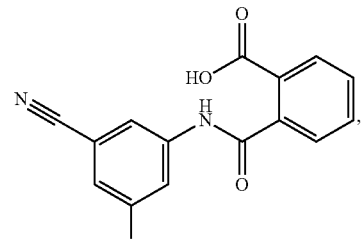

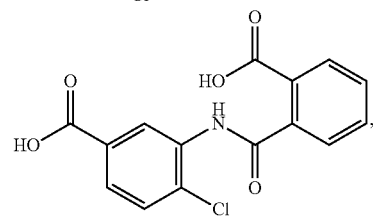

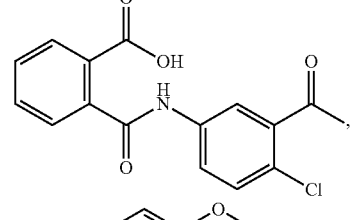

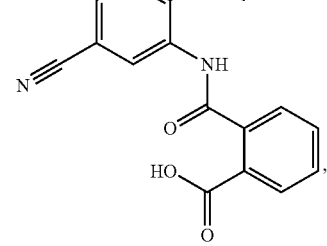

125
-continued
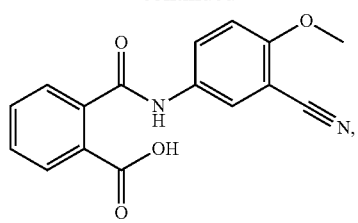
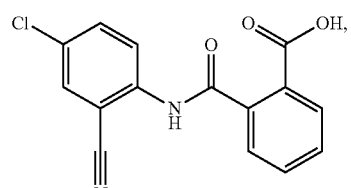
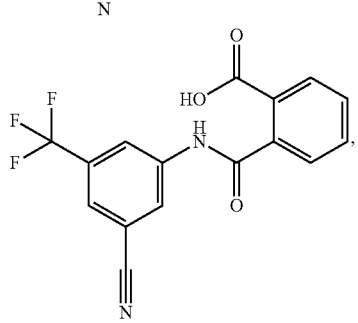
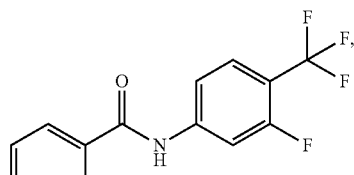
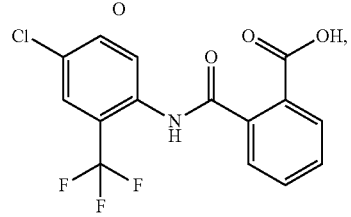
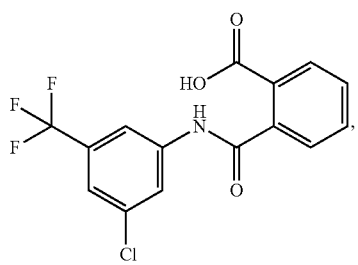
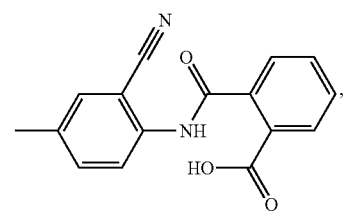
126
-continued
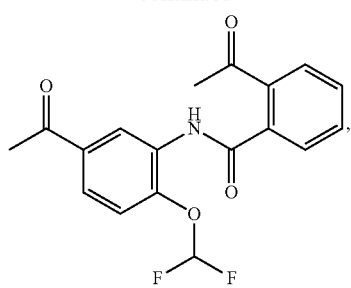
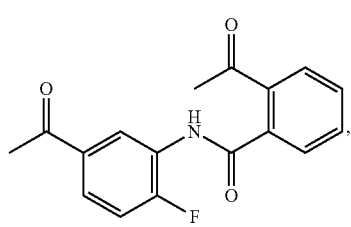
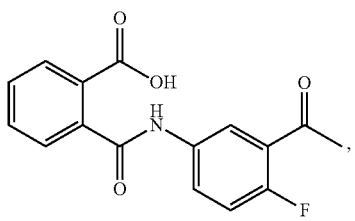
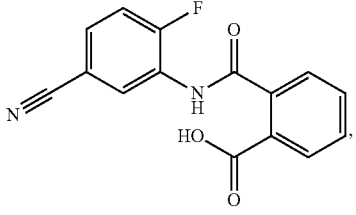
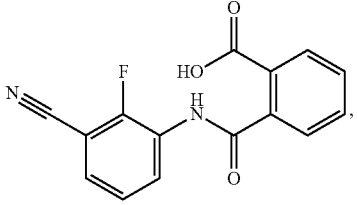
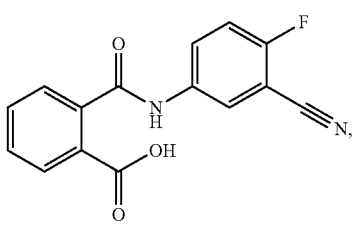
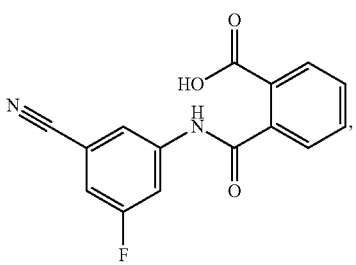

127
-continued
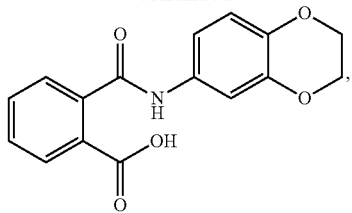
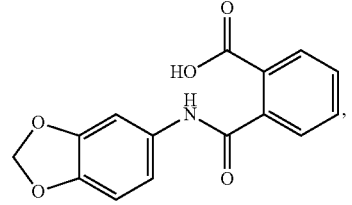
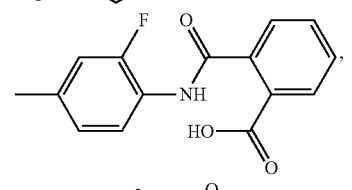
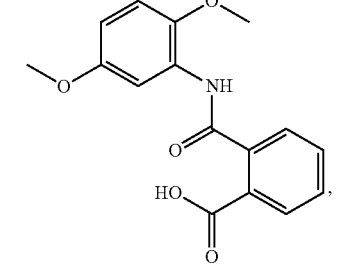
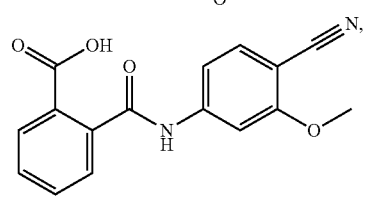
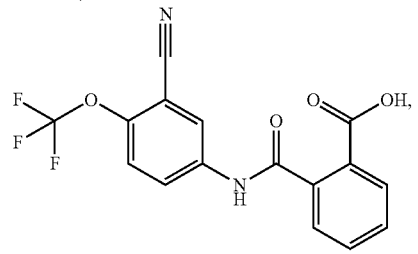
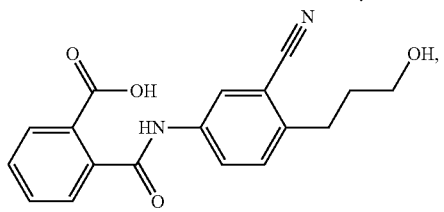
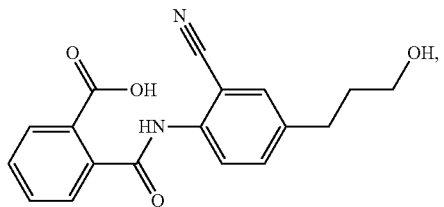
128
-continued
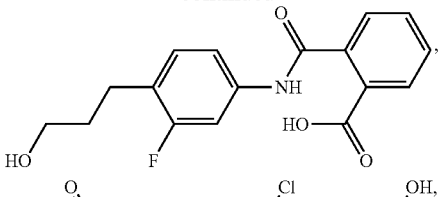
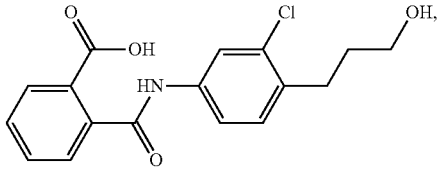
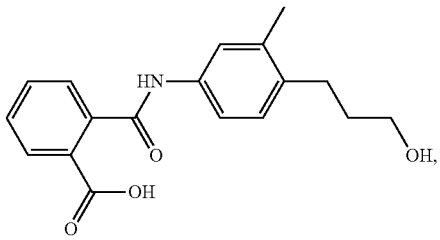
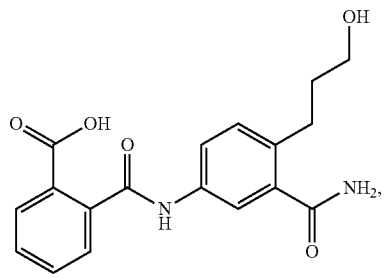
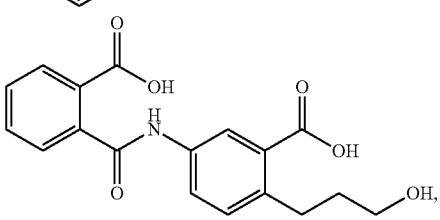
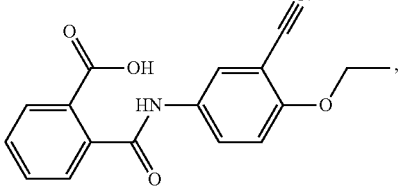
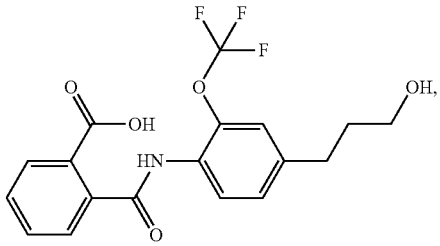
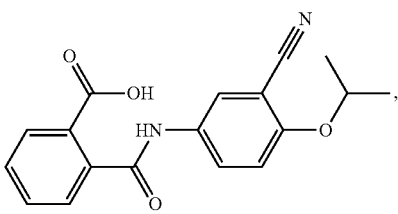

-continued
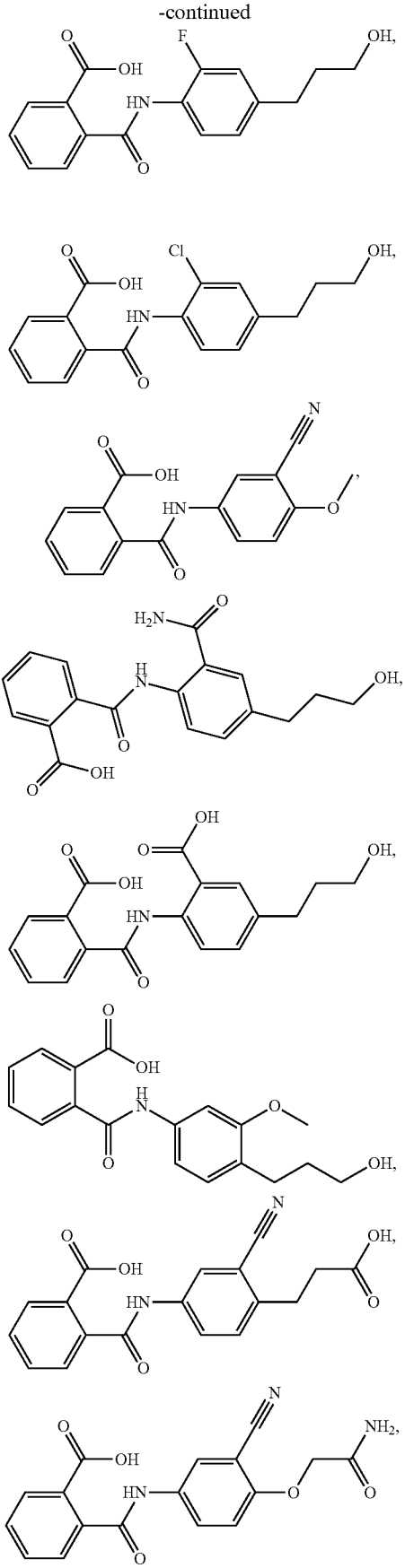
-continued
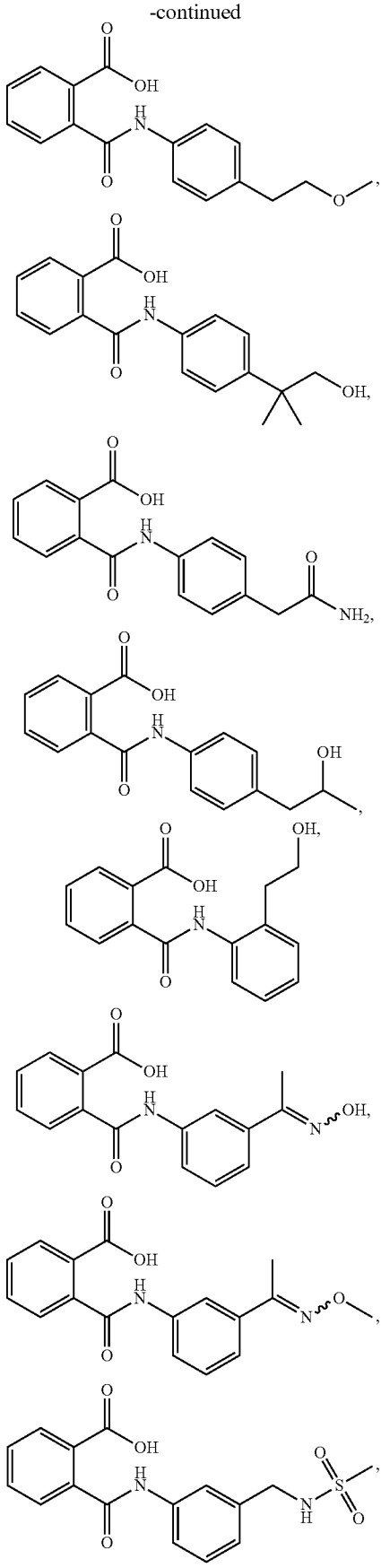

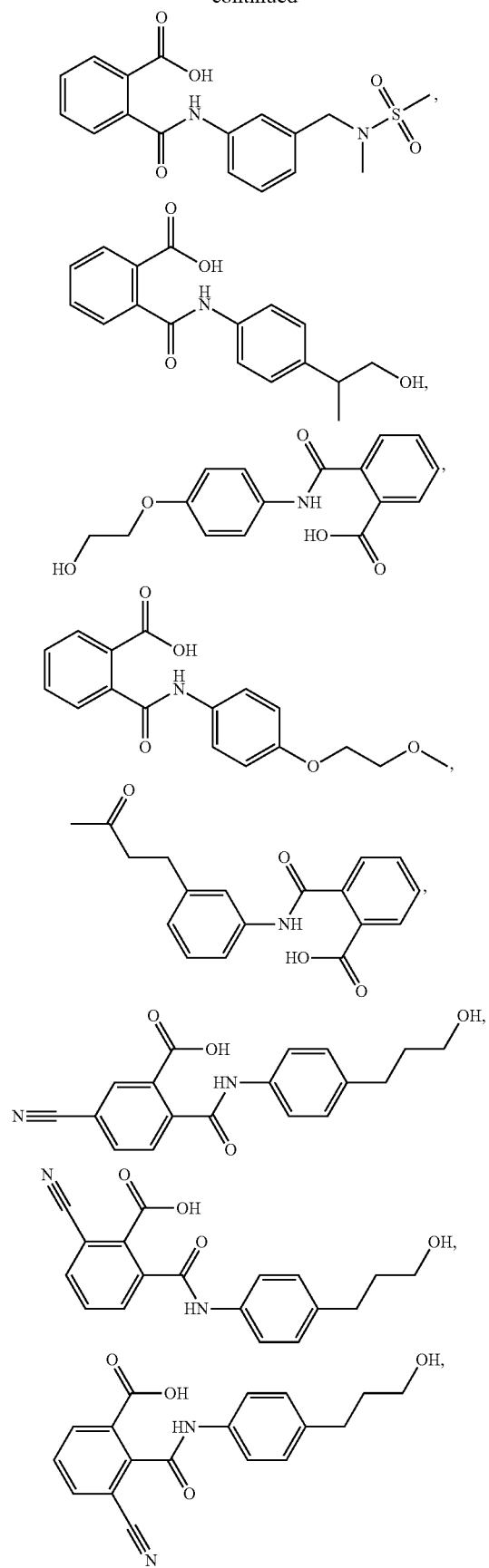
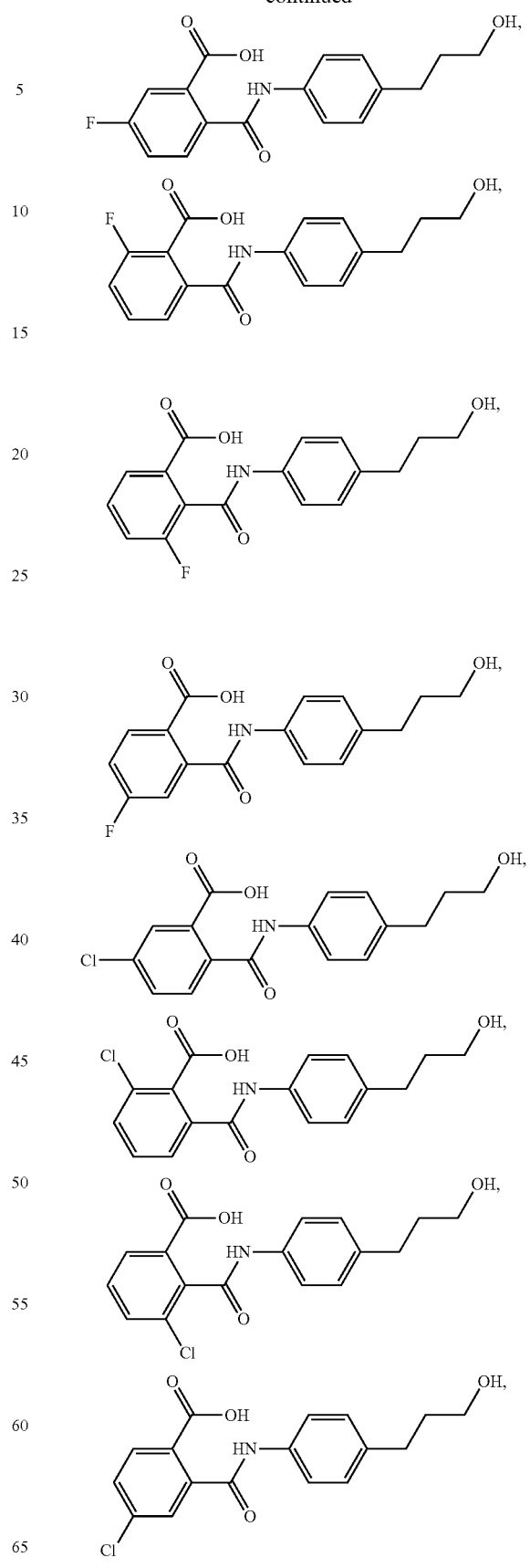

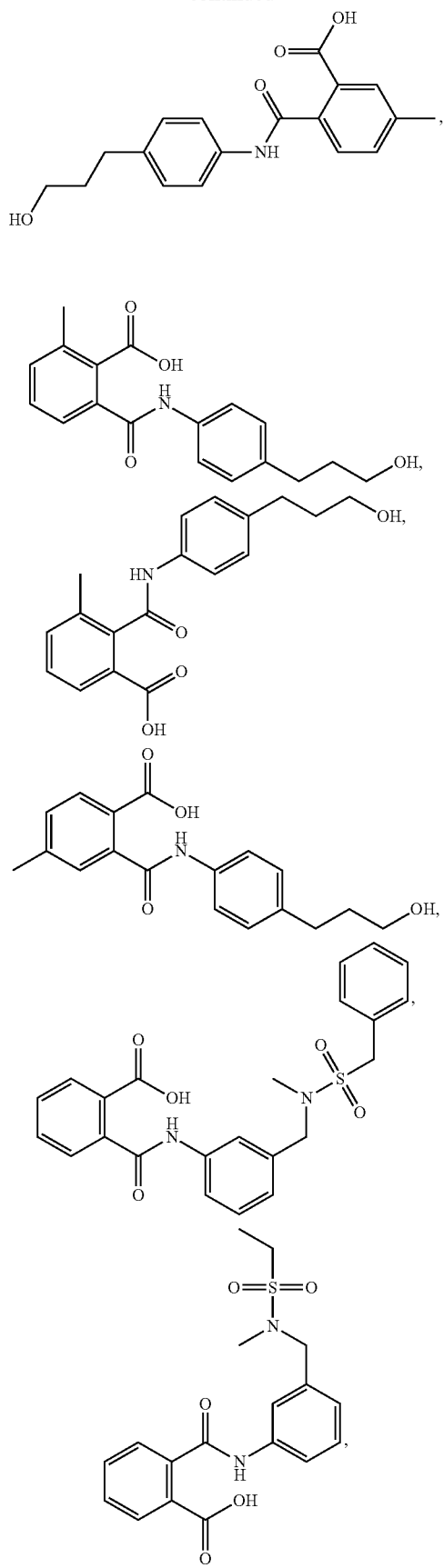
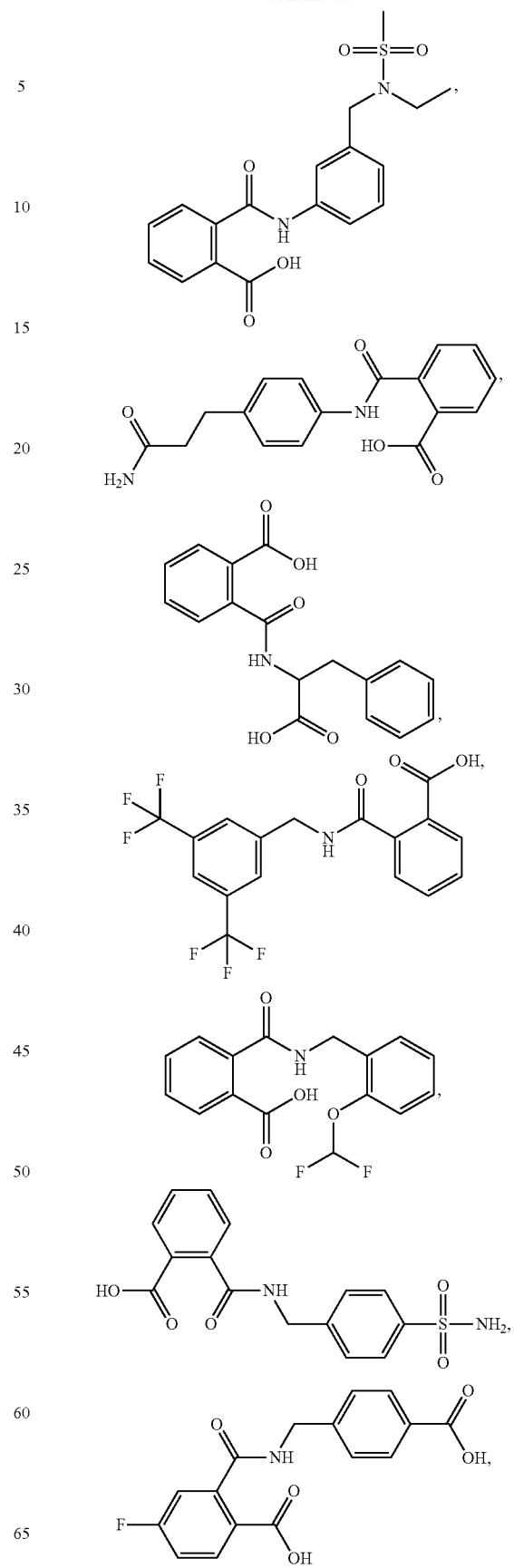

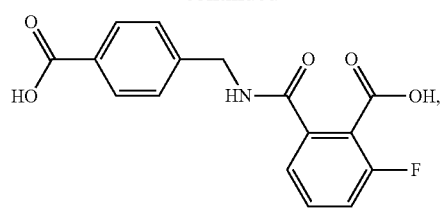
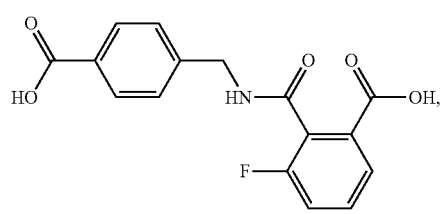
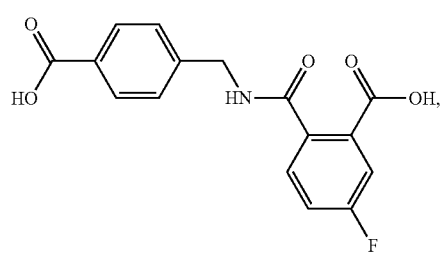
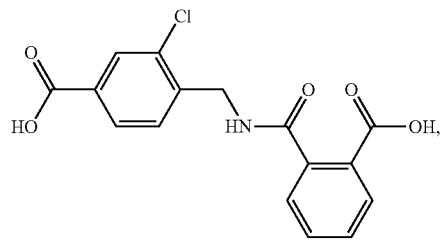
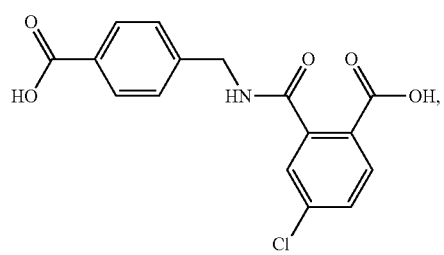
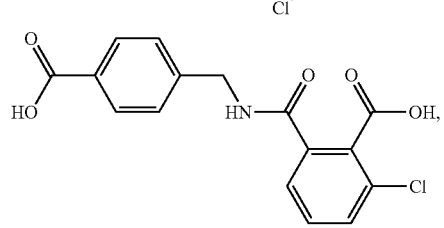
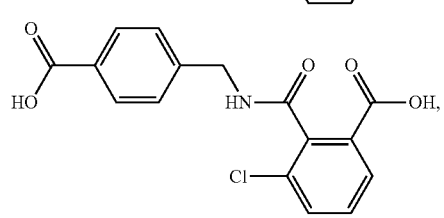
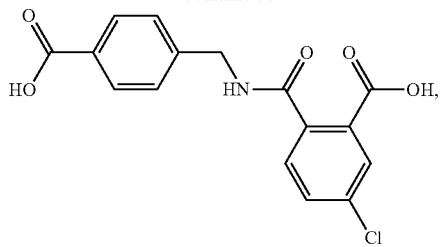
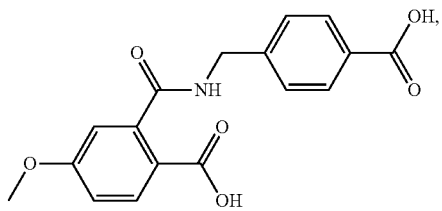
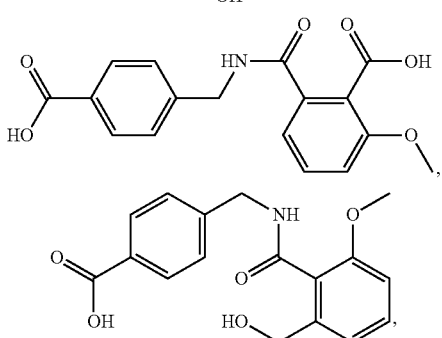
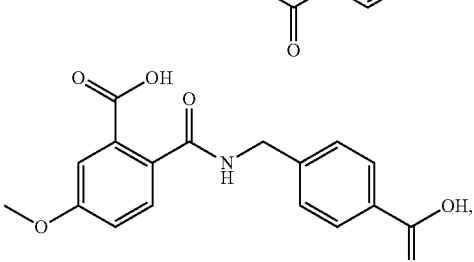
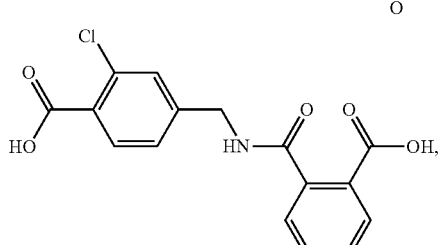
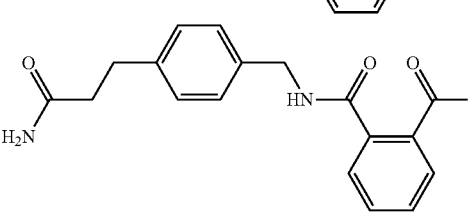
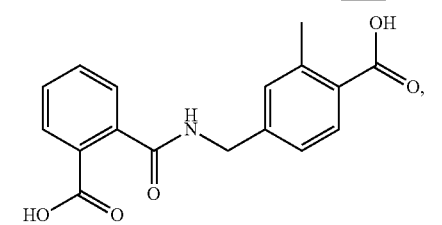

-continued
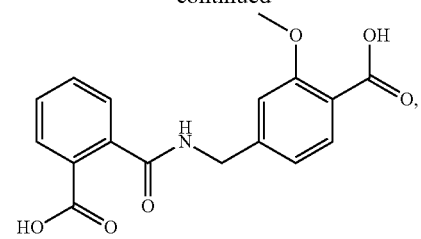
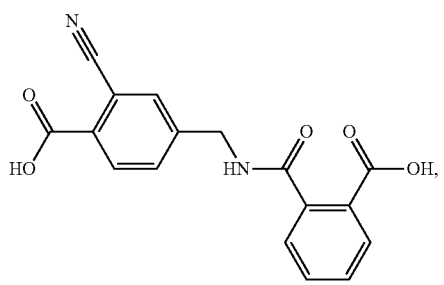
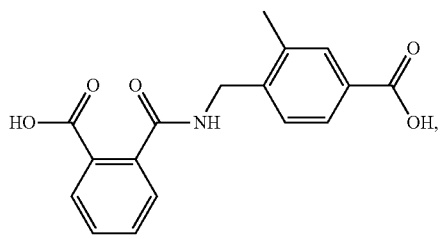
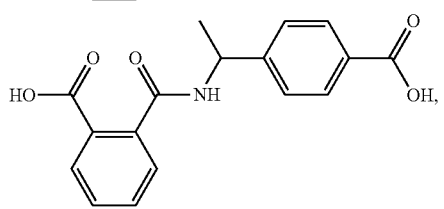
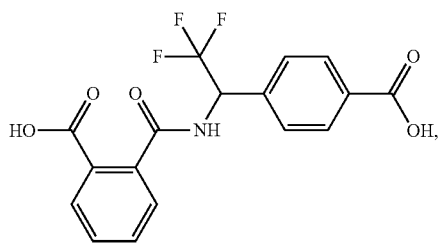
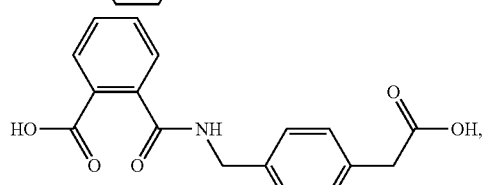
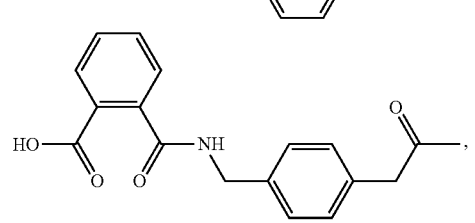
-continued
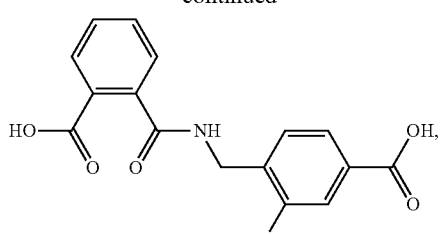
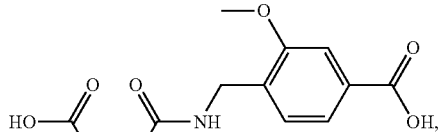
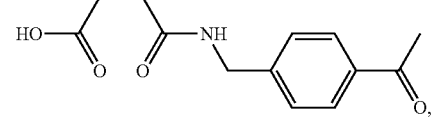
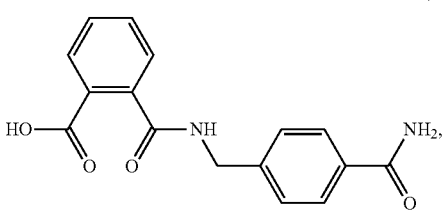
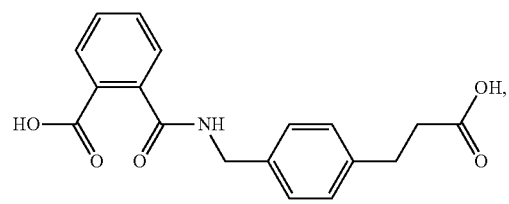
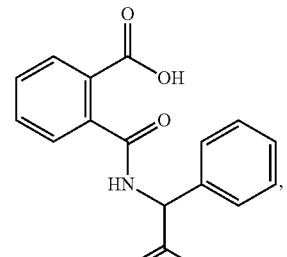
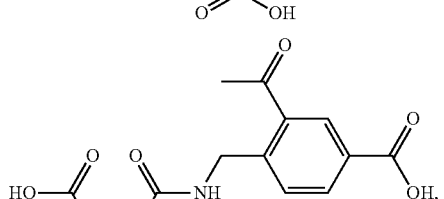
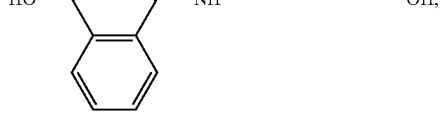

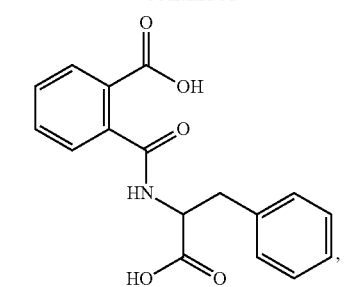
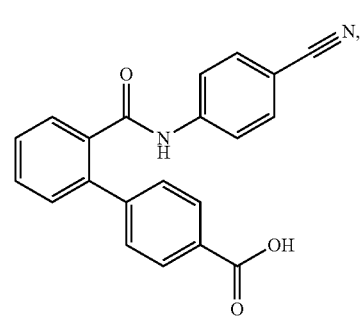
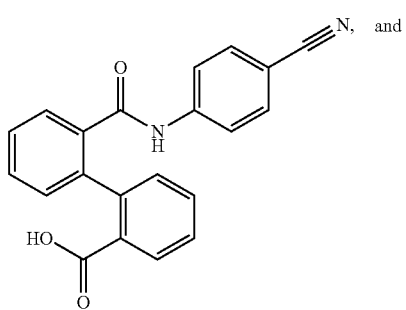
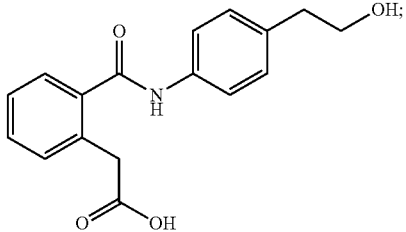
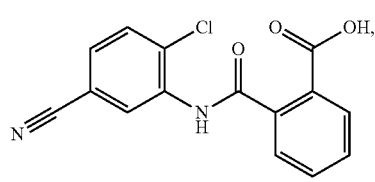
or a pharmaceutically acceptable salt, solvate, polymorph, prodrug, ester, metabolite, N-oxide, stereoisomer, or isomer thereof.
In some embodiments described above or below of a compound of Formula Ia, the compound is selected from:
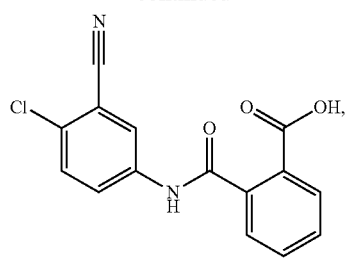
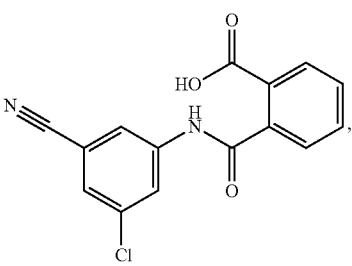
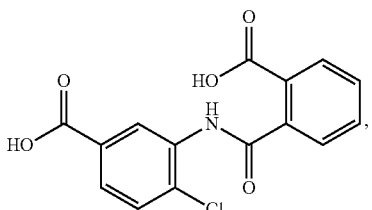
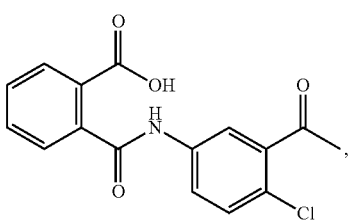
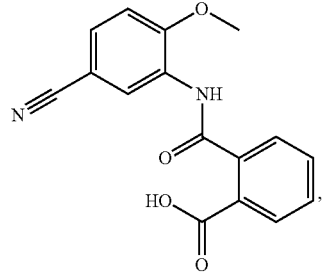
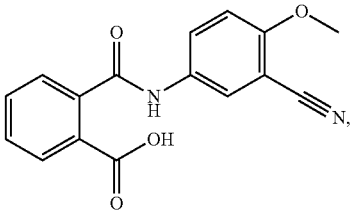
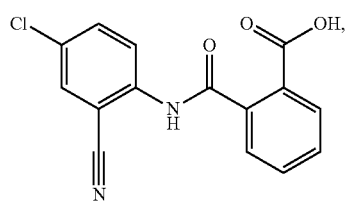

-continued
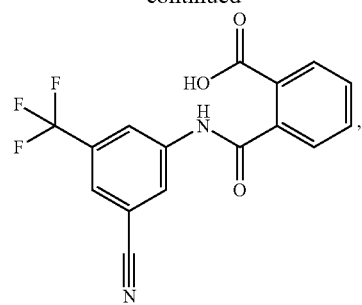
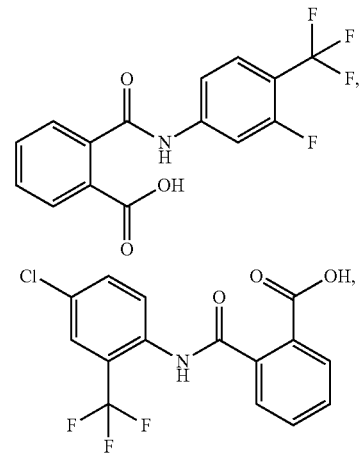
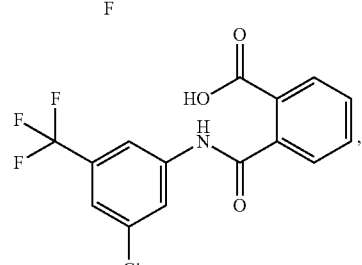
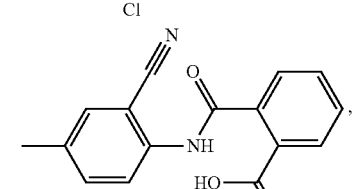
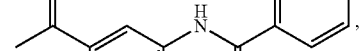
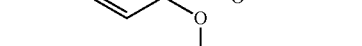
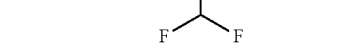
-continued
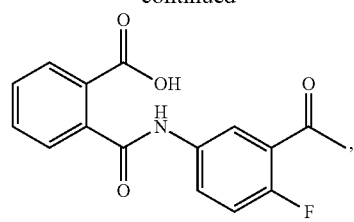
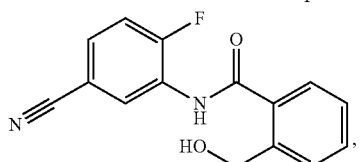
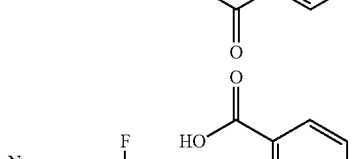
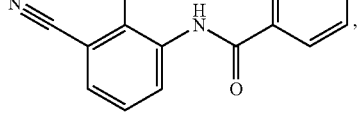
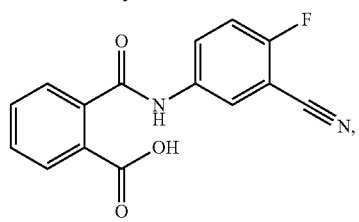
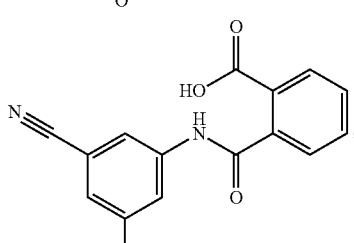
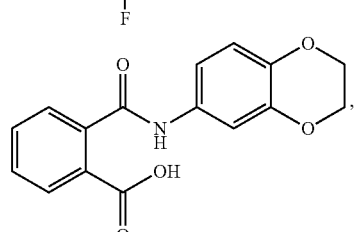
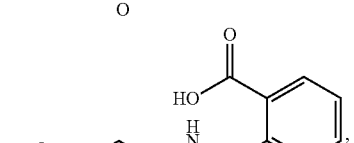
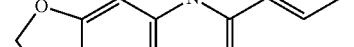
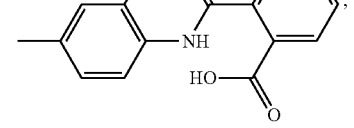

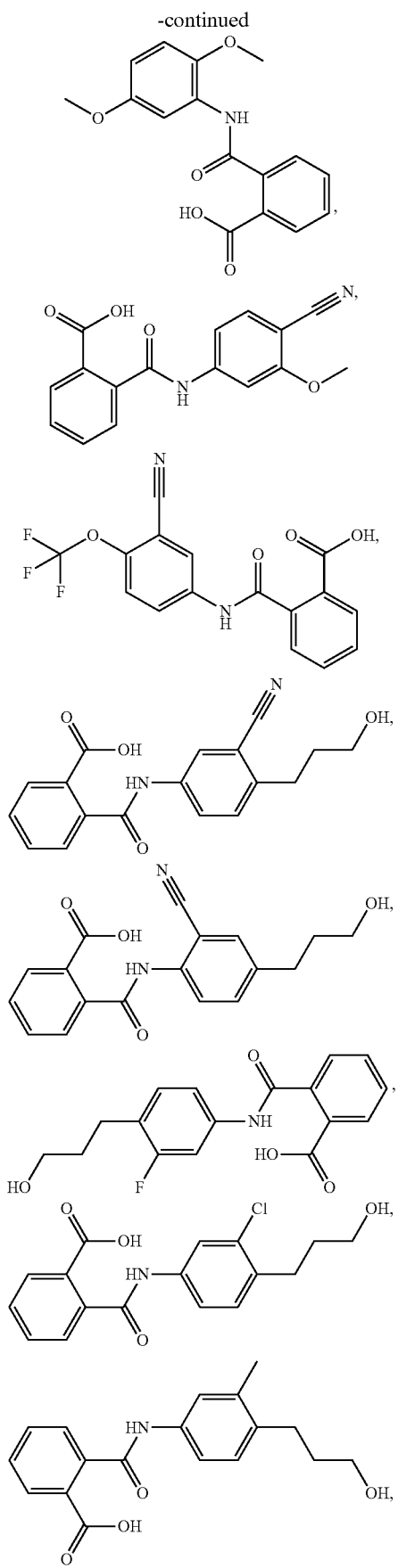
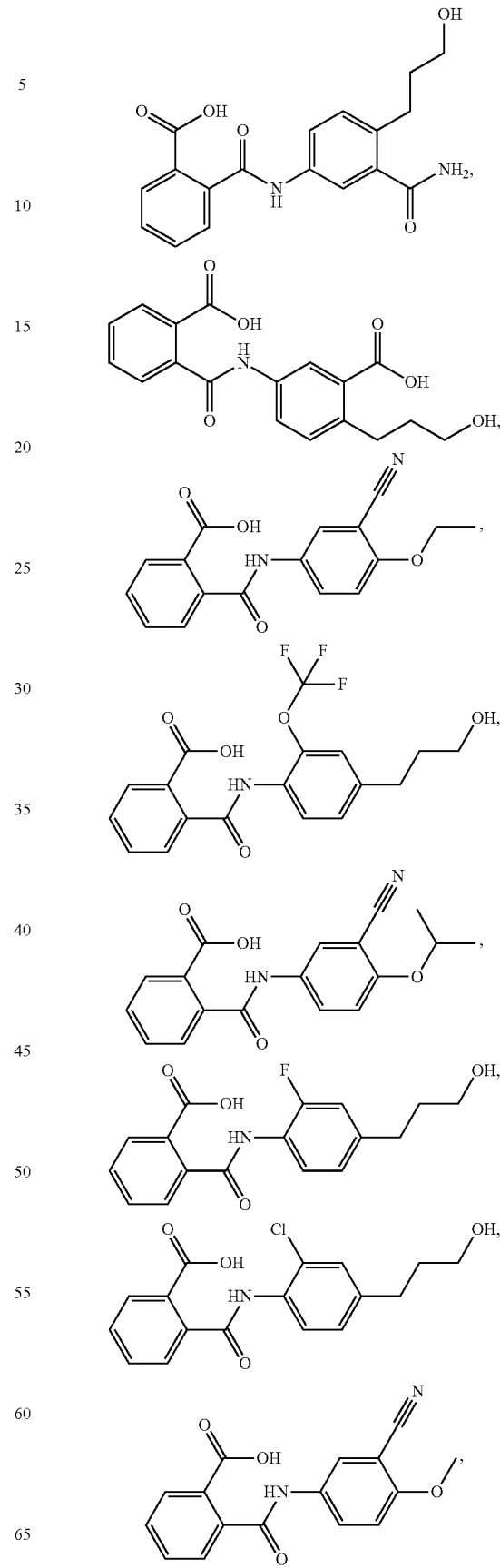

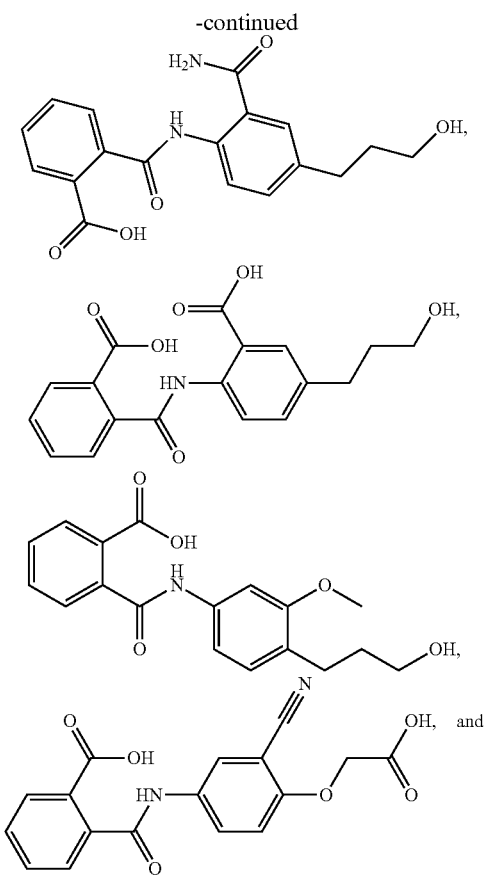
or a pharmaceutically acceptable salt, solvate, polymorph, prodrug, ester, metabolite, N-oxide, stereoisomer, or isomer thereof.
In some embodiments described above or below of a compound of Formula Ib, the compound is selected from
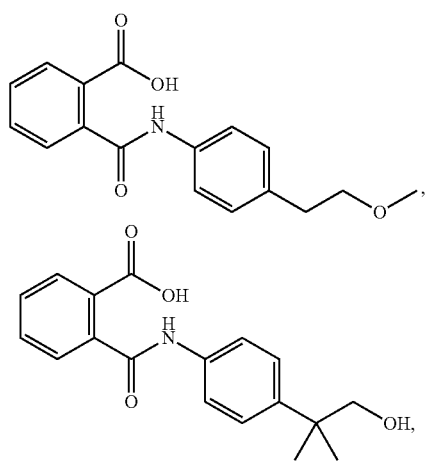
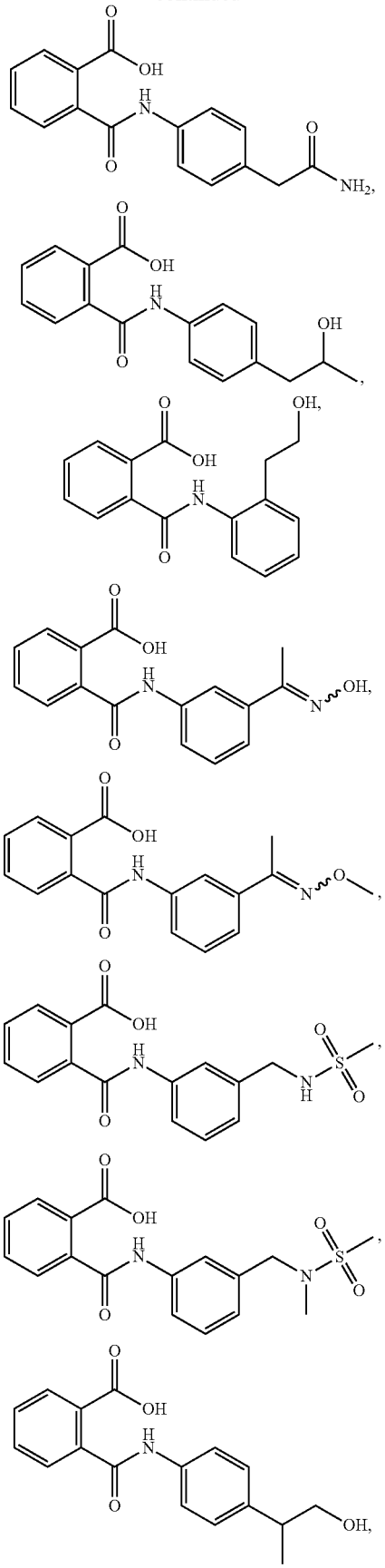

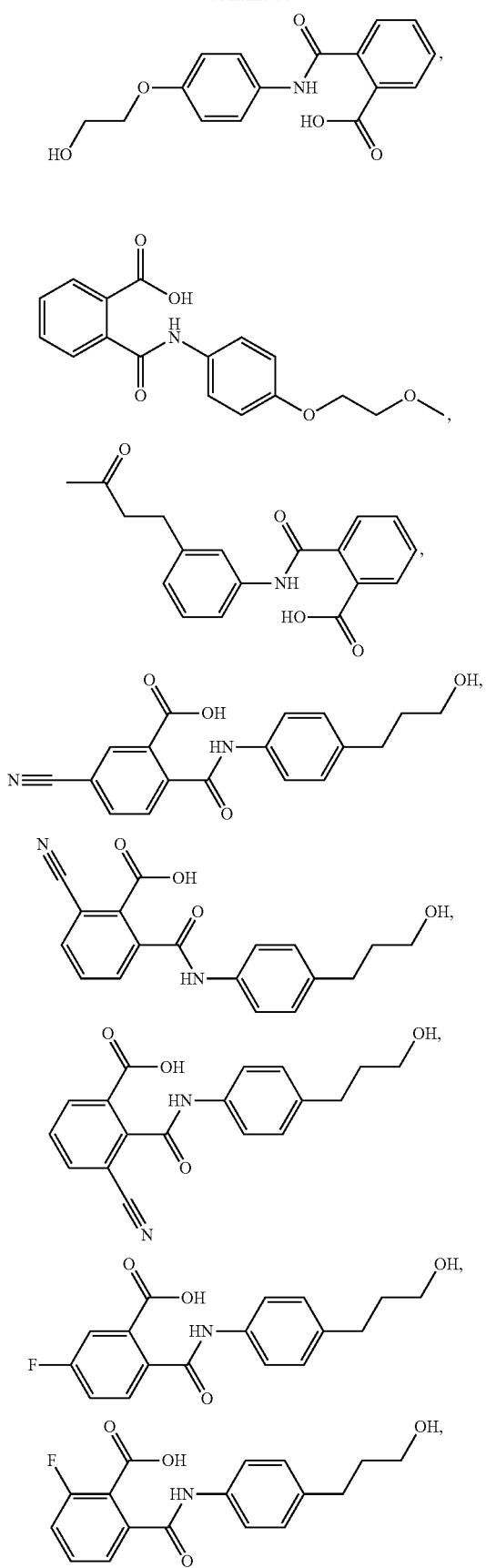
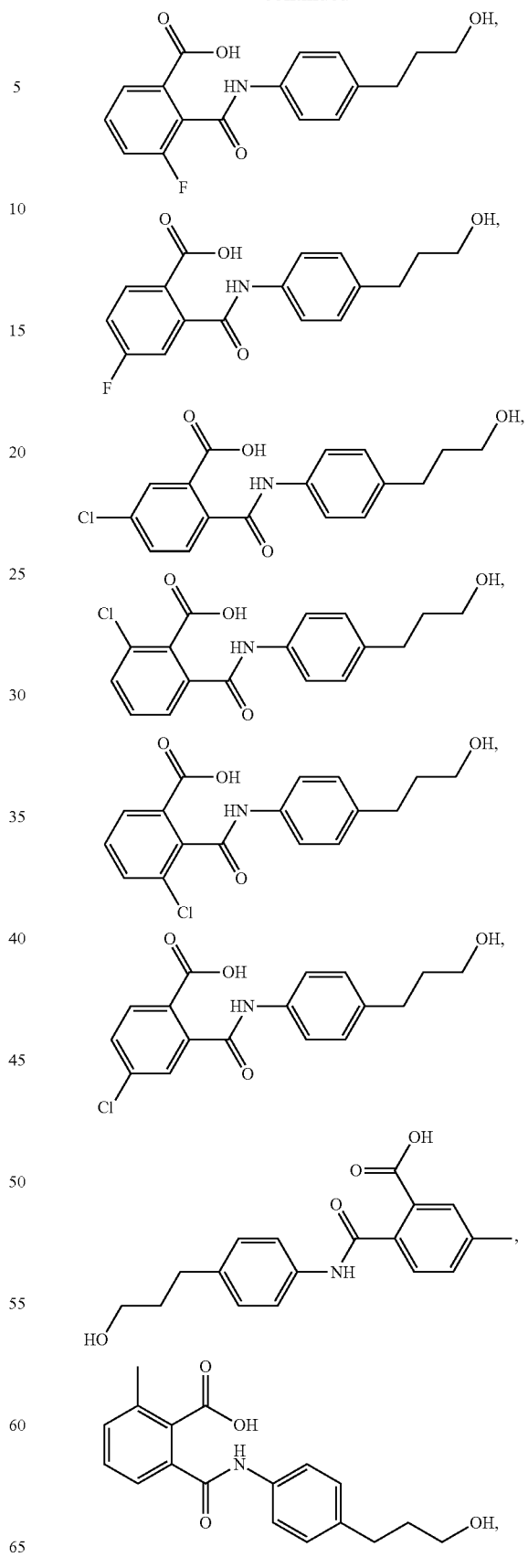

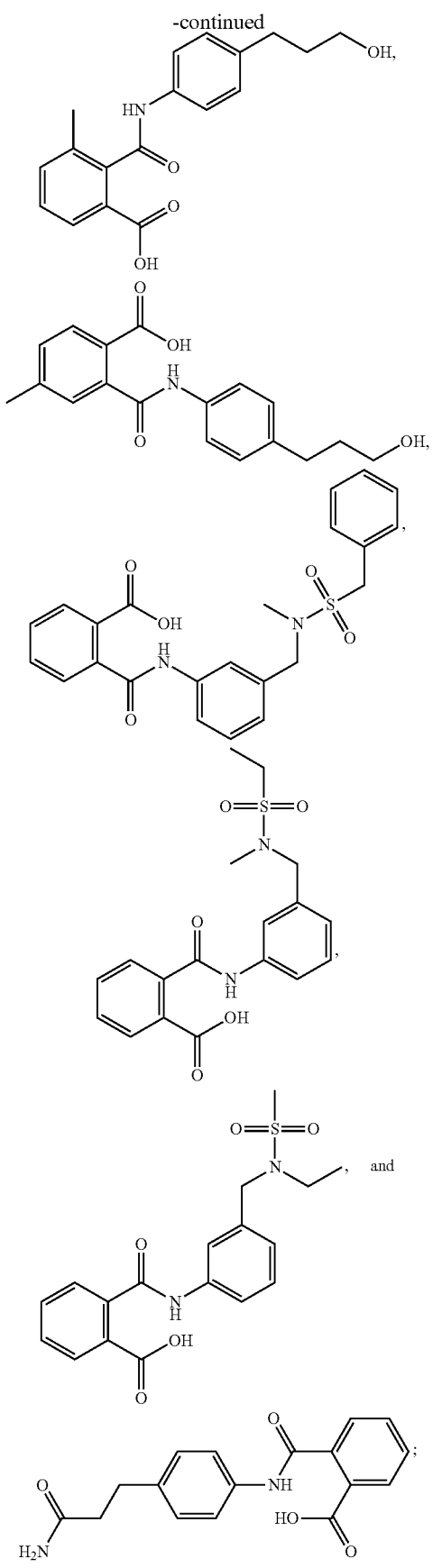
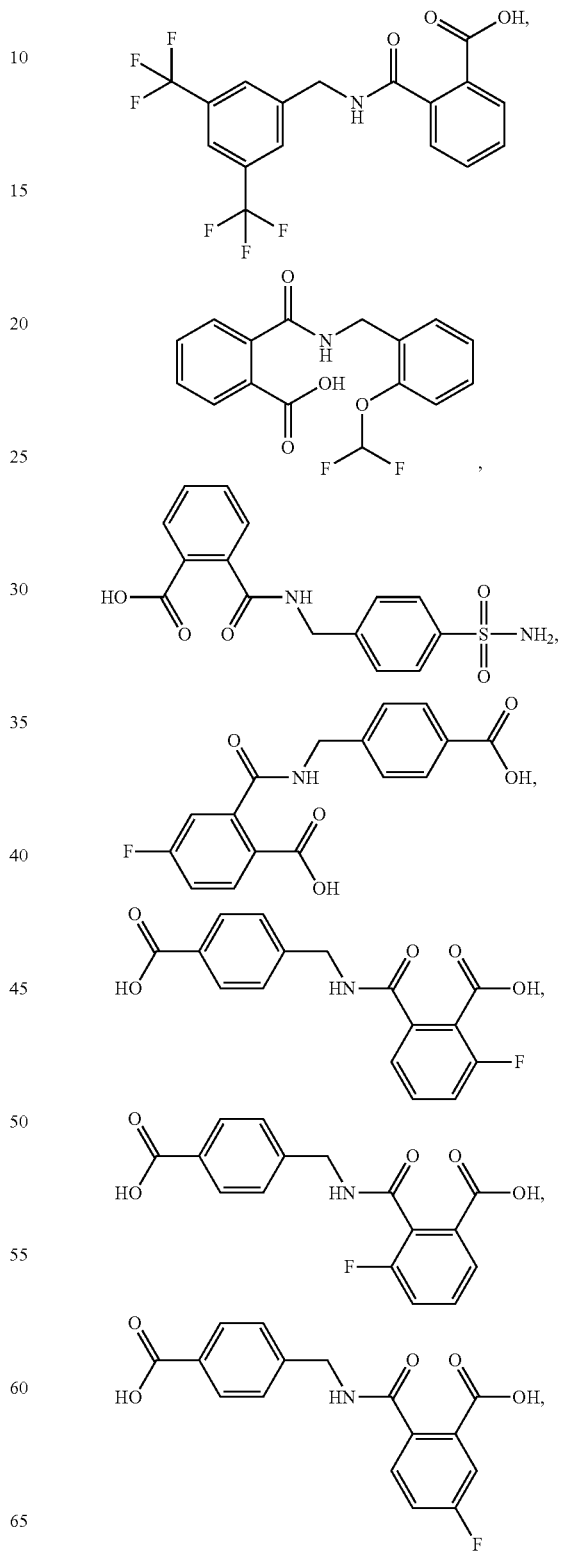
or a pharmaceutically acceptable salt, solvate, polymorph, prodrug, ester, metabolite, N-oxide, stereoisomer, or isomer thereof.
In some embodiments described above or below of a compound of Formula Ic, the compound is selected from:

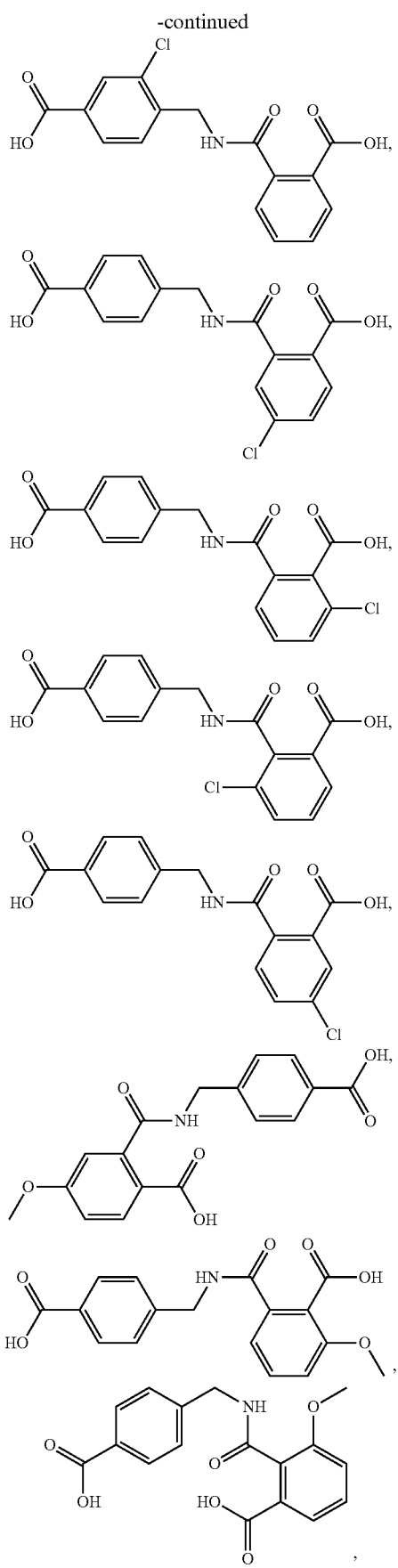
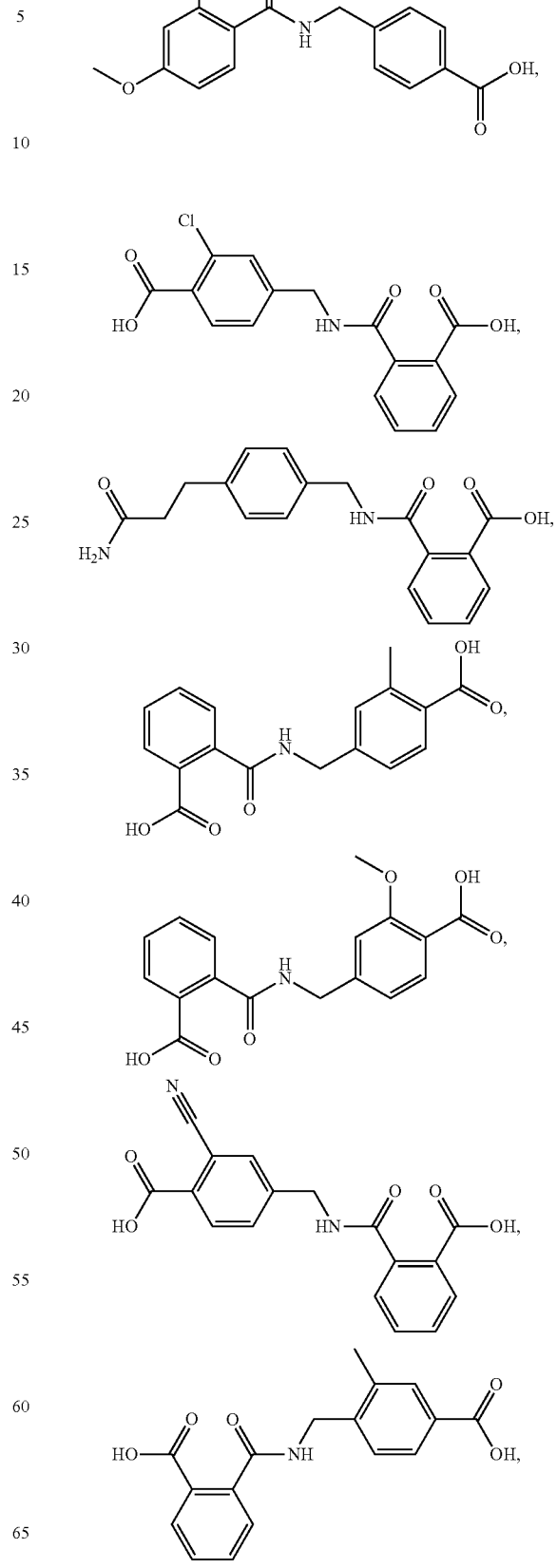

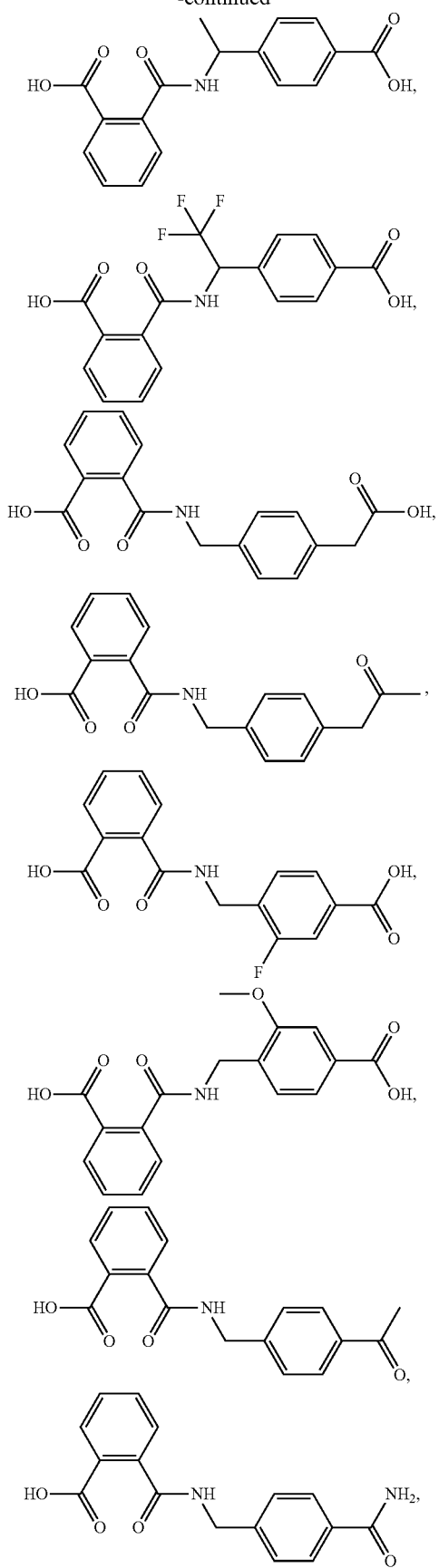
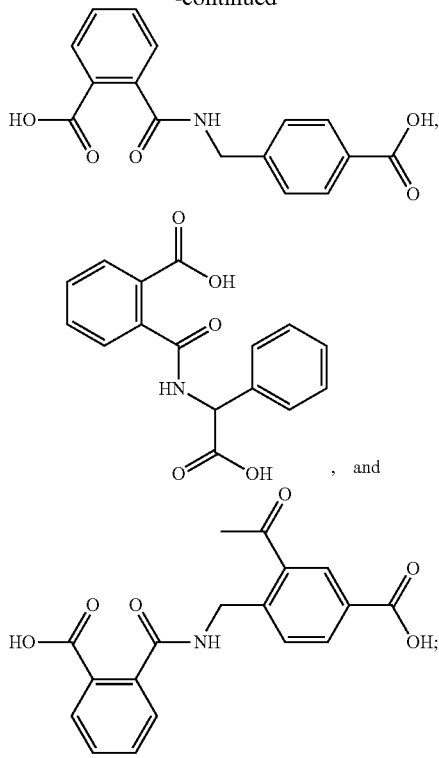
, and
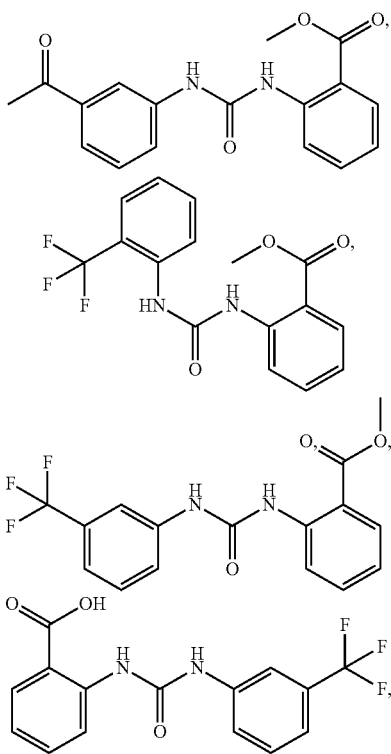
or a pharmaceutically acceptable salt, solvate, polymorph, prodrug, ester, metabolite, N-oxide, stereoisomer, or isomer thereof.
In some embodiments described above or below of a compound of Formula II, the compound is selected from:

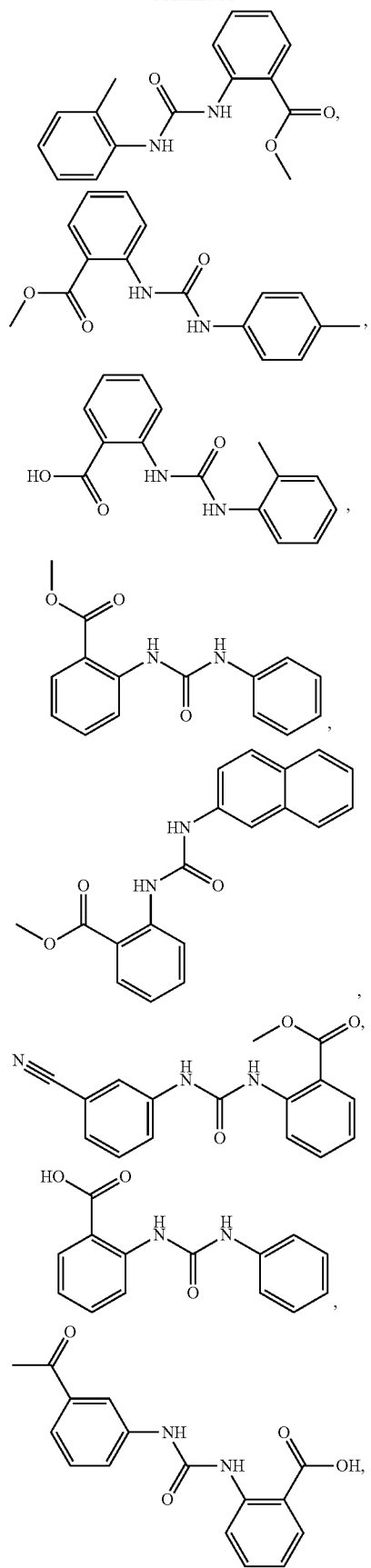
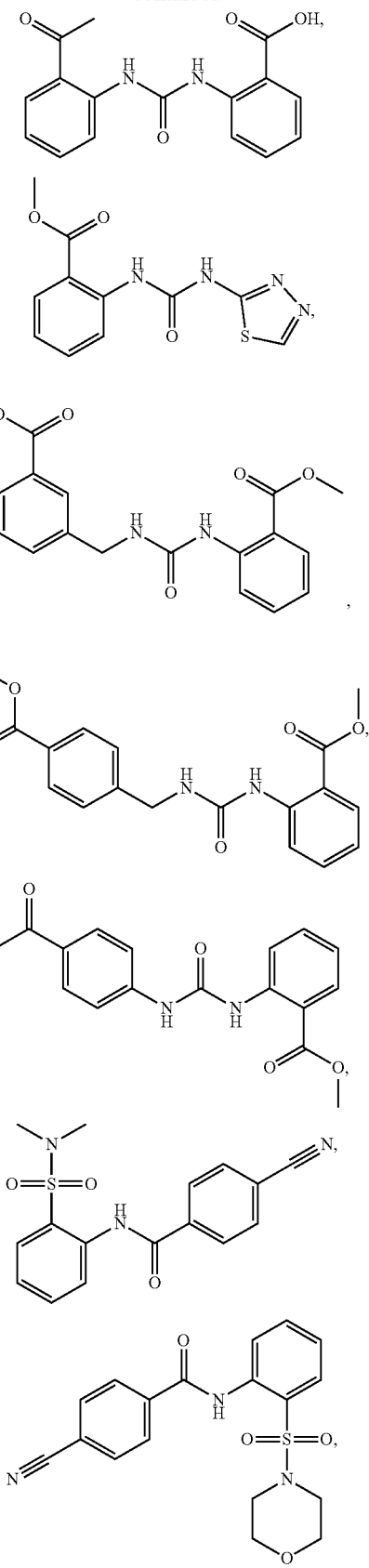

157
-continued
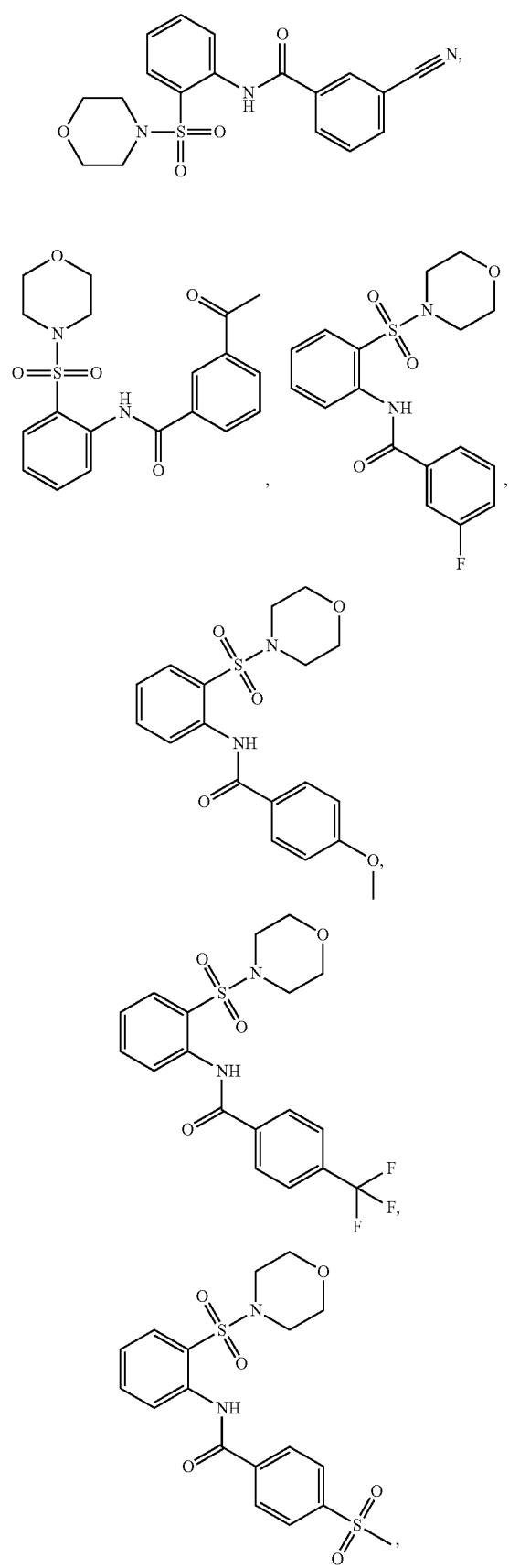
158
-continued
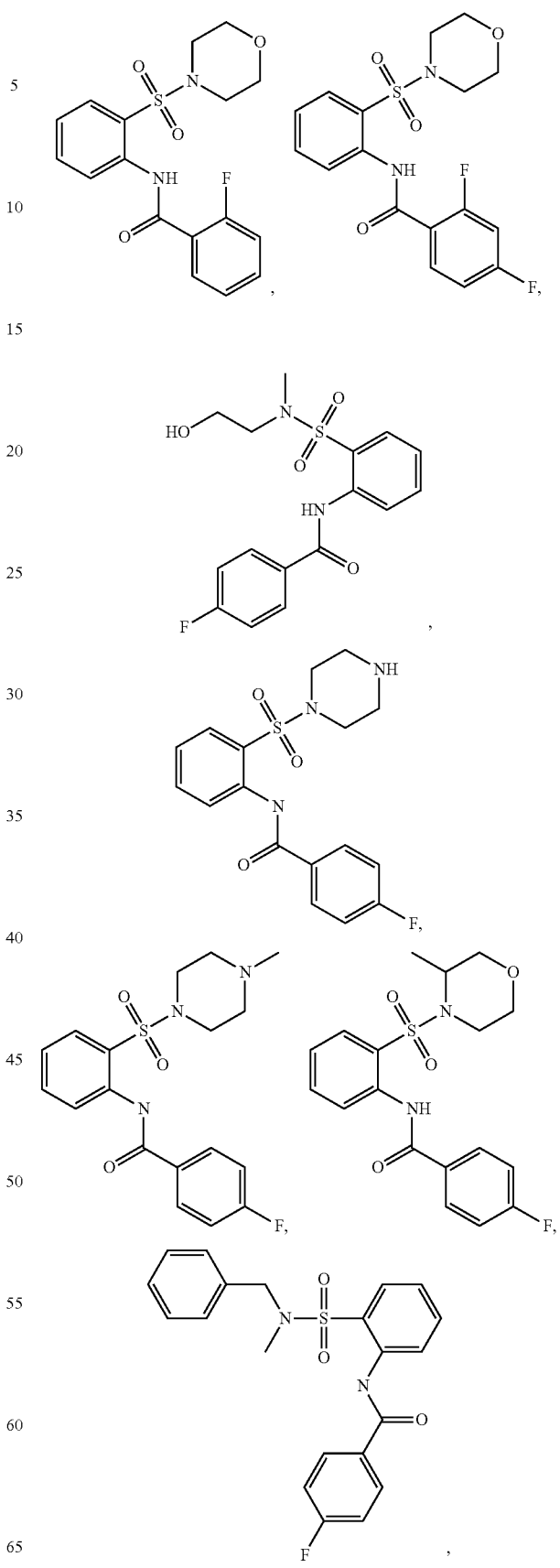

159
-continued
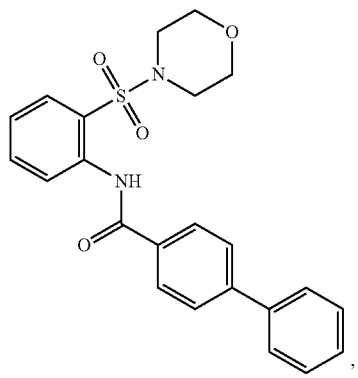
160
-continued
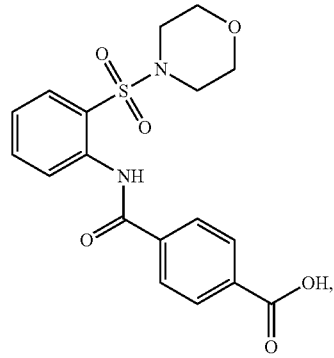
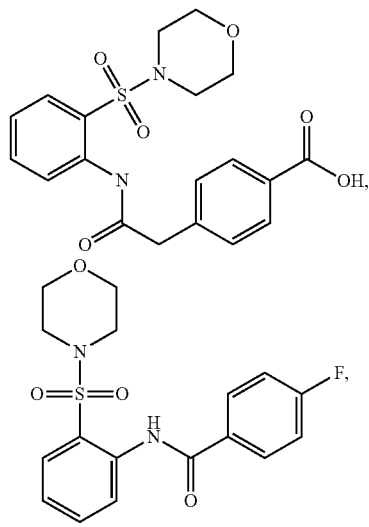
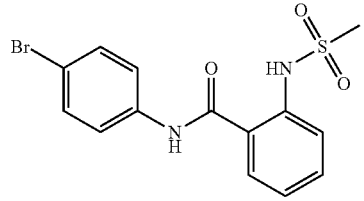
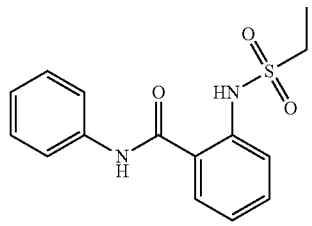
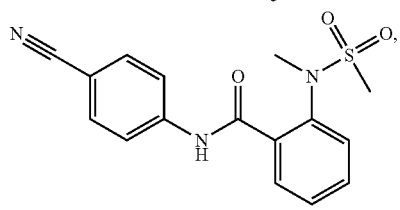

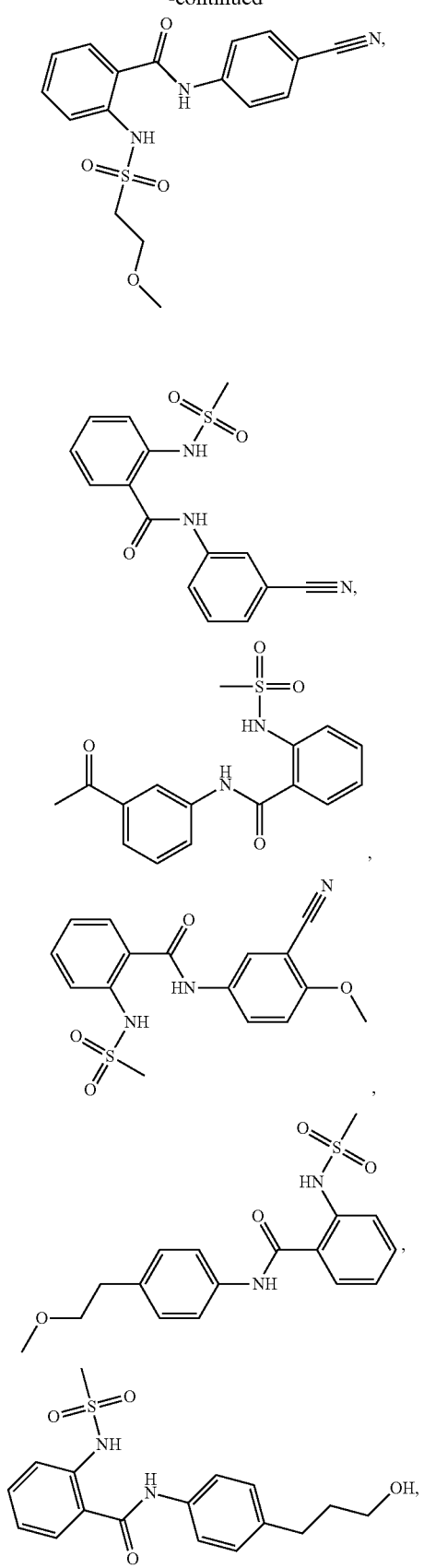
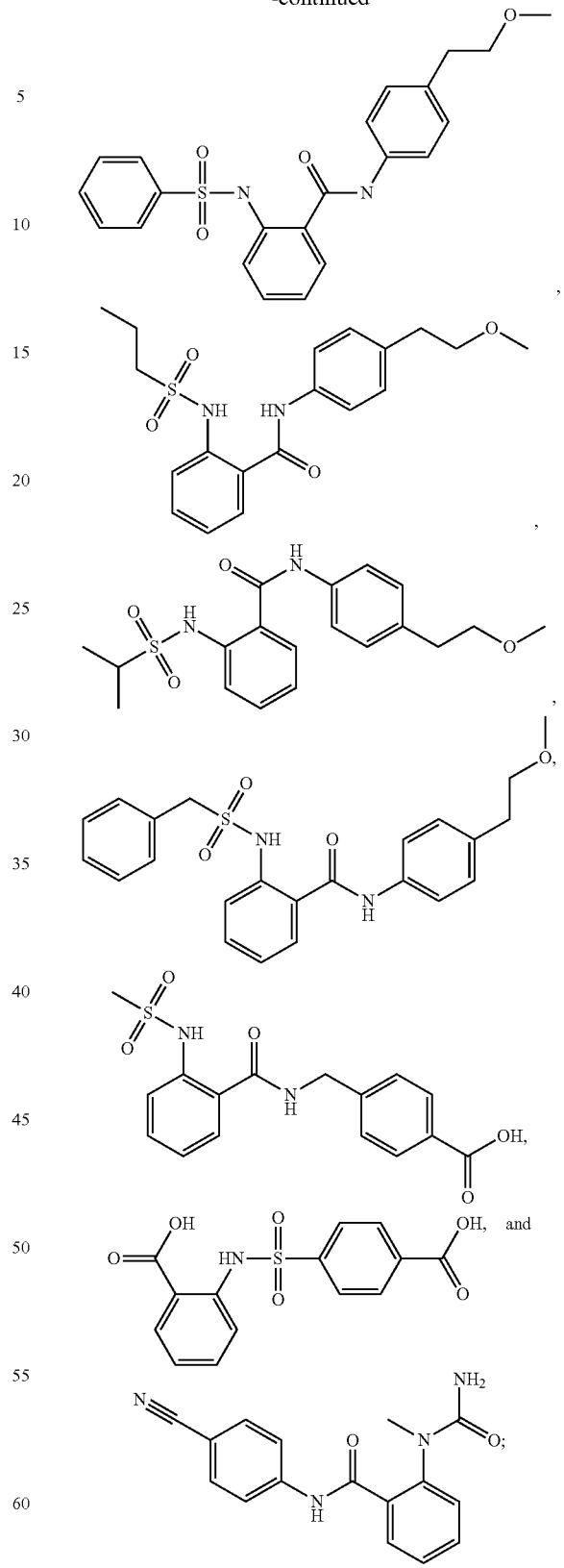
or a pharmaceutically acceptable salt, solvate, polymorph, prodrug, ester, metabolite, N-oxide, stereoisomer, or isomer thereof.

In some embodiments described above or below of a compound of Formula IIa, the compound is selected from:
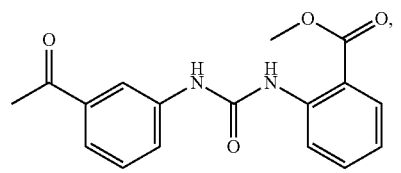
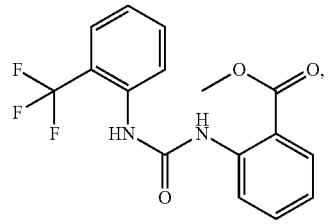
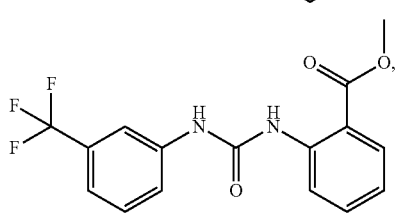
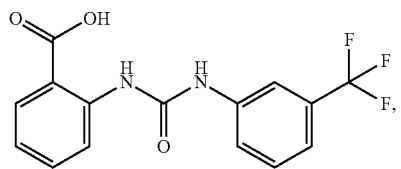
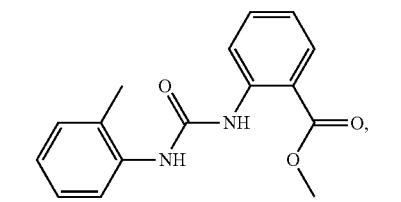
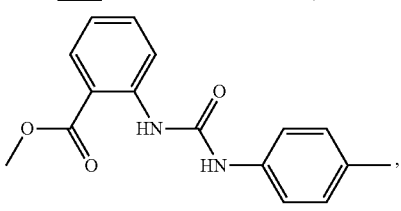
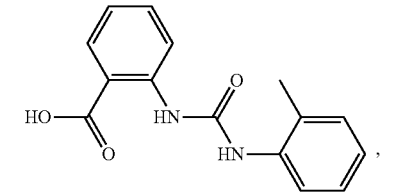
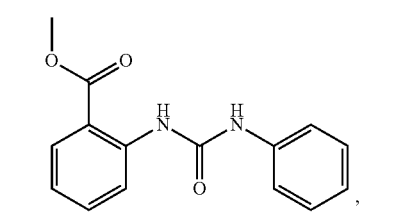
-continued
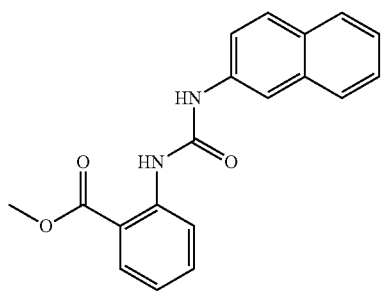
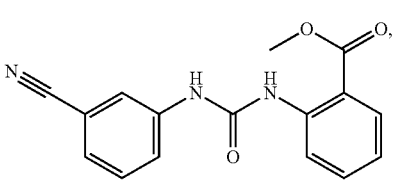
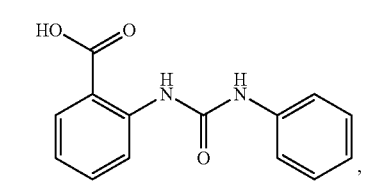
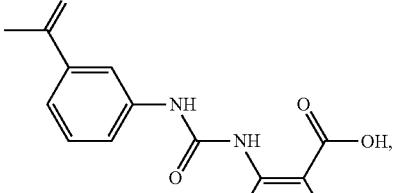
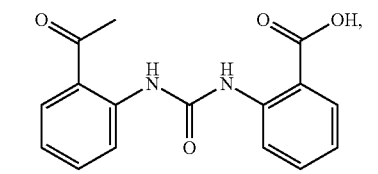
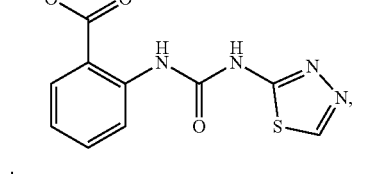
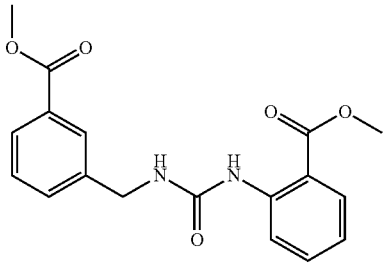

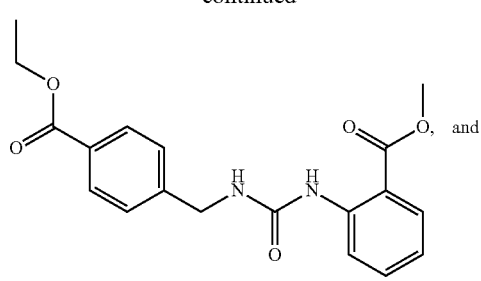
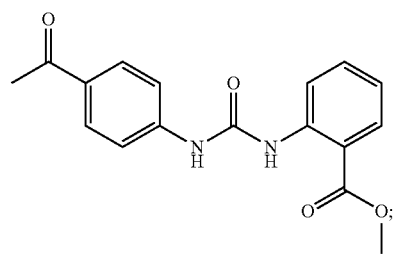
or a pharmaceutically acceptable salt, solvate, polymorph, prodrug, ester, metabolite, N-oxide, stereoisomer, or isomer thereof.
In some embodiments described above or below of a compound of Formula IIb, the compound is selected from:
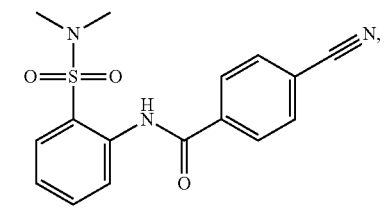
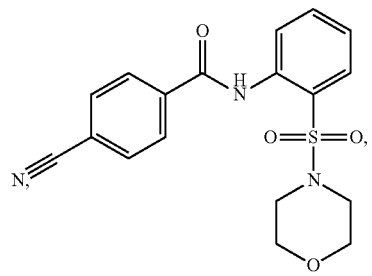
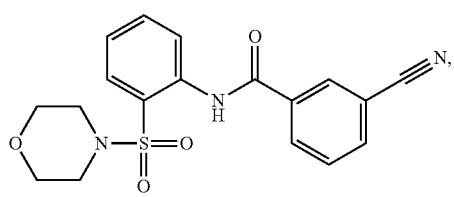
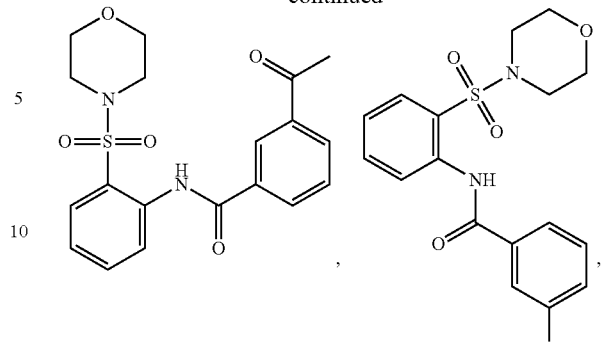
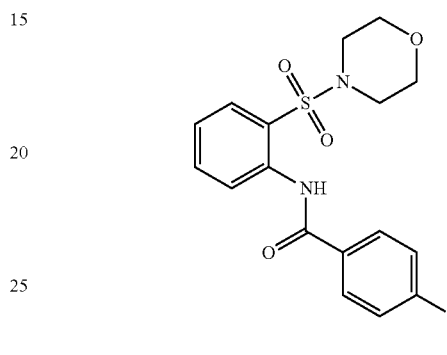
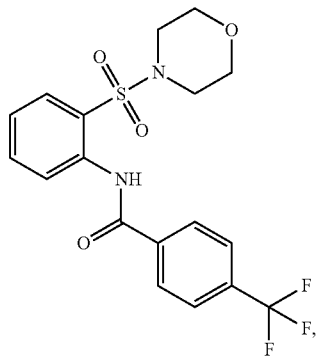
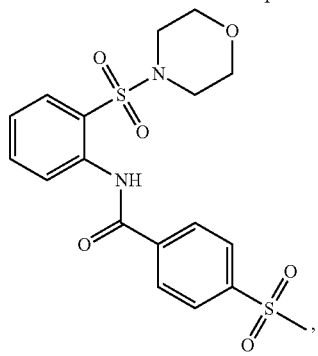
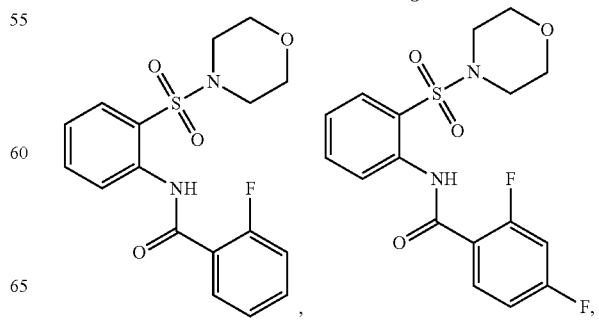

-continued
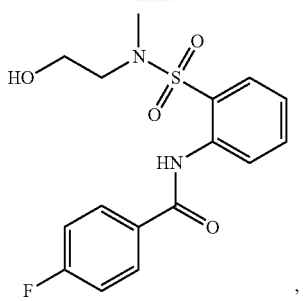
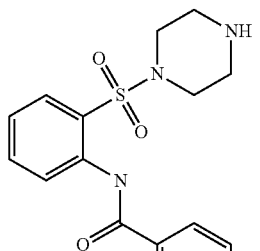
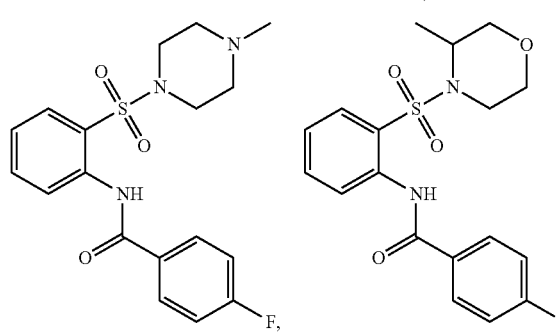
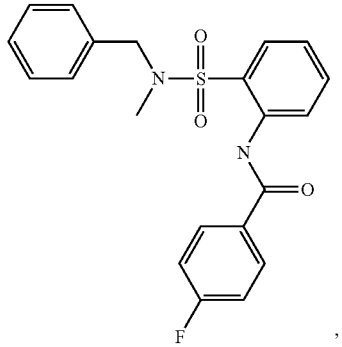
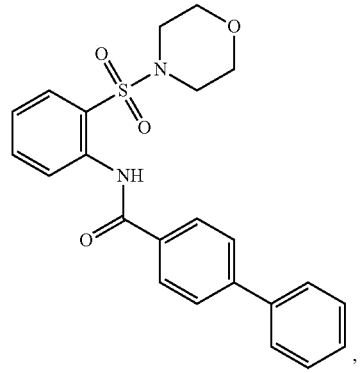
-continued
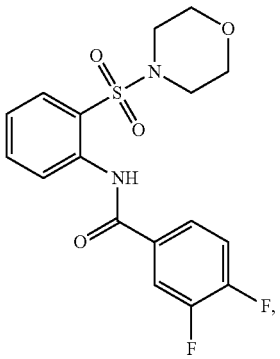
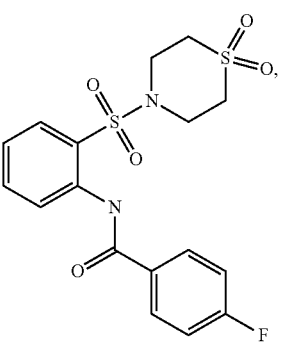
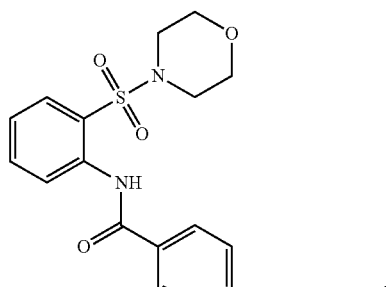
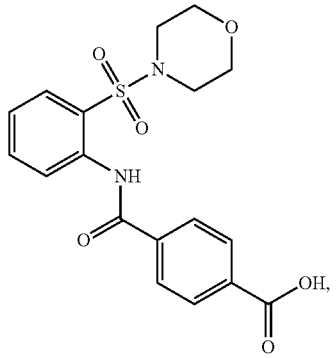
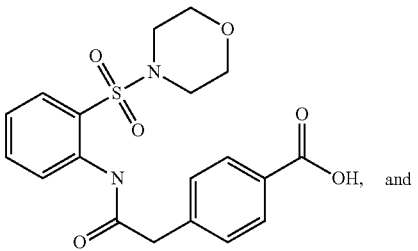, and

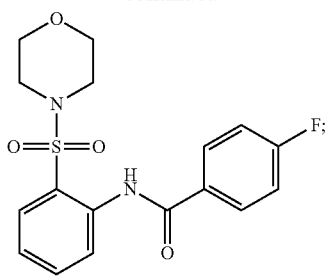
or, a pharmaceutically acceptable salt, solvate, polymorph, prodrug, ester, metabolite, N-oxide, stereoisomer, or isomer thereof.
In some embodiments described above or below of a compound of Formula IIc, the compound is selected from:
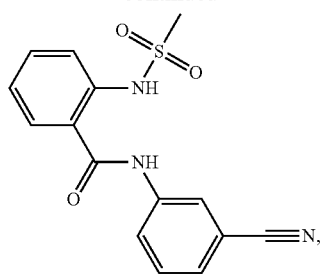
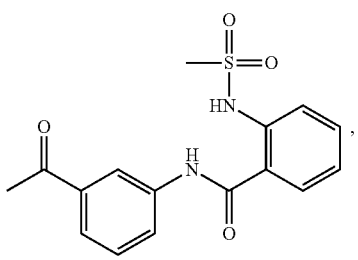
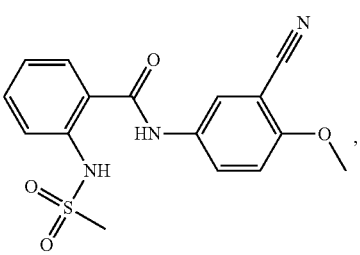
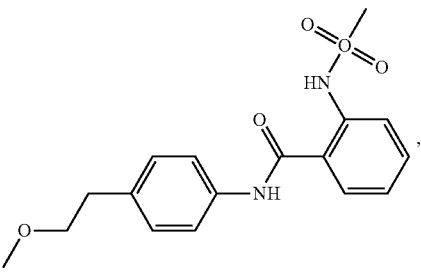
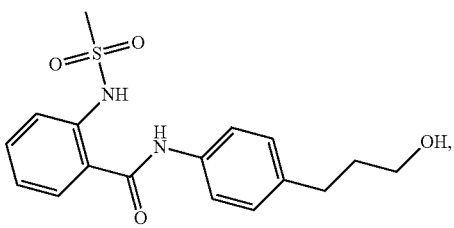
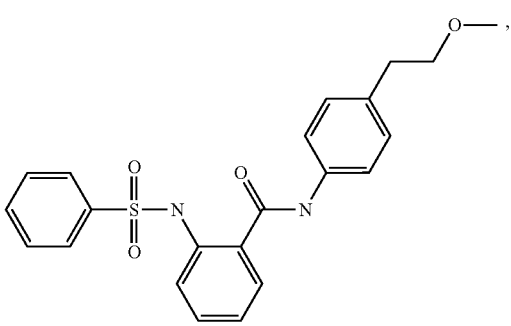

171
-continued

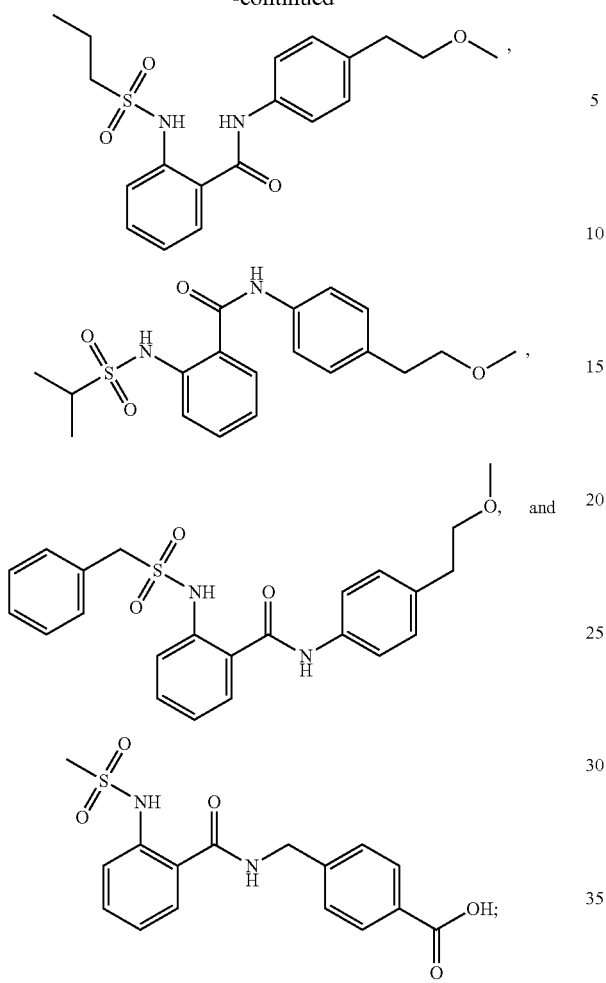

or a pharmaceutically acceptable salt, solvate, polymorph, prodrug, ester, metabolite, N-oxide, stereoisomer, or isomer thereof.

In some embodiments described above or below of a compound of Formula III, the compound is selected from:

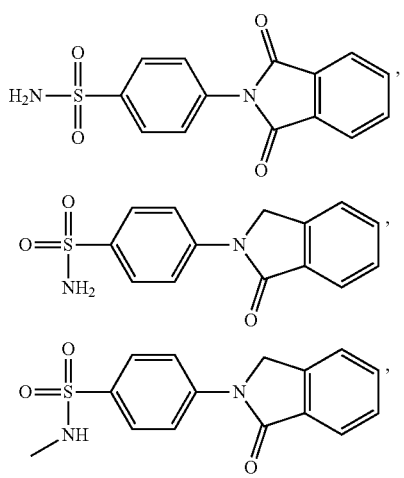

172
-continued

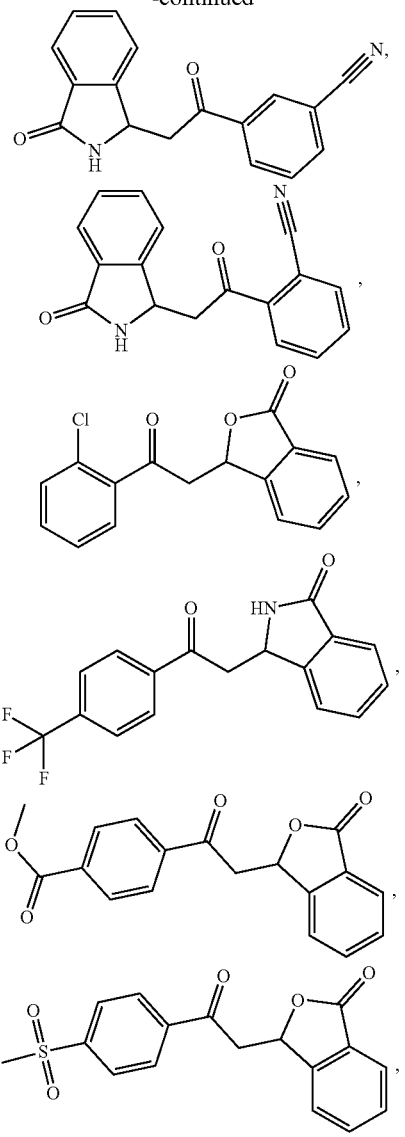

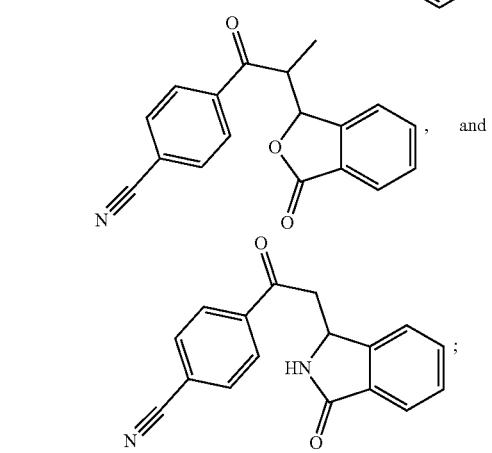

or a pharmaceutically acceptable salt, solvate, polymorph, prodrug, ester, metabolite, N-oxide, stereoisomer, or isomer thereof.

In one aspect, provided herein is a method of ameliorating arthritis or joint injury in a mammal, the method comprising administering to a joint of the mammal a composition comprising a therapeutically effective amount of a compound, or a pharmaceutically acceptable salt, solvate, polymorph, prodrug, ester, metabolite, N-oxide, stereoisomer, or isomer thereof, selected from:
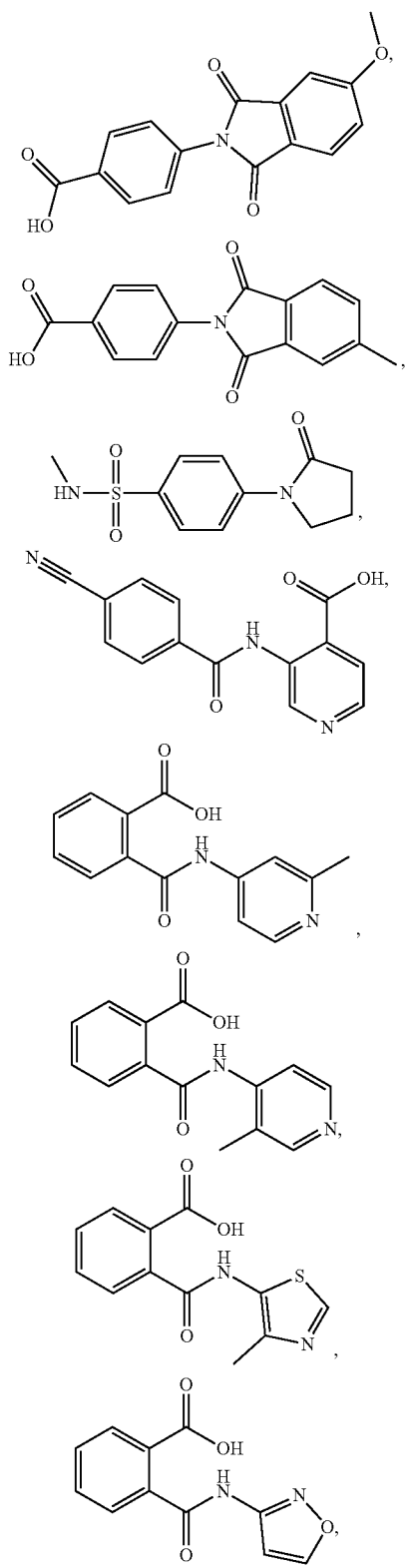
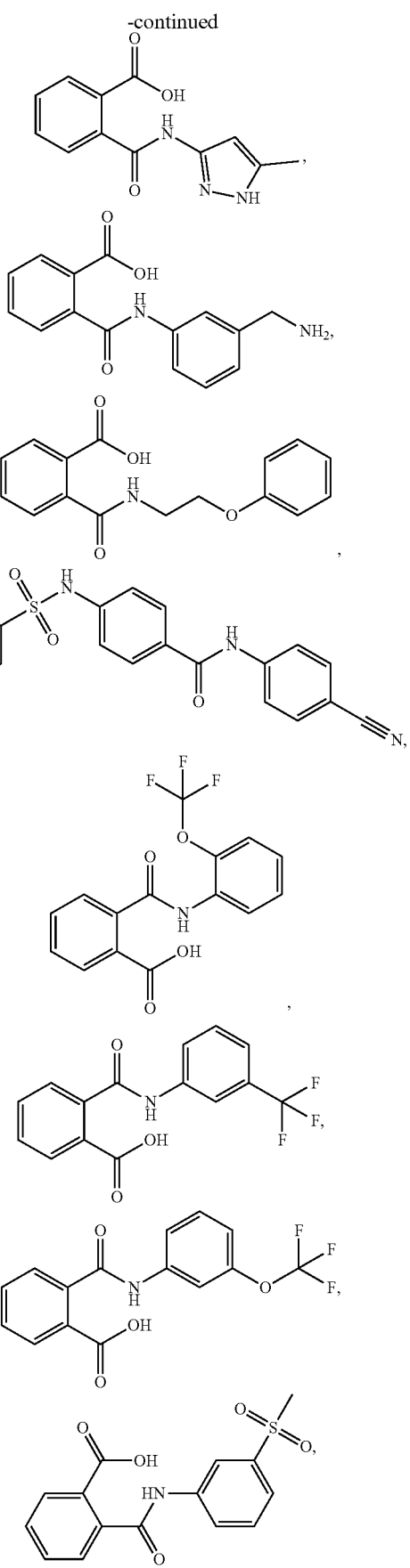

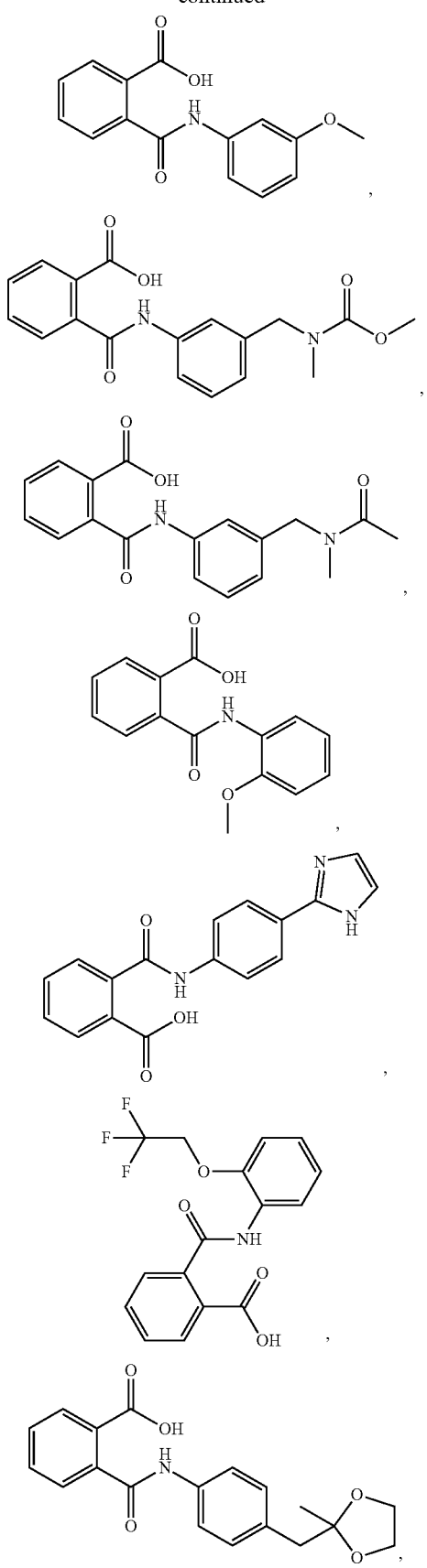

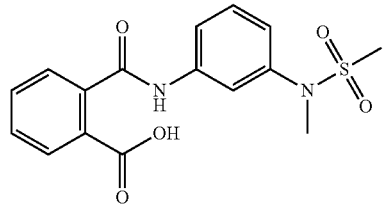

In another aspect, provided herein is a method of of inducing differentiation of mesenchymal stem cells into chondrocytes, the method comprising contacting mesenchymal stem cells with a sufficient amount of a compound, or a pharmaceutically acceptable salt, solvate, polymorph, prodrug, ester, metabolite, N-oxide, stereoisomer, or isomer thereof, selected from:

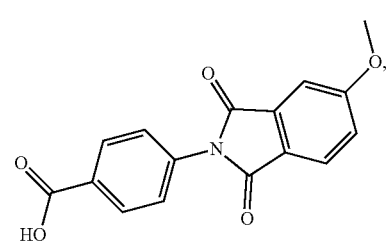

177
-continued
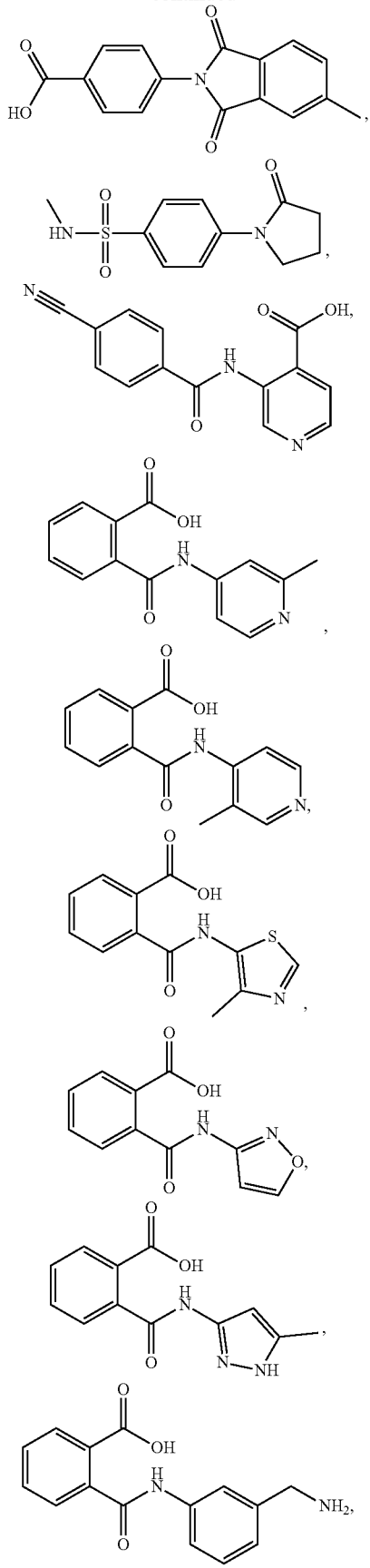
178
-continued
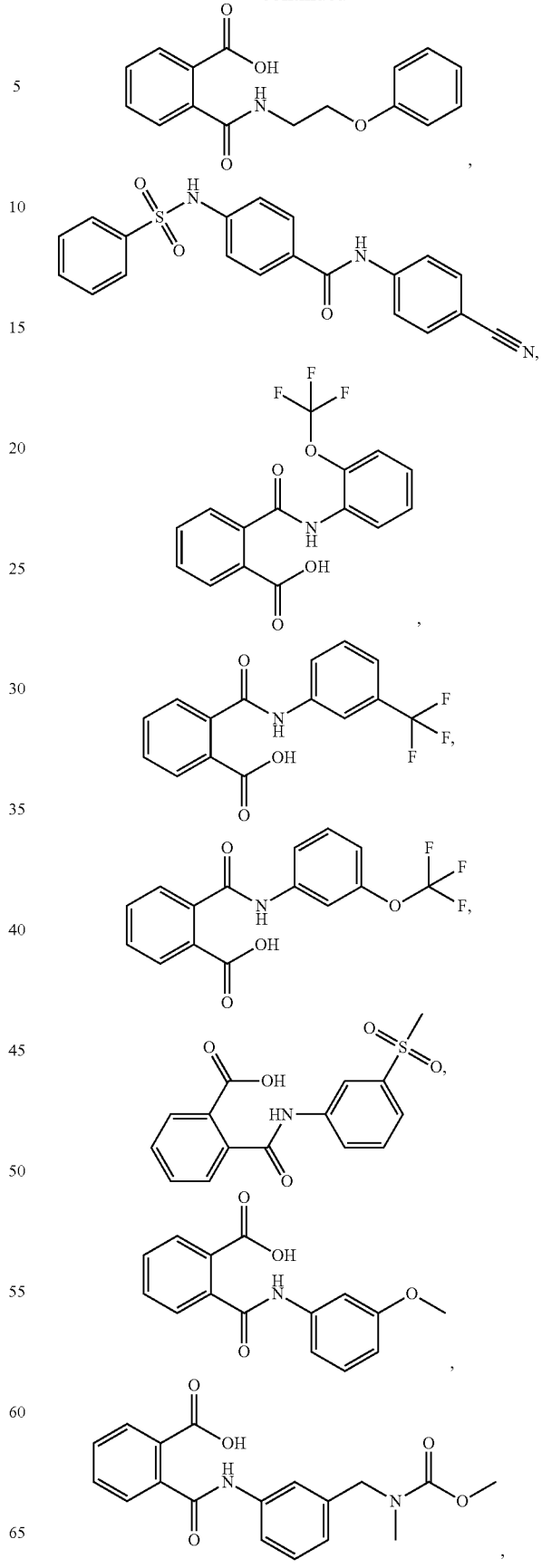

-continued

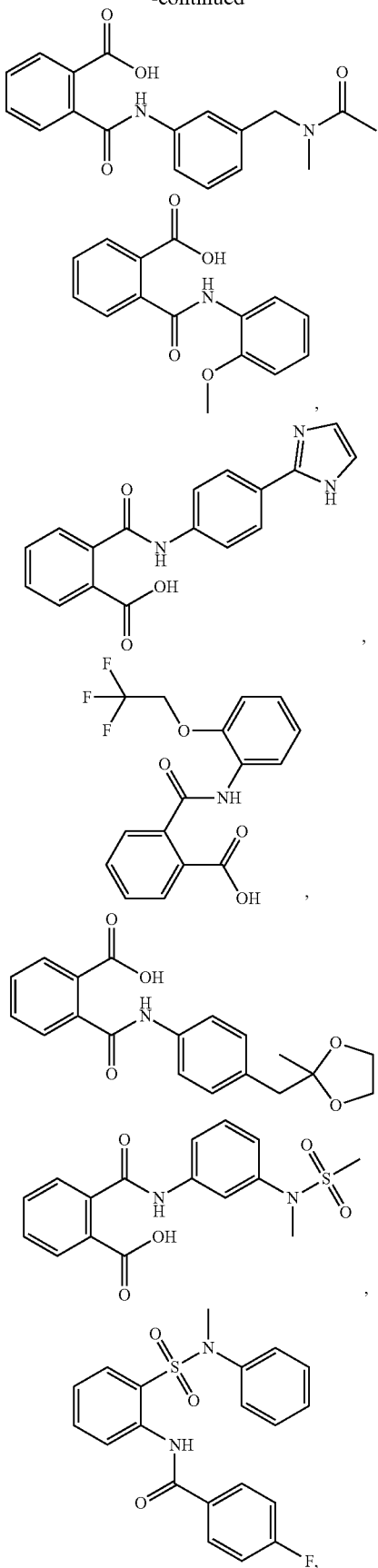

-continued

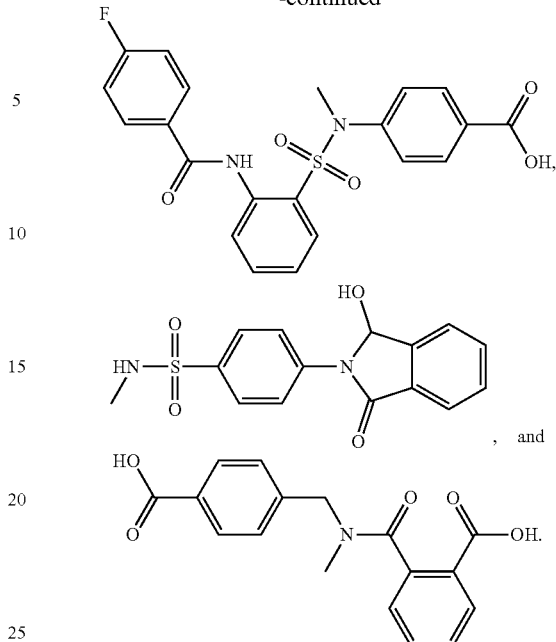

In some embodiments, the mammal does not have, but is at increased risk for, arthritis or joint injury.

It is contemplated that the compounds, compositions, and methods of the present invention may be used to ameliorate any type of arthritis or joint injury. It is further contemplated that the compounds, compositions, and methods of the present invention may be used to ameliorate various cartilagenous disorders. In some embodiments, the compounds and compositions of the present invention are administered to prevent arthritis or joint injury, for example where there is a genetic or family history of arthritis or joint injury or prior or during joint surgery or other circumstances where there is an increased risk of arthritis or joint injury. Exemplary conditions or disorders to be treated or prevented with the compounds, compositions, and methods of the invention, include, but are not limited to systemic rheumatoid arthritis, juvenile chronic arthritis, osteoarthritis, degenerative disc disease, spondyloarthropathies, and systemic sclerosis (scleroderma). In some embodiments of the invention, the compounds, compositions, and methods of the present invention may be used to treat osteoarthritis. In some embodiments, the arthritis can be osteoarthritis, trauma arthritis, degenerative disc disease, dupuytren disease, or tendon disease.

In some embodiments, the compounds, compositions, and methods of the present invention provide a method for stimulating chondrocyte proliferation and cartilage production in cartilagenous tissues that have been damaged due to traumatic injury or chondropathy. Traumatic injury can include, but is not limited to, blunt trauma to the joint, or damage to ligaments such as tearing the anterior cruciate ligament, medial collateral ligament, or a meniscal tear. Examples of tissues that exhibit articulated surfaces, and thus are particularly susceptible to treatment include, but are not limited to, spine, shoulder, elbow, wrist, joints of the fingers, hip, knee, ankle, and the joints of the feet. Examples of diseases that may benefit from treatment include osteoarthritis, rheumatoid arthritis, other autoimmune diseases, or osteochondritis dessicans. In addition, cartilage malformation is often seen in forms of dwarfism in humans suggesting that the compounds, compositions, and methods would be useful in these patients.

It is contemplated that the compounds, compositions, and methods of the present invention may be used to treat a mammal. As used herein a "mammal" refers to any mammal classified as a mammal, including humans, domestic and farm animals, and zoo, sports or pet animals, such as cattle (e.g. cows), horses, dogs, sheep, pigs, rabbits, goats, cats, etc. In some embodiments, the mammal can be a human, a dog, a cat, or a horse. In some embodiments of the invention, the mammal is a human. In some embodiments, the mammal is a dog, a cat, or a horse. In some embodiments, the mammal is cattle, sheep, pig, goat, or rabbit. In some embodiments, the mammal is a domesticated animal or livestock. In further embodiments, the domesticated animal or livestock is a dog, cat, or horse. In some embodiments, the mammal is a companion animal. As used herein, "companion animal" refers to dog, cat, rodent, and rabbit. In some embodiments, the mammal is a companion animal or livestock. In some embodiments, the mammal is livestock.

The compounds of the present invention are also useful for inducing differentiation of mesenchymal stem cells (MSCs) into chondrocytes. In some embodiments, the present invention provides a method of inducing differentiation of mesenchymal stem cells into chondrocytes, the method including contacting mesenchymal stem cells with a sufficient amount of a compound of the present invention, thereby inducing differentiation of the stem cells into chondrocytes.

MSCs are multipotent stem cells that can differentiate into several different types of cells including, but not limited to, osteoblasts, chondrocytes and adipocytes. Differentiation is the process by which a specialized cell type is formed from a less specialized cell type, for example, a chondrocyte from a MSC. In some embodiments, the method is performed in vitro. In some embodiments, the method is performed in vivo in a mammal and the stem cells are present in the mammal. In certain embodiments, the mammal is a human, a dog, a cat, or a horse. In certain embodiments, the mammal is a human. In certain embodiments, the mammal is a dog, a cat, or a horse.

Inducing differentiation of MSCs into chondrocytes can be accomplished using any suitable amount of a compound of the present invention. In some embodiments, the compound of the present invention can be present in an amount from about 0.1 mg to about 10000 mg, e.g., 1.0 mg to 1000 mg, e.g., 10 mg to 500 mg, according to the particular application and potency of the active component. In some embodiments, the compound of the present invention can be present in a concentration of 0.1 µM-100 µM in an intra-articular injection to the knee.

Assays for Identifying Compounds

The compounds of the present invention were identified using a variety of assays. The initial screen identified compounds that stimulated human mesenchymal stem cells (hMSCs) to develop into chondrocyte nodules. Additional assays were performed to determine toxicity and specificity of chondrocyte differentiation.

Compounds

Described herein are compounds that induce differentiation of mesenchymal stem cells into chondrocytes. In some embodiments, the compounds described herein ameliorate arthritis or joint injury in a mammal. In some embodiments, the compounds described herein treat arthritis or joint injury in a mammal.

In one aspect, provided herein are compounds of Formula I, or pharmaceutically acceptable salts, solvates, polymorphs, prodrugs, esters, metabolites, N-oxides, stereoisomers, or isomers thereof.

In another aspect, provided herein are compounds of Formula Ia, or pharmaceutically acceptable salts, solvates, polymorphs, prodrugs, esters, metabolites, N-oxides, stereoisomers, or isomers thereof.

In another aspect, provided herein are compounds of Formula Ib, or pharmaceutically acceptable salts, solvates, polymorphs, prodrugs, esters, metabolites, N-oxides, stereoisomers, or isomers thereof.

In another aspect, provided herein are compounds of Formula Ic, or pharmaceutically acceptable salts, solvates, polymorphs, prodrugs, esters, metabolites, N-oxides, stereoisomers, or isomers thereof.

In another aspect, provided herein are compounds of Formula II, or pharmaceutically acceptable salts, solvates, polymorphs, prodrugs, esters, metabolites, N-oxides, stereoisomers, or isomers thereof.

In another aspect, provided herein are compounds of Formula IIa, or pharmaceutically acceptable salts, solvates, polymorphs, prodrugs, esters, metabolites, N-oxides, stereoisomers, or isomers thereof.

In another aspect, provided herein are compounds of Formula IIb, or pharmaceutically acceptable salts, solvates, polymorphs, prodrugs, esters, metabolites, N-oxides, stereoisomers, or isomers thereof.

In another aspect, provided herein are compounds of Formula IIc, or pharmaceutically acceptable salts, solvates, polymorphs, prodrugs, esters, metabolites, N-oxides, stereoisomers, or isomers thereof.

In another aspect, provided herein are compounds of Formula III, or pharmaceutically acceptable salts, solvates, polymorphs, prodrugs, esters, metabolites, N-oxides, stereoisomers, or isomers thereof.

In another aspect, provided herein are compounds, or pharmaceutically acceptable salts, solvates, polymorphs, prodrugs, esters, metabolites, N-oxides, stereoisomers, or isomers thereof, selected from:

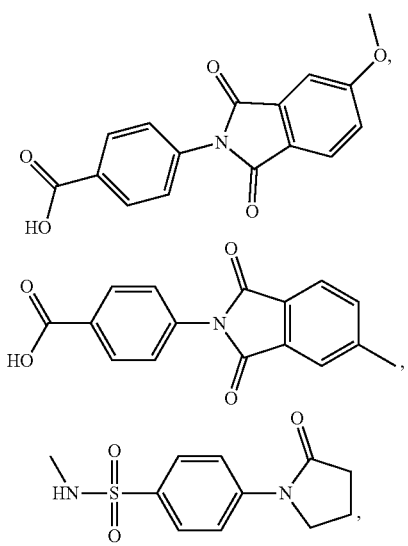

183
-continued
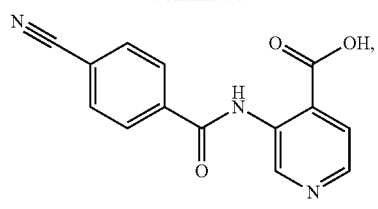
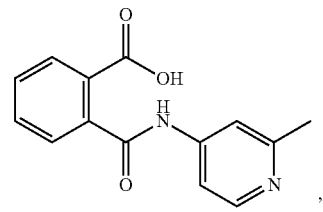
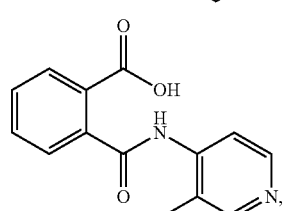
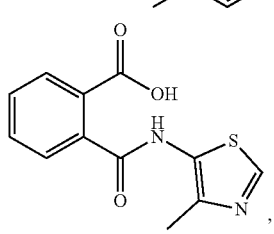
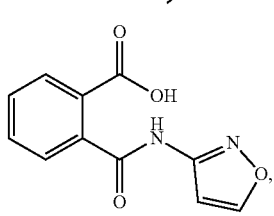
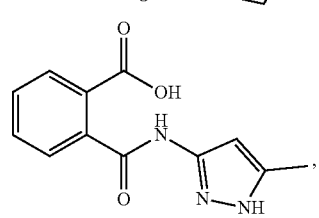
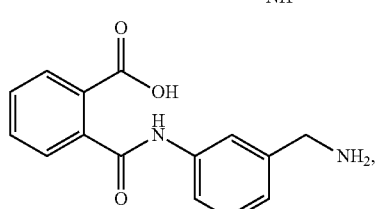
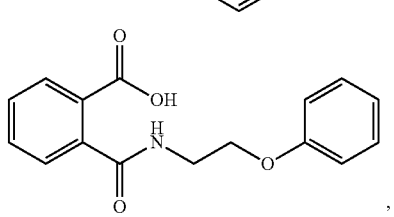
184
-continued
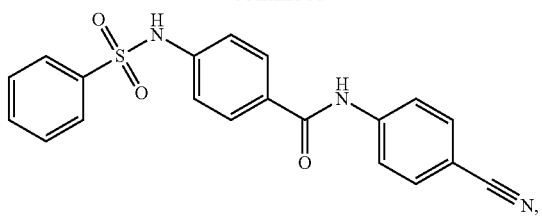
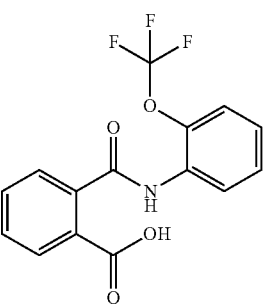
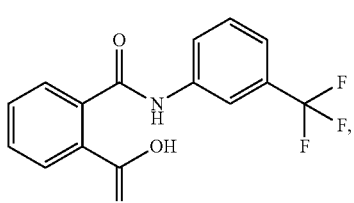
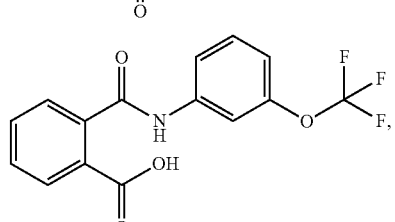
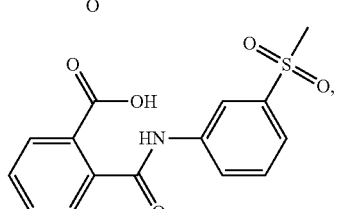
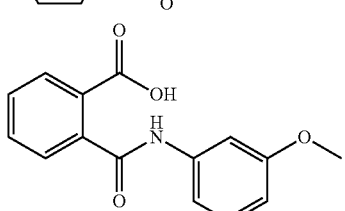
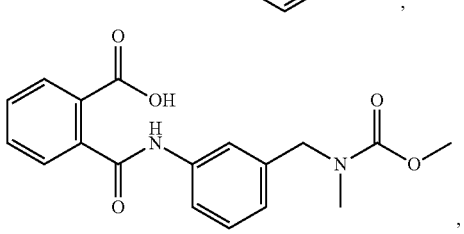

-continued

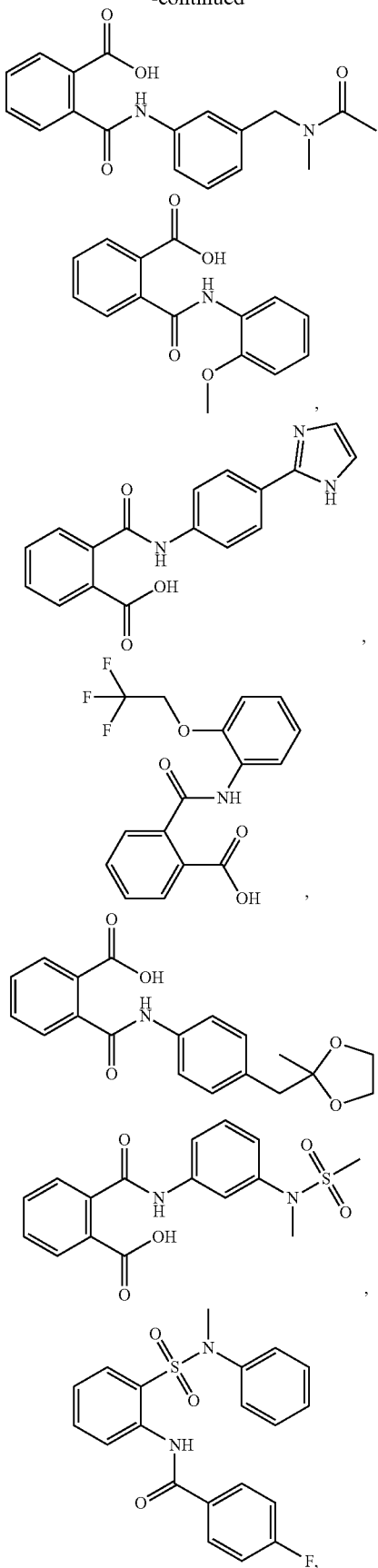

-continued

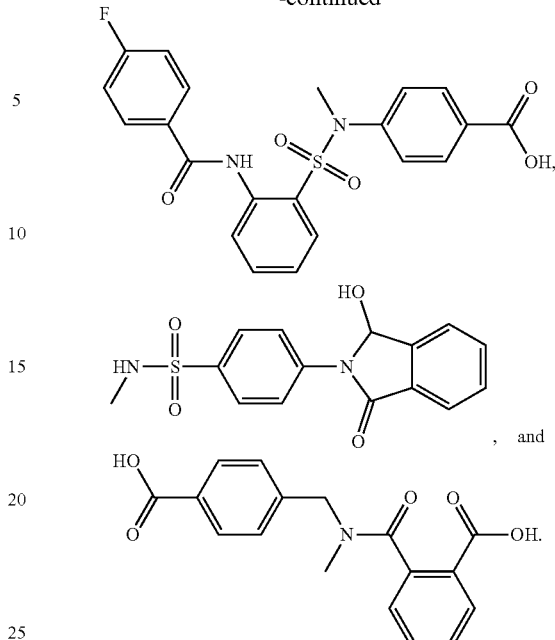

Preparation of Compounds

Described herein are compounds for inducing differentiation of mesenchymal stem cells into chondrocytes and for ameliorating arthritis or joint injury in a mammal, and processes for the preparation of these compounds. Also described herein are pharmaceutically acceptable salts, pharmaceutically acceptable solvates, pharmaceutically active metabolites, and pharmaceutically acceptable prodrugs of such compounds. Pharmaceutical compositions comprising at least one such compound or a pharmaceutically acceptable salt, pharmaceutically acceptable solvate, pharmaceutically active metabolite or pharmaceutically acceptable prodrug of such compound, and a pharmaceutically acceptable excipient are also provided.

Compounds described herein may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

Further Forms of Compounds Disclosed Herein

Isomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the metabolites, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds of the invention and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The invention provides for methods of treating diseases by administering such polymorphs. The invention further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

Prodrugs are generally drug precursors that, following administration to an individual and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. They are, for instance, bioavailable by oral administration whereas the parent is not. In certain instances, the prodrug also has improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety. (See for example Bundgaard, "Design and Application of Prodrugs" in *A Textbook of Drug Design and Development*, Krosgaard-Larsen and Bundgaard, Ed., 1991, Chapter 5, 113-191, which is incorporated herein by reference).

In some embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent.

In some embodiments, prodrugs are $C_1$-$C_6$ alkyl esters of the compounds disclosed herein.

Additionally, prodrug derivatives of compounds described herein can be prepared by methods described herein are otherwise known in the art (for further details see Saulnier et al., *Bioorganic and Medicinal Chemistry Letters*, 1994, 4, 1985). By way of example only, appropriate prodrugs can be prepared by reacting a non-derivatized compound with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are prodrugs for another derivative or active compound.

In some embodiments, prodrugs include compounds wherein an amino acid residue, or a polypeptide chain of two or more (e. g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e. g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Compounds having free amino, amido, hydroxy or carboxylic groups can be converted into prodrugs. For instance, free carboxyl groups can be derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

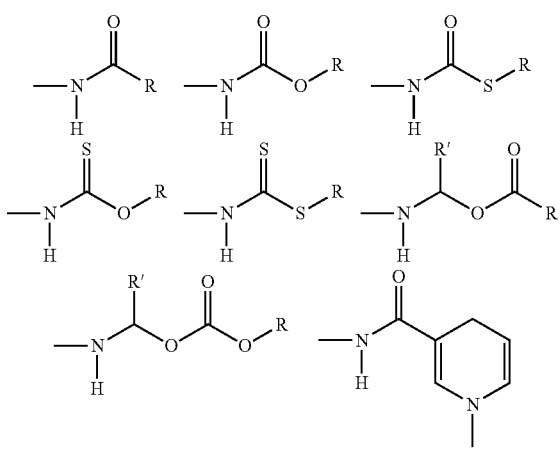

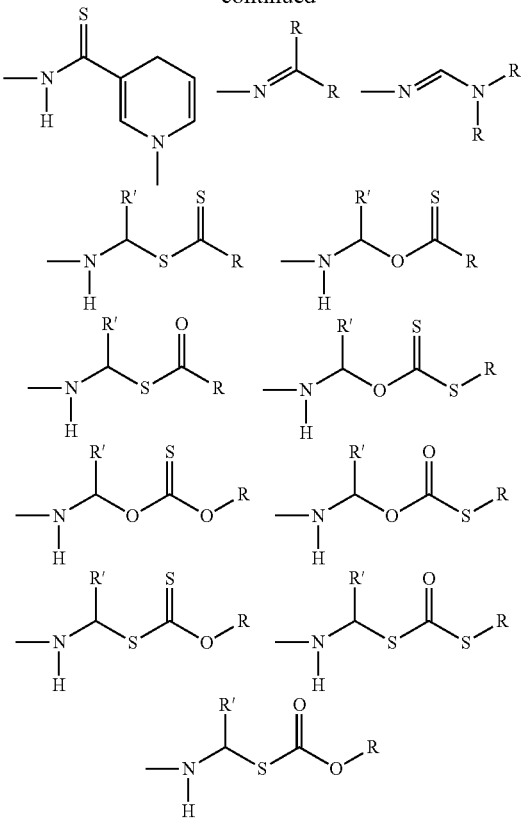

as well as sulfonamides and phosphonamides.

In certain instances, sites on any aromatic ring portions are susceptible to various metabolic reactions, therefore incorporation of appropriate substituents on the aromatic ring structures, can reduce, minimize or eliminate this metabolic pathway.

Metabolites

In some embodiments, compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen, or an alkyl group.

In additional or further embodiments, the compounds described herein are metabolized upon administration to an organism in need to produce a metabolite that is then used to produce a desired effect, including a desired therapeutic effect.

Pharmaceutical Compositions/Formulations

In another aspect, provided herein are pharmaceutical compositions comprising a compound described herein, or a pharmaceutically acceptable salt, polymorph, solvate, prodrug, N-oxide, or isomer thereof, and a pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound as described herein and at least one pharmaceutically acceptable inactive ingredient. In some embodiments, the compounds described herein are administered as pharmaceutical compositions in which a compound described herein is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound described herein with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human, a dog, a cat, or a horse. In some embodiments, the mammal is a human. In some embodiments, the mammal is a dog, a cat, or a horse. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular, intra-articular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including a compound described herein are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Combination Treatment

The compounds and compositions of the present invention can be used in combination with other components suitable for ameliorating arthritis or joint injury. In some embodiments, the composition can further comprise an additional compound which is therapeutically effective for the treatment of arthritis or joint injury and/or the symptoms associated with arthritis or joint injury in a mammal. In some embodiments, the composition can also include a non-steroidal anti-inflammatory drug (NSAID), an analgesic, a glucocorticoid, an angiopoietin-like 3 protein (ANGPTL3) or chondrogenic variant thereof, oral salmon calcitonin, SD-6010 (iNOS inhibitor), vitamin D3 (choliecalciferol), collagen hydrolyzate, FGF18, BMP7, avocado soy unsaponifiables (ASU) or hyaluronic acid. ANGPTL3 is described in more detail in WO2011/008773 (incorporated herein in its entirety). In some embodiments, the composition includes an agent with anti-inflammatory activity. In some embodiments, the composition includes an apoptosis modulator. In certain embodiments, the apoptosis modulator is a caspase inhibitor. One non-limiting example of an apoptosis/caspase inhibitor is emricasan. In some embodiments, the composition includes an iNOS inhibitor. One non-limiting example of an iNOS inhibitor is SD-6010.

NSAIDS include, but are not limited to, aspirin, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, nabumetone, diclofenac, piroxicam, meloxicam, tenoxicam, droxicam, lornoxicam, isoxicam, mefenamic acid, meclofenamic acid, flufenamic acid, tolfenamic acid, celecoxib, parecoxib, etoricoxib, lumiracoxib, and firocoxib.

Analgesics include, but are not limited to, acetaminophen and opioids (narcotics). Opioids include, but are not limited to, dextropropoxyphene, codeine, tramadol, tapentadol, anileridine, alphaprodine, pethidine, hydocodone, morphine, oxycodone, methadone, diamorphine, hydromorphone, oxymorphone, levorphanol, 7-hydroxymitragynine, buprenorphine, fentanyl, sufentanil, bromadol, etorphine, dihydroetorphine, and carfentanil.

Glucocorticoids include, but are not limited to, hydrocortisone, cortisone, prednisone, prednisolone, methylprednisolone, dexamethasone, betamethasone, triamcinolone, beclometasone, or fludrocortisones.

The compounds described herein may be used in combination with one or more compounds which are therapeutically effective for the treatment of arthritis or joint injury and/or the symptoms associated with arthritis or joint injury. Such additional compounds may be administered, by a route and in an amount commonly used therefore, contemporaneously or sequentially with a compound disclosed herein. When a compound disclosed herein is used contemporaneously with one or more such additional compounds, a pharmaceutical composition in unit dosage form containing such other drugs and the compound of the present invention is preferred. However, the combination therapy may also include therapies in which the compound disclosed herein and one or more additional compounds are administered on different overlapping schedules. It is also contemplated that when used in combination with one or more additional compounds, the compounds may be used in lower doses than when each is used singly.

The above combinations include combinations of a compound disclosed herein not only with one compound which is therapeutically effective for the treatment of arthritis or joint injury and/or the symptoms associated with arthritis or joint injury, but also with two or more such compounds. Likewise, compounds disclosed herein, either in combination with a compound which is therapeutically effective for the treatment of arthritis or joint injury and/or the symptoms associated with arthritis or joint injury or by themselves, may be used in combination with other drugs that are used in the prevention, treatment, control, or amelioration of osteoarthritis or joint injury or conditions associated with osteoarthritis or joint injury. Such other drugs may be administered, by a route and in an amount commonly used therefore, contemporaneously or sequentially with a compound disclosed herein. When a compound disclosed herein is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound disclosed herein. The weight ratio of the compound disclosed herein to the second active ingredient may be varied and will depend upon the effective dose of each ingredient. Generally, an effective dose of each will be used.

Administration of Pharmaceutical Composition

Suitable routes of administration include, but are not limited to, oral, intravenous, intra-articular, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, intra-articular, and intranasal injections.

In some embodiments, compounds disclosed herein and compositions thereof are administered in any suitable manner. The manner of administration can be chosen based on, for example, whether local or systemic treatment is desired, and on the area to be treated. For example, the compositions can be administered orally, parenterally (e.g., intravenous, subcutaneous, intraperitoneal, intra-articular, or intramuscular injection), by inhalation, extracorporeally, topically (including transdermally, ophthalmically, vaginally, rectally, intranasally) or the like. In some embodiments, the compositions can be administered by microneedle. In some embodiments, the compositions can be administered by a microneedle array in the form of a patch which can perform intracutaneous drug delivery. In some embodiments, the compositions can be administered by transdermal microneedle patch delivery.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
BOP benzotriazol-1-yl-oxytris (dimethylamino) phosphonium
t-Bu tert-butyl
Cbz benzyl carbamate
Cy Cyclohexyl
DBU 1,8-Diazabicyclo[5.4.0]undec-7-ene
DCC dicyclohexylcarbodiimide
DCM dichloromethane ($CH_2Cl_2$)
DIC 1,3-diisopropylcarbodiimide
DEAD diethyl azodicarboxylate
DIAD diisopropyl azodicarboxylate
DIPEA diisopropylethylamine
DMAP 4-(N,N-dimethylamino)pyridine DMP reagent Dess-Martin Periodinane reagent
DMF dimethylformamide
DMA N,N-Dimethylacetamide
DME 1,2-Dimethoxy-ethane
DMSO dimethylsulfoxide
Dppf 1,1'-Bis(diphenylphosphino)ferrocene
EDCI 1-ethyl-3-(3-dimethylaminopropyl) carbodiimide HCl
eq equivalent(s)
Et ethyl
$Et_2O$ diethyl ether
EtOH ethanol
EtOAc ethyl acetate
HOAt 1-hydroxy-7-azabenzotriazole
HOBT 1-hydroxybenztriazole
HOSu N-hydroxysuccinamide
HPLC high performance liquid chromatography
LAH lithium aluminum anhydride
Me methyl
MeI methyliodide
MeOH methanol
MOMCl methoxymethylchloride
MOM methoxymethyl
MS mass spectroscopy
NMP N-methyl-pyrrolidin-2-one
NMR nuclear magnetic resonance
PyBOP benzotriazole-1-yl-oxytris-pyrrolidino-phosphonium Hexafluorophosphate
SPHOS 2-Dicyclohexylphosphino-2',6'-dimethoxybiphenyl
TBD 1,5,7-triazabicyclo[4.4.0]-dec-5-ene
RP-HPLC reverse phase-high pressure liquid chromatography
TBS tert-butyldimethylsilyl
TBSCl tert-butyldimethylsilyl chloride
TBTU O-(Benzotriazol-1-yl)-N,N,N',N'-tetramethyluronium
TEOC 2-Trimethylsilylethyl Carbamate
TFA trifluoroacetic acid
$Tf_2O$ triflate anhydride
TMG 1,1,3,3-Tetramethylguanidine
THF tetrahydrofuran
THP tetrahydropyran
TLC thin layer chromatography
XPHOS 2-Dicyclohexylphosphino-2',4',6'-triisopropylbiphenyl General Examples for the Preparation of Compounds of the Invention The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). Details of reagent and reaction options are also available by structure and reaction searches using commercial computer search engines such as Scifinder (www.cas.org) or Reaxys (www.reaxys.com).

Synthetic Examples

The following preparations of compounds disclosed herein and intermediates are given to enable those of skill in the art to more clearly understand and to practice the present invention. They should not be considered as limiting the scope of the invention, but merely as illustrative and representative thereof.

Synthetic Scheme A: Sample Experimental for compound #1

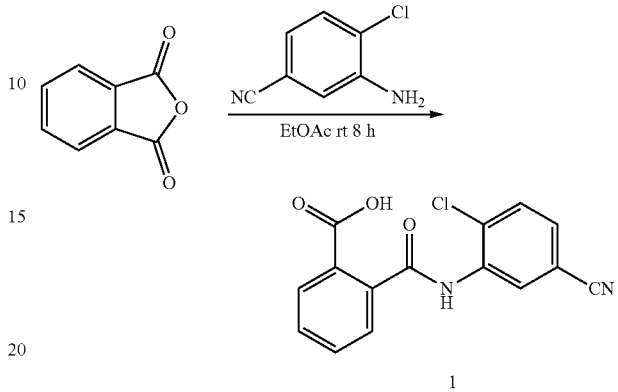

To a solution of phthalic anhydride (1.0 eq) in EtOAc was added 3-amino-4-chlorobenzonitrile (1 eq), then was stirred for 1-8 h at 20-30° C. TLC indicated starting material had disappeared. The reaction mixture was filtered and the solid was purified by recrystallization in EtOAc to afford compound 1 (12 mg). Final product 1 was confirmed by $^1$H NMR and LCMS. LCMS: Found 301.0 [M+H]. $^1$H NMR (400 MHz, MeOD-$d_4$): 8.35 (s, 1H), 8.09 (d, J=7.7 Hz, 1H), 7.71 (dd, J=8.0, 4.1 Hz, 1H), 7.67 (d, J=8.4 Hz, 1H), 7.61 (t, J=7.4 Hz. 2H), 7.57 (dd, J=8.4, 2.0 Hz, 1H).

Select compounds in Table 1 were obtained using analogous conditions as the reaction scheme given above, substituting 3-amino-4-chlorobenzonitrile with the appropriate aniline or amine. Reaction yields based on isolated products ranged from 20% to 80%.

Synthetic Scheme B-1: Sample Experimental for compound #15

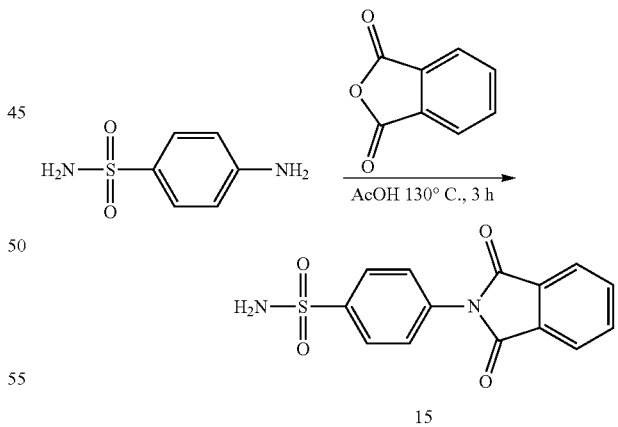

To a solution of 4-aminobenzenesulfonamide (100 mg, 0.58 mmol) in AcOH (20 mL), phthalic anhydride (82 mg, 0.55 mmol) was added. The mixture was stirred at 130° C. for 3 h. The mixture was diluted with $H_2O$ (30 mL) and stirred for 2 h. After filtration to get compound 15 (44 mg, yield: 26%) as a white solid. Final product 15 was confirmed by $^1$H NMR and LCMS. LCMS: Found 303.0 [M+H]. $^1$H NMR (400 MHz, DMSO-$d_6$): 7.10-7.36 (m, 6H), 6.56-6.70 (m, 2H), 6.62 (br s, 2H).

Select compounds in Table 1 were obtained using analogous conditions as the reaction scheme given above, substituting 4-aminobenzenesulfonamide with the appropriate aniline. In the case of compound 33, reaction time was 3 h and the reaction mixture was diluted with H₂O and stirred for 12 h for crystallization.

Synthetic Scheme B-2: Sample Experimental for compound #26

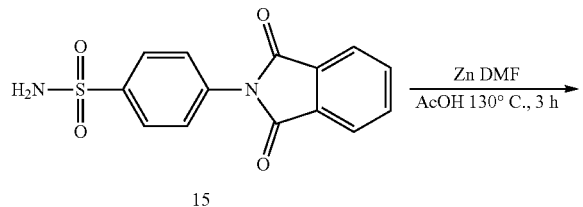

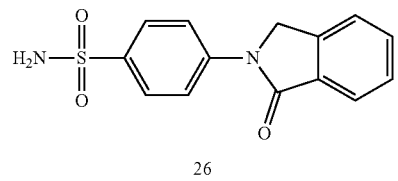

To a solution of compound 15 (276 mg, 0.913 mmol) in AcOH (5 mL), Zn (596.91 mg, 9.13 mmol) and DMF (0.1 mL) were added. The mixture was stirred at 130° C. for 3 h, then cooled to room temperature and concentrated to get the crude products as colorless oil. The residue was purified by prep-HPLC (0.1% TFA as additive), most CH₃CN was removed by evaporation under reduced pressure, and the remaining solvent was removed by lyophilization to afford compound 26 (80 mg, yield: 30%) as a white solid. LCMS: Found 289.1 [M+H].

Compound 27 (Table 1) was obtained using analogous conditions as the reaction scheme given above. In the preparation of compound 27, DMF was not used.

The starting material of product 27 was made by the following procedure.

Preparation of Compound 27-2

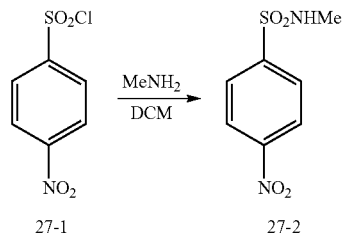

To a solution of compound 27-1 (3.8 g, 17 mmol) in DCM (50 ml), MeNH₂ (5.3 g, 51 mmol) in alcohol was added. The mixture was stirred at room temperature for 2 h. The mixture was diluted by DCM (30 ml) and washed with H₂O (30 ml). The organic layer was dried over anhydrous Na₂SO₄, filtered and concentrated to afford compound 27-2 (3.3 g, yield: 90%).

Preparation of Compound 27-3

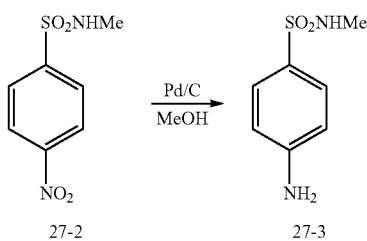

To a solution of compound 27-2 (3.3 g, 15.3 mol) in CH₃OH (50 mL) was added Pd/C (0.16 g) at room temperature. The mixture was stirred under H₂ (30 psi) at room temperature for 12 h. The mixture was filtered and the solvent was removed to give the compound 27-3 (2.3 g, yield: 80%) as a gray solid.

Preparation of Starting Material of Compound 27

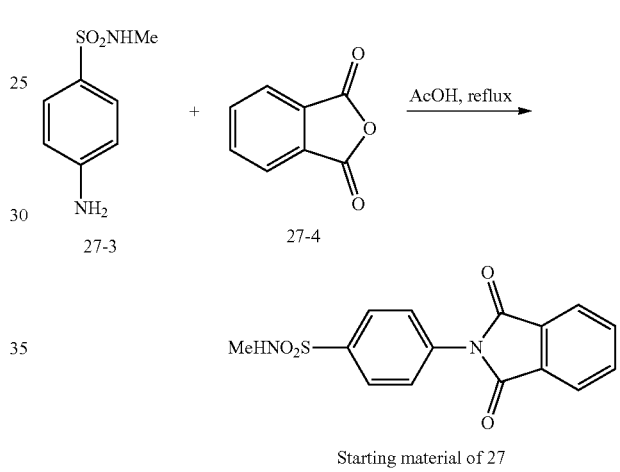

To a solution of 27-3 (0.5 g, 2.68 mmol) in AcOH (40 mL) was added 27-4 (0.433 g, 2.92 mmol). The reaction mixture was stirred at 130° C. for 3 h. The reaction mixture was cooled down, and the solvent was removed to afford crude product which was used directly in the next step.

Synthetic Scheme B-3: Sample Experimental for compound #117

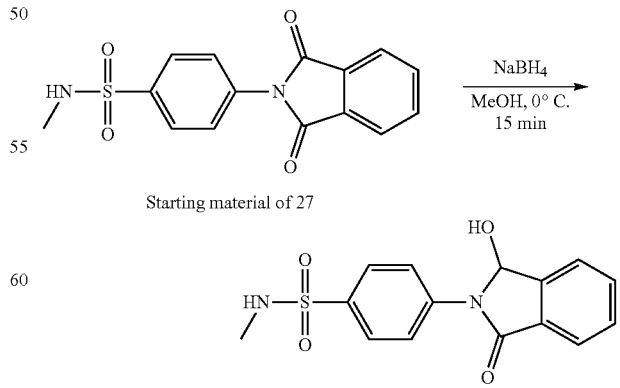

To a solution of the starting material for compound 27 (1.0 g, 3.16 mmol) in CH$_3$OH (20 mL) at 0° C. was added NaBH$_4$ (239 mg, 6.32 mmol). The mixture was stirred at 0° C. for 15 min before the solvent was removed under reduced pressure. Water (20 mL) and sat'd. aq. NH$_4$Cl (20 mL) was added to the crude residue. The mixture was stirred for 30 min at room temperature. Filtration provided compound 177 (840 mg, yield: 83%) as an off-white solid.

Synthetic Scheme C: General procedure for compounds C

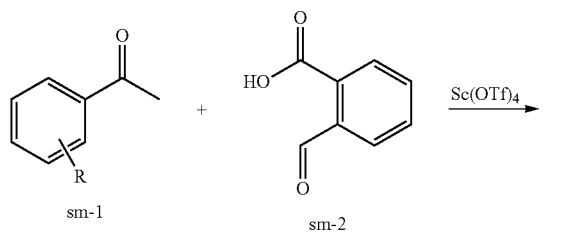

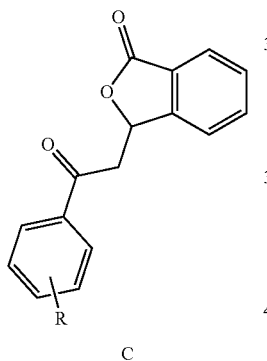

C

To a solution of ketone sm-1 (1.0 eq) in dioxane (V/M=10:1) was added carboxybenzaldehyde sm-2 (1.2 eq), followed by Sc(OTf)$_4$. The mixture heated to reflux for 12 h. Upon cooling to room temperature, the mixture was concentrated and purified by prep-HPLC to afford compound C.

Select compounds in Table 1 were obtained using Synthetic Scheme C. Reaction yields based on isolated products ranged from 5% to 50%.

Synthetic Scheme D: General procedure for compounds D

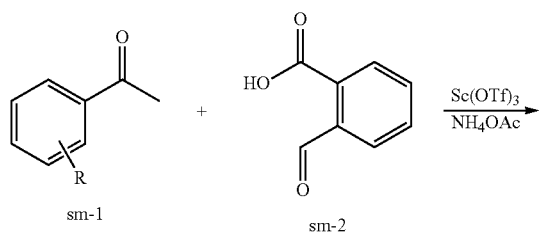

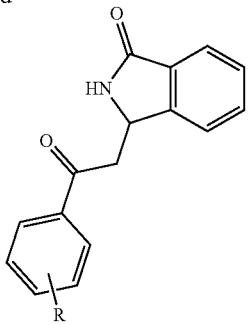

D

To a solution of ketone sm-1 (1.0 eq) in dioxane (V/M=15:1) was added carboxybenzaldehyde sm-2 (1.2 eq), followed by Sc(OTf)$_4$ (2 eq). The mixture was heated to reflux for 12 h. NH$_4$OAc (5 eq) was added, and the reaction mixture was heated to reflux for an additional 12 h. Upon cooling to room temperature, the mixture was concentrated and purified by prep-HPLC to afford compound D.

Select compounds in Table 1 were obtained using Synthetic Scheme D. Reaction yields based on isolated products ranged from 3% to 20%.

Synthetic Scheme E: General procedure for compounds E

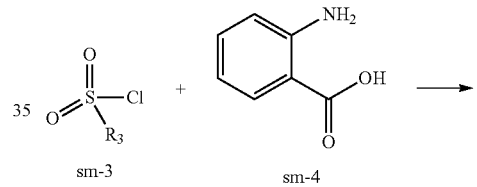

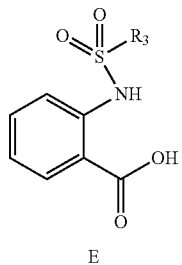

E

To a solution of 2-aminobenzoic acid sm-4 (1 eq) in 2 M NaHCO$_3$ (V=10 eq) was added sulfonyl chloride sm-3 (1.0 eq), and the mixture was stirred at room temperature for 2 h. TLC indicated starting material had disappeared. The mixture was extracted with EtOAc. The organic layer was dried over anhydrous Na$_2$SO$_4$, concentrated and purified by pre-HPLC to afford pure product E.

Compound 53 (Table 1) was obtained using Synthetic Scheme E. Reaction yields based on isolated product ranged from 60% to 80%.

Synthetic Scheme F: General procedure for compounds F

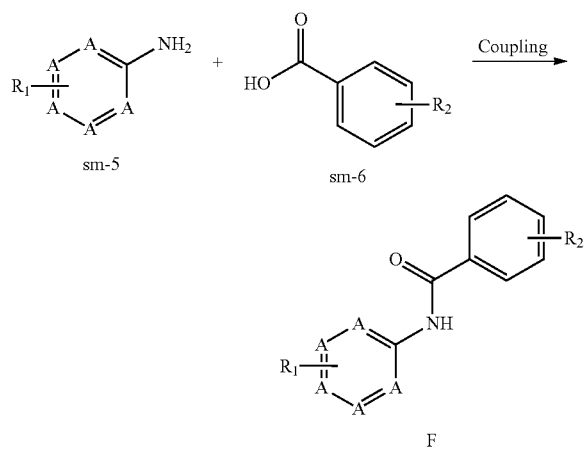

To a solution of benzoic acid sm-6 (1 eq) in DMF (10 eq) was added EDCI (1.5 eq) and HOBT (1.5 eq) at 0° C. prior to stirring at room temperature for about 2 h. Amine sm-5 (1.5 eq) was added to the reaction mixture, which was stirred at room temperature for an additional 12 h. Water was added, and the mixture was extracted with EtOAc, dried over anhydrous Na$_2$SO$_4$ and concentrated. The residue was purified by column chromatography to give the product F.

Select compounds in Table 1 were obtained using Synthetic Scheme F. Reaction yields based on isolated products ranged from 20% to 40%.

Synthetic Scheme G: Sample Experimental for compound #56

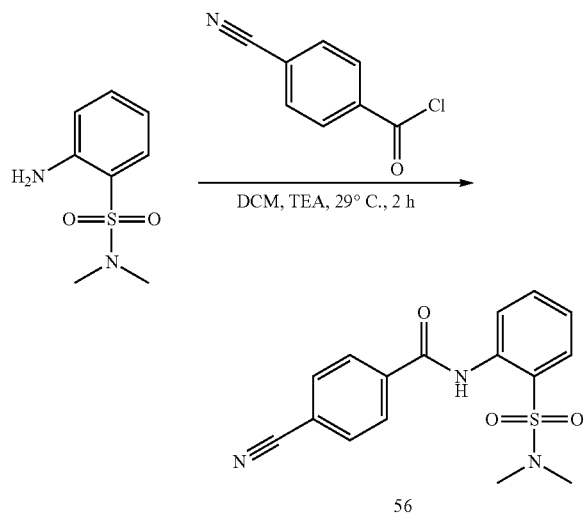

4-Cyanobenzoyl chloride (1.0 eq) was added to a solution of 2-amino-N,N-dimethylbenzenesulfonamide (1.0 eq) and TEA (1.5 eq) in DCM. The reaction mixture was stirred at 29° C. for about 2 h. TLC indicated starting material had disappeared. The reaction mixture was quenched with sat'd. aq. NaHCO$_3$, extracted with DCM, dried over anhydrous Na$_2$SO$_4$ and concentrated. The residue was purified by prep-HPLC to afford compound 56 (yield: 70%). LCMS: Found 330.1 [M+H].

Compound 62 (Table 1) was obtained using analogous conditions as the reaction scheme given above. Reaction yields based on isolated products ranged from 70% to 80%.

The requisite aniline starting material I of compounds 56 and 62 were made by the following procedure.

Preparation of Intermediates Sm-8

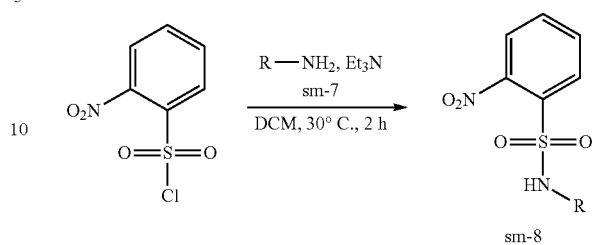

A solution of 2-nitrobenzene-1-sulfonyl chloride (1.0 eq) and amine sm-7 (1.0 eq) in DCM was stirred at 30° C. for about 2 h. TLC indicated starting material had disappeared. The reaction mixture was washed with brine, dried over anhydrous Na$_2$SO$_4$ and concentrated to afford intermediate sm-8 (yield: 72-91%).

Preparation of Aniline Starting Materials I

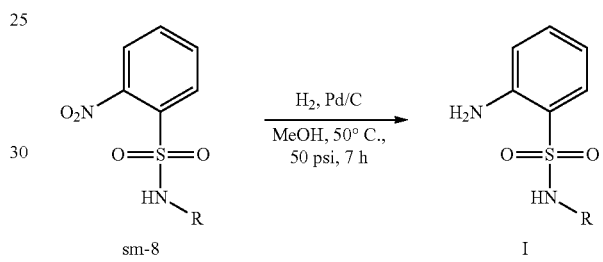

To a solution of intermediate sm-8 (1.0 eq) in MeOH was added Pd/C. The reaction mixture was stirred at 50° C. under 50 psi of H$_2$ for 7 h. TLC indicated starting material had disappeared. The mixture was filtered, and the filtrate was concentrated to afford compound I (yield: 89-91%).

Synthetic Scheme H: General procedure for compounds H

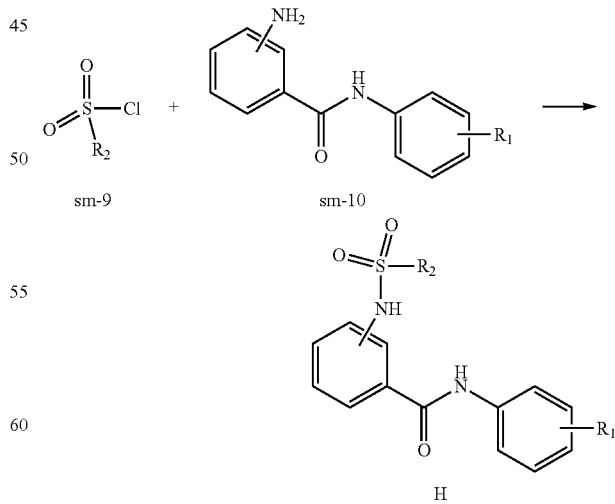

To a solution of amide sm-10 (1 eq) in THF (V=10 eq) was added dropwise LiHMDS(1 eq) at 0° C. After 30 min, sulfonyl chloride sm-9 (1.0 eq) was added, and the mixture was stirred at room temperature for 2 h. TLC indicated starting material had disappeared. The mixture was extracted with EtOAc. The organic layer was dried over anhydrous Na₂SO₄, concentrated and purified by pre-HPLC to afford compound H.

Select compounds in Table 1 were obtained using Synthetic Scheme H. Reaction yields based on isolated products ranged from 50% to 80%.

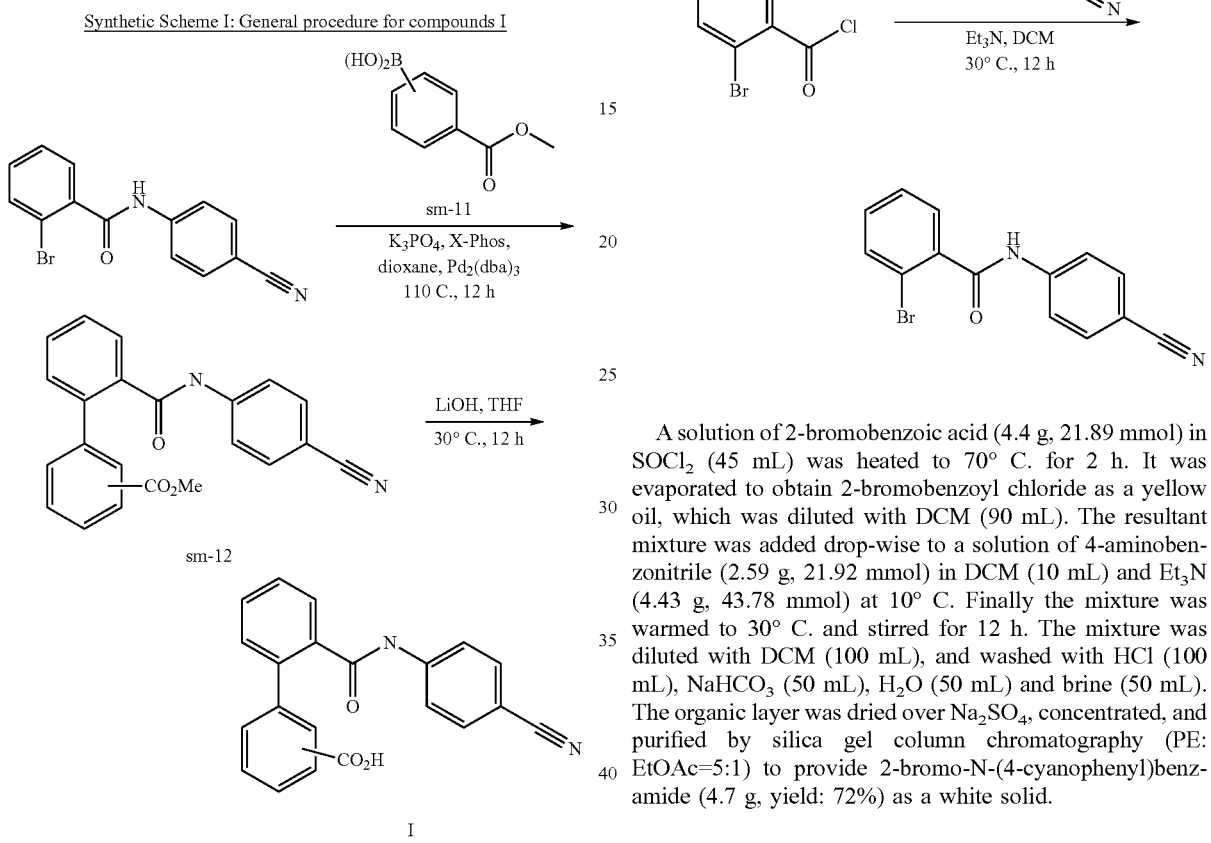

To a stirring mixture of 2-bromo-N-(4-cyanophenyl)benzamide (1.66 mmol) and boronic acid sm-11 (3.32 mmol) in dioxane (10 mL) was added K₃PO₄ (1.06 g, 4.98 mmol). Pd₂(dba)₃ (45.61 mg, 49.81 umol) and X-Phos (39.58 mg, 83.02 umol) were added under N₂. Finally the mixture was heated to 110° C. and stirred for 12 h. After filtration, the mixture was concentrated to give intermediate sm-12 as a brown oil. To a solution of sm-12 (770 mg, 2.16 mmol) in THF (30 mL) was added LiOH (4.32 mL, 4.32 mmol) drop-wise and stirred for 12 h. The solution was acidified to pH 4 at 10° C., extracted with EtOAc (30 mL), washed with H₂O (50 mL) and brine (50 mL), concentrated and purified by prep-HPLC (0.1% TFA as additive). Solvents were removed by evaporation under reduced pressure and lyophilization to afford compound I as a white solid.

Select compounds in Table 1 were obtained using Synthetic Scheme I. Reaction yields based on isolated products ranged from 15% to 30%.

2-Bromo-N-(4-cyanophenyl)benzamide was prepared by the following procedure.

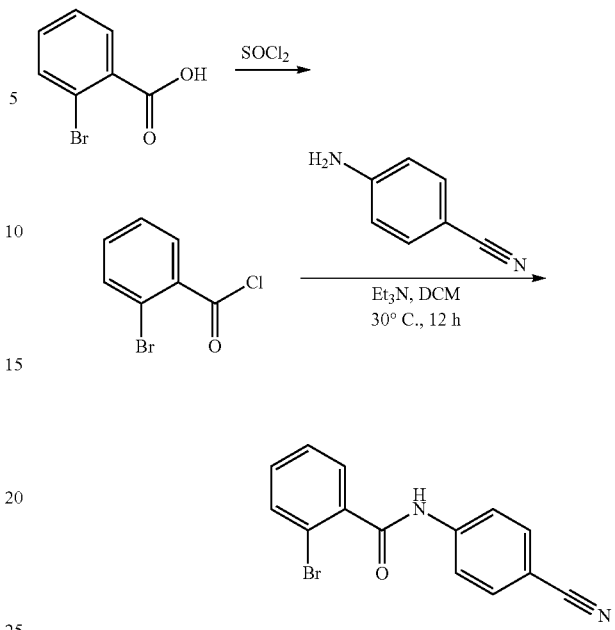

A solution of 2-bromobenzoic acid (4.4 g, 21.89 mmol) in SOCl₂ (45 mL) was heated to 70° C. for 2 h. It was evaporated to obtain 2-bromobenzoyl chloride as a yellow oil, which was diluted with DCM (90 mL). The resultant mixture was added drop-wise to a solution of 4-aminobenzonitrile (2.59 g, 21.92 mmol) in DCM (10 mL) and Et₃N (4.43 g, 43.78 mmol) at 10° C. Finally the mixture was warmed to 30° C. and stirred for 12 h. The mixture was diluted with DCM (100 mL), and washed with HCl (100 mL), NaHCO₃ (50 mL), H₂O (50 mL) and brine (50 mL). The organic layer was dried over Na₂SO₄, concentrated, and purified by silica gel column chromatography (PE:EtOAc=5:1) to provide 2-bromo-N-(4-cyanophenyl)benzamide (4.7 g, yield: 72%) as a white solid.

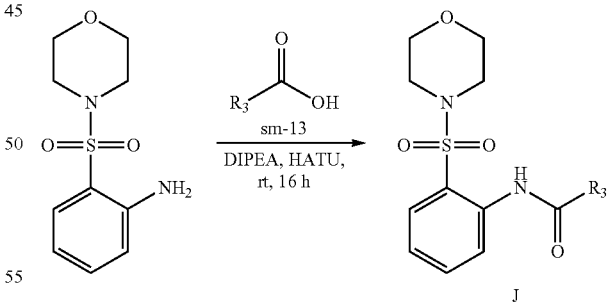

To a solution of 2-(morpholinosulfonyl)aniline (1.0 eq) in DMF was added carboxylic acid sm-13 (1.0 eq), DIPEA (1.5 eq) and HATU (1.3 eq). The resultant mixture was stirred at 10-15° C. for 16-24 h. TLC indicated starting material had disappeared. The reaction mixture was concentrated and the solid was purified by silica gel column chromatography to afford compound J.

Select compounds in Table 1 were obtained using Synthetic Scheme J.

Synthetic Scheme K-1: Sample Experimental for compound #193

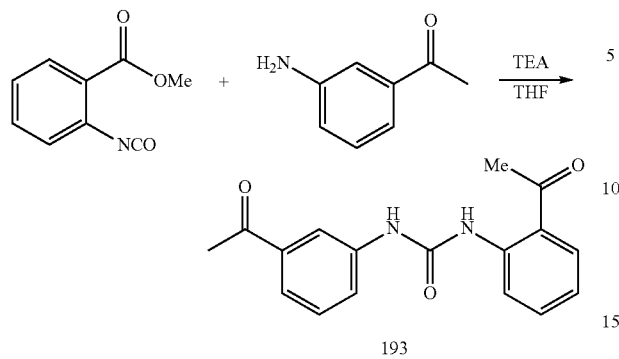

193

Methyl 2-isocyanatobenzoate (200 mg 1.13 mmol) and 1-(3-aminophenyl)ethanone (167 mg, 1.24 mmol) were dissolved in THF (2.5 ml) and heated using microwave heating at 100° C. for 15 min. The reaction mixture was washed with sat'd. aq. NaHCO$_3$ and purified via column chromatography (EtOAc:hexanes) to provide the final product 193 (262 mg, yield: 75%), which was confirmed by $^1$H NMR and LCMS.

Select compounds in Table 1 were obtained using analogous conditions as the reaction scheme given above. In these reactions, DIPEA was used instead of TEA and the temperature was increased to 120° C. Reaction yields based on isolated products ranged from 47-90%.

Synthetic Scheme K-2: Sample Experimental compound #196

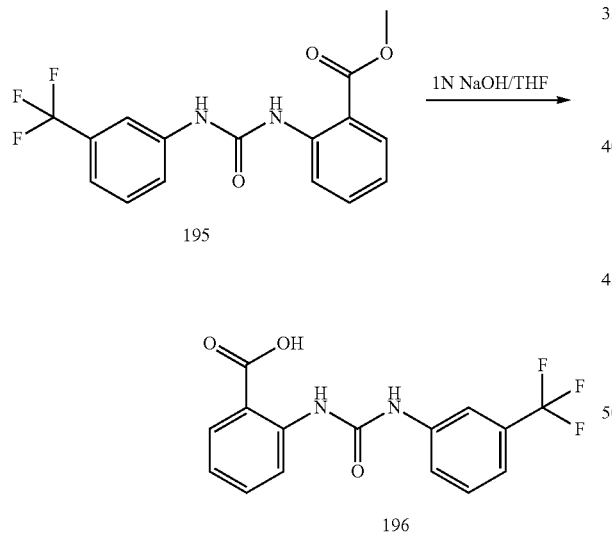

195

196

Compound 195 was dissolved in THF (2 mL) and 1 N NaOH (1 mL). The reaction mixture was stirred at room temperature for 15 h. The mixture was diluted with EtOAc (20 mL) prior to the drop-wise addition of 1 N HCl (3 mL) with constant stirring. The organic layer was extracted, dried, and concentrated. The crude product was recrystallized from EtOAc to provide compound 196 (25 mg).

Select compounds in Table 1 were obtained using analogous conditions as the reaction scheme given above. Reaction yields based on isolated products ranged from 80-90%.

Synthetic Scheme L: General procedure for compounds L

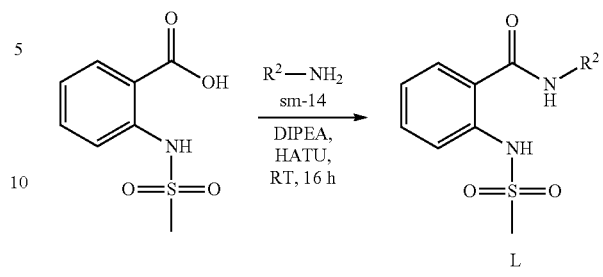

L

To a solution of 2-(methylsulfonamido)benzoic acid (1.0 eq) in DMF was added sm-14 (1.0 eq), DIPEA (1.5 eq) and HATU (1.3 eq). The mixture was stirred at 10-15° C. for 16-24 h. Upon reaction completion as indicated by TLC, the reaction mixture was concentrated, and the solid was purified by silica gel chromatography to afford compound L.

Select compounds in Table 1 were obtained using Synthetic Scheme L.

Synthetic Scheme for Compound 28

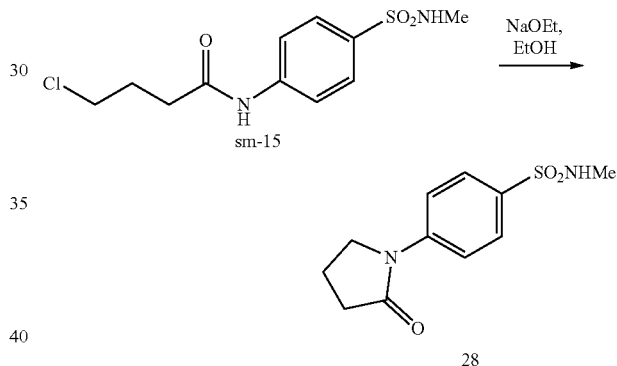

28

A solution of compound I (320 g, 1.1 mmol) in EtOH (10 mL) was added dropwisely NaOEt (571.6 mg, 8.4 mmol) at 0° C. for 3 h. The reaction was acidific with 1N HCl and removed the solvent to get the crude product. The residue was purified by pre-HPLC (0.1% TFA as additive), most CH$_3$CN was removed by evaporation under reduced pressure, and the remained solvent was removed by hyophilization to afford the compound 28 (17 mg, 6% yield) as white solid. LCMS: Found 255.0 [M+H]. $^1$H NMR (400 MHz, CDCl$_3$): 7.50-7.72 (m, 4H), 4.85 (br s, 1H), 3.90 (t, 2H, J=7.2 Hz), 2.53-2.72 (m, 5H), 2.14-2.28 (m, 2H).

The intermediate sm-15 was made by the following procedure.

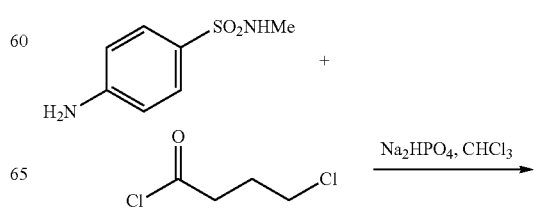

-continued

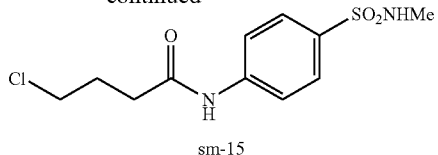

sm-15

To a solution of 4-amino-N-methylbenzenesulfonamide (200 mg, 1.1 mmol) and $Na_2HPO_4$ (300 mg, 2.2 mmol) in $CHCl_3$ (10 mL) was added 4-chlorobutanoyl chloride (151 mg, 1.1 mol) drop-wise at 0° C. After reagent addition, the mixture was allowed to stir at room temperature. The mixture was concentrated to give crude sm-15, which was used directly in the next step without further purification.

Synthetic Scheme for Compound 47

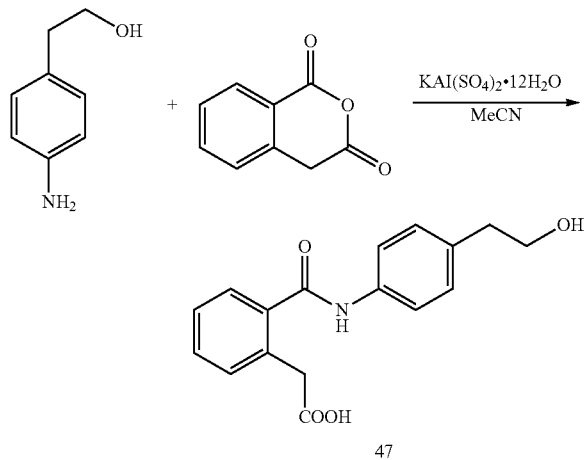

A solution of 2-(4-aminophenyl)ethanol (300 mg, 2.2 mmol), isochroman-1,3-dione (355 mg, 2.2 mmol) and $KAl(SO_4)_2 \cdot 12H_2O$ (522 mg, 11 mmol) in MeCN (10 mL) was stirred at room temperature for 1-1.5 h. The solvent was removed to obtain crude product. The residue was purified by prep-HPLC (0.1% TFA as additive). Solvents were removed by evaporation under reduced pressure and lyophilization to afford compound 47 (25 mg, 5.5% yield) as a white solid. LCMS: Found 300.1 [M+H].

BIOLOGICAL EXAMPLES

Example 1: Human Chondrocyte Differentiation Assay

Human MSCs (50,000) were plated into each well of a 96-well plate and cultured overnight. Compounds (in DMSO solution) were added to the cells at a final concentration of 1 μM, and the cells were cultured for 7 days at 5% $CO_2$, 37° C. The cells were fixed with 10% formalin solution at room temperature for 10 min, and immunostained using antibodies specific for type II collagen (Abcam), Sox9 (Santa Cruz) and cartilage oligomeric matrix protein (COMP, Santa Cruz), and fluorescently labeled secondary antibodies (Li-Cor). The total intensity of the staining was measured using Oddyssey CLx imaging system (Li-Cor). Vehicle (DMSO) was used as control to determine the basal level of chondrocyte differentiation. Compounds exhibiting 30% or higher increase in staining intensity compared to vehicle control were selected as active hits. Representative data are shown in Table 1 [A: >50% increase in staining intensity compared to vehicle control; B: 30-50% increase in staining intensity compared to vehicle control].

TABLE 1

| Cmpd # | Structure | Synthetic Scheme | Characterization Data (NMR and/or LCMS) | Biological Activity |
|---|---|---|---|---|
| 1 | 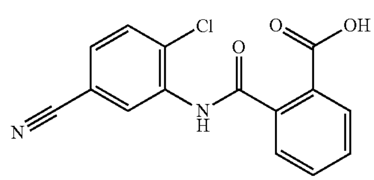 [SMILES: N#Cc1ccc(Cl)c(NC(=O)c2ccccc2C(=O)O)c1] | A | LCMS: Found 301.0 [M + H] | B |
| 2 | 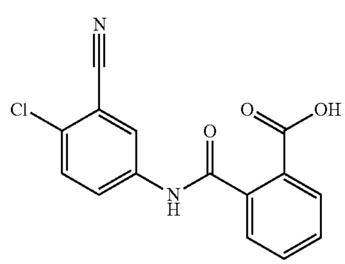 [SMILES: N#Cc1cc(NC(=O)c2ccccc2C(=O)O)ccc1Cl] | A | LCMS: Found 301.0 [M + H]<br>LCMS: Found: 323.0 [M + Na] | B |

TABLE 1-continued

| Cmpd # | Structure | Synthetic Scheme | Characterization Data (NMR and/or LCMS) | Biological Activity |
|---|---|---|---|---|
| 3 | 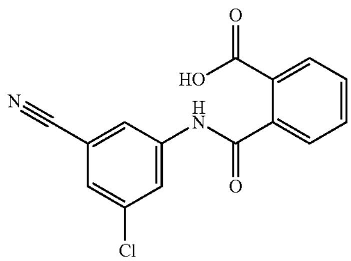 [SMILES: N#Cc1cc(Cl)cc(NC(=O)c2ccccc2C(=O)O)c1] | A | LCMS: Found 301.0 [M + H] | A |
| 4 | 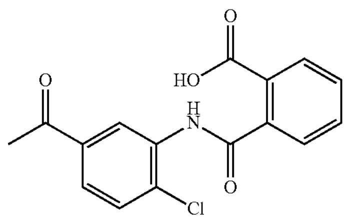 [SMILES: CC(=O)c1ccc(Cl)c(NC(=O)c2ccccc2C(=O)O)c1] | A | LCMS: Found 318.0 [M + H]<br>LCMS: Found 340.0 [M + Na] | A |
| 5 | 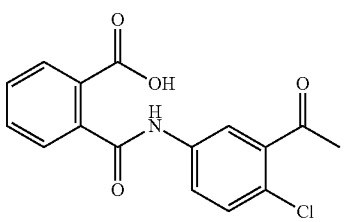 [SMILES: CC(=O)c1cc(NC(=O)c2ccccc2C(=O)O)ccc1Cl] | A | LCMS: Found 318.0 [M + H]<br>LCMS: Found 340.0 [M + Na] | B |
| 6 | 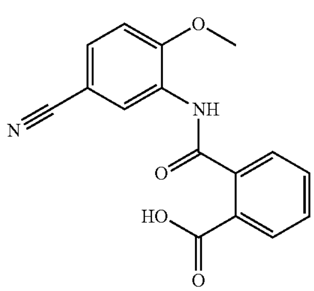 [SMILES: COc1ccc(C#N)cc1NC(=O)c1ccccc1C(=O)O] | A | LCMS: Found 297.0 [M + H]<br>LCMS: Found 615.2 [2M + Na] | A |
| 7 | 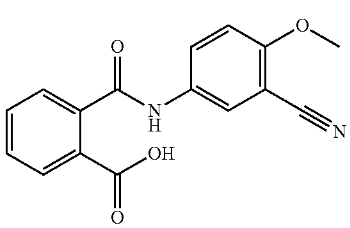 [SMILES: COc1ccc(NC(=O)c2ccccc2C(=O)O)cc1C#N] | A | LCMS: Found 297.0 [M + H]<br>LCMS: Found 615.2 [2M + Na] | A |
| 8 | 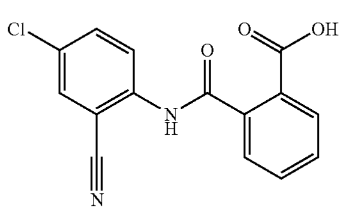 [SMILES: N#Cc1cc(Cl)ccc1NC(=O)c1ccccc1C(=O)O] | A | LCMS: Found 301.1 [M + H]<br>LCMS: Found 322.9 [M + Na]<br>$^1$H NMR (400 MHz, DMSO-$d_6$): 13.19 (S, 1H), 10.72 (S, 1H), 8.05 (D, J = 2.5 Hz, 1H), 7.94 (DD, J = 7.7, 1.3 Hz, 1H), 7.84 (DD, J = 8.8, 2.5 Hz, 1H), 7.72-7.55 (M, 4H) | B |

TABLE 1-continued

| Cmpd # | Structure | Synthetic Scheme | Characterization Data (NMR and/or LCMS) | Biological Activity |
|---|---|---|---|---|
| 9 | 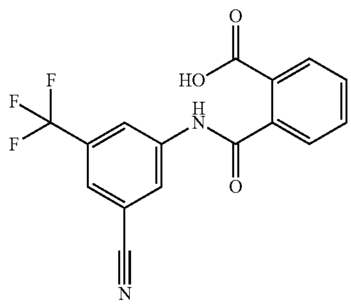 [SMILES: N#Cc1cc(NC(=O)c2ccccc2C(=O)O)cc(C(F)(F)F)c1] | A | LCMS: Found 335.0 [M + H]<br>LCMS: Found 691.0 [2M + Na]<br>LCMS: Found 357.0 [M + Na] | A |
| 10 | 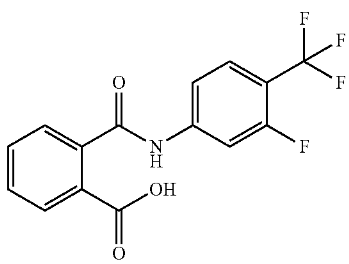 [SMILES: O=C(O)c1ccccc1C(=O)Nc1ccc(C(F)(F)F)c(F)c1] | A | LCMS: Found 328 [M + H]<br>LCMS: Found 350 [M + Na]<br>LCMS: Found 677 [2M + Na] | B |
| 11 | 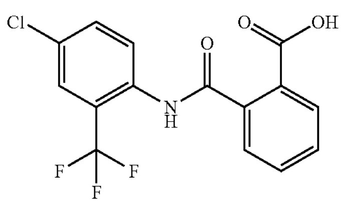 [SMILES: O=C(O)c1ccccc1C(=O)Nc1ccc(Cl)cc1C(F)(F)F] | A | LCMS: Found 344 [M + H]<br>LCMS: Found 366 [M + Na]<br>$^1$H NMR (400 MHz, DMSO-$d_6$): 13.19 (S, 1H), 10.19 (S, 1H), 7.93-7.86 (M, 3H), 7.71-7.58 (M, 4H) | B |
| 12 | 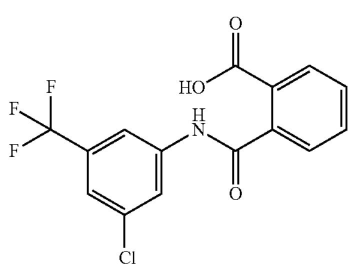 [SMILES: O=C(O)c1ccccc1C(=O)Nc1cc(Cl)cc(C(F)(F)F)c1] | A | LCMS: Found 344 [M + H] | B |
| 13 | 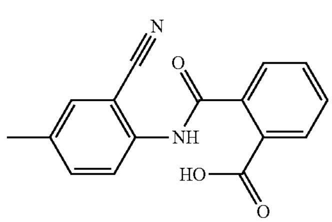 [SMILES: Cc1ccc(NC(=O)c2ccccc2C(=O)O)c(C#N)c1] | A | LCMS: Found 281.0 [M + H] | B |

TABLE 1-continued

| Cmpd # | Structure | Synthetic Scheme | Characterization Data (NMR and/or LCMS) | Biological Activity |
|---|---|---|---|---|
| 14 | 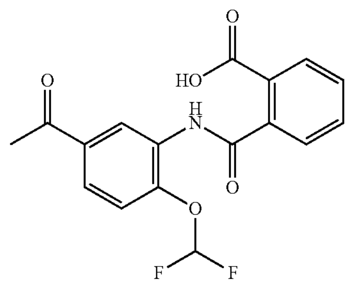 [SMILES: CC(=O)c1ccc(OC(F)F)c(NC(=O)c2ccccc2C(=O)O)c1] | A | LCMS: Found 350 [M + H]<br>LCMS: Found 372 [M + Na] | B |
| 15 | 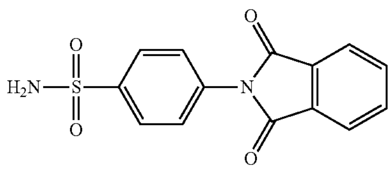 [SMILES: NS(=O)(=O)c1ccc(N2C(=O)c3ccccc3C2=O)cc1] | B-1 | LCMS: Found 303.0 [M + H]<br>$^1$H NMR (400 MHz, DMSO-$d_6$): 7.10-7.36 (M, 6H), 6.56-6.70 (M, 2H), 6.62 (br s, 2H) | B |
| 16 | 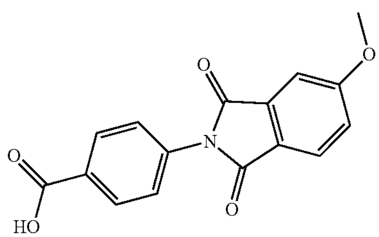 [SMILES: COc1ccc2c(c1)C(=O)N(c1ccc(C(=O)O)cc1)C2=O] | B-1 | LCMS: Found 298.0 [M + H] | A |
| 17 | 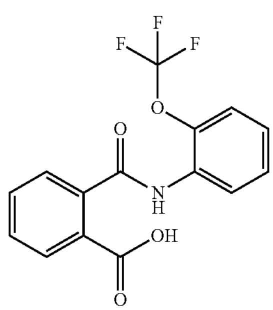 [SMILES: O=C(O)c1ccccc1C(=O)Nc1ccccc1OC(F)(F)F] | A | LCMS: Found 326 [M + H]<br>LCMS: Found 348 [M + Na] | B |
| 18 | 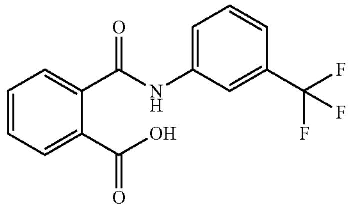 [SMILES: O=C(O)c1ccccc1C(=O)Nc1cccc(C(F)(F)F)c1] | A | LCMS: Found 308.0 [M − H] NEG<br>$^1$H NMR (400 MHz, DMSO-$d_6$): 13.12 (S, 1H), 10.69 (S, 1H), 8.21 (S, 1H), 7.93-7.85 (M, 2H), 7.71-7.67 (M, 1H), 7.63-7.61 (M 3H), 7.46-7.44 (M, 1H) | A |
| 19 | 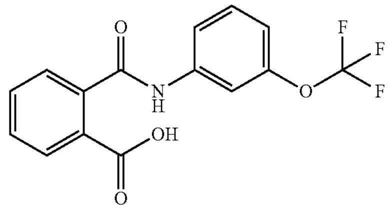 [SMILES: O=C(O)c1ccccc1C(=O)Nc1cccc(OC(F)(F)F)c1] | A | LCMS: Found 326 [M + H]<br>LCMS: Found 348 [M + Na]<br>LCMS: Found 673 [2M + Na]<br>$^1$H NMR (400 MHz, DMSO-$d_6$): 13.05 (S, 1H), 10.65 (S, 1H), 7.92-7.87 (M, 2H), 7.69-7.45 (M, 5H), 7.09-7.07 (D, J = 8 Hz, 1H) | A |

TABLE 1-continued

| Cmpd # | Structure | Synthetic Scheme | Characterization Data (NMR and/or LCMS) | Biological Activity |
|---|---|---|---|---|
| 21 | 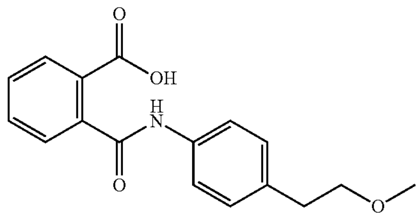 [SMILES: COCCc1ccc(NC(=O)c2ccccc2C(=O)O)cc1] | A | LCMS: Found 300 [M + H]<br>LCMS: Found 322 [M + Na]<br>LCMS: Found 622 [2M + Na] | A |
| 22 | 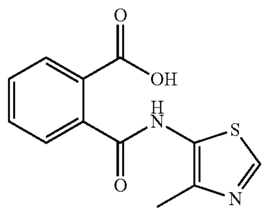 [SMILES: Cc1ncsc1NC(=O)c1ccccc1C(=O)O] | A | LCMS: Found 263.1 [M + H]<br>LCMS: Found 571.1 [2M + Na] | B |
| 23 | 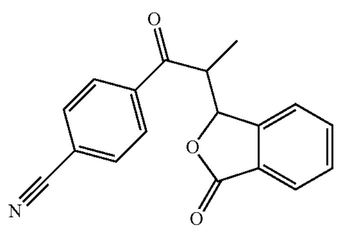 [SMILES: CC(C(=O)c1ccc(C#N)cc1)C1OC(=O)c2ccccc21] | C | LCMS: Found 314.0 [M + Na]<br>LCMS: Found 292.0 [M + H] | A |
| 24 | 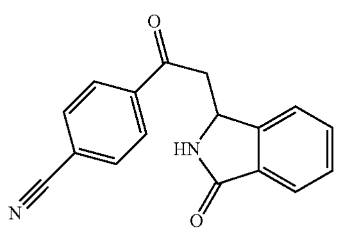 [SMILES: N#Cc1ccc(C(=O)CC2NC(=O)c3ccccc32)cc1] | D | LCMS: Found 277.2 [M + H]<br>LCMS: Found 299.1 [M + Na] | A |
| 25 | 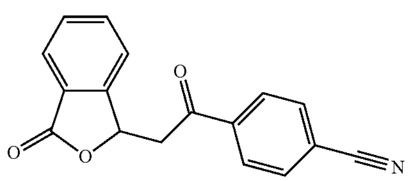 [SMILES: N#Cc1ccc(C(=O)CC2OC(=O)c3ccccc32)cc1] | C | LCMS: Found 278.0 [M + H]<br>LCMS: Found 300.0 [M + Na] | B |
| 26 | 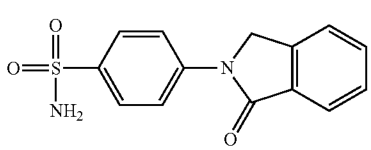 [SMILES: NS(=O)(=O)c1ccc(N2Cc3ccccc3C2=O)cc1] | B-2 | LCMS: Found 289.1 [M + H] | B |
| 27 | 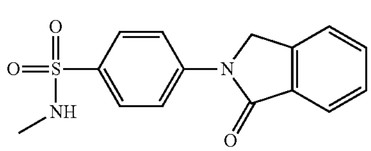 [SMILES: CNS(=O)(=O)c1ccc(N2Cc3ccccc3C2=O)cc1] | B-2 | LCMS: Found 303.1 [M + H] | A |

TABLE 1-continued

| Cmpd # | Structure | Synthetic Scheme | Characterization Data (NMR and/or LCMS) | Biological Activity |
|---|---|---|---|---|
| 28 | 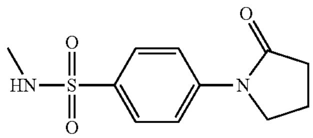 [SMILES: CNS(=O)(=O)c1ccc(N2CCCC2=O)cc1] | 28 | LCMS: Found 255.0 [M + H] <br> $^1$H NMR (400 MHz, CDCl$_3$): 7.50-7.72 (M, 4H), 4.85 (br s, 1H), 3.90 (T, 2H, J = 7.2 Hz), 2.53-2.72 (M, 5H), 2.14-2.28 (M, 2H) | B |
| 29 | 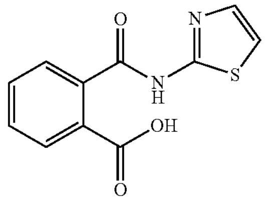 [SMILES: O=C(O)c1ccccc1C(=O)Nc1nccs1] | A | LCMS: Found 249 [M + H] <br> LCMS: Found 271 [M + Na] | B |
| 30 | 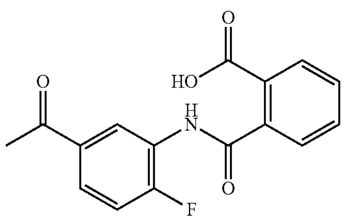 | A | LCMS: Found 302 [M + H] <br> LCMS: Found 324 [M + Na] <br> LCMS: Found 625 [2M + Na] | B |
| 31 | 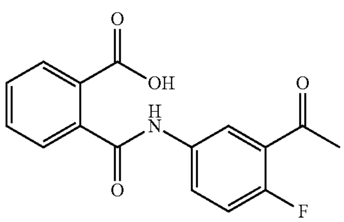 [SMILES: CC(=O)c1cc(NC(=O)c2ccccc2C(=O)O)ccc1F] | A | LCMS: Found 302 [M + H] <br> LCMS: Found 324 [M + Na] <br> LCMS: Found 625 [2M + Na] | B |
| 32 | 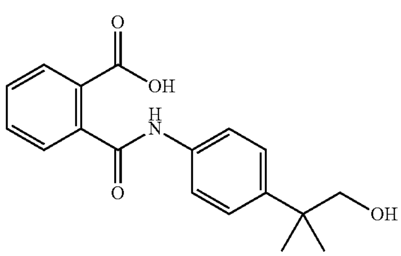 [SMILES: CC(C)(CO)c1ccc(NC(=O)c2ccccc2C(=O)O)cc1] | A | LCMS: Found 314 [M + H] | B |
| 33 | 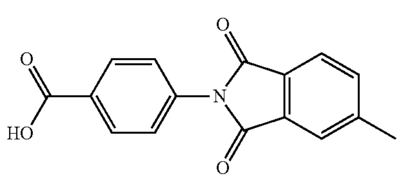 [SMILES: Cc1ccc2c(c1)C(=O)N(c1ccc(C(=O)O)cc1)C2=O] | B-1 | LCMS: Found 282.2 [M + H] | B |
| 34 | 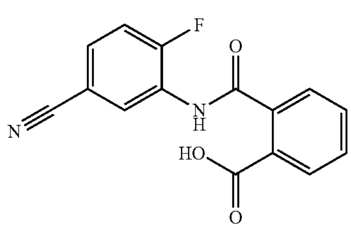 [SMILES: N#Cc1ccc(F)c(NC(=O)c2ccccc2C(=O)O)c1] | A | LCMS: Found 307 [M + Na] <br> LCMS: Found 591 [2M + Na] | B |

TABLE 1-continued

| Cmpd # | Structure | Synthetic Scheme | Characterization Data (NMR and/or LCMS) | Biological Activity |
| --- | --- | --- | --- | --- |
| 35 | 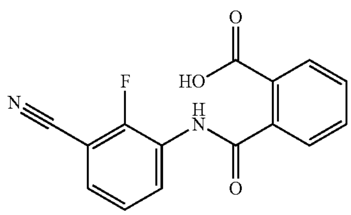 [SMILES: N#Cc1cccc(NC(=O)c2ccccc2C(=O)O)c1F] | A | LCMS: Found 307 [M + Na]<br>LCMS: Found 591 [2M + Na]<br>$^1$H NMR (400 MHz, DMSO-$d_6$): 13.15 (S, 1H), 10.54 (S, 1H), 8.21-8.19 (D, J = 7.6 Hz, 1H), 7.92-7.90 (D, J = 7.6 Hz, 1H), 7.72-7.44 (M, 5H) | B |
| 36 | 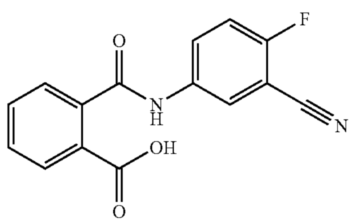 [SMILES: N#Cc1cc(NC(=O)c2ccccc2C(=O)O)ccc1F] | A | LCMS: Found 284 [M + H]<br>LCMS: Found 307 [M + Na]<br>LCMS: Found 591 [2M + Na] | B |
| 37 | 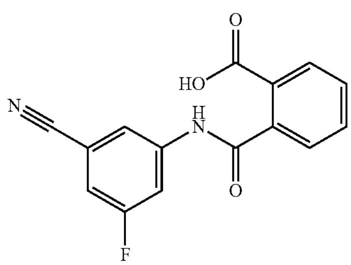 [SMILES: N#Cc1cc(F)cc(NC(=O)c2ccccc2C(=O)O)c1] | A | LCMS: Found 284 [M + H]<br>LCMS: Found 307 [M + Na]<br>LCMS: Found 591 [2M + Na]<br>$^1$H NMR (400 MHz, DMSO-$d_6$): 13.23 (S, 1H), 10.91 (S, 1H), 7.95-7.88 (S, 3H), 7.71-7.69 (M, 1H), 7.65-7.58 (M, 3H) | A |
| 38 | 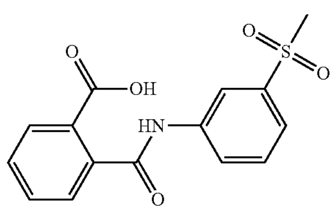 [SMILES: CS(=O)(=O)c1cccc(NC(=O)c2ccccc2C(=O)O)c1] | A | LCMS: Found 320.0 [M + H]<br>LCMS: Found 342.0 [M + Na]<br>LCMS: Found 661.0 [2M + Na] | B |
| 39 | 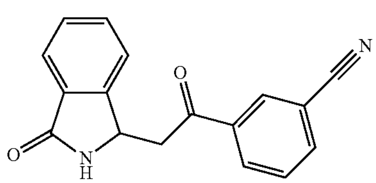 [SMILES: N#Cc1cccc(C(=O)CC2NC(=O)c3ccccc32)c1] | D | LCMS: Found 277.1 [M + H]<br>LCMS: Found 299.1 [M + Na]<br>$^1$H NMR (400 MHz, DMSO-$d_6$): 8.60 (S, 1H), 8.47 (S, 1H), 8.29 (D, 1H), 8.13 (D, 1 H), 7.78-7.49 (M, 5H), 5.13-5.10 (M, 1H), 3.80 (DD, 1H), 3.41 (DD, 1H) | B |
| 40 | 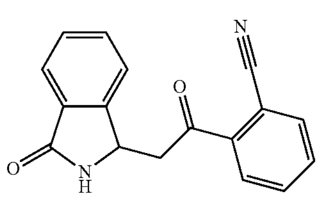 [SMILES: N#Cc1ccccc1C(=O)CC1NC(=O)c2ccccc21] | C | LCMS: Found 278.1 [M + H] | B |
| 41 | 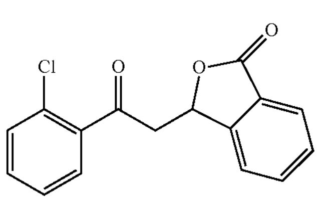 [SMILES: O=C(CC1OC(=O)c2ccccc21)c1ccccc1Cl] | C | LCMS: Found 287.1 [M + H]<br>LCMS: Found 309.0 [M + Na]<br>$^1$H NMR (400 MHz, DMSO-$d_6$): 7.87-7.75 (M, 4H), 7.64-7.45 (M, 4H), 6.09 (M, 1H), 3.86 (DD, 1 H), 3.62 (DD, 1H) | A |

TABLE 1-continued

| Cmpd # | Structure | Synthetic Scheme | Characterization Data (NMR and/or LCMS) | Biological Activity |
|---|---|---|---|---|
| 42 | 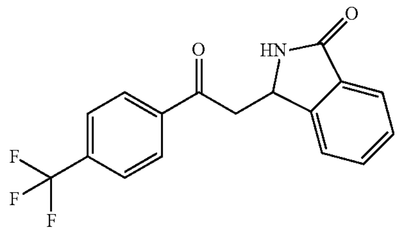 [SMILES: O=C(CC1NC(=O)c2ccccc21)c1ccc(C(F)(F)F)cc1] | D | LCMS: Found 320.1 [M + H] $^1$H NMR (400 MHz, DMSO-$d_6$): 8.61 (S, 1H), 8.20 (D, J = 8.1 Hz, 2H), 7.92 (D, J = 8.2 Hz, 2H), 7.69-7.59 (M, 3H), 7.50 (TD, J = 7.3, 1.3 Hz, 1H), 5.13 (DD, J = 8.0, 4.4 Hz, 1H), 3.80 (DD, J = 18.1, 4.4 Hz, 1H), 3.43 (DD, J = 18.1. 8.1 Hz, 1H) | B |
| 43 | 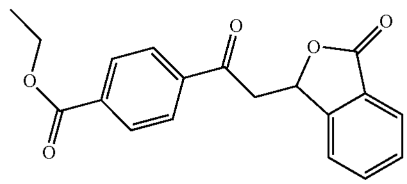 | C | LCMS: Found 311.0 [M + H] LCMS: Found 333.0 [M + Na] | B |
| 44 | 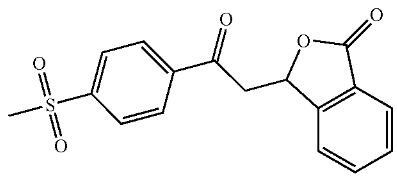 | C | LCMS: Found 311.0 [M + H] LCMS: Found 352.0 [M + Na] | B |
| 45 | 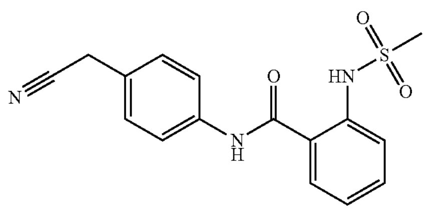 [SMILES: CS(=O)(=O)Nc1ccccc1C(=O)Nc1ccc(CC#N)cc1] | H | LCMS: Found 330.0 [M + H] LCMS: Found 352.0 [M + Na] | B |
| 46 | 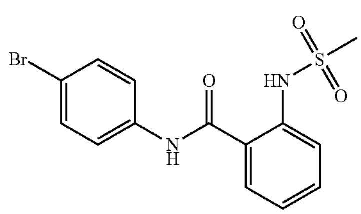 [SMILES: CS(=O)(=O)Nc1ccccc1C(=O)Nc1ccc(Br)cc1] | H | LCMS: Found 369.0 [M + H] LCMS: Found 391.0 [M + Na] | B |
| 47 | 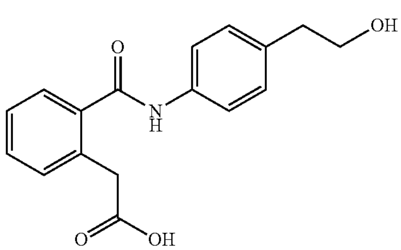 [SMILES: O=C(O)Cc1ccccc1C(=O)Nc1ccc(CCO)cc1] | 47 | LCMS: Found 300.1 [M + H] | B |
| 48 | 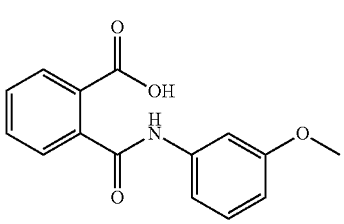 [SMILES: COc1cccc(NC(=O)c2ccccc2C(=O)O)c1] | A | LCMS: Found 272.0 [M + H] LCMS: Found 294.0 [M + Na] LCMS: Found 565.1 [2M + Na] | B |

TABLE 1-continued

| Cmpd # | Structure | Synthetic Scheme | Characterization Data (NMR and/or LCMS) | Biological Activity |
|---|---|---|---|---|
| 49 | 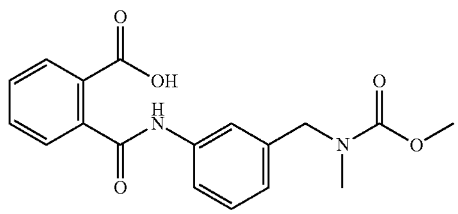 [SMILES: COC(=O)N(C)Cc1cccc(NC(=O)c2ccccc2C(=O)O)c1] | A | LCMS: Found 365.0 [M + Na]<br>LCMS: Found 707.2 [2M + Na] | B |
| 50 | 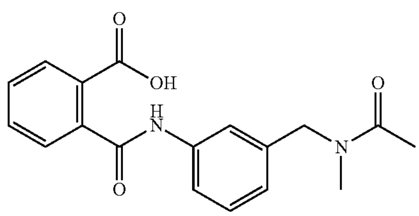 [SMILES: CC(=O)N(C)Cc1cccc(NC(=O)c2ccccc2C(=O)O)c1] | A | LCMS: Found 349.1 [M + Na] | B |
| 51 | 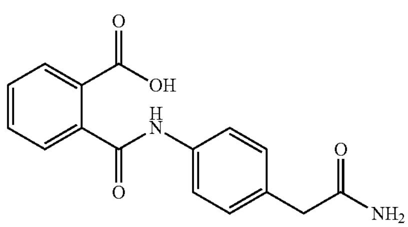 [SMILES: NC(=O)Cc1ccc(NC(=O)c2ccccc2C(=O)O)cc1] | A | LCMS: Found 299.1 [M + H]<br>LCMS: Found 321.0 [M + Na]<br>$^1$H NMR (400 MHz, DMSO-$d_6$): 13.03 (S, 1H), 10.29 (S, 1H), 7.88 (T, 1H), 7.62 (M, 5 H), 7.43 (S, 1H), 7.22 (D, J = 8.4 Hz, 1H), 6.86 (S, 1H), 3.17 (S, 2H) | B |
| 52 | 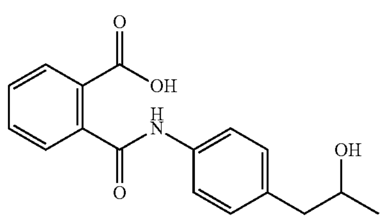 [SMILES: CC(O)Cc1ccc(NC(=O)c2ccccc2C(=O)O)cc1] | A | LCMS: Found 300.1 [M + H]<br>LCMS: Found 322.0 [M + Na] | B |
| 53 | 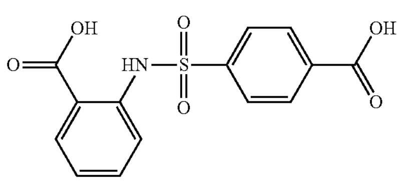 [SMILES: O=C(O)c1ccc(S(=O)(=O)Nc2ccccc2C(=O)O)cc1] | E | LCMS: Found 322.0 [M + H]<br>LCMS: Found 344.0 [M + Na] | B |
| 54 | 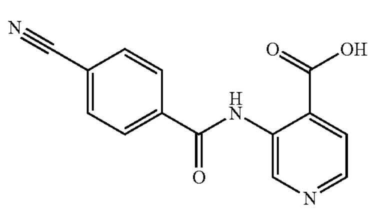 [SMILES: N#Cc1ccc(C(=O)Nc2cnccc2C(=O)O)cc1] | F | LCMS: Found 268.1 [M + H] | B |
| 55 | 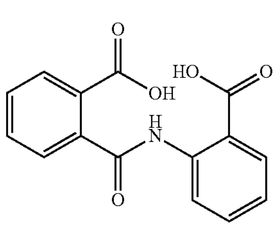 [SMILES: O=C(O)c1ccccc1NC(=O)c1ccccc1C(=O)O] | A | LCMS: Found 289.0 [M + H]<br>LCMS: Found 308.0 [M + Na]<br>LCMS: Found 593.0 [2M + Na]<br>$^1$H NMR (400 MHz, MeOD): 8.71 (D, J = 8 Hz, 1H), 8.13 (M, 1H), 8.01 (D, J = 8 Hz, 1H), 7.65 (M, 4H), 7.20 (M, 1H) | A |

TABLE 1-continued

| Cmpd # | Structure | Synthetic Scheme | Characterization Data (NMR and/or LCMS) | Biological Activity |
| --- | --- | --- | --- | --- |
| 56 | 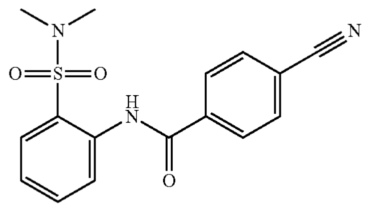 [SMILES: CN(C)S(=O)(=O)c1ccccc1NC(=O)c1ccc(C#N)cc1] | G | LCMS: Found 330.1 [M + H] | A |
| 57 | 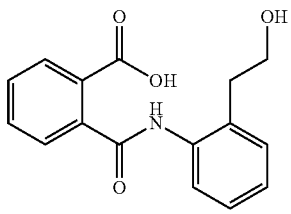 [SMILES: O=C(O)c1ccccc1C(=O)Nc1ccccc1CCO] | A | LCMS: Found 286.2 [M + H]<br>LCMS: Found 308.1 [M + Na]<br>LCMS: Found 593.3 [2M + Na] | B |
| 58 | 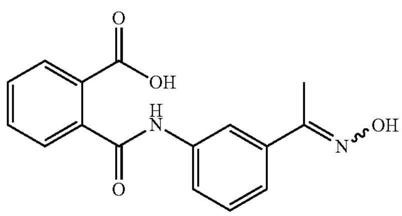 [SMILES: CC(=NO)c1cccc(NC(=O)c2ccccc2C(=O)O)c1] | A | LCMS: Found 299.2 [M + H]<br>LCMS: Found 321.2 [M + Na]<br>LCMS: Found 619.1 [2M + Na] | B |
| 59 | 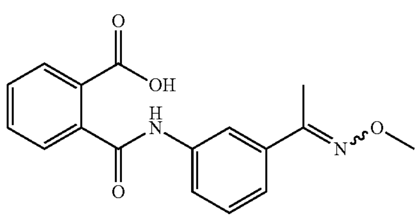 [SMILES: CON=C(C)c1cccc(NC(=O)c2ccccc2C(=O)O)c1] | A | LCMS: Found 313.1 [M + H]<br>LCMS: Found 335.0 [M + Na]<br>LCMS: Found 647.1 [2M + Na] | B |
| 60 | 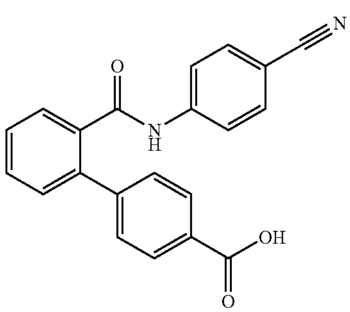 [SMILES: N#Cc1ccc(NC(=O)c2ccccc2-c2ccc(C(=O)O)cc2)cc1] | I | LCMS: Found 343.1 [M + H]<br>$^1$H NMR (400 MHz, DMSO-$d_6$): 13.00 (br s, 1H), 10.72 (br s, 1H), 8.03 (S, 1H), 7.82-7.91 (M, 1H), 7.58-7.80 (M, 7H), 7.42-7.58 (M, 3H) | A |
| 61 | 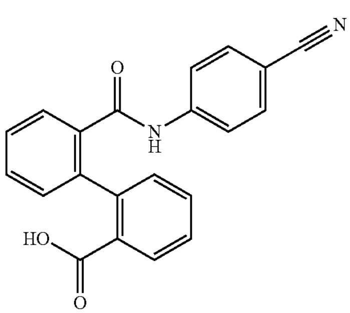 [SMILES: N#Cc1ccc(NC(=O)c2ccccc2-c2ccccc2C(=O)O)cc1] | I | LCMS: Found 343.1 [M + H] | A |

TABLE 1-continued

| Cmpd # | Structure | Synthetic Scheme | Characterization Data (NMR and/or LCMS) | Biological Activity |
|---|---|---|---|---|
| 62 | 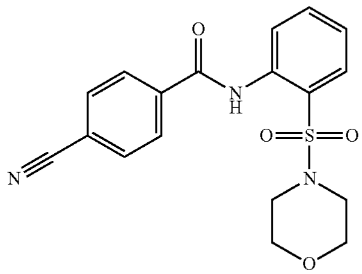 [SMILES: N#Cc1ccc(C(=O)Nc2ccccc2S(=O)(=O)N2CCOCC2)cc1] | G | LCMS: Found 372.2 [M + H]<br>LCMS: Found 394.1 [M + Na] | A |
| 63 | 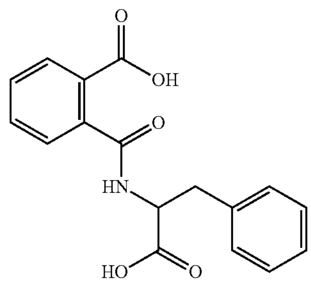 [SMILES: O=C(O)c1ccccc1C(=O)NC(Cc1ccccc1)C(=O)O] | A | LCMS: Found 249 [M + H]<br>LCMS: Found 271 [M + Na] | A |
| 64 | 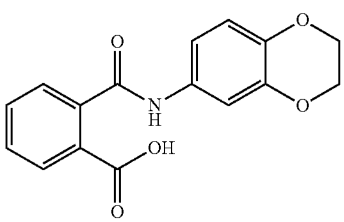 [SMILES: O=C(O)c1ccccc1C(=O)Nc1ccc2c(c1)OCCO2] | A | LCMS: Found 300.2 [M + H]<br>LCMS: Found 621.2 [2M + Na]<br>$^1$H NMR (400 MHz, DMSO-$d_6$): 12.99 (S, 1H), 10.13 (S, 1H), 7.86 (M, 1H), 7.63 (M, 1H), 7.51 (M, 2H), 7.31 (S, 1H), 7.07 (M, 1H), 6.80 (D, J = 8.4 Hz, 1 H), 4.23 (M, 4H) | B |
| 65 | 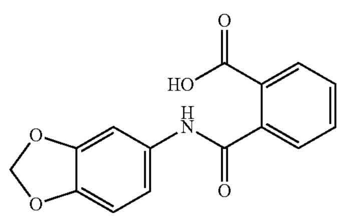 [SMILES: O=C(O)c1ccccc1C(=O)Nc1ccc2c(c1)OCO2] | A | LCMS: Found 286.2 [M + H]<br>LCMS: Found 593.2 [2M + Na] | A |
| 66 | 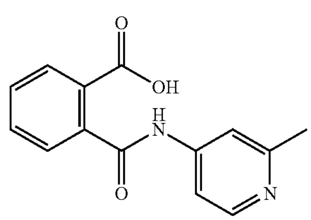 [SMILES: Cc1cc(NC(=O)c2ccccc2C(=O)O)ccn1] | A | LCMS: Found 257.0 [M + H] | B |
| 67 | 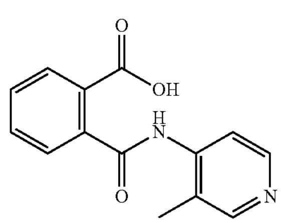 [SMILES: Cc1cnccc1NC(=O)c1ccccc1C(=O)O] | A | LCMS: Found 257.0 [M + H] | A |

TABLE 1-continued

| Cmpd # | Structure | Synthetic Scheme | Characterization Data (NMR and/or LCMS) | Biological Activity |
|---|---|---|---|---|
| 68 | 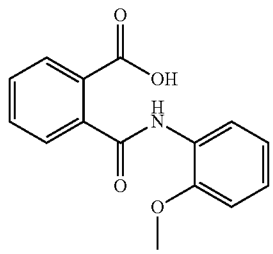 [SMILES: COc1ccccc1NC(=O)c1ccccc1C(=O)O] | A | LCMS: Found 272.0 [M + H]<br>LCMS: Found 294.0 [M + Na]<br>LCMS: Found 565.1 [2M + Na]<br>$^1$H NMR (400 MHz, DMSO-$d_6$): 9.37 (S, 1H), 7.98 (D, J = 7.6 Hz, 1H), 7.85 (D, J = 7.6 Hz, 1H), 7.65 (M, 1H), 7.58 (M, 2H), 7.15 (M, 1H), 7.07 (M, 1H), 6.98 (M, 1H) | A |
| 69 | 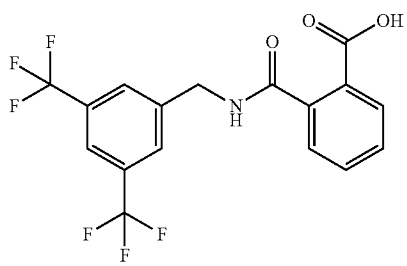 [SMILES: O=C(O)c1ccccc1C(=O)NCc1cc(C(F)(F)F)cc(C(F)(F)F)c1] | A | LCMS: Found 392.1 [M + H]<br>LCMS: Found 414.1 [M + Na] | B |
| 70 | 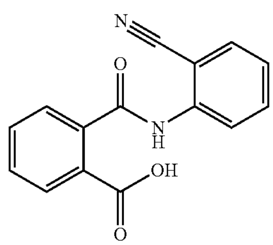 [SMILES: N#Cc1ccccc1NC(=O)c1ccccc1C(=O)O] | A | LCMS: Found 267.1 [M + H] | A |
| 71 | 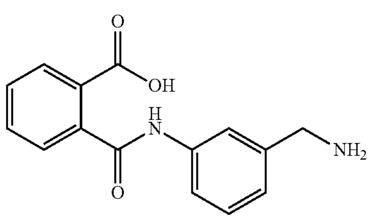 [SMILES: NCc1cccc(NC(=O)c2ccccc2C(=O)O)c1] | A | LCMS: Found 271.0 [M + H] | A |
| 72 | 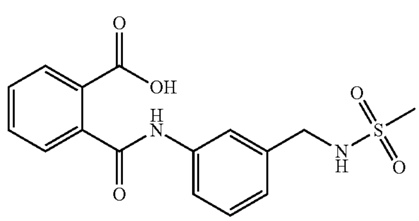 [SMILES: CS(=O)(=O)NCc1cccc(NC(=O)c2ccccc2C(=O)O)c1] | A | LCMS: Found 349.0 [M + H]<br>LCMS: Found 371.0 [M + Na]<br>$^1$H NMR (400 MHz, DMSO-$d_6$): 10.38 (S, 1H), 7.89 (T, 1H), 7.23 (S, 1H), 7.66 (M, 1H), 7.58 (M, 4H), 7.07 (D, J = 7.6 Hz, 1H), 4.15 (D, J = 6 Hz, 2H), 2.89 (S, 3H) | A |
| 73 | 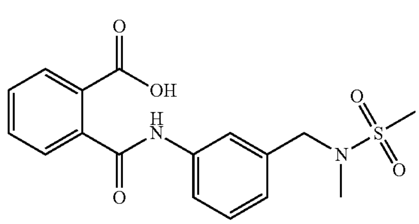 [SMILES: CN(Cc1cccc(NC(=O)c2ccccc2C(=O)O)c1)S(C)(=O)=O] | A | LCMS: Found 363.0 [M + H]<br>LCMS: Found 385.0 [M + Na]<br>LCMS: Found 747.0 [2M + Na]<br>$^1$H NMR (400 MHz, DMSO-$d_6$): 13.02 (S, 1H), 10.41 (S, 1H), 7.87 (D, J = 7.2 Hz, 1H), 7.65 (M, 3H), 7.35 (T, 1H), 7.04 (D, J = 7.6 Hz, 1H), 4.21 (S, 1H), 2.96 (S, 1H), 2.67 (S, 1H) | A |

| Cmpd # | Structure | Synthetic Scheme | Characterization Data (NMR and/or LCMS) | Biological Activity |
|---|---|---|---|---|
| 74 | 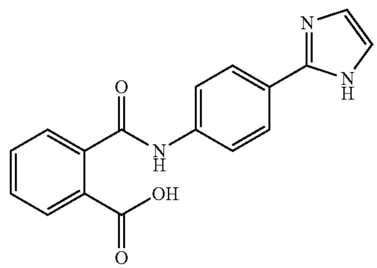 [SMILES: O=C(O)c1ccccc1C(=O)Nc1ccc(-c2ncc[nH]2)cc1] | A | LCMS: Found 308.2 [M + H] $^1$H NMR (400 MHz, DMSO-$d_6$): 10.53 (S, 1H), 7.88 (D, J = 8.4 Hz, 3H), 7.56 (D, J = 8.8 Hz, 2H), 7.65 (M, 1H), 7.59 (M, 2H), 7.10 (S, 1H) | B |
| 75 | 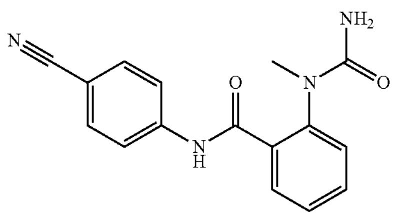 [SMILES: CN(C(N)=O)c1ccccc1C(=O)Nc1ccc(C#N)cc1] | F | LCMS: Found 295.1 [M + H] LCMS: Found 317.1 [M + Na] $^1$H NMR (400 MHz, CDCl$_3$): ) 9.47 (br s, 1 H), 7.86 (D, 1H), 7.79 (D, 2H), 7.57-7.66 (M, 3H), 7.48-7.54 (M, 1H), 7.31 (D, 1H), 4.74 (Br s, 2H), 3.25 (S, 3H) | B |
| 76 | 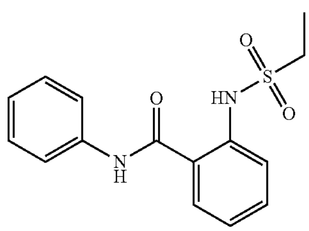 | H | LCMS: Found 330.1 [M + H] | B |
| 77 | 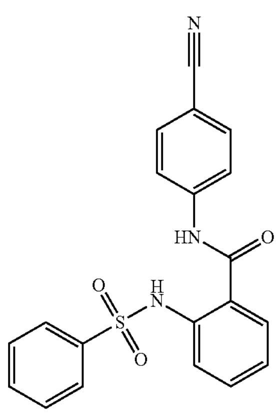 [SMILES: N#Cc1ccc(NC(=O)c2ccccc2NS(=O)(=O)c2ccccc2)cc1] | H | LCMS: Found 378.1 [M + H] | A |
| 78 | 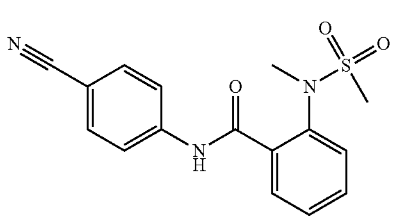 [SMILES: CN(c1ccccc1C(=O)Nc1ccc(C#N)cc1)S(C)(=O)=O] | H | LCMS: Found 330.1 [M + H] $^1$H NMR (400 MHz, DMSO-$d_6$): 10.70 (S, 1H), 7.90 (D, 2H), 7.82 (D, 2H), 7.64-7.49 (M, 4H), 3.26 (S, 3H), 3.00 (S, 3H) | B |

TABLE 1-continued

| Cmpd # | Structure | Synthetic Scheme | Characterization Data (NMR and/or LCMS) | Biological Activity |
|---|---|---|---|---|
| 79 | 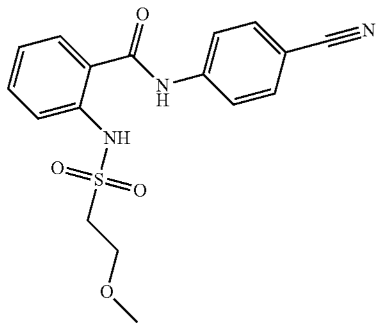 [SMILES: COCCS(=O)(=O)Nc1ccccc1C(=O)Nc1ccc(C#N)cc1] | H | LCMS: Found 360.1 [M + H]<br>$^1$H NMR (400 MHz, CDCl3) 10.85 (S, 1H), 9.97 (S, 1H), 7.94 (D, 2H), 7.84 (D, 2H), 7.59-7.63 (M, 2H), 7.30-7.32 (M, 1H), 3.61-3.64 (M, 2H), 3.44-3.47 (M, 2H), 3.06 (S, 3H) | B |
| 80 | 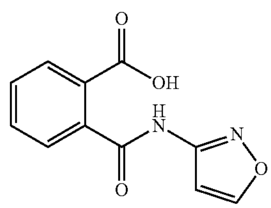 [SMILES: O=C(O)c1ccccc1C(=O)Nc1ccon1] | A | LCMS: Found 233.1 [M + H]<br>LCMS: Found 255.1 [M + Na]<br>LCMS: Found 487.0 [2M + Na] | B |
| 81 | 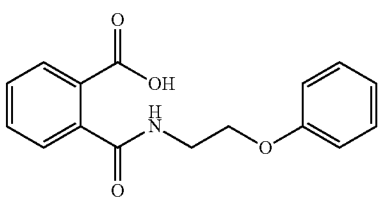 [SMILES: O=C(O)c1ccccc1C(=O)NCCOc1ccccc1] | A | LCMS: Found 286.0 [M + H]<br>LCMS: Found 308.0 [M + Na] | B |
| 82 | 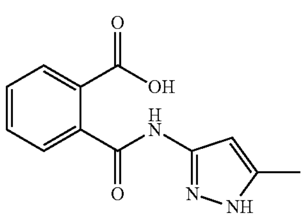 [SMILES: Cc1cc(NC(=O)c2ccccc2C(=O)O)n[nH]1] | A | LCMS: Found 246.2 [M + H]<br>LCMS: Found 513.2 [2M + Na] | A |
| 83 | 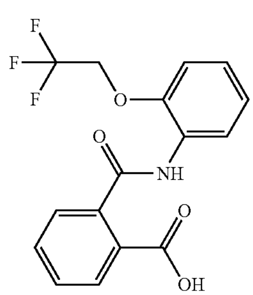 [SMILES: O=C(O)c1ccccc1C(=O)Nc1ccccc1OCC(F)(F)F] | A | LCMS: Found 340.0 [M + H]<br>LCMS: Found 362.0 [M + Na]<br>LCMS: Found 701.1 [2M + Na] | A |
| 84 | 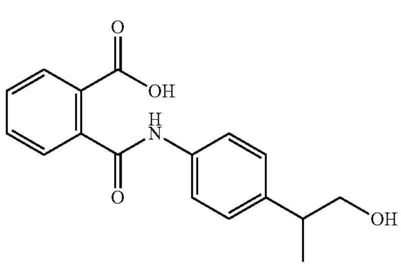 [SMILES: CC(CO)c1ccc(NC(=O)c2ccccc2C(=O)O)cc1] | A | LCMS: Found 300.2 [M + H]<br>LCMS: Found 322.1 [M + Na]<br>$^1$H NMR (400 MHz, DMSO-$d_6$): 10.24 (S, 1H), 7.84 (D, J = 6.8 Hz, 1H), 7.56 (M, 4H), 7.15 (D, J = 8.8 Hz, 1H), 4.61 (T, 1H), 3.47 (M, 1H), 2.75 (M, 1H), 1.14 (D, J = 6.8 Hz, 3H) | A |

TABLE 1-continued

| Cmpd # | Structure | Synthetic Scheme | Characterization Data (NMR and/or LCMS) | Biological Activity |
|---|---|---|---|---|
| 85 | 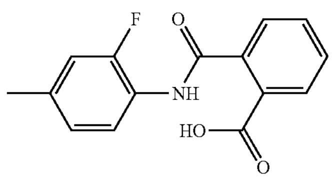 [SMILES: Cc1ccc(NC(=O)c2ccccc2C(=O)O)c(F)c1] | A | LCMS: Found 274.2 [M + H]<br>LCMS: Found 296.1 [M + Na] | B |
| 86 | 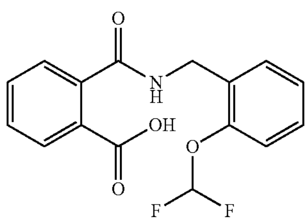 [SMILES: O=C(O)c1ccccc1C(=O)NCc1ccccc1OC(F)F] | A | LCMS: Found 322.1 [M + H]<br>LCMS: Found 344.0 [M + Na] | B |
| 87 | 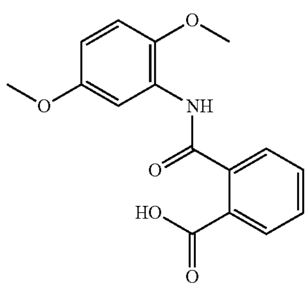 [SMILES: COc1ccc(OC)c(NC(=O)c2ccccc2C(=O)O)c1] | A | LCMS: Found 302.0 [M + H]<br>LCMS: Found 625.1 [2M + Na] | B |
| 88 | 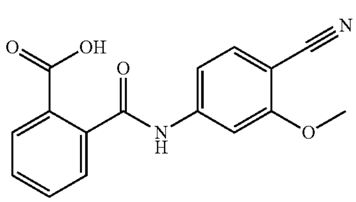 [SMILES: COc1cc(NC(=O)c2ccccc2C(=O)O)ccc1C#N] | A | LCMS: Found 297.1 [M + H]<br>LCMS: Found 316.0 [M + Na]<br>$^1$H NMR (400 MHz, CD$_3$OD): 8.06-8.04 (D, 1H), 7.75-7.65 (M, 2H), 7.61-7.53 (M, 3H), 7.24-7.24 (D, 2H), 3.95 (S, 3H) | — |
| 89 | 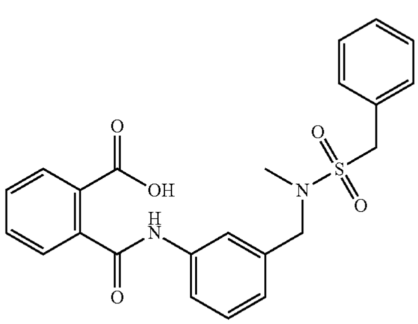 [SMILES: CN(Cc1cccc(NC(=O)c2ccccc2C(=O)O)c1)S(=O)(=O)Cc1ccccc1] | A | LCMS: Found 461.0 [M + Na]<br>$^1$H NMR (400 MHz, CD$_3$OD): 8.05 (D, 1H), 7.69-7.57 (M, 5H), 7.46-7.35 (M, 6H), 7.20 (D, 1H), 4.45 (S, 2H), 4.16 (S, 2H), 2.69 (S, 3H). | — |

| Cmpd # | Structure | Synthetic Scheme | Characterization Data (NMR and/or LCMS) | Biological Activity |
|---|---|---|---|---|
| 90 | 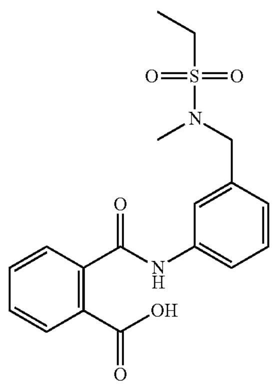 [SMILES: CCS(=O)(=O)N(C)Cc1cccc(NC(=O)c2ccccc2C(=O)O)c1] | A | LCMS: Found 377.0 [M + H], LCMS: Found 399.0 [M + Na] $^1$H NMR (400 MHz, CD$_3$OD): 8.05 (D, 1H), 7.72-7.57 (M, 5H), 7.37 (T, 1H), 7.18 (D, 1H), 4.39 (S, 2H), 3.15 (Q, 2H), 2.81 (S, 3H), 1.38 (T, 3H). | — |
| 91 | 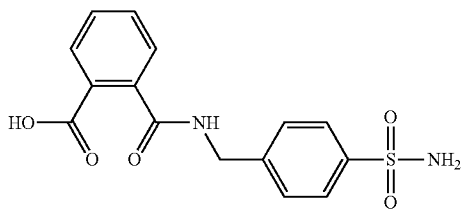 [SMILES: NS(=O)(=O)c1ccc(CNC(=O)c2ccccc2C(=O)O)cc1] | A | LCMS: Found 335.1 [M + H] | — |
| 92 | 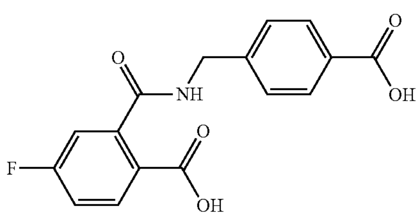 [SMILES: O=C(O)c1ccc(CNC(=O)c2cc(F)ccc2C(=O)O)cc1] | A | LCMS: Found 318.1 [M + H] $^1$H NMR (400 MHz, DMSO-d$_6$): 13.05 (br s, 2H), 9.04-8.98 (M, 1H), 7.92-7.88 (D, 2H), 7.58-7.45 (M, 3H), 7.37-7.33 (M, 1H), 4.50 (D, 2H) | — |
| 93 | 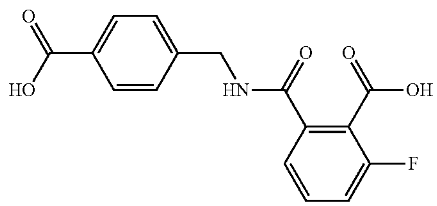 [SMILES: O=C(O)c1ccc(CNC(=O)c2cccc(F)c2C(=O)O)cc1] | A | LCMS: Found 318.1 [M + H] $^1$H NMR (400 MHz, DMSO-d$_6$): 13.20 (br s, 2H), 9.03 (S, 1H), 7.90 (D, 2H), 7.74 (D, 1H), 7.55-7.50 (M, 4H), 4.52 (D, 2H) | B |
| 94 | 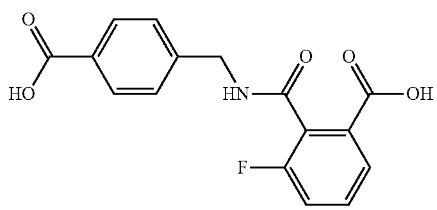 | A | LCMS: Found 318.1 [M + H] | B |
| 95 | 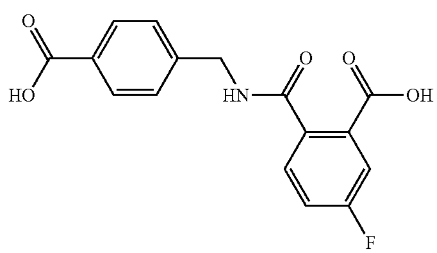 [SMILES: O=C(O)c1ccc(CNC(=O)c2ccc(F)cc2C(=O)O)cc1] | A | LCMS: Found 318.1 [M + H] | — |

TABLE 1-continued

| Cmpd # | Structure | Synthetic Scheme | Characterization Data (NMR and/or LCMS) | Biological Activity |
|---|---|---|---|---|
| 96 | 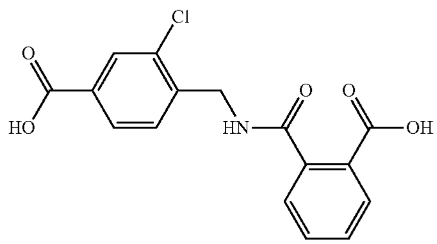 [SMILES: O=C(O)c1ccc(CNC(=O)c2ccccc2C(=O)O)c(Cl)c1] | A | LCMS: Found 334.0 [M + H] | B |
| 97 | 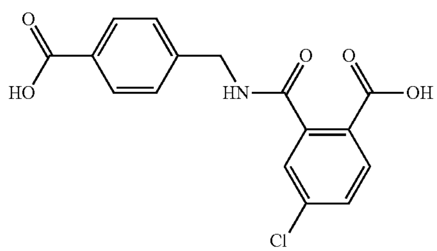 [SMILES: O=C(O)c1ccc(CNC(=O)c2cc(Cl)ccc2C(=O)O)cc1] | A | LCMS: Found 334.0 [M + H] <br> $^1$H NMR (400 MHz, DMSO-$d_6$): 9.74 (br s, 1H), 9.39 (br s, 1H), 7.90 (D, 2H), 7.59-7.56 (M, 3H), 7.51-7.47 (M, 2H), 4.50 (D, 2H) | — |
| 98 | 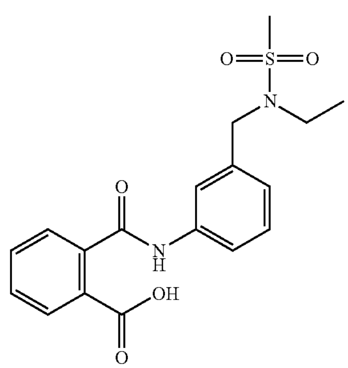 [SMILES: CCN(Cc1cccc(NC(=O)c2ccccc2C(=O)O)c1)S(C)(=O)=O] | A | LCMS: Found 377.0 [M + H], LCMS: Found 399.0 [M + Na] <br> $^1$H NMR (400 MHz, CD$_3$OD): 8.05 (D, 1H), 7.76-7.57 (M, 5H), 7.37 (T, 1H), 7.20 (D, 1H), 4.43 (S, 2H), 3.32-3.27 (M, 2H), 2.96 (S, 3H), 1.15 (T, 3H). | — |
| 99 | 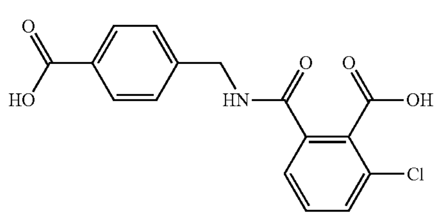 [SMILES: O=C(O)c1ccc(CNC(=O)c2cccc(Cl)c2C(=O)O)cc1] | A | LCMS: Found 334.0 [M + H] <br> $^1$H NMR (400 MHz, DMSO-$d_6$): 13.10 (br s, 2H), 8.93-8.90 (M, 1H), 7.90 (D, 2H), 7.74 (D, 1H), 7.56-7.51 (M, 3H), 4.51 (D, 2H) | B |
| 100 | 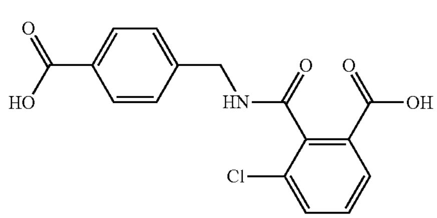 | A | LCMS: Found 334.0 [M + H] | B |

TABLE 1-continued

| Cmpd # | Structure | Synthetic Scheme | Characterization Data (NMR and/or LCMS) | Biological Activity |
|---|---|---|---|---|
| 101 | 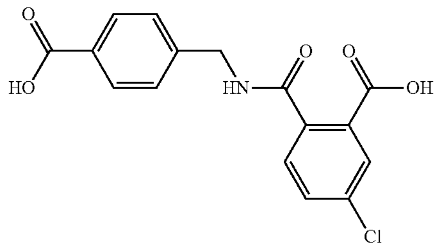 [SMILES: O=C(O)c1ccc(CNC(=O)c2ccc(Cl)cc2C(=O)O)cc1] | A | LCMS: Found 334.1 [M + H] | — |
| 102 | 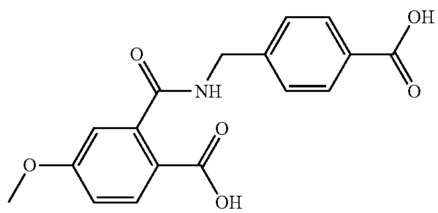 [SMILES: COc1ccc(C(=O)O)c(C(=O)NCc2ccc(C(=O)O)cc2)c1] | A | LCMS: Found 330.1 [M + H]<br>$^1$H NMR (400 MHz, DMSO-$d_6$): 12.96 (br s, 2H), 7.90 (D, 2H), 7.51-7.47 (M, 3H), 7.19 (D, 1H), 7.10 (DD, 1H), 4.49 (D, 2H), 3.82 (S, 3H) | — |
| 103 | 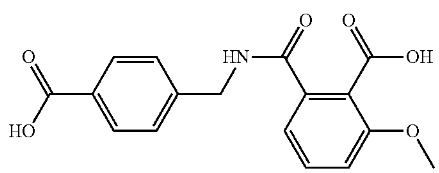 [SMILES: COc1cccc(C(=O)NCc2ccc(C(=O)O)cc2)c1C(=O)O] | A | LCMS: Found 330.0 [M + H]<br>$^1$H NMR (400 MHz, DMSO-$d_6$): 12.90 (br s, 2H), 8.65 (T, 1H), 7.91 (D, 2H), 7.54 (D, 2H), 7.45 (D, 2H), 7.32 (DD, 1H), 4.48 (D, 1H), 3.83 (S, 3H) | A |
| 104 | 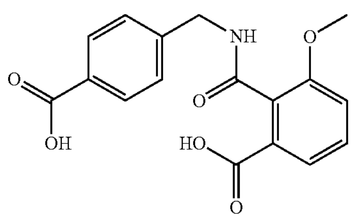 [SMILES: COc1cccc(C(=O)O)c1C(=O)NCc1ccc(C(=O)O)cc1] | A | LCMS: Found 330.0 [M + H] | A |
| 105 | 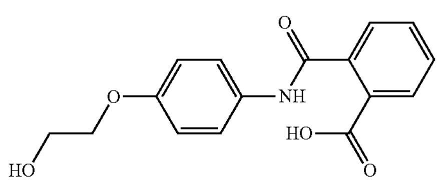 [SMILES: O=C(O)c1ccccc1C(=O)Nc1ccc(OCCO)cc1] | A | LCMS: Found 302.1 [M + H]<br>$^1$H NMR (400 MHz, DMSO-$d_6$): 12.98 (br s, 1H), 10.19 (S, 1H), 7.86 (D, 1H), 7.67-7.52 (M, 5H), 6.91 (D, 2H), 4.87 (br s, 1H), 3.96 (T, 2H), 3.71 (Q, 2H) | B |
| 106 | 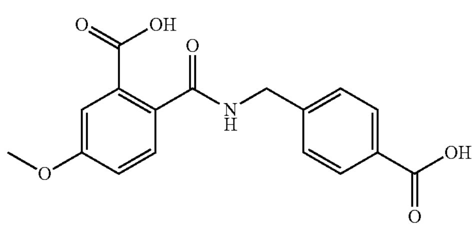 [SMILES: COc1ccc(C(=O)NCc2ccc(C(=O)O)cc2)c(C(=O)O)c1] | A | LCMS: Found 330.1 [M + H]<br>$^1$H NMR (400 MHz, DMSO-$d_6$): 12.80 (br s, 2H), 7.90 (D, 2H), 7.81 (D, 1H), 7.52 (D, 2H), 7.05 (DD, 1H), 6.95 (D, 1H), 4.49 (D, 2H), 3.85 (S, 3H) | B |
| 107 | 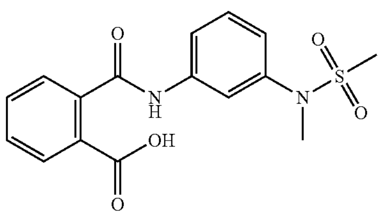 [SMILES: CN(c1cccc(NC(=O)c2ccccc2C(=O)O)c1)S(C)(=O)=O] | A | LCMS: Found 349.0 [M + H],<br>LCMS: Found 371.0 [M + Na]<br>$^1$H NMR (400 MHz, CD$_3$OD): 8.06 (D, 1H), 7.83 (S, 1H), 7.69-7.56 (M, 4H), 7.39 (T, 1H), 7.23 (D, 1H), 3.32 (S, 3H), 2.95 (S, 3H). | B |

TABLE 1-continued

| Cmpd # | Structure | Synthetic Scheme | Characterization Data (NMR and/or LCMS) | Biological Activity |
|---|---|---|---|---|
| 108 | 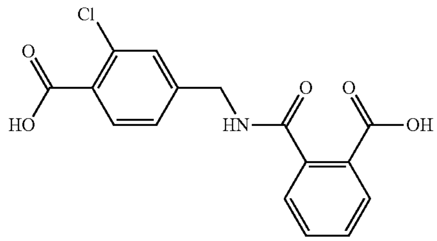 [SMILES: O=C(O)c1ccc(CNC(=O)c2ccccc2C(=O)O)cc1Cl] | A | LCMS: Found 334.1 [M + H] $^1$H NMR (400 MHz, DMSO-$d_6$): 13.18 (br s, 2H), 9.01 (S, 1H), 7.92 (D, 1H), 7.88 (DD, 1H), 7.80 (DD, 1H), 7.71 (D, 1H), 7.63-7.53 (M, 3H), 4.53 (D, 2H) | — |
| 109 | 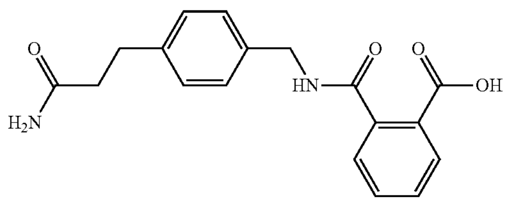 [SMILES: NC(=O)CCc1ccc(CNC(=O)c2ccccc2C(=O)O)cc1] | A | LCMS: Found 327.2 [M + H] $^1$H NMR (400 MHz, DMSO-$d_6$): 12.98 (br s, 1H), 8.81 (S, 1H), 7.76 (D, 2H), 7.58-7.44 (M, 3H), 7.28 (D, 2H), 7.15 (D, 2H), 4.40 (D, 2H), 2.77 (Q, 2H), 2.34 (Q, 2H) | — |
| 110 | 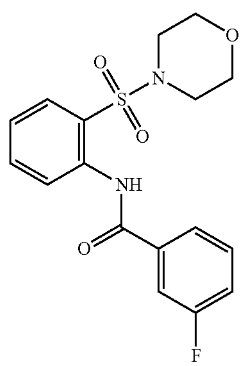 [SMILES: O=C(Nc1ccccc1S(=O)(=O)N1CCOCC1)c1cccc(F)c1] | G | LCMS: Found 365.2 [M + H] $^1$H NMR (400 MHz, CDCl$_3$): 10.50 (S, 1H), 8.76 (D, 1H), 7.82-7.70 (M, 4H), 7.54-7.53 (M, 1H), 7.34-7.30 (m, 2H), 3.71-3.69 (M, 4H), 3.05-3.03 (m, 4H). | B |
| 111 | 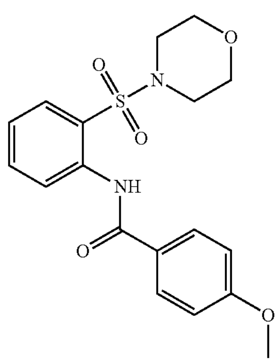 [SMILES: COc1ccc(C(=O)Nc2ccccc2S(=O)(=O)N2CCOCC2)cc1] | G | LCMS: Found 377.2 [M + H] $^1$H NMR (400 MHz, CDCl$_3$): 10.38 (S, 1H), 8.74 (D, 1H), 7.94-8.07 (M, 2H), 7.80 (D, 1H), 7.68 (D, 1H), 7.25-7.31 (M, 1H), 6.95-7.14 (M, 2H), 3.91 (S, 3H), 3.62-3.72 (M, 4H), 2.96-3.11 (M, 4H). | — |
| 112 | 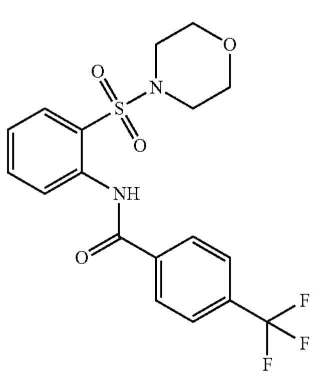 [SMILES: O=C(Nc1ccccc1S(=O)(=O)N1CCOCC1)c1ccc(C(F)(F)F)cc1] | G | LCMS: Found 415.1 [M + H] $^1$H NMR (400 MHz, CDCl$_3$): 10.62 (S, 1H), 8.78 (D, 1H), 8.14 (D, 2H), 7.84-7.82 (M, 3H), 7.51-7.46 (M, 1H), 7.36-7.32 (M, 1H), 3.72-3.69 (M, 4H), 3.05-3.03 (M, 4H). | — |

| Cmpd # | Structure | Synthetic Scheme | Characterization Data (NMR and/or LCMS) | Biological Activity |
|---|---|---|---|---|
| 113 | 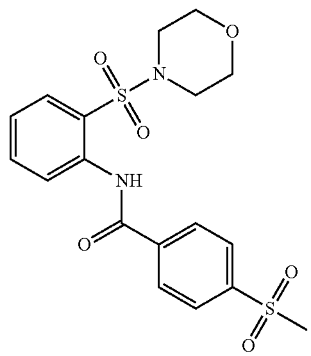 [SMILES: CS(=O)(=O)c1ccc(C(=O)Nc2ccccc2S(=O)(=O)N2CCOCC2)cc1] | G | LCMS: Found 425.1 [M + H]<br>¹H NMR (400 MHz, CDCl₃): 10.68 (S, 1H), 8.78 (D, 1H), 8.22 (D, 2H), 8.14 (D, 2H), 7.81 (D, 1H), 7.76-7.68 (M, 1H), 7.37-7.33 (M, 1H), 3.73-3.70 (M, 4H), 3.05-3.03 (M, 4H). | A |
| 114 | 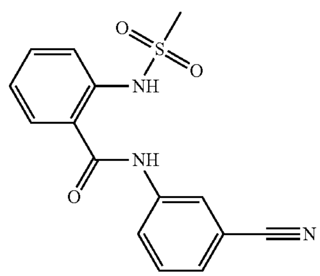 [SMILES: CS(=O)(=O)Nc1ccccc1C(=O)Nc1cccc(C#N)c1] | L | LCMS: Found 316.1 [M + H]<br>¹H NMR (400 MHz, DMSO-d₆): 10.76 (S, 1H), 9.98 (S, 1H), 8.21 (S, 1H), 7.98 (T, 1H), 7.83 (D, 1H), 7.62-7.57 (M, 4H), 7.32 (T, 1H), 3.12 (S, 3H) | — |
| 115 | 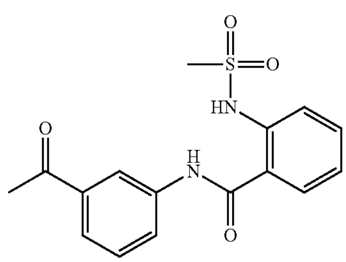 [SMILES: CC(=O)c1cccc(NC(=O)c2ccccc2NS(C)(=O)=O)c1] | L | LCMS: Found 333.1 [M + H]<br>¹H NMR (400 MHz, DMSO-d₆): 10.70 (br s, 1H), 10.18 (br s, 1H), 8.33 (S, 1H), 7.99 (d, 1H), 7.89 (D, 1H), 7.76 (D, 1H), 7.58-7.52 (M, 3H), 7.30 (T, 1H), 3.13 (S, 3H), 2.60 (S, 3H) | — |
| 116 | 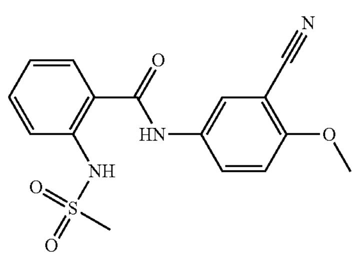 [SMILES: COc1ccc(NC(=O)c2ccccc2NS(C)(=O)=O)cc1C#N] | L | LCMS: Found 346.1 [M + H]<br>¹H NMR (400 MHz, DMSO-d₆): 10.60 (S, 1H), 10.16 (S, 1H), 8.07 (S, 1H), 7.90 (DD, 2H), 7.59-7.57 (M, 2H), 7.31-7.29 (M, 2H), 3.92 (S, 3H), 3.12 (S, 3H) | — |
| 117 | 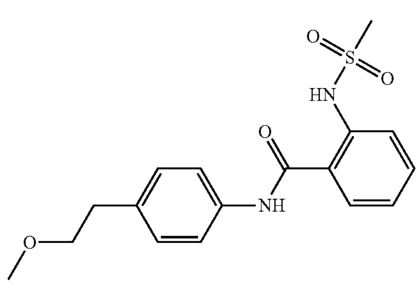 [SMILES: COCCc1ccc(NC(=O)c2ccccc2NS(C)(=O)=O)cc1] | L | LCMS: Found 349.2 [M + H]<br>¹H NMR (400 MHz, DMSO-d₆): 10.44 (S, 1H), 10.29 (S, 1H), 7.88 (D, 1H), 7.64-7.55 (M, 4H), 7.31-7.22 (M, 3H), 3.52 (Q, 2H), 3.25 (s, 3H), 3.13 (S, 3H), 2.79 (q, 2H) | A |

TABLE 1-continued

| Cmpd # | Structure | Synthetic Scheme | Characterization Data (NMR and/or LCMS) | Biological Activity |
|---|---|---|---|---|
| 118 | 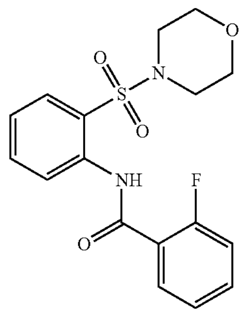 [SMILES: O=C(Nc1ccccc1S(=O)(=O)N1CCOCC1)c1ccccc1F] | G | LCMS: Found 365.1 [M + H] $^1$H NMR (400 MHz, CDCl$_3$): 10.40 (D, 1H), 8.67 (D, 1H), 8.14-8.10 (M, 2H), 7.87 (D, 1H), 7.72-7.68 (M, 1H), 7.61-7.55 (M, 1H), 7.36-7.30 (M, 4H), 3.71-3.68 (M, 4H), 3.10-3.07 (M, 4H). | B |
| 119 | 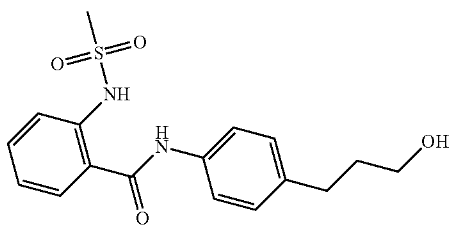 [SMILES: CS(=O)(=O)Nc1ccccc1C(=O)Nc1ccc(CCCO)cc1] | L | LCMS: Found 349.1 [M + H] $^1$H NMR (400 MHz, DMSO-d$_6$): 10.31 (br s, 2H), 7.90 (D, 1H), 7.62 (D, 2H), 7.53 (S, 2H), 7.20-7.18 (M, 3H), 4.49-4.46 (M, 1H), 3.43-3.39 (M, 2H), 3.08 (S, 3H), 2.65-2.55 (M, 2H), 1.74-1.67 (M, 2H) | — |
| 120 | 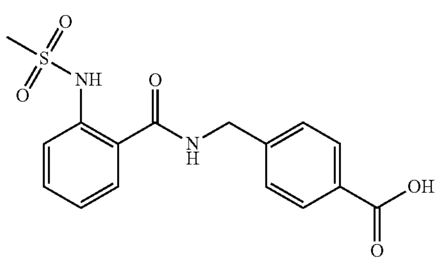 [SMILES: CS(=O)(=O)Nc1ccccc1C(=O)NCc1ccc(C(=O)O)cc1] | L | LCMS: Found 349.1 [M + H] $^1$H NMR (400 MHz, DMSO-d$_6$): 12.91 (br s, 1H), 11.13 (br s, 1H), 9.51 (T, 1H), 7.94-7.91 (M, 3H), 7.57 (S, 2H), 7.46 (D, 2H), 7.24-7.21 (M, 1H), 4.56 (D, 2H), 3.12 (S, 3H) | B |
| 121 | 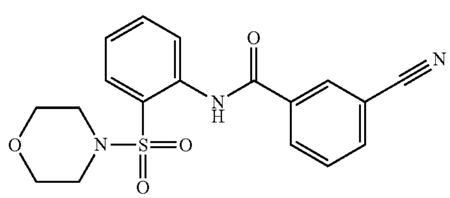 [SMILES: N#Cc1cccc(C(=O)Nc2ccccc2S(=O)(=O)N2CCOCC2)c1] | J | LCMS: Found 372.1 [M + H] $^1$H NMR (400 MHz, DMSO-d$_6$): 10.37 (S, 1H), 8.37 (S, 1H), 8.26 (M, 1H), 8.14-8.12 (M, 2H), 7.86-7.79 (M, 3H), 7.52 (M, 1H), 3.56-3.54 (T, 4H), 2.83-2.86 (T, 4H) | — |
| 122 | 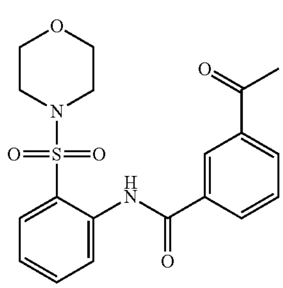 [SMILES: CC(=O)c1cccc(C(=O)Nc2ccccc2S(=O)(=O)N2CCOCC2)c1] | J | LCMS: Found 389.1 [M + H] $^1$H NMR (400 MHz, DMSO-d$_6$): 10.42 (S, 1H), 8.51 (S, 1H), 8.30 (D, 1H), 8.23-8.19 (M, 2H), 7.87-7.74 (M, 3H), 7.50 (T, 1H), 3.57-3.55 (M, 4H), 2.92-2.89 (M, 4H), 2.67 (S, 3H) | A |

TABLE 1-continued

| Cmpd # | Structure | Synthetic Scheme | Characterization Data (NMR and/or LCMS) | Biological Activity |
|---|---|---|---|---|
| 123 | 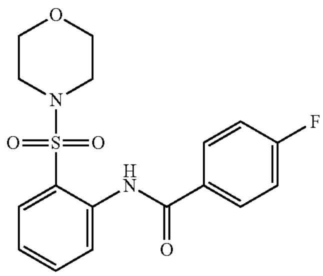 [SMILES: O=C(Nc1ccccc1S(=O)(=O)N1CCOCC1)c1ccc(F)cc1] | J | LCMS: Found 365.1 [M + H] $^1$H NMR (400 MHz, DMSO-$d_6$): 10.27 (S, 1H), 8.30 (D, 1H), 8.05-8.01 (M, 2H), 7.84-7.80 (M, 2H), 7.47-7.41 (M, 3H), 3.62-3.55 (M, 4H), 2.95-2.88 (M, 4H) | A |
| 124 | 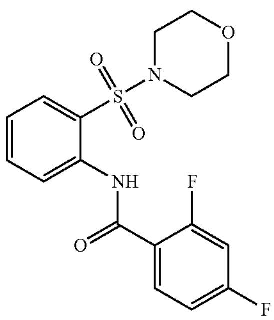 [SMILES: O=C(Nc1ccccc1S(=O)(=O)N1CCOCC1)c1ccc(F)cc1F] | G | LCMS: Found 383.1 [M + H] $^1$H NMR (400 MHz, CDCl$_3$): 10.36 (D, 1H), 8.64 (D, 1H), 8.20-8.14 (M, 1H), 7.85 (D, 1H), 7.69 (T, 1H), 7.35-7.29 (M, 2H), 7.10-6.95 (M, 2H), 3.71-3.69 (M, 4H), 3.09-3.06 (M, 4H). | — |
| 125 | 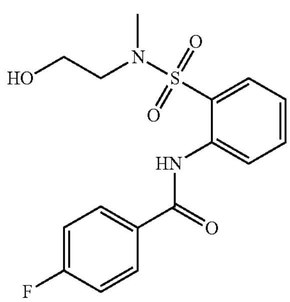 [SMILES: CN(CCO)S(=O)(=O)c1ccccc1NC(=O)c1ccc(F)cc1] | G | LCMS: Found 353.1 [M + H] $^1$H NMR (400 MHz, CDCl$_3$): 10.40 (S, 1H), 8.66 (D, 1H), 8.07-8.04 (M, 2H), 7.85 (D, 1H), 7.60 (T, 1H), 7.32-7.20 (M, 3H), 3.73-3.71 (M, 2H), 3.25-3.23 (M, 2H), 2.86 (S, 3H). | B |
| 126 | 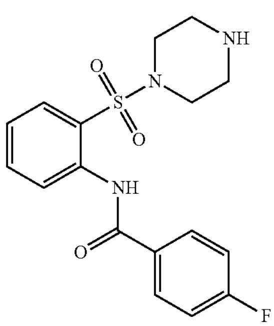 [SMILES: O=C(Nc1ccccc1S(=O)(=O)N1CCNCC1)c1ccc(F)cc1] | G | LCMS: Found 364.2 [M + H] $^1$H NMR (400 MHz, CDCl$_3$ + CD$_3$OD): 8.60 (D, 1H), 7.97-7.94 (M, 2H), 7.80 (D, 1H), 7.70 (T, 1H), 7.32-7.16 (M, 3H), 3.37-3.33 (M, 4H), 3.18-3.15 (M, 4H). | — |
| 127 | 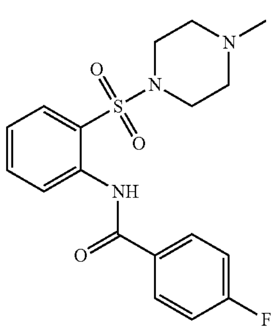 [SMILES: CN1CCN(S(=O)(=O)c2ccccc2NC(=O)c2ccc(F)cc2)CC1] | G | LCMS: Found 378.2 [M + H] $^1$H NMR (400 MHz, CDCl$_3$): 10.17 (S, 1H), 8.73 (D, 1H), 8.03-8.00 (M, 2H), 7.80 (D, 1H), 7.74 (T, 1H), 7.35-7.22 (M, 3H), 3.81 (br s, 2H), 3.56 (br s, 2H), 3.29 (br s, 2H), 2.90 (br s, 2H), 2.81 (S, 3H). | — |

TABLE 1-continued

| Cmpd # | Structure | Synthetic Scheme | Characterization Data (NMR and/or LCMS) | Biological Activity |
|---|---|---|---|---|
| 128 | 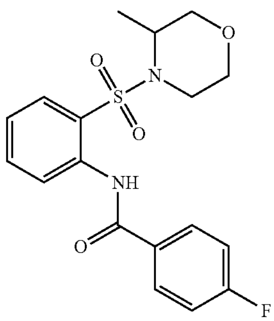 [SMILES: CC1COCCN1S(=O)(=O)c1ccccc1NC(=O)c1ccc(F)cc1] | G | LCMS: Found 379.2 [M + H] $^1$H NMR (400 MHz, CDCl$_3$): 10.28 (S, 1H), 8.64 (D, 1H), 8.06-8.03 (M, 2H), 7.89 (D, 1H), 7.65 (T, 1H), 7.30-7.21 (M, 3H), 3.87-3.85 (M, 1H), 3.75 (D, 1H), 3.55-3.26 (M, 5H), 1.19 (D, 3H). | A |
| 129 | 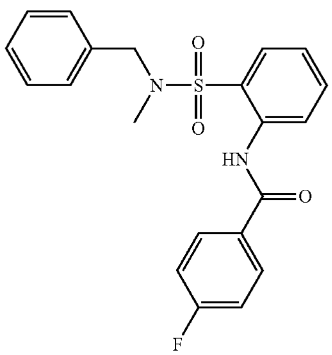 [SMILES: CN(Cc1ccccc1)S(=O)(=O)c1ccccc1NC(=O)c1ccc(F)cc1] | G | LCMS: Found 399.2 [M + H] $^1$H NMR (400 MHz, CDCl$_3$): 10.55 (S, 1H), 8.76 (D, 1H), 8.05-8.02 (M, 2H), 7.90 (D, 1H), 7.69 (T, 1H), 7.33-7.17 (M, 8H), 4.19 (S, 2H), 2.63 (S, 3H). | — |
| 130 | 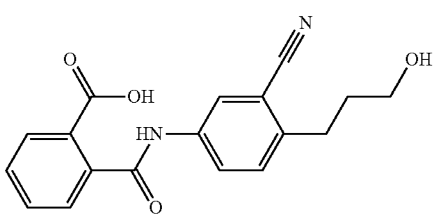 [SMILES: N#Cc1cc(NC(=O)c2ccccc2C(=O)O)ccc1CCCO] | A | LCMS: Found 325.1 [M + H] | — |
| 131 | 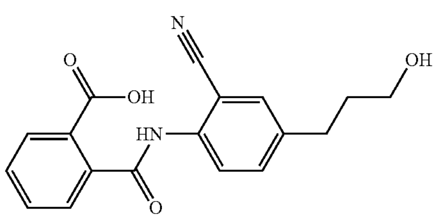 [SMILES: N#Cc1cc(CCCO)ccc1NC(=O)c1ccccc1C(=O)O] | A | LCMS: Found 325.1 [M + H] $^1$H NMR (400 MHz, DMSO-d$_6$): 13.15 (br s, 1H), 10.58 (S, 1H), 7.92 (D, 1H), 7.72-7.53 (M, 6H), 4.54 (T, 1H), 4.42-4.39 (M, 2H), 2.68-2.65 (M, 2H), 1.76-1.69 (M, 2H) | — |
| 132 | 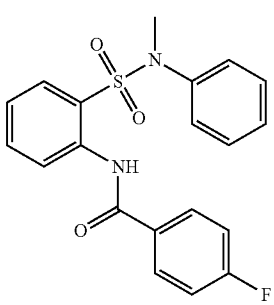 [SMILES: CN(c1ccccc1)S(=O)(=O)c1ccccc1NC(=O)c1ccc(F)cc1] | G | LCMS: Found 385.1 [M + H] $^1$H NMR (400 MHz, CDCl$_3$): 9.84 (S, 1H), 8.63 (D, 1H), 7.89 (D, 1H), 7.67-7.59 (M, 3H), 7.30-7.28 (M, 1H), 7.11-7.05 (m, 6H), 6.95-6.93 (M, 1H), 3.19 (S, 3H). | — |

TABLE 1-continued

| Cmpd # | Structure | Synthetic Scheme | Characterization Data (NMR and/or LCMS) | Biological Activity |
|---|---|---|---|---|
| 133 | 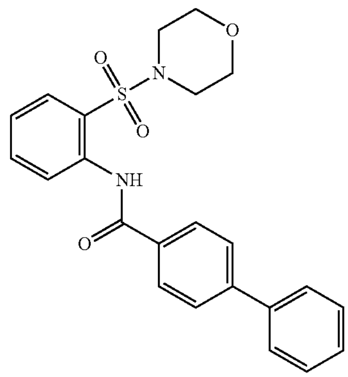 [SMILES: O=C(Nc1ccccc1S(=O)(=O)N1CCOCC1)c1ccc(-c2ccccc2)cc1] | G | LCMS: Found 423.1 [M + H] $^1$H NMR (400 MHz, CDCl$_3$): 10.54 (S, 1H), 8.79 (D, 1H), 8.10 (D, 2H), 7.83-7.66 (M, 6H), 7.54-7.42 (M, 3H), 7.33-7.29 (M, 1H), 3.71-3.69 (M, 4H), 3.07-3.05 (M, 4H). | B |
| 134 | 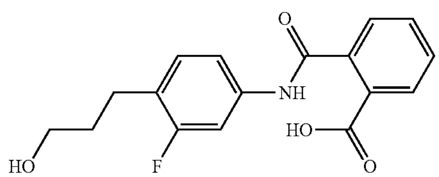 [SMILES: O=C(O)c1ccccc1C(=O)Nc1ccc(CCCO)c(F)c1] | A | LCMS: Found 318.2 [M + H] $^1$H NMR (400 MHz, DMSO-d$_6$): 13.10 (br s, 1H), 10.49 (S, 1H), 7.89 (D, 1H), 7.63-7.53 (M, 4H), 7.31 (D, 2H), 7.23 (T, 1H), 4.51 (T, 1H), 3.45-3.42 (M, 2H), 2.62-2.58 (M, 2H), 1.71-1.65 (M, 2H) | — |
| 135 | 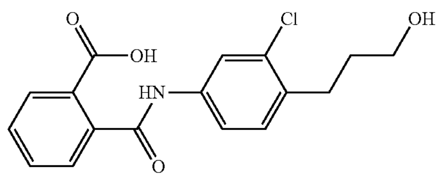 [SMILES: O=C(O)c1ccccc1C(=O)Nc1ccc(CCCO)c(Cl)c1] | A | LCMS: Found 334.1 [M + H] $^1$H NMR (400 MHz, DMSO-d$_6$): 13.09 (br s, 1H), 10.44 (S, 1H), 7.90-7.84 (M, 2H), 7.67-7.49 (M, 4H), 7.28 (D, 2H), 4.53 (T, 1H), 3.46-3.42 (M, 2H), 2.70-2.66 (M, 2H), 1.73-1.66 (M, 2H) | — |
| 136 | 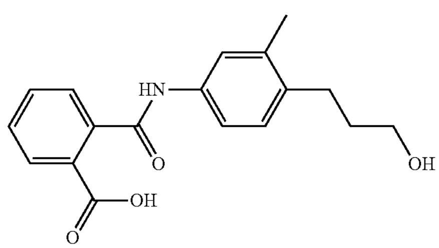 [SMILES: Cc1cc(NC(=O)c2ccccc2C(=O)O)ccc1CCCO] | A | LCMS: Found 314.1 [M + H] $^1$H NMR (400 MHz, CDCl$_3$): 10.17 (S, 1H), 7.86-7.84 (D, 1H), 7.63-7.62 (D, 1H), 7.55-7.47 (M, 3H), 7.40-7.35 (D, 1H), 7.06-7.04 (D, 1H), 4.49-4.47 (T, 1H), 3.45-3.41 (M, 2H), 2.57-2.53 (M, 2H), 2.24 (S, 3H), 1.67-1.60 (M, 2H) | — |
| 137 | 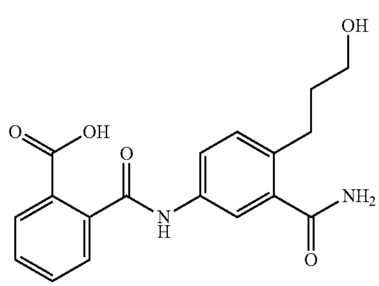 [SMILES: NC(=O)c1cc(NC(=O)c2ccccc2C(=O)O)ccc1CCCO] | A | LCMS: Found 343.0 [M + H] | — |
| 138 | 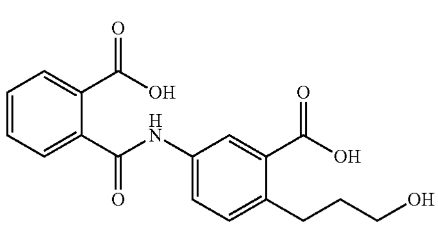 [SMILES: O=C(O)c1cc(NC(=O)c2ccccc2C(=O)O)ccc1CCCO] | A | LCMS: Found 344.1 [M + H] | — |

TABLE 1-continued

| Cmpd # | Structure | Synthetic Scheme | Characterization Data (NMR and/or LCMS) | Biological Activity |
|---|---|---|---|---|
| 139 | 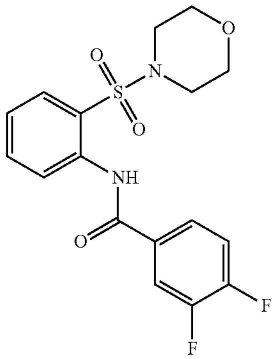 [SMILES: O=C(Nc1ccccc1S(=O)(=O)N1CCOCC1)c1ccc(F)c(F)c1] | G | LCMS: Found 383.2 [M + H] <br> ¹H NMR (400 MHz, CDCl₃): 10.50 (S, 1H), 8.73 (D, 1H), 7.92 (T, 1H), 7.82-7.70 (M, 3H), 7.40-7.29 (M, 2H), 3.72-3.70 (M, 4H), 3.05-3.02 (M, 4H). | — |
| 140 | 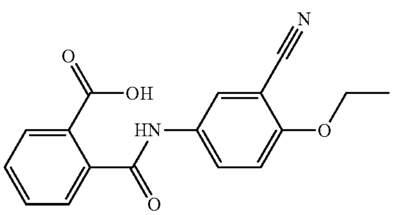 [SMILES: CCOc1ccc(NC(=O)c2ccccc2C(=O)O)cc1C#N] | A | LCMS: Found 311.2 [M + H] <br> ¹H NMR (400 MHz, DMSO-d₆): 13.10 (br s, 1H), 10.51 (S, 1H), 8.02 (S, 1H), 7.90-7.82 (M, 2H), 7.67-7.55 (M, 3H), 7.26 (D, 1H), 4.18 (Q, 2H), 1.37 (T, 3H) | — |
| 141 | 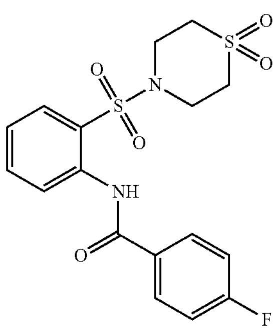 [SMILES: O=C(Nc1ccccc1S(=O)(=O)N1CCS(=O)(=O)CC1)c1ccc(F)cc1] | G | LCMS: Found 412.9 [M + H] <br> ¹H NMR (400 MHz, CD₃OD): 8.33 (D, 1H), 8.11-8.08 (M, 2H), 7.98 (D, 1H), 7.79 (T, 1H), 7.49 (T, 1H), 7.36-7.31 (M, 2H), 3.68-3.66 (M, 4H), 3.28-3.16 (M, 4H). | B |
| 142 | 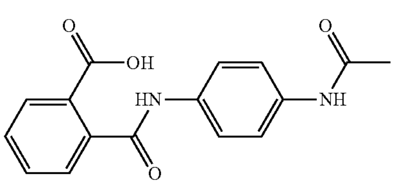 [SMILES: CC(=O)Nc1ccc(NC(=O)c2ccccc2C(=O)O)cc1] | A | LCMS: Found 299.1 [M + H] <br> ¹H NMR (400 MHz, DMSO-d₆): 12.99 (br s, 1H), 10.27 (S, 1H), 9.89 (S, 1H), 7.87 (D, 1H), 7.67-7.50 (M, 7H), 2.03 (S, 3H) | B |
| 143 | 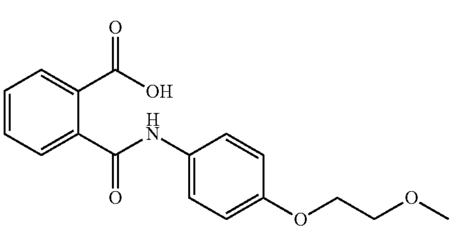 [SMILES: COCCOc1ccc(NC(=O)c2ccccc2C(=O)O)cc1] | A | LCMS: Found 316.1 [M + H] <br> ¹H NMR (400 MHz, CD₃OD): 8.03-8.01 (T, 1H), 7.66-7.63 (T, 1H), 7.58-7.52 (M, 4H), 6.94-6.92 (M, 2H), 4.12-4.10 (M, 2H), 3.75-3.73 (M, 2H), 3.42 (S, 3H) | — |

TABLE 1-continued

| Cmpd # | Structure | Synthetic Scheme | Characterization Data (NMR and/or LCMS) | Biological Activity |
|---|---|---|---|---|
| 144 | 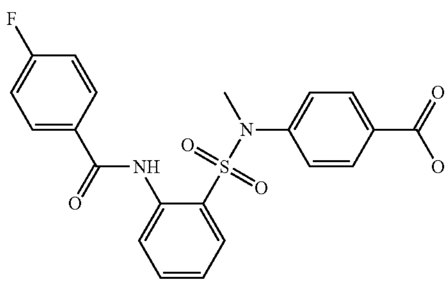 [SMILES: CN(c1ccc(C(=O)O)cc1)S(=O)(=O)c1ccccc1NC(=O)c1ccc(F)cc1] | G | LCMS: Found 429.0 [M + H]<br>¹H NMR (400 MHz, CD₃OD): 8.40 (D, 1H), 7.99 (D, 1H), 7.74 (T, 1H), 7.65-7.57 (M, 4H), 7.42 (T, 1H), 7.20-7.11 (M, 4H), 3.19 (S, 3H). | — |
| 145 | 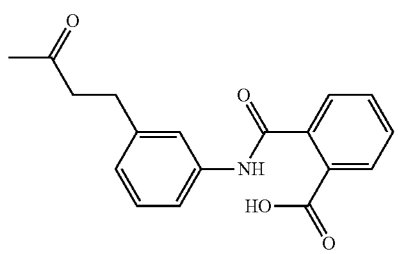 [SMILES: CC(=O)CCc1cccc(NC(=O)c2ccccc2C(=O)O)c1] | A | LCMS: Found 312.1 [M + H]<br>¹H NMR (400 MHz, DMSO-d₆): 11.18 (br s, 1H), 7.80 (D, 1H), 7.62-7.50 (M, 5H), 7.22 (T, 1H), 6.91 (D, 1H), 2.75 (S, 3H), 2.12-2.09 (M, 2H) | B |
| 146 | 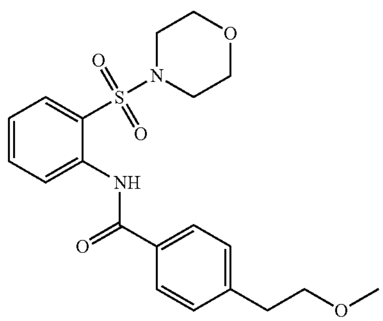 [SMILES: COCCc1ccc(C(=O)Nc2ccccc2S(=O)(=O)N2CCOCC2)cc1] | G | LCMS: Found 405.0 [M + H], LCMS: Found 427.0 [M + Na]<br>¹H NMR (400 MHz, CD₃OD): 8.53 (D, 1H), 7.93 (D, 2H), 7.88 (D, 1H), 7.76 (T, 1H), 7.47 (D, 2H), 7.42 (D, 1H), 3.68 (T, 2H), 3.64-3.62 (M, 4H), 3.36 (S, 3H), 3.01-2.96 (M, 6H). | — |
| 147 | 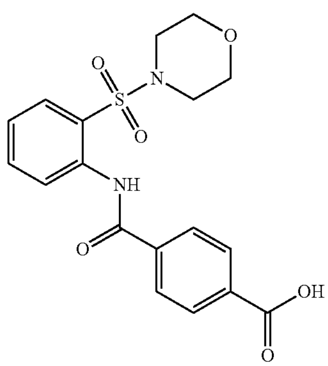 [SMILES: O=C(O)c1ccc(C(=O)Nc2ccccc2S(=O)(=O)N2CCOCC2)cc1] | G | LCMS: Found 391.0 [M + H]<br>¹H NMR (400 MHz, CD₃OD): 8.53 (D, 1H), 8.22 (D, 2H), 8.12 (D, 2H), 7.92 (D, 1H), 7.80 (T, 1H), 7.44 (T, 1H), 3.65-3.63 (M, 4H), 3.02-3.00 (M, 4H). | B |
| 148 | 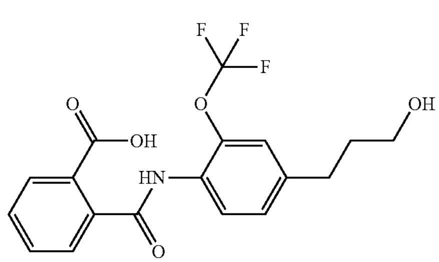 [SMILES: O=C(O)c1ccccc1C(=O)Nc1ccc(CCCO)cc1OC(F)(F)F] | A | LCMS: 384.1 [M + H]<br>¹H NMR (400 MHz, DMSO-d₆): 11.18 (br s, 1H), 7.80 (D, 1H), 7.62-7.50 (M, 5H), 7.22 (T, 1H), 6.91 (D, 1H), 2.75 (S, 3H), 2.12-2.09 (M, 2H) | B |

| Cmpd # | Structure | Synthetic Scheme | Characterization Data (NMR and/or LCMS) | Biological Activity |
|---|---|---|---|---|
| 149 | 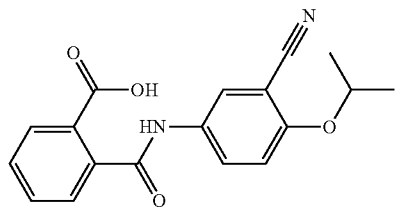 [SMILES: CC(C)Oc1ccc(NC(=O)c2ccccc2C(=O)O)cc1C#N] | A | LCMS: Found 325.2 [M + H] $^1$H NMR (400 MHz, DMSO-$d_6$): 13.09 (S, 1H), 10.48 (S, 1H), 8.01-8.01 (D, 1H), 7.90-7.88 (D, 1H), 7.81-7.80 (D, 1H), 7.67 (S, 1H), 7.59-7.56 (D, 2H), 7.31-7.28 (D, 2H), 4.77-4.72 (M, 1H), 1.32-1.31 (D, 6H) | — |
| 150 | 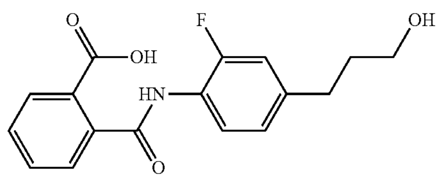 [SMILES: O=C(O)c1ccccc1C(=O)Nc1ccc(CCCO)cc1F] | A | LCMS: Found 318.1 [M + H] $^1$H NMR (400 MHz, DMSO-$d_6$): 13.03 (S, 1H), 10.05 (S, 1H), 7.88-7.86 (D, 2H), 7.07-7.65 (M, 2H), 7.57-5.52 (M, 2H), 7.11-7.03 (M, 2H), 4.50 (S, 1H), 3.42-3.41 (D, 2H), 2.64-2.60 (T, 2H), 1.76-1.69 (M, 2H) | — |
| 151 | 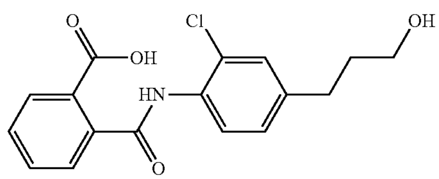 [SMILES: O=C(O)c1ccccc1C(=O)Nc1ccc(CCCO)cc1Cl] | A | LCMS: Found 334.1 [M + H] $^1$H NMR (400 MHz, DMSO-$d_6$): 13.13 (S, 1H), 9.93 (S, 1H), 7.88-7.86 (D, 1H), 7.66-7.65 (M, 1H), 7.59-7.54 (M, 3H), 7.35 (S, 1H), 7.22-7.20 (D, 1H), 4.50 (S, 1H), 3.43-3.39 (M, 2H), 2.64-2.60 (T, 2H), 1.74-1.68 (M, 2H) | — |
| 152 | 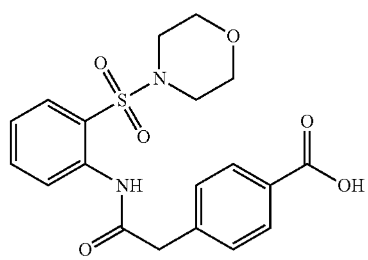 [SMILES: O=C(Cc1ccc(C(=O)O)cc1)Nc1ccccc1S(=O)(=O)N1CCOCC1] | G | LCMS: Found 405.0 [M + H] $^1$H NMR (400 MHz, CD$_3$OD): 8.36 (D, 1H), 8.05 (D, 2H), 7.76 (D, 1H), 7.67 (T, 1H), 7.53 (D, 2H), 7.35 (T, 1H), 3.88 (S, 2H), 3.51-3.48 (M, 4H), 2.64-2.62 (M, 4H). | — |
| 153 | 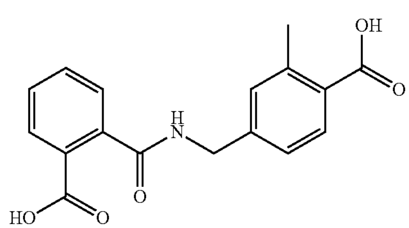 [SMILES: Cc1cc(CNC(=O)c2ccccc2C(=O)O)ccc1C(=O)O] | A | LCMS: Found 314.1 [M + H] $^1$H NMR (400 MHz, DMSO-$d_6$): 12.91 (br s, 2H), 8.98 (S, 1H), 7.80-7.75 (M, 2H), 7.58-7.50 (M, 3H), 7.31-7.28 (M, 2H), 4.46-4.04 (M, 2H) | — |
| 154 | 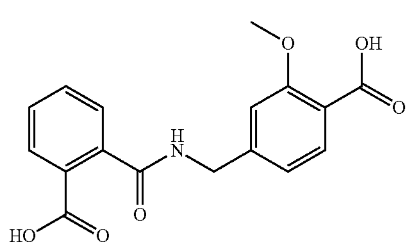 [SMILES: COc1cc(CNC(=O)c2ccccc2C(=O)O)ccc1C(=O)O] | A | LCMS: Found 330.0 [M + H] $^1$H NMR (400 MHz, DMSO-$d_6$): 12.95 (br s, 1H), 12.55 (br s, 1H), 8.93 (S, 1H), 7.78 (D, 1H), 7.62-7.49 (M, 4H), 7.16 (D, 1H), 4.47 (D, 2H), 3.84 (S, 3H) | B |

TABLE 1-continued

| Cmpd # | Structure | Synthetic Scheme | Characterization Data (NMR and/or LCMS) | Biological Activity |
|---|---|---|---|---|
| 155 | 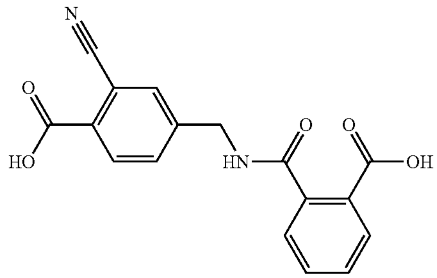 [SMILES: N#Cc1cc(CNC(=O)c2ccccc2C(=O)O)ccc1C(=O)O] | A | LCMS: Found 325.0 [M + H] $^1$H NMR (400 MHz, DMSO-$d_6$): 13.37 (br s, 1H), 8.99 (T, 1H), 8.07 (D, 1H), 7.97 (S, 1H), 7.83-7.80 (M, 2H), 7.62-7.51 (M, 3H), 4.54 (D, 2H) | A |
| 156 | 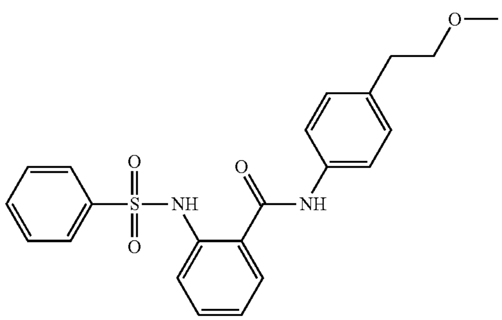 | H | LCMS: Found 455.1 [M + 2NA − H] $^1$H NMR (400 MHz, CDCl$_3$): 10.36 (S, 1H), 7.82-7.75 (M, 3H), 7.51-7.43 (M, 5H), 7.37-7.33 (M, 2H), 7.29-7.27 (M, 2H), 7.16 (T, 1H), 4.38 (T, 2H), 3.81 (S, 3H), 3.02 (T, 2H). | A |
| 157 | 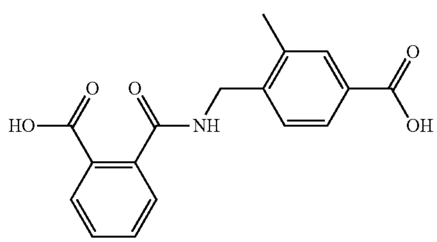 [SMILES: Cc1cc(C(=O)O)ccc1CNC(=O)c1ccccc1C(=O)O] | A | LCMS: Found 314.1 [M + H] $^1$H NMR (400 MHz, DMSO-$d_6$): 12.92 (br s, 2H), 8.86 (T, 1H), 7.79-7.73 (M, 3H), 7.60-7.48 (M, 4H), 4.45 (D, 2H), 2.38 (S, 3H) | — |
| 158 | 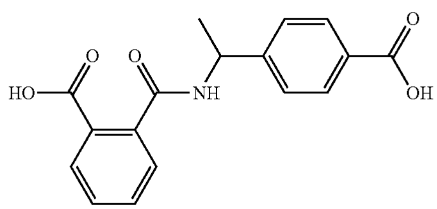 [SMILES: CC(NC(=O)c1ccccc1C(=O)O)c1ccc(C(=O)O)cc1] | A | LCMS: 314.1 [M + H] $^1$H NMR (400 MHz, DMSO-$d_6$): 12.97 (br s, 2H), 8.83 (D, 1H), 8.02 (D, 1H), 7.91 (D, 1H), 7.79 (D, 1H), 7.61-7.55 (M, 3H), 7.44 (D, 1H), 5.18-5.11 (M, 1H), 1.44 (D, 3H) | — |
| 159 | 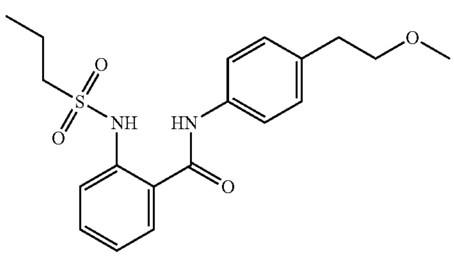 | H | LCMS: Found 421.2 [M + 2Na − H] $^1$H NMR (400 MHz, CDCl$_3$): 10.36 (S, 1H), 7.96 (S, 1H), 7.79 (D, 1H), 7.67 (D, 1H), 7.56-7.51 (M, 3H), 7.29-7.27 (M, 1H), 7.19 (T, 1H), 4.36 (T, 2H), 3.80 (S, 3H), 3.14 (T, 2H), 3.01 (T, 2H), 1.91-1.85 (M, 2H), 1.02 (T, 3H). | B |
| 160 | 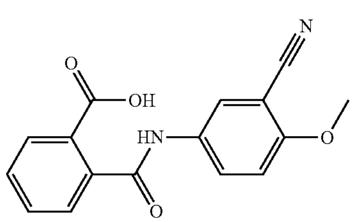 [SMILES: COc1ccc(NC(=O)c2ccccc2C(=O)O)cc1C#N] | A | LCMS: Found 297.1 [M + H] | — |

TABLE 1-continued

| Cmpd # | Structure | Synthetic Scheme | Characterization Data (NMR and/or LCMS) | Biological Activity |
|---|---|---|---|---|
| 161 | 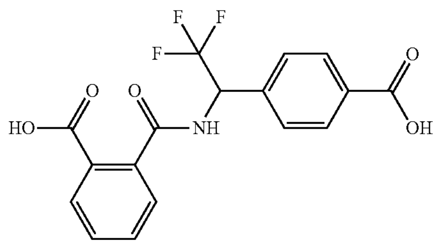 [SMILES: O=C(O)c1ccc(C(NC(=O)c2ccccc2C(=O)O)C(F)(F)F)cc1] | A | LCMS: Found 368.1 [M + H]<br>$^1$H NMR (400 MHz, CD$_3$OD): 8.08-8.06 (D, 2H), 8.01-7.99 (D, 1H), 7.68-7.64 (M, 3H), 7.56-7.56 (D, 1H), 7.42-7.40 (D, 1H), 6.03-5.97 (M, 1H) | — |
| 162 | 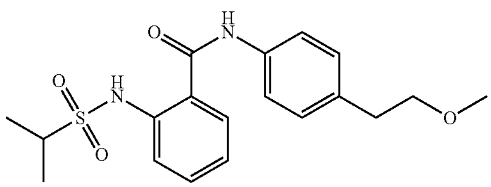 | H | LCMS: Found 421.2 [M + 2Na − H]<br>$^1$H NMR (400 MHz, CDCl$_3$): 10.35 (S, 1H), 7.95 (S, 1H), 7.85 (D, 1H), 7.65 (D, 1H), 7.56-7.48 (M, 3H), 7.31-7.27 (M, 1H), 7.16 (T, 1H), 4.36 (T, 2H), 3.80 (S, 3H), 3.37-3.32 (M, 1H), 3.01 (T, 2H), 1.41 (S, 6H). | B |
| 163 | 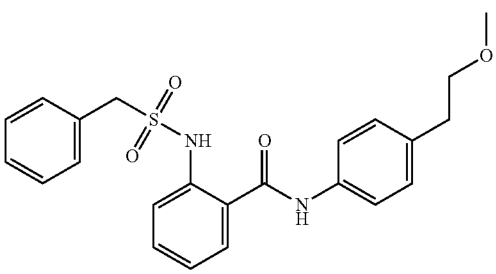 | H | LCMS: Found 469.2 [M + 2Na − H]<br>$^1$H NMR (400 MHz, CDCl$_3$): 10.42 (S, 1H), 7.80 (S, 1H), 7.67 (D, 1H), 7.61 (D, 1H), 7.50-7.44 (M, 3H), 7.29-7.24 (M, 6H), 7.16 (T, 1H), 4.42 (S, 2H), 4.37 (T, 2H), 3.80 (s, 3H), 3.01 (T, 2H) | — |
| 164 | 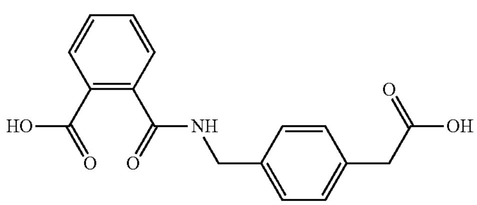 [SMILES: O=C(O)Cc1ccc(CNC(=O)c2ccccc2C(=O)O)cc1] | A | LCMS: Found 314.1 [M + H]<br>$^1$H NMR (400 MHz, DMSO-d$_6$): 12.70 (br s, 2H), 8.83 (T, 1H), 7.76 (D, 1H), 7.59-7.45 (M, 3H), 7.32 (D, 2H), 7.20 (D, 2H), 4.41 (D, 2H), 3.55 (S, 2H) | A |
| 165 | 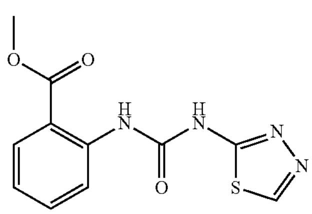 [SMILES: COC(=O)c1ccccc1NC(=O)Nc1nncs1] | K-1 | LCMS: Found 279.0 [M + H]<br>$^1$H NMR (400 MHz, CDCl$_3$): 10.98 (S, 1H), 8.80 (S, 1H), 8.46 (D, 1H), 8.03 (D, 1H), 7.61-7.56 (M, 1H), 7.28-7.11 (M, 1H), 3.92 (S, 3H) | — |
| 166 | 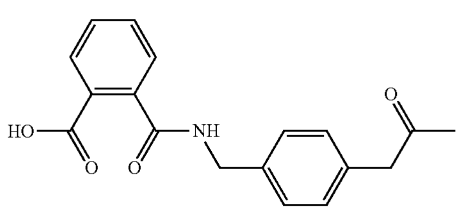 [SMILES: CC(=O)Cc1ccc(CNC(=O)c2ccccc2C(=O)O)cc1] | A | LCMS: Found 312.1 [M + H]<br>$^1$H NMR (400 MHz, DMSO-d$_6$): 12.99 (br s, 1H), 8.84 (T, 1H), 7.76 (D, 1H), 7.59-7.47 (M, 3H), 7.33 (D, 2H), 7.14 (D, 2H), 4.41 (D, 2H), 3.74 (S, 2H), 2.12 (S, 3H) | B |

TABLE 1-continued

| Cmpd # | Structure | Synthetic Scheme | Characterization Data (NMR and/or LCMS) | Biological Activity |
|---|---|---|---|---|
| 167 | 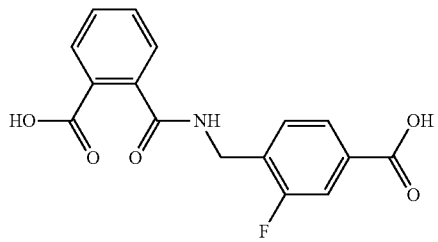 [SMILES: O=C(O)c1ccc(CNC(=O)c2ccccc2C(=O)O)c(F)c1] | A | LCMS: Found 318.1 [M + H] | — |
| 168 | 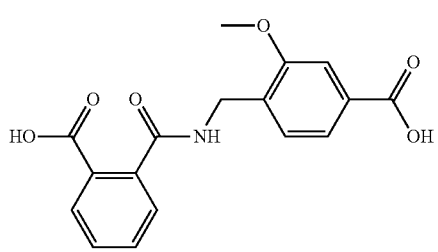 [SMILES: COc1cc(C(=O)O)ccc1CNC(=O)c1ccccc1C(=O)O] | A | LCMS: Found 330.1 [M + H]<br>$^1$H NMR (400 MHz, DMSO-$d_6$): 9.39 (br s, 2H), 7.71 (D, 1H), 7.59-7.47 (M, 6H), 4.43 (D, 2H), 3.55 (S, 2H) | — |
| 169 | 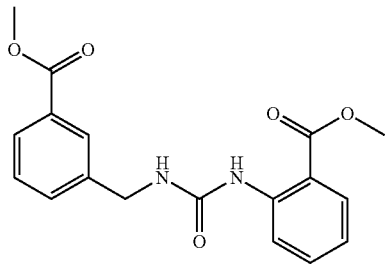 [SMILES: COC(=O)c1cccc(CNC(=O)Nc2ccccc2C(=O)OC)c1] | K-1 | LCMS: Found 343.0 [M + H]<br>LCMS: Found 365.0 [M + Na]<br>$^1$H NMR (400 MHz, CDCl$_3$): 10.48 (S, 1H), 8.56 (D, 1H), 8.04-7.79 (M, 3H), 7.60 (D, 1H), 7.53 (T, 1H), 7.45 (T, 1H), 7.02-6.98 (M, 1H), 5.11 (br s, 1H), 4.56 (D, 2H), 3.94 (S, 3H), 3.91 (S, 3H) | — |
| 170 | 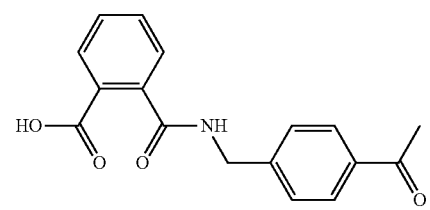 [SMILES: CC(=O)c1ccc(CNC(=O)c2ccccc2C(=O)O)cc1] | A | LCMS: Found 298.1 [M + H]<br>$^1$H NMR (400 MHz, DMSO-$d_6$): 13.03 (br s, 1H), 8.94 (T, 1H), 7.92 (D, 2H), 7.78 (D, 2H), 7.61-7.49 (M, 5H), 4.50 (D, 2H), 2.58 (S, 3H) | — |
| 171 | 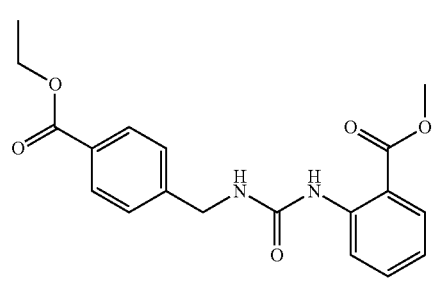 [SMILES: CCOC(=O)c1ccc(CNC(=O)Nc2ccccc2C(=O)OC)cc1] | K-1 | LCMS: Found 357.0 [M + H]<br>LCMS: Found 379.0 [M + Na]<br>$^1$H NMR (400 MHz, CDCl$_3$): 10.50 (S, 1H), 8.56 (D, 1H), 8.05-8.01 (M, 3H), 7.53 (T, 1H), 7.44 (D, 1H), 7.00 (t, 1H), 5.10 (br s, 1H), 4.57 (D, 2H), 4.38 (Q, 2H), 3.91 (S, 3H), 1.41 (T, 3H) | — |
| 172 | 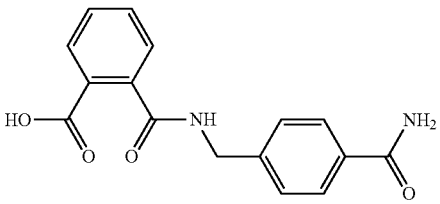 [SMILES: NC(=O)c1ccc(CNC(=O)c2ccccc2C(=O)O)cc1] | A | LCMS: Found 299.1 [M + H] | B |

TABLE 1-continued

| Cmpd # | Structure | Synthetic Scheme | Characterization Data (NMR and/or LCMS) | Biological Activity |
|---|---|---|---|---|
| 173 | 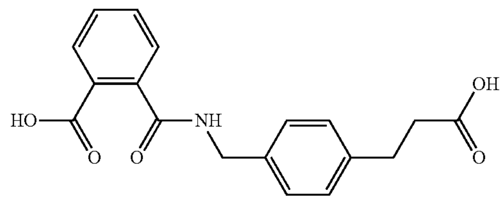 [SMILES: O=C(O)CCc1ccc(CNC(=O)c2ccccc2C(=O)O)cc1] | A | LCMS: Found 328.2 [M + H] | — |
| 174 | 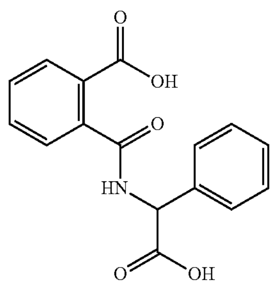 [SMILES: O=C(O)c1ccccc1C(=O)NC(C(=O)O)c1ccccc1] | A | LCMS: Found 300.1 [M + H]<br>$^1$H NMR (400 MHz, CD$_3$OD): 7.98-7.97 (D, 1H), 7.63-7.51 (M, 5H), 7.39-7.36 (T, 3H), 5.68 (S, 1H) | — |
| 175 | 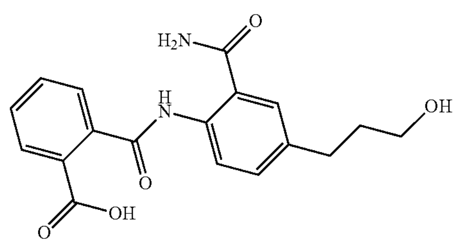 [SMILES: NC(=O)c1cc(CCCO)ccc1NC(=O)c1ccccc1C(=O)O] | A | LCMS: Found 365.1 [M + Na]<br>$^1$H NMR (400 MHz, DMSO-d$_6$): 13.09 (br s, 1H), 12.09 (S, 1H), 8.49 (D, 1H), 8.30 (S, 1H), 7.82 (D, 1H), 7.7-7.61 (M, 4H), 7.36 (D, 1H), 4.52 (T, 1H), 3.44-3.41 (M, 2H), 2.63-2.60 (M, 2H), 1.78-1.71 (M, 2H) | — |
| 176 | 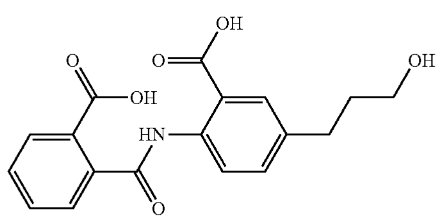 [SMILES: O=C(O)c1cc(CCCO)ccc1NC(=O)c1ccccc1C(=O)O] | A | LCMS: Found 344.1 [M + H]<br>$^1$H NMR (400 MHz, DMSO-d$_6$): 13.12 (S, 1H), 11.42 (S, 1H), 8.52-8.50 (D, 1H), 7.86-7.83 (M, 2H), 7.70-7.64 (M, 3H), 7.62 (D, 1H), 4.49 (S, 1H), 3.41 (M, 2H), 2.65-2.62 (T, 2H), 1.75-1.68 (M, 2H) | B |
| 177 | 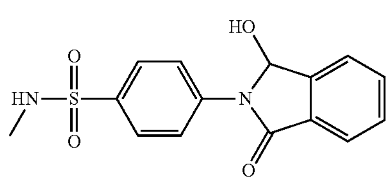 [SMILES: CNS(=O)(=O)c1ccc(N2C(=O)c3ccccc3C2O)cc1] | B-3 | LCMS: Found 318.9 [M + H]<br>LCMS: Found 301.0 [M − H$_2$O]<br>$^1$H NMR (400 MHz, DMSO-d$_6$): 8.07 (D, 2H), 7.84 (D, 2H), 7.83-7.71 (M, 3H), 7.64 (T, 1H), 7.42 (br s, 1H), 7.03 (br s, 1H), 6.66 (S, 1H), 2.44 (S, 3H). | — |
| 178 | 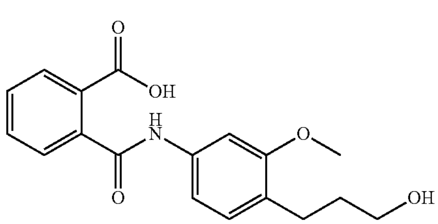 [SMILES: COc1cc(NC(=O)c2ccccc2C(=O)O)ccc1CCCO] | A | LCMS: Found 330.2 [M + H]<br>$^1$H NMR (400 MHz, DMSO-d$_6$): 13.03 (S, 1H), 10.26 (S, 1H), 7.88 (D, 1H), 7.64 (D, 1H), 7.59-7.52 (M, 2H), 7.41 (S, 1H), 7.17 (D, 1H), 7.06 (D, 1H), 4.43 (T, 1H), 3.75 (S, 3H), 3.43-3.38 (M, 2H), 2.51-2.50 (M, 2H), 1.67-1.65 (M, 2H) | B |

TABLE 1-continued

| Cmpd # | Structure | Synthetic Scheme | Characterization Data (NMR and/or LCMS) | Biological Activity |
|---|---|---|---|---|
| 179 | 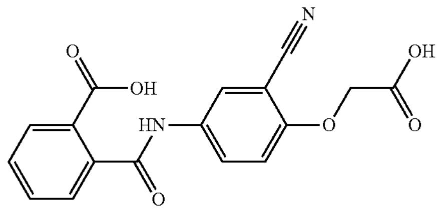 [SMILES: N#Cc1cc(NC(=O)c2ccccc2C(=O)O)ccc1OCC(=O)O] | A | LCMS: Found 341.1 [M + H] <br> $^1$H NMR (400 MHz, DMSO-$d_6$): 13.21 (br s, 1H), 10.56 (S, 1H), 8.03 (D, 1H), 7.90 (D, 1H), 7.80 (D, 1H), 7.69-7.55 (M, 3H), 7.17 (D, 1H), 4.87 (S, 2H) | — |
| 180 | 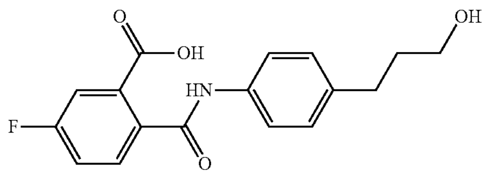 [SMILES: O=C(O)c1cc(F)ccc1C(=O)Nc1ccc(CCCO)cc1] | A | LCMS: Found 318.1 [M + H] <br> $^1$H NMR (400 MHz, DMSO-$d_6$): 13.13 (br s, 1H), 10.31 (S, 1H), 7.96 (D, 1H), 7.63-7.39 (M, 5H), 7.15 (D, 2H), 4.47 (T, 1H), 3.42-3.40 (M, 2H), 2.59-2.53 (M, 2H), 1.73-1.66 (M, 2H) | B |
| 181 | 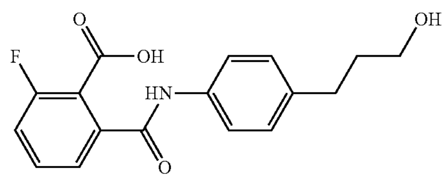 [SMILES: O=C(Nc1ccc(CCCO)cc1)c1cccc(F)c1C(=O)O] | A | LCMS: Found 318.1 [M + H] <br> $^1$H NMR (400 MHz, DMSO-$d_6$): 13.25 (br s, 1H), 10.46 (S, 1H), 7.64-7.45 (M, 6H), 7.15 (D, 2H), 4.47 (T, 1H), 3.43-3.37 (M, 2H), 2.60-2.56 (M, 2H), 1.74-1.66 (m, 2H) | B |
| 182 | 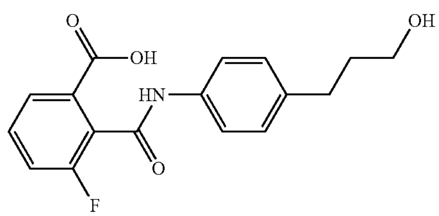 [SMILES: O=C(O)c1cccc(F)c1C(=O)Nc1ccc(CCCO)cc1] | A | LCMS: Found 318.1 [M + H] | B |
| 183 | 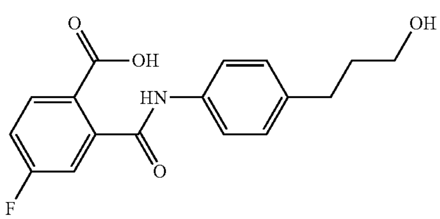 [SMILES: O=C(O)c1ccc(F)cc1C(=O)Nc1ccc(CCCO)cc1] | A | LCMS: Found 318.1 [M + H] | B |
| 184 | 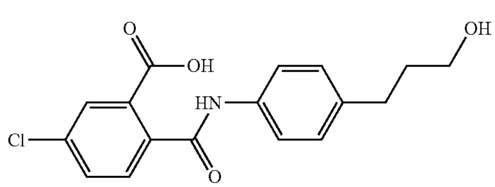 [SMILES: O=C(O)c1cc(Cl)ccc1C(=O)Nc1ccc(CCCO)cc1] | A | LCMS: Found 334.1 [M + H] <br> $^1$H NMR (400 MHz, DMSO-$d_6$): 13.30 (br s, 1H), 10.31 (S, 1H), 7.90-7.55 (M, 6H), 7.15 (D, 2H), 4.47 (br s, 1H), 3.43-3.38 (M, 2H), 2.60-2.55 (M, 2H), 1.73-1.68 (M, 2H) | B |
| 185 | 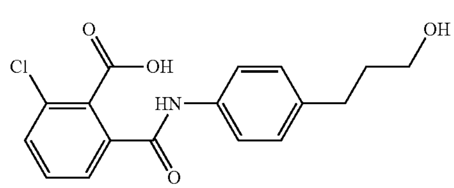 [SMILES: O=C(Nc1ccc(CCCO)cc1)c1cccc(Cl)c1C(=O)O] | A | LCMS: Found 334.1 [M + H] <br> $^1$H NMR (400 MHz, DMSO-$d_6$): 10.46 (S, 1H), 7.727.68 (M, 2H), 7.61-7.54 (M, 3H), 7.16 (D, 2H), 4.47 (S, 1H), 3.43-3.39 (M, 2H), 2.60-2.50 (M, 2H), 1.74-1.66 (M, 2H) | B |

TABLE 1-continued
| Cmpd # | Structure | Synthetic Scheme | Characterization Data (NMR and/or LCMS) | Biological Activity |
|---|---|---|---|---|
| 186 | 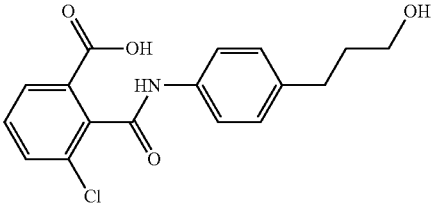 | A | LCMS: Found 334.1 [M + H] | B |
| 187 | 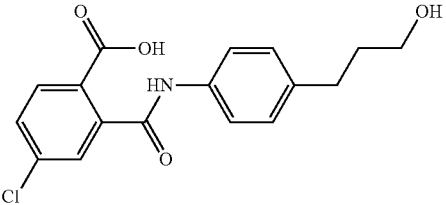 [SMILES: O=C(O)c1ccc(Cl)cc1C(=O)Nc1ccc(CCCO)cc1] | A | LCMS: Found 334.1 [M + H] | B |
| 188 | 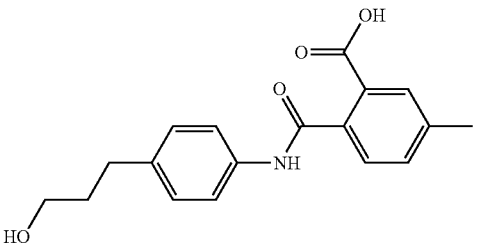 [SMILES: Cc1ccc(C(=O)Nc2ccc(CCCO)cc2)c(C(=O)O)c1] | A | LCMS: Found 314.2 [M + H] $^1$H NMR (400 MHz, DMSO-$d_6$): 12.85 (br s, 1H), 10.19 (S, 1H), 7.79-7.56 (M, 3H), 7.44-7.33 (M, 2H), 7.13 (D, 2H), 4.47 (T, 1H), 3.42-3.39 (M, 2H), 2.59-2.51 (M, 2H), 1.73-1.66 (M, 2H) | — |
| 189 | 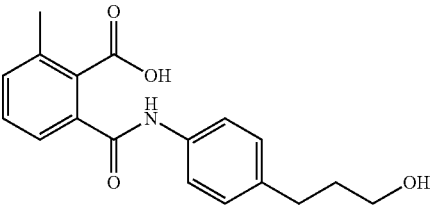 [SMILES: Cc1cccc(C(=O)Nc2ccc(CCCO)cc2)c1C(=O)O] | A | LCMS: Found 314.2 [M + H] $^1$H NMR (400 MHz, MeOD): 7.59-7.53 (M, 3H), 7.48-7.41 (M, 2H), 7.18-7.14 (M, 2H), 3.60-3.57 (T, 2H), 2.72-2.67 (M, 2H), 2.47 (S, 3H), 1.88-1.81 (M, 2H) | A |
| 190 | 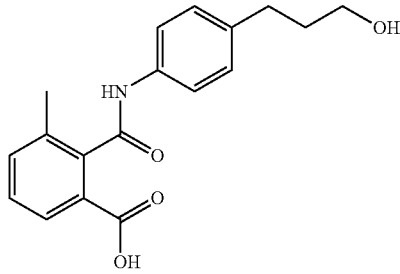 [SMILES: Cc1cccc(C(=O)O)c1C(=O)Nc1ccc(CCCO)cc1] | A | LCMS: Found 314.2 [M + H] | A |
| 191 | 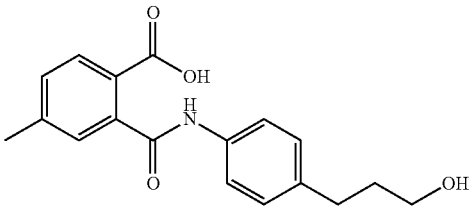 [SMILES: Cc1ccc(C(=O)O)c(C(=O)Nc2ccc(CCCO)cc2)c1] | A | LCMS: Found 314.2 [M + H] | — |

TABLE 1-continued

| Cmpd # | Structure | Synthetic Scheme | Characterization Data (NMR and/or LCMS) | Biological Activity |
|---|---|---|---|---|
| 192 | 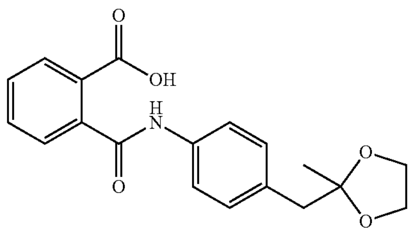 [SMILES: CC1(Cc2ccc(NC(=O)c3ccccc3C(=O)O)cc2)OCCO1] | A | LCMS: Found 342.2 [M + H] $^1$H NMR (400 MHz, DMSO-$d_6$): 13.04 (br s, 1H), 10.28 (S, 1H), 7.86 (D, 1H), 7.65-7.53 (M, 5H), 7.19 (D, 2H), 3.86-3.77 (M, 4H), 2.81 (S, 2H), 1.19 (S, 3H) | — |
| 193 | 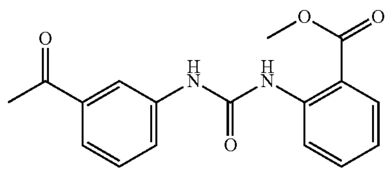 [SMILES: COC(=O)c1ccccc1NC(=O)Nc1cccc(C(C)=O)c1] | K-1 | LCMS: Found 313.2 [M + H] $^1$H NMR (400 MHz, DMSO-$d_6$): 10.63 (S, 1H), 8.53 (D, 1H), 8.03 (M, 2H), 7.75 (D, 1H), 7.68 (D, 1H), 7.53 (T, 1H), 7.42 (T, 1H), 7.04 (M, 1H), 3.90 (S, 3H), 2.30 (S, 3H) | B |
| 194 | 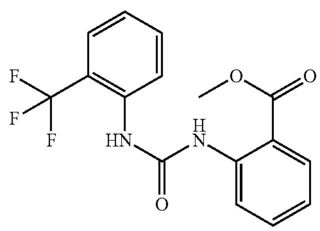 [SMILES: COC(=O)c1ccccc1NC(=O)Nc1ccccc1C(F)(F)F] | K-1 | LCMS: Found 339.2 [M + H] $^1$H NMR (400 MHz, DMSO-$d_6$): 10.70 (S, 1H), 8.50 (D, 1H), 8.00 (T, 2H), 7.65 (D, 1H), 7.55 (M, 2H), 7.26 (m, 1H), 6.67 (S, 1H), 3.88 (s, 3H) | B |
| 195 | 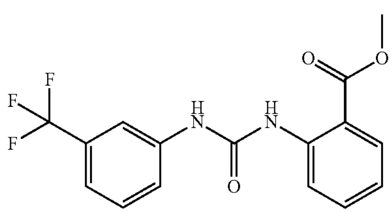 [SMILES: COC(=O)c1ccccc1NC(=O)Nc1cccc(C(F)(F)F)c1] | K-1 | LCMS: Found 339.2 [M + H] $^1$H NMR (400 MHz, DMSO-$d_6$): 10.65 (S, 1H), 8.55 (D, 1H), 8.02 (D, 1H), 7.81 (S, 1H), 7.62 (D, 1H), 7.55 (T, 1H), 7.45 (T, 1H), 7.26 (D, 1H), 7.05 (T, 1H), 6.95 (S, 1H), 3.91 (S, 3H) | B |
| 196 | 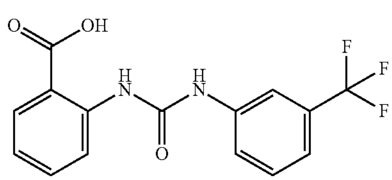 [SMILES: O=C(Nc1cccc(C(F)(F)F)c1)Nc1ccccc1C(=O)O] | K-2 | LCMS: Found 307.1 [M − $H_2O$ + H] $^1$H NMR (400 MHz, DMSO-$d_6$): 11.63 (S, 1H), 7.95 (D, 1H), 7.82 (M, 1H), 7.81 (S, 1H), 7.73 (M, 2H), 7.68 (M, 1H), 7.24 (M, 2H) | B |
| 197 | 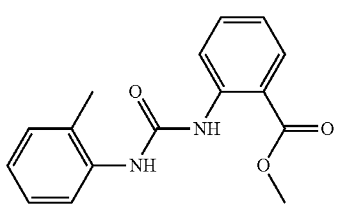 [SMILES: COC(=O)c1ccccc1NC(=O)Nc1ccccc1C] | K-1 | LCMS: Found 285.2 [M + H] $^1$H NMR (400 MHz, DMSO-$d_6$): 9.96 (S, 1H), 9.01 (S, 1H), 8.29 (D, 1H), 7.92 (DD, 1H), 7.55 (T, 1H), 7.46 (DD, 1H), 7.22-7.16 (M, 2H), 7.07-7.04 (M, 2H), 3.87 (S, 3H), 2.25 (S, 3H) | B |
| 198 | 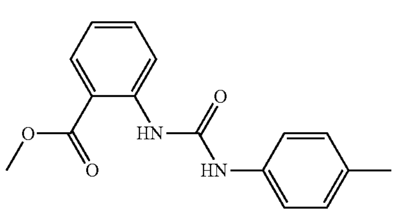 | K-1 | LCMS: Found 285.2 [M + H] $^1$H NMR (400 MHz, CDCl$_3$): 10.47 (S, 1H), 8.55 (D, 1H), 7.99 (D, 1H), 7.51 (T, 1H), 7.30 (D, 2H), 7.16 (D, 2H), 7.0 (T, 1H), 6.68 (S, 1H), 3.87 (S, 3H), 2.33 (S, 3H) | B |

TABLE 1-continued

| Cmpd # | Structure | Synthetic Scheme | Characterization Data (NMR and/or LCMS) | Biological Activity |
|---|---|---|---|---|
| 199 | 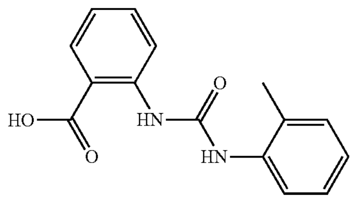 [SMILES: Cc1ccccc1NC(=O)Nc1ccccc1C(=O)O] | K-2 | LCMS: Found 253.2 [M − H₂O + H]<br>¹H NMR (400 MHz, DMSO-d₆): 11.60 (S, 1H), 7.96 (D, 1H), 7.72 (T, 1H), 7.35 (M, 2H), 7.30 (M, 1H), 7.22 (M, 3H), 3.32 (S, 3H) | B |
| 200 | 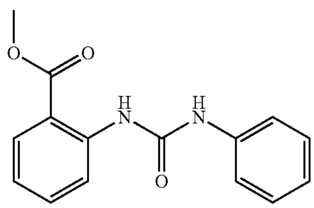 [SMILES: COC(=O)c1ccccc1NC(=O)Nc1ccccc1] | K-1 | LCMS: Found 271.2 [M + H]<br>¹H NMR (400 MHz, DMSO-d₆): 10.50 (S, 1H), 8.55 (D, 1H, J = 6 Hz), 7.97 (D, 1H, J = 7.8 Hz), 7.52 (M, 1H), 7.44 (M, 1H), 7.34 (M, 2H), 7.11 (M, 1H), 7.00 (M, 1H), 6.84 (S, 1H), 3.88 (S, 3H) | B |
| 201 | 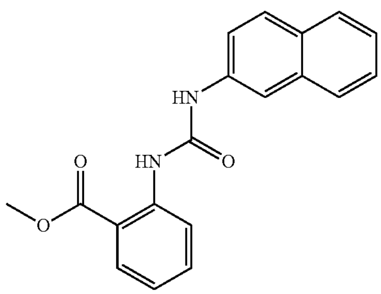 [SMILES: COC(=O)c1ccccc1NC(=O)Nc1ccc2ccccc2c1] | K-1 | LCMS: Found 321.2 [M + H]<br>¹H NMR (400 MHz, CDCl₃): 10.64 (S, 1H), 8.60 (DD, 1H), 8.08-7.98 (M, 2H), 7.83-7.74 (M, 3H), 7.55 (DD, 1H), 7.49-7.34 (M, 3H), 7.06-6.97 (M, 1H), 6.95 (S, 1H), 3.89 (S, 3H) | B |
| 202 | 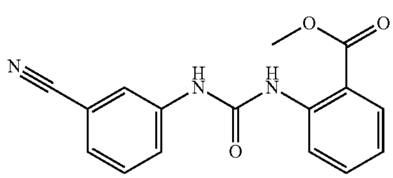 [SMILES: COC(=O)c1ccccc1NC(=O)Nc1cccc(C#N)c1] | K-1 | LCMS: Found 296.2 [M + H]<br>¹H NMR (400 MHz, CDCl₃): 10.70 (S, 1H), 8.52 (DD, 1H), 8.02 (DD, 1H), 7.89 (T, 1H), 7.64 (DD, 1H), 7.56 (DD, 1H), 7.45-7.33 (M, 2H), 7.05 (DD, 1H), 6.92 (S, 1H), 3.93 (S, 3H) | A |
| 203 | 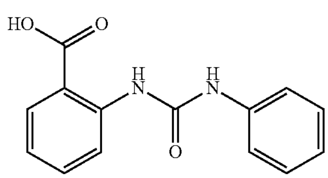 [SMILES: O=C(Nc1ccccc1)Nc1ccccc1C(=O)O] | K-2 | LCMS: Found 238.07 [M − H₂O + H]<br>¹H NMR (400 MHz, DMSO-d₆): 11.56 (S, 2H), 7.94 (D, 1H, J = 8 Hz), 7.70 (T, 1H, J = 6 Hz), 7.48 (M, 2H), 7.42 (M, 1H), 7.32 (M, 2H), 7.22 (m, 2H) | B |
| 204 | 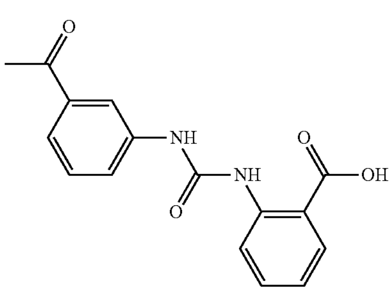 | K-2 | LCMS: Found 280.08 [M − H₂O + H]<br>¹H NMR (400 MHz, DMSO-d₆): 11.60 (S, 2H), 8.03 (D, 2H, J = 6 Hz), 7.95 (M, 2H), 7.72 (T, 2H, J = 6 Hz), 7.25 (D, 2H, J = 6.4 Hz), 3.32 (S, 3H) | B |

TABLE 1-continued

| Cmpd # | Structure | Synthetic Scheme | Characterization Data (NMR and/or LCMS) | Biological Activity |
|---|---|---|---|---|
| 205 | 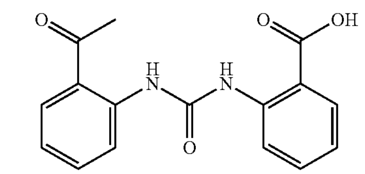 [SMILES: CC(=O)c1ccccc1NC(=O)Nc1ccccc1C(=O)O] | K-2 | LCMS: Found 281.2 [M − $H_2O$ + H] $^1$H NMR (400 MHz, DMSO-$d_6$): 11.55 (S, 1H), 8.05 (D, 1H), 7.90 (D, 1H), 7.70 (M, 2H), 7.61 (M, 1H), 7.42 (D, 1H), 7.23 (M, 2H), 2.46 (S, 3H) | B |
| 206 | 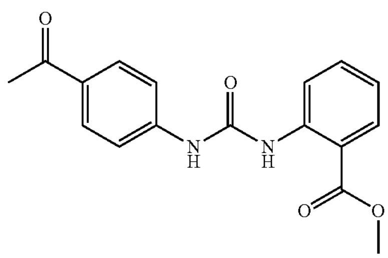 [SMILES: COC(=O)c1ccccc1NC(=O)Nc1ccc(C(C)=O)cc1] | K-1 | LCMS: Found 313.2 [M + H] $^1$H NMR (400 MHz, DMSO-$d_6$): 10.67 (S, 2H), 8.52 (D, 1H, J = 7.8 Hz), 8.00 (D, 1H), 7.94 (D, 2H, J = 8 Hz), 7.55 (M, 3H), 7.03 (T, 1H, J = 6 Hz), 3.88 (S, 3H), 2.58 (S, 3H) | B |

Example 2: Cell Viability Assay

Human MSCs, chondrocytes, osteoblasts and synoviocytes are plated into 384-well plates at 10,000 cells per well. Compounds are added at a final concentration of 100 µM. The cells are cultured for 48 h. Cell viability is analyzed by Cell Titer-Glo (Promega) assay using EnVision plate reader (PerkinElmer). Apoptosis activity is analyzed by Caspase 3/7-Glo (Promega) assay using EnVision plate reader (PerkinElmer).

Example 3: PK Study Via Intra-Articular Injection in Rats

A 30 µl-compound solution (100 µM in PBS containing 0.1% DMSO) is injected into the articular space of the right knee of each rat. The animals are bled at 1, 3, 4, 6, 7, 8, 9, and 10 hours post-injection. The animals are terminated at 2 or 12 hours post-dose. Plasma and joint lavage of the injected knees are collected. The quantities of the injected compounds are analyzed using LCMS.

Example 4: Rat Medial Meniscal Tear (MMT) Osteoarthritis (OA) Model

The medial meniscus of the right knee of each animal is surgically torn to induce OA. Dosing of the compound solutions (30 µl of 100 µM in PBS containing 0.1% DMSO) is begun 7 days post-surgery at one dose per week for three weeks. Body weights and gait deficits are monitored weekly right before dosing. Animals are terminated at day 28 post-surgery. The joints of the operated knees are processed and histochemically stained for cartilage, and the cartilage is evaluated.

Following 4-6 days in 5% formic acid decalcifier, the operated joints are cut into two approximately equal halves in the frontal plane and embedded in paraffin. Three sections are cut from each operated right knee (g1-8) at approximately 200 µm steps and stained with toluidine blue. Left knees of group 1 and right knees from group 9 have a single section prepared and stained with toluidine blue.

All three sections of each operated knee are analyzed microscopically. The worst-case scenario for the two halves on each slide is determined for general cartilage degeneration, proteoglycan loss, collagen damage, and osteophyte formation. The values for each parameter are then averaged across the three sections to determine overall subjective scores.

In addition, for some parameters (noted below), regional differences across the tibial plateau are taken into consideration by dividing each section into three zones (1-outside, 2-middle, 3-inside). In the surgical OA model, the outside (z1) and middle (z2) thirds are most severely affected, and milder changes are present on the inside third (z3). When zones are scored individually, scores are assigned based on percent area of the zone affected. Zone areas are delineated using an ocular micrometer.

The following parameters are measured and/or scored:

General cartilage degeneration includes the important parameters of chondrocyte death/loss, proteoglycan loss, and collagen loss or fibrillation. Cartilage degeneration in the tibia is scored none to severe (numerical values 0-5) for each zone using the following criteria:

0=no degeneration

1=minimal degeneration, within the zone 5-10% of the matrix appears non viable as a result of significant chondrocyte loss (greater than 50% of normal cell density). PG loss is usually present in these areas of cell loss and collagen matrix loss may be present.

2=mild degeneration, within the zone 11-25% of the matrix appears non viable as a result of significant chondrocyte loss (greater than 50% of normal cell density). PG loss is usually present in these areas of cell loss and collagen matrix loss may be present.

3=moderate degeneration, within the zone 26-50% of the matrix appears non viable as a result of significant chondrocyte loss (greater than 50% of normal cell density). PG loss is usually present in these areas of cell loss and collagen matrix loss may be present.

4=marked degeneration, within the zone 51-75% of the matrix appears non viable as a result of significant chondrocyte loss (greater than 50% of normal cell density). PG loss is usually present in these areas of cell loss and collagen matrix loss may be present.

5=severe degeneration, within the zone 76-100% of the matrix appears non viable as a result of significant chondrocyte loss (greater than 50% of normal cell density). PG loss is usually present in these areas of cell loss and collagen matrix loss may be present.

In some cases, image analysis may be used to determine the exact % of matrix viability and/or loss in each zone or in selected zones so that absolute % rather than scores (0-5) can be compared. A 3-zone sum for cartilage degeneration is calculated in addition to expressing the data for each zone.

The same process is applied to evaluation of the femoral cartilage with the exception that lesions are not analyzed based on zones since the lesions are not generally distributed over the surface in a zonal pattern. The total width of the load-bearing surface (approximately 2000 µm for the femur) is determined and the above criteria is applied to the most severely affected 1/3, 2/3 or 3/3. For example, if 1/3 of the total area (lesion may be in the center of the plateau covering about 667 µm) has minimal degeneration (5-10% of total area has loss of chondrocytes and/or matrix), a score of 1 is assigned. If that minimal degeneration extends over the entire surface (3/3) then the score is 3. If the entire femoral cartilage is absent as a result of severe diffuse degeneration, then the score is 15.

In addition to this overall cartilage degeneration score, collagen matrix damage is scored separately in order to identify more specific effects of agents. Collagen damage across the medial tibial plateau (most severely affected section of the two halves) is quantified by measuring the total width of the following:

Any damage (fibrillation ranging from superficial to full thickness loss).

Severe damage (total or near total loss of collagen to tidemark, >90% thickness)

Marked damage (extends through 61-90% of the cartilage thickness)

Moderate damage (extends thru 31-60% of the cartilage thickness)

Mild damage (extends through 11-30% of the cartilage thickness)

Minimal damage (very superficial, affecting upper 10% only)

In addition to the above subjective general cartilage scoring, two cartilage degeneration width measurements are taken:

Total Tibial Cartilage Degeneration Width (µm) is a micrometer measurement of total extent of tibial plateau affected by any type of degeneration (cell loss, proteoglycan loss or collagen damage). This measurement extends from the origination of the osteophyte with adjacent cartilage degeneration (outside 1/3) across the surface to the point where tangential layer and underlying cartilage appear histologically normal.

Substantial Cartilage Degeneration Width (µm) reflects areas of tibial cartilage degeneration in which both chondrocyte and proteoglycan loss extend through greater than 50% of the cartilage thickness. In general, the collagen damage is mild (25% depth) or greater for this parameter but chondrocyte and proteoglycan loss extend to at least 50% or greater of the cartilage depth.

A micrometer depth of any type of lesion (both chondrocyte and proteoglycan loss, but may have good retention of collagenous matrix and no fibrillation), expressed as a ratio of depth of changed area vs. depth to tidemark, is taken in the area of greatest lesion severity in each of the three zones across the tibial surface at the midpoint of the zone. This measurement is the most critical analysis of any type of microscopic change present. The denominator can serve as an average measure of cartilage thickness in each of the three zones for comparison of anabolics when measures are taken at the midpoint of the zone.

Scoring of the osteophytes and categorization into small, medium and large is done with an ocular micrometer. Marginal zone proliferative changes have to be >200 µm in order to be measured and designated as osteophytes. Scores are assigned to the largest osteophyte in each section (typically found in the tibia) according to the following criteria:

1=small up to 299 µm
2=moderate 300-399 µm
3=large 400-499 µm
4=very large 500-599
5=very large ≥600

The actual osteophyte measurement (tidemark to furthest distance point extending toward synovium) is also recorded.

The femoral cartilage degeneration score and the three-zone sum of the tibial cartilage degeneration scores (mean of three levels) are summed to create a total cartilage degeneration score. The mean osteophyte score for each joint is added to this value to produce a total joint score.

Image Analysis

In order to quantify and compare the cartilage matrix preservation, cartilage area measurements are taken from the most severely affected section of each animal. Photomicrographs are taken with a CoolSNAP-Pro microscope camera and loaded into ImagePro Plus software. The following measurements are taken from tracings of these photomicrographs, four per page, which are included in the report:

Total area from the tidemark to the surface (or projected surface in degenerated areas) over 9 cm (photomicrograph) of the tibial plateau, measured from the inner edge of the osteophyte Area of non-viable matrix (cartilage with less than 50% chondrocytes, proteoglycan, and intact collagen) and no matrix within the total area Area of no matrix within the total area The area of non-viable matrix is subtracted from the total area to get the area of viable matrix, and the area of no matrix is subtracted from the total area to get the area of any matrix (collagen matrix with or without chondrocytes and proteoglycan). These two values are then compared back to the total area to derive the percent viable matrix area and the percent any matrix area, which are compared between groups. Five left knees from the vehicle group are included in this process as normal controls. This process may be used to analyze the entire surface or selected zones depending on lesion severity and apparent treatment effects.

Synovial reaction, if abnormal, is described (should be mainly fibrosis) and characterized with respect to inflammation type and degree but is not included in the OA score.

Damage to the calcified cartilage layer and subchondral bone (worst case scenario for all sections) is scored using the following criteria:

0=No changes
1=Increased basophilia at tidemark, no fragmentation of tidemark, no marrow changes or if present minimal and focal
2=Increased basophilia at tidemark, minimal to mild focal fragmentation of calcified cartilage of tidemark, mesenchymal change in marrow involves 1/4 of total area but generally is restricted to subchondral region under lesion
3=Increased basophilia at tidemark, mild to marked focal or multifocal fragmentation of calcified cartilage (multifocal), mesenchymal change in marrow is up to 3/4 of total area, areas of marrow chondrogenesis may be evident but no major collapse of articular cartilage into epiphyseal bone (definite depression in surface)

4=Increased basophilia at tidemark, marked to severe fragmentation of calcified cartilage, marrow mesenchymal change involves up to 3/4 of area and articular cartilage has collapsed into the epiphysis to a depth of 250 µm or less from tidemark (see definite depression in surface cartilage)

5=Increased basophilia at tidemark, marked to severe fragmentation of calcified cartilage, marrow mesenchymal change involves up to 3/4 of area and articular cartilage has collapsed into the epiphysis to a depth of greater than 250 µm from tidemark In addition, measurements are made of the thickness of the medial synovial/collateral ligament repair in a non-tangential area of the section.

Growth plate thickness is measured in all knees on medial and lateral sides (2 measures/joint) at the approximate midpoint of the medial and lateral physis (assuming a non tangential area of the section).

Example 5: Extraction and Quantitation of Chondrogenesis Compounds in Joint and Plasma Rat Samples LC-MS/MS analysis for Chondrogenesis compounds were performed using an API 3000 equipped with an Agilent 1100 HPLC and a Leap Technologies autosampler. A HPLC Phenomenex 5 micron, 100 A Luna C18 (2) analytical column with dimensions of 2.0×50 mm (Part No. 00B-4252-B0) at a temperature of 30 C, flow rate of 0.6 mL/min, injection volume of 10 uL, and a 6.0 min run time was used. Mobile phase A1 was 0.1% formic acid in water and Mobile phase B1 was 0.1% formic acid in acetonitrile. The gradient was 90% A1/10% B1 at time 0; 90% A1/10% B1 at time 1.0 min; 10% A1/90% B1 at time 2.0 min; 10% A1/90% B1 at time 4.0 min; 90% A1/10% B1 at time 4.10 min; 90% A1/10% B1 at time 6.0 min. Analytes and internal standard quantitation were performed using Multiple Reaction Monitoring (MRM) quantitation method. Listed below are specific methods used to dose and measure exposure in plasma and the observed concentration in joint extract.

Rat Plasma Samples:

Calibration standard curve was prepared by serial dilution of a concentrated, spike solution of the compound in control rat plasma. Calibration standards and rat plasma samples were prepared via protein precipitation by adding aliquots of Acetonitrile and internal standard to each aliquot of standards and samples. Following vortex mixing and centrifugation, aliquots of the supernatants from each standards and samples were diluted with formic acid in water, mixed and injected. All plasma samples collected after IA dosing (starting at t=0, 0.5, 1, 2, 4, and 6 h) indicated no systemic exposure for any of the compounds listed in Table 2.

Rat Knee Joint Samples:

Calibration standard curve was prepared by serial dilution of a concentrated, spike solution of the compound in internal standard diluents. Internal standard diluent was prepared by dissolving the internal standard compound at a certain concentration in acetonitrile.

Rat knee joint samples for each time points were individually crushed and transferred into each centrifuge tube and added 1.0-mL of internal standard diluent. Each centrifuge tube was vortexed and centrifuged for 30 minutes. From each tube, supernatant was removed and injected onto the column for analysis. In addition, plasma samples were obtained by retro-orbital bleeds into heparin coated tubes and stored at −80 C and later processed by analogy to the protocol described above for rat plasma samples.

Compound Administration and Tissue Processing:

30 µL of 100 µM compound solution (PBS with 0.1% DMSO) was injected into the intra-articular space of the right hinder knee of each animal. The animals were euthanized at indicated time points (0 hr, 0.5 hr, 1 hr, 2 hr, 4 hr and 6 hr). Four animals were used for each timepoint. The injected knee joints were harvested, flash freeze in liquid nitrogen. The whole joints were grounded into powder while frozen, mixed with 1 mL internal standard-containing acetonitrile, incubated at 4° C. overnight, vortexed and centrifuged for 30 min. The supernatant from each sample was analyzed using LC-MS/MS. Data shown in Table 2 indicates the observed concentration in knee extract. ND=Not determined.

TABLE 2

| Compound # | Concentration observed in extract (ng/mL) | | | | | |
|---|---|---|---|---|---|---|
| | T = 0 h | T = 0.5 h | T = 1 h | T = 2 h | T = 4 h | T = 6 h |
| 21 | 433.5 | 9.1 | 4.9 | 0 | ND | ND |
| 27 | 592 | 35.4 | 6.3 | 2.5 | ND | ND |
| 62 | 411 | 108.75 | 52.6 | 15.7 | ND | ND |
| 73 | 587 | 28.5 | 9.41 | 2.6 | ND | ND |
| 113 | 565.5 | 25.3 | 4.2 | 0 | ND | ND |
| 117 | 925.5 | 50.6 | 4.4 | 0 | ND | ND |
| 123 | 4430 | 1102 | 741.25 | 337.5 | 38 | 0 |
| 128 | 7280 | 2942.5 | 1365 | 546 | ND | ND |
| 156 | 108.8 | 3.5 | 0 | 0 | ND | ND |

Example 6: Parenteral Composition of a Compound Presented Herein

To prepare a parenteral pharmaceutical composition suitable for administration by injection, 100 mg of a compound presented herein, or a water soluble pharmaceutically acceptable salt thereof, is dissolved in DMSO and then mixed with 10 ml of 0.9% sterile saline solution. The mixture is incorporated into a dosage unit suitable for administration by injection.

Example 7: Oral Composition of a Compound Presented Herein

To prepare a pharmaceutical composition for oral delivery, 400 mg of a compound presented herein, and the following ingredients are mixed intimately and pressed into single scored tablets.

| Tablet Formulation | |
|---|---|
| Ingredient | Quantity per tablet mg |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
|---|---|
| Ingredient | Quantity per capsule mg |
| compound | 200 |
| lactose spray dried | 148 |
| magnesium stearate | 2 |

What is claimed is:

1. A method of (a) ameliorating arthritis or joint injury in a mammal, the method comprising administering to a joint of the mammal a composition comprising a therapeutically effective amount of a compound of Formula IIb, or a pharmaceutically acceptable salt, solvate, polymorph, prodrug, ester, metabolite, N-oxide, stereoisomer, or isomer thereof; or (b) inducing differentiation of mesenchymal stem cells into chondrocytes, the method comprising contacting mesenchymal stem cells with a sufficient amount of a compound of Formula IIb, or a pharmaceutically acceptable salt, solvate, polymorph, prodrug, ester, metabolite, N-oxide, stereoisomer, or isomer thereof:

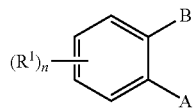

(Formula IIb)

wherein each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;

n is 0, 1, 2, 3, or 4;

B is $NHC(O)R^2$;

$R^2$ is optionally substituted phenyl, optionally substituted heteroaryl, optionally substituted heterocyclyl, optionally substituted aralkyl, or optionally substituted alkyl;

$R^4$ is optionally substituted phenyl, optionally substituted heteroaryl, optionally substituted heterocyclyl, optionally substituted aralkyl, or optionally substituted alkyl;

$R^5$ is H, optionally substituted alkyl, $C(O)R^4$, $C(O)OR^4$, $C(O)NR^4R^4$, or $SO_2R^4$;

A is $SO_2NR^aR^b$; and each $R^a$ and $R^b$ is independently optionally substituted alkyl or together with the N to which they are attached make a ring.

2. The method of claim 1, wherein each $R^a$ and $R^b$ is independently optionally substituted alkyl.

3. The method of claim 1, wherein $R^a$ and $R^b$ together with the N to which they are attached make a ring.

4. The method of claim 1, wherein $R^2$ is optionally substituted phenyl.

5. The method of claim 1, wherein the phenyl of $R^2$ is monosubstituted or disubstituted.

6. The method of claim 5, wherein substitution on the phenyl of $R^2$ is independently selected from F, Cl, $CO_2H$, CN, $OCH_3$, $C(O)CH_3$, $CF_3$, $CH_3$, $CH_2OH$, $CH_2CH_2OH$, and $CH_2CH_2CH_2OH$.

7. The method of claim 1, wherein the compound is:

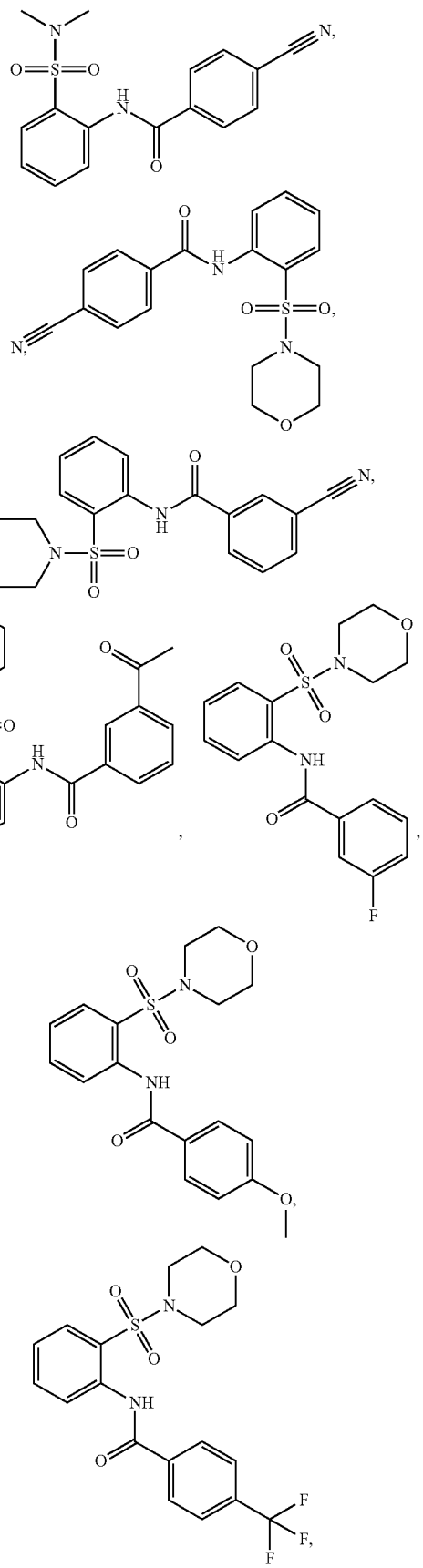

287
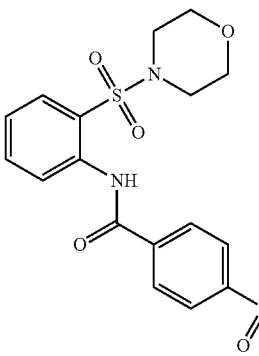
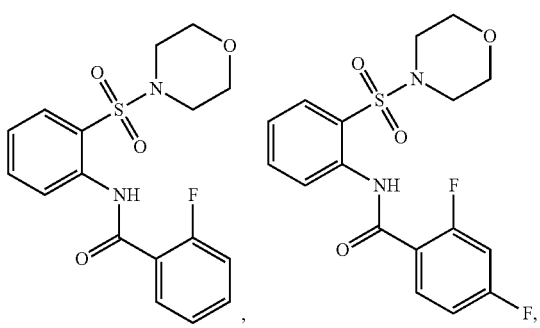
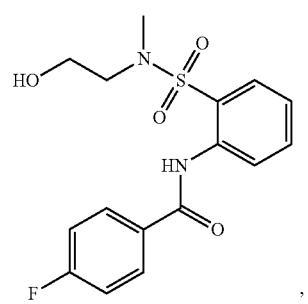
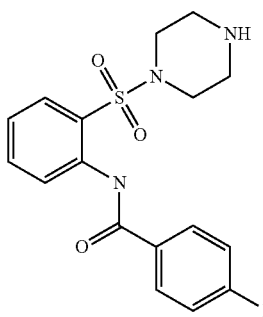
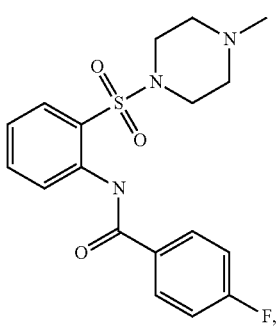 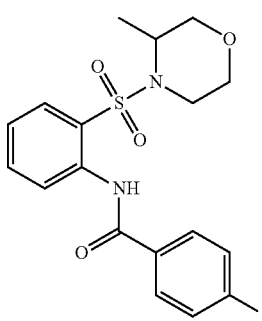
288
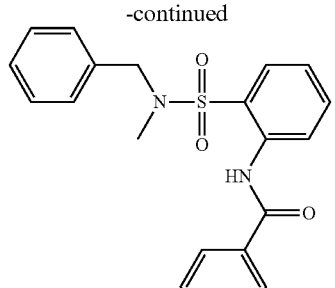
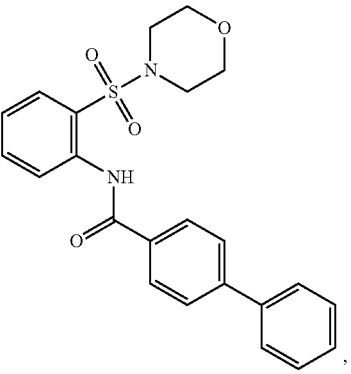
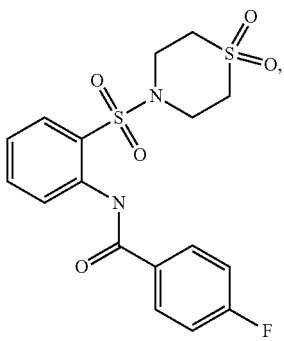
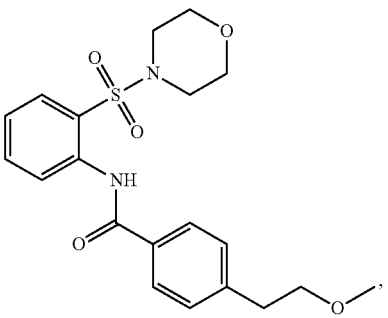

289
-continued

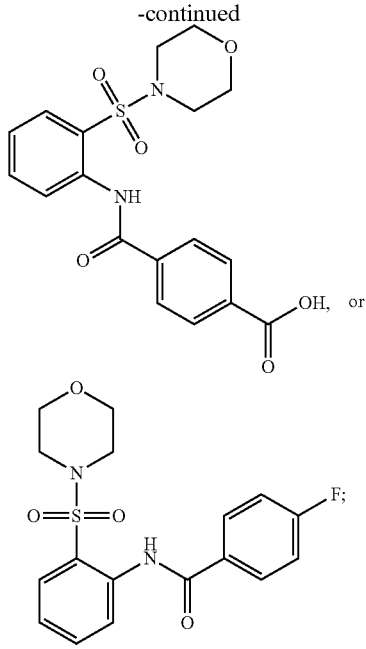

or a pharmaceutically acceptable salt, solvate, polymorph, prodrug, ester, metabolite, N-oxide, stereoisomer, or isomer thereof.

8. A method of (a) ameliorating arthritis or joint injury in a mammal, the method comprising administering to a joint of the mammal a composition comprising a therapeutically effective amount of a compound of Formula III, or a pharmaceutically acceptable salt, solvate, polymorph, prodrug, ester, metabolite, N-oxide, stereoisomer, or isomer thereof; or (b) inducing differentiation of mesenchymal stem cells into chondrocytes, the method comprising contacting mesenchymal stem cells with a sufficient amount of a compound of Formula III, or a pharmaceutically acceptable salt, solvate, polymorph, prodrug, ester, metabolite, N-oxide, stereoisomer, or isomer thereof:

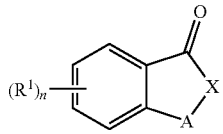 (Formula III)

wherein
each $R^1$ is independently halo, optionally substituted alkyl, optionally substituted alkoxy, optionally substituted aryloxy, CN, $NO_2$, $SR^4$, $S(O)R^4$, $SO_2R^4$, $NHR^5$, $NR^4R^5$, $CO_2H$, or $CO_2R^4$;
n is 0, 1, 2, 3, or 4;
X is O or NH and A is CH—$CR^3R^4$—$C(O)R^2$; or
X is $NR^6$ and A is C(O) or $CH_2$;
$R^2$ is optionally substituted aryl or optionally substituted heteroaryl;
each $R^3$ and $R^4$ is independently H or optionally substituted alkyl;
$R^5$ is H, optionally substituted alkyl, $C(O)R^4$, $C(O)OR^4$, $C(O)NR^4R^4$, or $SO_2R^4$; and
$R^6$ is optionally substituted phenyl;
provided that

290 if n is 0, A is $CHCH_2C(O)R^2$ and X is O, then $R^2$ is not

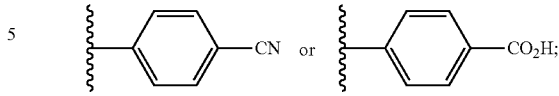

and
if A is C(O) or $CH_2$, then X is $NR^6$ and $R^6$ is not

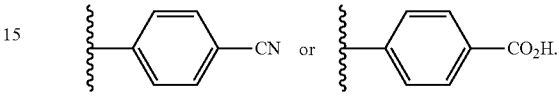

9. The method of claim 8, wherein $R^2$ is phenyl and the phenyl of $R^2$ is monosubstituted or disubstituted.

10. The method of claim 9, wherein substitution on the phenyl is independently selected from F, Cl, $CO_2H$, CN, $OCH_3$, $C(O)CH_3$, $CF_3$, $CH_3$, $CH_2OH$, $CH_2CH_2OH$, and $CH_2CH_2CH_2OH$.

11. The method of claim 8, wherein n is 0 or 1.

12. The method of claim 11, wherein $R^1$ is independently selected from Cl, F, $CH_2OH$, $CH_2NH_2$, $OCH_3$, $OCF_3$, $OCHF_2$, CN, $NO_2$, $CO_2H$, and $CO_2CH_3$.

13. The method of claim 8, wherein the compound is

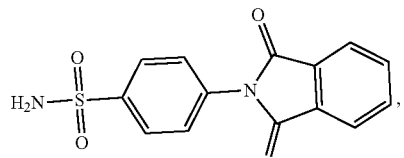

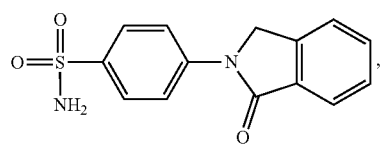

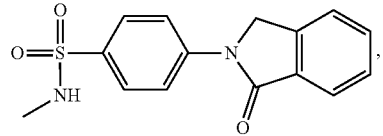

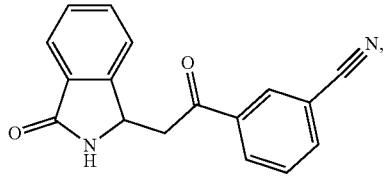

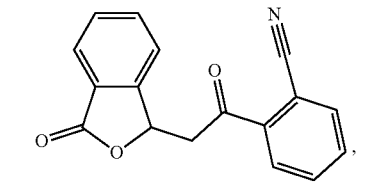

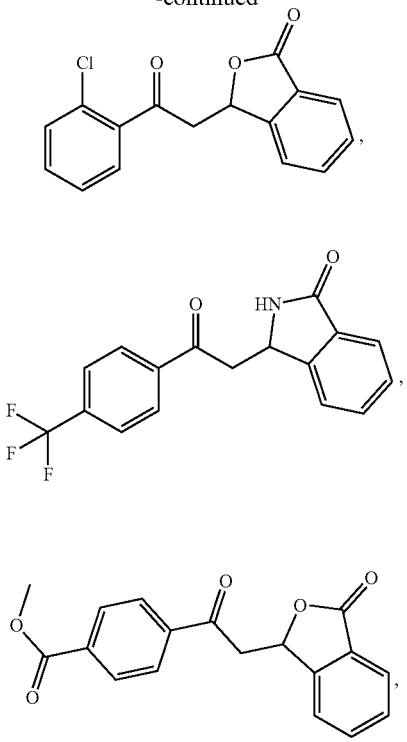
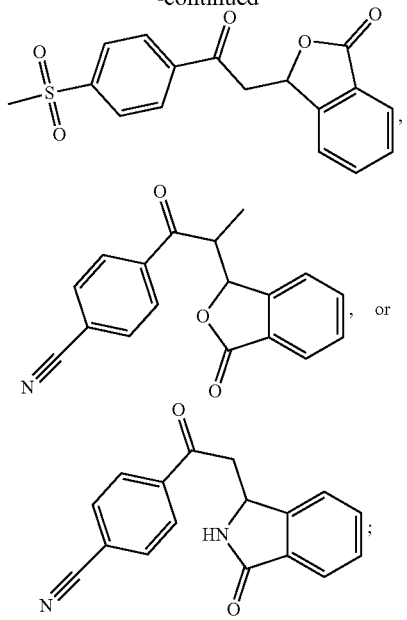
or a pharmaceutically acceptable salt, solvate, polymorph, prodrug, ester, metabolite, N-oxide, stereoisomer, or isomer thereof.
* * * * *